US012680121B2

(12) United States Patent
Louis et al.

(10) Patent No.: US 12,680,121 B2
(45) Date of Patent: Jul. 14, 2026

(54) HYALURONIC ACID-PRODUCING RECOMBINANT CELLS

(71) Applicant: GIVAUDAN SA, Vernier (CH)

(72) Inventors: Dominique Louis, Orsay (FR);
Valentina Bevilacqua, Orsay (FR);
Lionel Durant, Orsay (FR); **Karine
Jaillardon, Orsay (FR); Dominique
Thomas**, Argenteuil (FR)

(73) Assignee: GIVAUDAN SA, Vernier (CH)

( * ) Notice: Subject to any disclaimer, the term of this patent is extended or adjusted under 35 U.S.C. 154(b) by 111 days.

(21) Appl. No.: 18/553,487

(22) PCT Filed: Mar. 31, 2022

(86) PCT No.: PCT/EP2022/058558
§ 371 (c)(1),
(2) Date: Sep. 29, 2023

(87) PCT Pub. No.: WO2022/207786
PCT Pub. Date: Oct. 6, 2022

(65) Prior Publication Data
US 2025/0146037 A1        May 8, 2025

(30) Foreign Application Priority Data

Apr. 1, 2021  (EP) ..................................... 21166743
Oct. 26, 2021  (EP) ..................................... 21306488

(51) Int. Cl.
| | |
|---|---|
| *C12P 19/26* | (2006.01) |
| *C12N 9/00* | (2006.01) |
| *C12N 9/04* | (2006.01) |
| *C12N 9/06* | (2006.01) |
| *C12N 9/10* | (2006.01) |
| *C12N 9/26* | (2006.01) |

(52) U.S. Cl.
CPC ............ *C12P 19/26* (2013.01); *C12N 9/0006* (2013.01); *C12N 9/0016* (2013.01); *C12N 9/1051* (2013.01); *C12N 9/2474* (2013.01); *C12N 9/93* (2013.01); *C12Y 101/01022* (2013.01); *C12Y 104/01014* (2013.01); *C12Y 204/01212* (2013.01); *C12Y 302/01035* (2013.01); *C12Y 603/01002* (2013.01)

(58) Field of Classification Search
None
See application file for complete search history.

(56) References Cited

U.S. PATENT DOCUMENTS

| | | | |
|---|---|---|---|
| 2014/0038235 A1* | 2/2014 | Sloma ..................... | C12P 19/26 |
| | | | 435/252.31 |
| 2017/0073719 A1 | 3/2017 | Chen | |
| 2020/0224230 A1* | 7/2020 | Louis ..................... | C12N 15/52 |

FOREIGN PATENT DOCUMENTS

| | | |
|---|---|---|
| CN | 104263666 B | 7/2017 |

OTHER PUBLICATIONS

Gomes, A. et al., "Heterologous Hyaluronic Acid Production in *Kluyveromyces lactis*".
National Library of Medicine, "PubChem ID 24759", 2024.
Pavicic et al, "Efficacy of Cream-Based Novel Formulations of Hyaluronic Acid of Different Molecular Weights in Anti-Wrinkle Treatment", Journal of Drugs in Dermatology, 10(9), pp. 990-1000, https://pubmed.ncbi.nlm.nih.gov/22052267/, Sep. 1, 2011 (Sep. 1, 2011).
De Oliveira et al, "Genetic basis for hyper production of hyaluronic acid in natural and engineered microorganisms", Microbial Cell Factories, 15(119), pp. 1-19, DOI 10.1186/s12934-016-0517-4, Jul. 1, 2016 (Jul. 1, 2016).
Sahu Umakant et al, "Methanol Expression Regulator 1 (Mxr1p) Is Essential for the Utilization of Amino Acids as the Sole Source of Carbon by the Methylotrophic Yeast, Pichia pastoris", US vol. 291, No. 39.
Wray Lewis V et al, "Bacillus subtilis Glutamine Synthetase Controls Gene Expression through a Protein-Protein Interaction with Transcription Factor TnrA", Cell,vol. 107, No. 4, Nov. 16, 2001 (Nov. 16, 2001), p. 427-435.
Du Yan et al, "Indirect Pathway Metabolic Engineering Strategies for Enhanced Biosynthesis of Hyaluronic Acid in Engineered *Corynebacterium glutamicum*", Frontiers in Bioengineering and Biotechnology,vol. 9, Dec. 20, 2021 (Dec. 20, 2021).

* cited by examiner

*Primary Examiner* — Blaine Lankford
(74) *Attorney, Agent, or Firm* — WCF IP

(57) ABSTRACT

The present invention relates to the field of bio-production of hyaluronic acid.
There is a need in the art for hyaluronic acid production methods allowing its highly efficient synthesis and secretion. The solution proposed in the present invention is the use of a genetically modified cell comprising many modifications as described in the present text.
The present invention further proposes methods allowing the bio-production of hyaluronic acid having a controlled molecular weight using the genetically modified cells of the invention.

17 Claims, 2 Drawing Sheets

Specification includes a Sequence Listing.

HYALURONIC ACID-PRODUCING RECOMBINANT CELLS

SEQUENCE LISTING

This application includes as the Sequence Listing the complete contents of the accompanying text file "2024-06-12_13390125US_seqlisting.txt", created Jun. 12, 2024, containing 268,138 bytes, hereby incorporated by reference.

FIELD OF THE INVENTION

The present invention relates to the field of bio-production of hyaluronic acid.

BACKGROUND OF THE INVENTION

Hyaluronic acid, also known as hyaluronan or HA, is a naturally occurring high molecular weight polysaccharide composed of D-glucuronic acid and N-acetyl-D-glucosamine, linked via alternating $\beta$-(1→4) and $\beta$-(1→3) glycosidic bonds and having the chemical formula $(C_{14}H_{21}NO_{11})n$. Hyaluronic acid can be 25,000 disaccharide repeats in length. Polymers of hyaluronic acid can range in size from 5,000 to 20,000,000 Da in vivo.

HA has many applications in the medical and cosmetic fields including scaffolding for tissue engineering, dermatological fillers, and viscosupplementation for osteoarthritis treatment. In particular, a reduction in HA mass or molecular weight via degradation or slowing of synthesis affects physical and chemical properties such as tissue volume, viscosity, and elasticity. There is therefore a constant need for HA production.

Today's main known sources of HA are human ombilical cords, rooster combs and fermentation of certain microorganisms.

Fermentation methods for preparing HA from microorganisms are particularly of interest since they facilitate the production of a large quantity of HA through possible scale-up, at a reduced cost. Contrary to isolating HA from animal sources which provide hyaluronic acid of very high molecular weights, microbial fermentation allows to control, to a certain extent, the size of the starting molecular weight. This avoids the need for further fractionation steps by mechanical, physical or chemical means.

In this aim, bacterial cultures such as group A and C hemolytic streptococci have been shown to represent good sources of HA (U.S. Pat. Nos. 5,316,926, 4,801,539, JP2009011315). However, such bacteria, and in particular *Streptococcus zooepidemicus* which is mainly used in the art, is not generally recognized as safe. Recombinant *Bacillus* host cells have also shown the ability to produce HA in the range of 20 to 800 KDa (US2008038780). It has also been demonstrated in US2006168690 that transforming plant cells to include a DNA encoding hyaluronic acid synthase successfully allowed for the production of HA. Finally, production of small molecules of HA has also been demonstrated in yeasts such as in a recombinant *Pichia pastoris* in CN104263666.

Contrary to other microorganisms that are commonly used for the production of biological molecules, yeasts are generally recognised as safe. They can grow rapidly and be cultivated at higher density, compared to bacteria, and do not require an aseptic environment. Furthermore, yeast cells can be more easily separated from the culture medium than bacteria, greatly simplifying the process for product extraction and purification. Finally, yeasts present the advantage of being more resistant to pH changes in the culture medium, and as such represent stronger fermentation systems.

However, among yeasts, distinguishing features between species may also present certain challenges. This is mainly due to the difference in metabolisms between the species. For example, genome integrations in *P. pastoris* are stable but often a high variability of clones from one transformation is encountered, displaying various productivity characteristics or changes in their physiology. This requires a time-consuming screening process so as to find the clone with the optimal features for the desired application. This clonal variability is an important drawback for the further development of *P. pastoris* as a platform for producing value-added chemicals. Another drawback of using *P. pastoris* is that it is a methanotrophic organism.

On the contrary, *Saccharomyces cerevisiae* is particularly useful as a tool for the production of molecules of interest since it has a long safe history when it comes to being used by humans (such as in wine, beer, or bread) and as such is a well-established model whose genetic information is well known in the art. *S. cerevisiae* further presents the advantage of being generally recognised as safe for humans and animals. What's more, the acidification of the medium which occurs when cultivating this yeast reduces the possibility of contamination of the bio fermenters, and therefore eliminates the need to add antibiotics to the medium. Finally, many genetic tools have been developed allowing for stable modifications of its genome (integration within the chromosome).

Accordingly, there is still a need in the art for further hyaluronic acid production methods allowing its highly efficient synthesis and secretion. In particular, there is still a need to provide production methods that are cost-efficient and supply hyaluronic acid which is safe for human application.

In a particular case, there is still a need in the art for hyaluronic acid methods allowing to obtain large amounts of hyaluronic acid of a particular and controlled size.

SUMMARY OF THE INVENTION

The present invention accordingly relates to the following items:

Item 1: a recombinant yeast cell producing hyaluronic acid (HA) wherein the recombinant cell comprises:

(a) one or more recombinant nucleic acids encoding a polypeptide having hyaluronan synthase activity;

(b) one or more recombinant nucleic acids encoding a polypeptide having UDP-Glucose dehydrogenase (UDP-GlcDH or HASB) activity;

(c) one or more recombinant nucleic acids encoding a polypeptide having hyaluronidase activity wherein the polypeptide having hyaluronidase activity comprises a secretion signal so that hyaluronic acid, in particular of a desired molecular weight (HAMW) is produced by the recombinant yeast cell, and (d) (i) one or more recombinant nucleic acids encoding a polypeptide having a glutamine synthetase (GLN1) activity; and/or (ii) one or more disrupted endogeneous nucleic acids encoding a glutamate synthase (GLT1);

wherein said recombinant yeast cell belongs to the *Saccharomyces* genus, or to the *Candida* genus, or to the *Kluyveromyces* genus, or to the *Ogataea* genus, or to the *Yarrowia* genus, or to the *Debaryomyces* genus, or to the *Ashbya* genus.

As illustrated in the examples, the recombinant yeasts of the invention allow for the production of hyaluronic acid in a yeast cell which is not naturally able to produce hyaluronic acid. It is further demonstrated in the examples that the size of the hylaruonic acid produced by the recombinant yeast may be controlled.

Said advantageous properties can be further increased by recombining the yeast with additional modifications described here-after.

Item 2: A recombinant host cell producing hyaluronic acid (HA) wherein the recombinant host cell comprises:

(a) one or more recombinant nucleic acids encoding a polypeptide having hyaluronan synthase activity;

(b) one or more recombinant nucleic acids encoding a polypeptide having UDP-Glucose dehydrogenase (UDP-GlcDH or HASB) activity;

(c) one or more recombinant nucleic acids encoding a polypeptide having hyaluronidase activity wherein the polypeptide having hyaluronidase activity comprises a secretion signal and an anchoring signal so that hyaluronic acid, in particular of a desired molecular weight (HAMW) is produced by the host cell; and (d) (i) one or more recombinant nucleic acids encoding a polypeptide having a glutamine synthetase (GLN1) activity; and/or (ii) one or more disrupted endogeneous nucleic acids encoding a glutamate synthase (GLT1).

Item 3: The recombinant cell according to item 1 or 2, wherein the molecular weight of the HA is in the range of less than 50 kDa, preferably in the range of about 20 kDa to about 50 kDa.

Item 4: The recombinant cell according to item 1 or 2, wherein the molecular weight of the HA is in the range of greater than 50 kDa, preferably in the range of about 50 kDa to about 250 kDa.

Item 5: The recombinant cell according to item 1 or 2, wherein the molecular weight of the HA is in the range of greater than 100 kDa, preferably in the range of about 100 kDa to about 1500 kDa.

Item 6: The recombinant cell according to any one of items 1 to 5, wherein the nucleic acid encoding a polypeptide having a glutamine synthetase activity is obtained or derived from *Saccharomyces cerevisiae*.

Item 7: The recombinant cell according to any one of items 1 to 6, wherein the nucleic acid encoding a polypeptide having hyaluronidase activity is obtained or derived from at least one of *Cupiennius salei, Loxosceles intermedia, Hirudo nipponia, Bothrops atrox* or *Tityus serrulatus*.

Item 8: The recombinant cell according to any one of items 1 to 7 wherein the nucleic acid encoding a polypeptide having hyaluronan synthase activity is obtained or derived from at least one of *Streptococcus zooepidemicus, Chlorella* virus PBCV1, *Chlorella* virus CviK1, *Chlorella* virus IL-5-2s1, *Chlorella* virus CZ-2, *Chlorella* virus CVG-1, *Xenopus laevis* or *Pasteurella multocida*, and is in particular obtained or derived from at least one of *Streptococcus zooepidemicus, Chlorella* virus PBCV1, *Chlorella* virus CviK1, *Chlorella* virus IL-5-2s1, *Chlorella* virus CZ-2, *Chlorella* virus CVG-1, or *Xenopus laevis*.

Item 9: The recombinant cell according to any one of items 1 to 8, wherein the nucleic acid encoding a polypeptide having UDP-Glucose dehydrogenase activity is obtained or derived from at least one of *Arabidopsis thaliana, Chlorella* virus PBCV1 or *Strep-*

*tococcus zooepidemicus*, and in particular from *Arabidopsis thaliana* or *Chlorella* virus PBCV1.

Item 10: The recombinant cell according to any one of items 1 to 9, wherein the recombinant cell comprises a recombinant nucleic acid encoding one or more of:

(i) a polypeptide having glutamine-fructose-6-phosphate amidotransferase (GFA1) activity; and/or (ii) a polypeptide having UDP-N-acetylglucosamine pyrophosphorylase (QRI1) activity.

Item 11: The recombinant cell according to any one of items 1 to 10, wherein the recombinant cell comprises at least one recombinant nucleic acid encoding one or more of:

(i) a polypeptide having Phosphoglucomutase-1 (PGM1) activity; and/or (ii) a polypeptide having UTP-glucose-1-phosphate uridylyltransferase (UGP1) activity; and/or (iii) a polypeptide having Glucosamine-6-phosphate N-acetyltransferase (GNA1) activity; and/or (iv) a polypeptide having phosphoacetylglucosamine mutase (PCM1) activity.

Item 12: The recombinant yeast cell according to any one of items 1 and 3 to 11, wherein the recombinant yeast cell is selected from the group consisting of *Saccharomyces cerevisiae, Saccharomyces boulardii, Saccharomyces bayanus, Saccharomyces paradoxus, Saccharomyces mikatae, Saccharomyces castelli, Candida albicans, Candida glabrata, Candida tropicalis, Kluyveromyces lactis, Kluyveromyces marxianus, Kluyveromyces polysporus, Kluyveromyces thermotolerens, Ogataea polymorpha, Yarrowia lypolytica, Debaryomyces hansenii*, and *Ashbya gossypii*, and is preferably *Saccharomyces cerevisiae*.

Item 13: The recombinant host cell according to any one of items 2 to 11 wherein the recombinant host cell belongs to the Saccharomycesales order, in particular to the Saccharomycesaceae family, and is in particular selected from the group consisting of *Saccharomyces cerevisiae, Saccharomyces boulardii, Saccharomyces bayanus, Saccharomyces paradoxus, Saccharomyces mikatae, Saccharomyces castelli, Candida albicans, Candida glabrata, Candida tropicalis, Kluyveromyces lactis, Kluyveromyces marxianus, Kluyveromyces polysporus, Kluyveromyces thermotolerens, Ogataea polymorpha, Yarrowia lypolytica, Debaryomyces hansenii*, and *Ashbya gossypii*, and is preferably *Saccharomyces cerevisiae*.

Item 14: A method of producing hyaluronic acid (HA) of a desired molecular weight (HAMW) comprising:

(a) cultivating a recombinant cell as defined in any one of items 1 to 13 in a cultivation medium for a time sufficient to produce hyaluronic acid (HA) of the desired molecular weight; and (b) optionally isolating or recovering the hyaluronic acid (HA) from the recombinant cell and/or from the cultivation medium.

Item 15: The method according to item 14, wherein the HA has a molecular weight of from about 20 kDa to about 50 kDA, and preferably from about 20 kDa to about 30 kDa.

Item 16: The method according to item 15, wherein the HA has a molecular weight of from about 30 kDa to about 50 kDa.

Item 17: The method according to item 14, wherein the molecular weight of the HA is of from about 50 kDa to about 150 kDa.

Item 18: The method according to item 14, wherein the molecular weight of the HA is of from about 150 kDa to about 1500 kDa.

Item 19: The method according to any one of items 14 to 18 wherein the recombinant cell comprises at least one recombinant nucleic acid encoding one or more of:

(i) a polypeptide having glutamine-fructose-6-phosphate amidotransferase (GFA1) activity; and/or (ii) a polypeptide having UDP-N-acetylglucosamine pyrophosphorylase (QRI1) activity.

Item 20: The method according to any one of items 14 to 19, wherein the recombinant cell comprises at least one recombinant nucleic acid encoding one or more of:

(i) a polypeptide having Phosphoglucomutase-1 (PGM1) activity;

(ii) a polypeptide having UTP-glucose-1-phosphate uridylyltransferase (UGP1) activity;

(iii) a polypeptide having Glucosamine-6-phosphate N-acetyltransferase (GNA1) activity; and/or (iv) a polypeptide having phosphoacetylglucosamine mutase (PCM1) activity.

Item 21: The method according to any one of items 14 to 20, wherein the recombinant cell is a member of the genus *Saccharomyces*, and in particular is *Saccharomyces cerevisiae*.

Item 22: The method according according to any one of items 14 to 21, wherein the time sufficient to produce hyaluronic acid (HA) of the desired molecular weight is a period of from about 35 hours to about 50 hours, preferably from about 40 hours to about 50 hours, preferably about 48 hours.

Item 23: The method according according to any one of items 14 to 22, wherein the molecular weight of the hyaluronic acid is controlled by regulating the pH of the cultivation medium.

Item 24: The method according to any one of items 14 to 23, wherein the method is carried out on an industrial scale, preferably where the cultivation medium is at least about 100 L, more preferably in the range of about 1000 L to about 3000 L, even more preferably about 10,000 L, even more preferably about 100,000 L, or even about 250,000 L.

Item 25: Hyaluronic acid (HA) obtainable from a recombinant cell of any one of items 1 to 10 or from the method according to any one of items 14 to 24.

Item 26: A cultivation medium comprising the HA according to item 25.

Item 27: A composition comprising the Hyaluronic acid (HA) according to item 24.

Item 28: An industrial product or a consumer product or a consumable comprising (i) the HA according to item 25, (ii) the cultivation medium of item 26 or (iii) the composition of item 27.

Item 29: The industrial product or the consumer product or the consumable of item 27, wherein the industrial product or the consumer product or the consumable is a cosmetic product, a flavour product, a fragrance product, a food product, a food, a beverage, a texturant, a pharmaceutical composition, a dietary supplement, a nutraceutical, a cleaning product and/or a dental and/or an oral hygiene composition.

Item 30: Use of a recombinant cell as defined in any one of items 1 to 13 for the production of hyaluronic acid (HA) having a molecular weight in the range of from about 20 kDa to about 50 kDa or from about 50 kDa to about 1000 kDa.

Item 31: A method for producing hyaluronic acid comprising the steps of:

(a) culturing a recombinant yeast as defined in any one of items 1 and 3 to 12 in a culture medium; and (b) recovering the hyaluronic acid from said culture medium, wherein the hyaluronic acid recovered in step (b) has a molecular weight controlled through the selection of:

the nature and origin of the nucleic acid encoding the hyaluronidase of the recombinant yeast, the nature and origin of the promoter controlling the expression of the nucleic acid encoding the hyaluronidase(s) of the recombinant yeast, the presence of an anchoring and/or of a secretion signal associated to the encoded hyaluronidase(s) of the recombinant yeast, the pH of the culture medium during the step of culturing the recombinant yeast, and/or the duration of the culturing of the recombinant yeast.

Certain embodiments of the present invention may provide one or more of the following advantages:

a process for producing Hyaluronic acid of controlled molecular weight;

a process for producing Hyaluronic acid of controlled molecular weight in a *Saccharomyces* yeast cell; and a process for producing Hyaluronic acid of controlled molecular weight by varying genetic parameters (eg regulatory sequences) and/or process parameters (pH or fermentation time).

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

SUMMARY OF THE SEQUENCES

Figure 1:
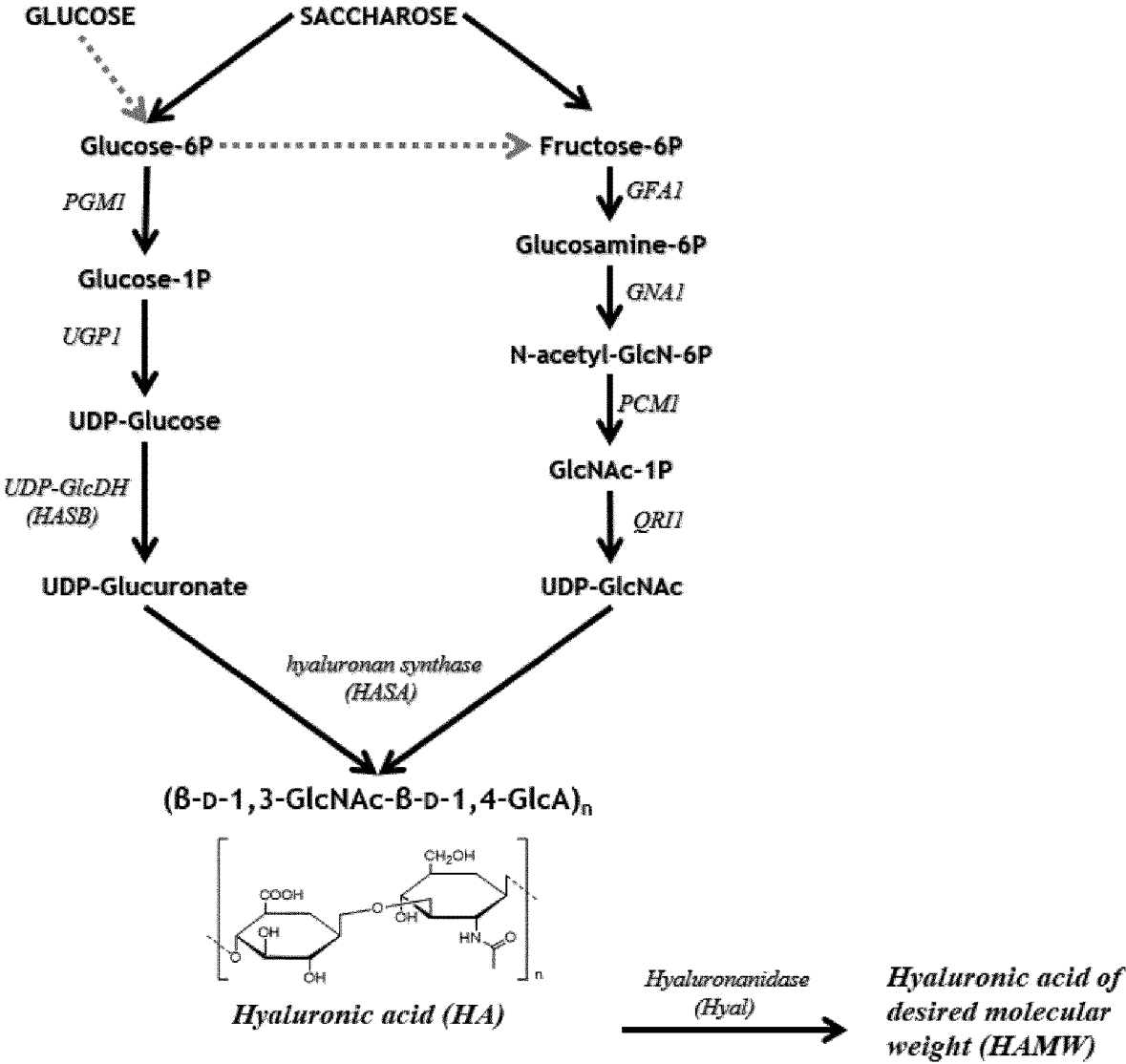
FIG. 1 shows a schematic pathway for the production of hyaluronic acid

SEQ ID NO: 1 is a reencoded nucleic acid sequence of hyaluronan synthase (HASA) originating from *Chlorella* virus PBCV-1

SEQ ID NO: 2 is a reencoded nucleic acid sequence of hyaluronan synthase (HASA) originating from *Chlorella* virus PBCV-1

SEQ ID NO: 3 is a reencoded nucleic acid sequence of hyaluronan synthase (HASA) originating from *Pasteurella multocida*

SEQ ID NO: 4 is a reencoded nucleic acid sequence of hyaluronan synthase (HASA) originating from *Pasteurella multocida*

SEQ ID NO: 5 is a reencoded nucleic acid sequence of hyaluronan synthase (HASA) originating from *Pasteurella multocida*

SEQ ID NO: 6 is a reencoded nucleic acid sequence of hyaluronan synthase (HASA) originating from *Xenopus laevis*

SEQ ID NO: 7 is a reencoded nucleic acid sequence of hyaluronan synthase (HASA) originating from *Streptococcus zooepidemicus*

SEQ ID NO: 8 is an amino acid sequence of hyaluronan synthase (HASA) originating from *Chlorella* virus PBCV-1

SEQ ID NO: 9 is an amino acid sequence of hyaluronan synthase (HASA) originating from *Pasteurella multocida*

SEQ ID NO: 10 is an amino acid sequence of hyaluronan synthase (HASA) originating from *Xenopus laevis*

SEQ ID NO: 11 is an amino acid sequence of hyaluronan synthase (HASA) originating from *Streptococcus zooepidemicus*

SEQ ID NO: 12 is a nucleic acid sequence of UDP-Glucose dehydrogenase (HASB) originating from *Arabidopsis thaliana*

SEQ ID NO: 13 is a reencoded nucleic acid sequence of UDP-Glucose dehydrogenase (HASB) originating from *Chlorella* virus PBCV-1

SEQ ID NO: 14 is a reencoded nucleic acid sequence of UDP-Glucose dehydrogenase (HASB) originating from *Chlorella* virus PBCV-1

SEQ ID NO: 15 is a reencoded nucleic acid sequence of UDP-Glucose dehydrogenase (HASB) originating from *Streptococcus zooepidemicus*

SEQ ID NO: 16 is an amino acid sequence of UDP-Glucose dehydrogenase (HASB) originating from *Arabidopsis thaliana*

SEQ ID NO: 17 is an amino acid sequence of UDP-Glucose dehydrogenase (HASB) originating from *Chlorella* virus PBCV1

SEQ ID NO: 18 is an amino acid sequence of UDP-Glucose dehydrogenase (HASB) originating from *Streptococcus zooepidemicus*

SEQ ID NO: 19 is a reencoded nucleic acid sequence of hyaluronidase (HYAL) originating from *Bothrops atrox* with a N-terminal secretion signal SEQ ID NO: 20 is a reencoded nucleic acid sequence of hyaluronidase (HYAL) originating from *Bothrops atrox* with a N-terminal secretion signal and a C-terminal anchoring signal SEQ ID NO: 21 is a reencoded nucleic acid sequence of hyaluronidase (HYAL) originating from *Cupiennius salei* with a N-terminal secretion signal SEQ ID NO: 22 is a reencoded nucleic acid sequence of hyaluronidase (HYAL) originating from *Cupiennius salei* with a N-terminal secretion signal and a C-terminal anchoring signal SEQ ID NO: 23 is a reencoded nucleic acid sequence of hyaluronidase (HYAL) originating from *Hirudo nipponia* with a N-terminal secretion signal SEQ ID NO: 24 is a reencoded nucleic acid sequence of hyaluronidase (HYAL) originating from *Hirudo nipponia* with a N-terminal secretion signal and a C-terminal anchoring signal SEQ ID NO: 25 is a reencoded nucleic acid sequence of hyaluronidase (HYAL) originating from *Loxosceles intermedia* with a N-terminal secretion signal SEQ ID NO: 26 is a reencoded nucleic acid sequence of hyaluronidase (HYAL) originating from *Loxosceles*

*intermedia* with a N-terminal secretion signal and a C-terminal anchoring signal SEQ ID NO: 27 is a reencoded nucleic acid sequence of hyaluronidase (HYAL) originating from *Tityus serrulatus* with a N-terminal secretion signal SEQ ID NO: 28 is a reencoded nucleic acid sequence of hyaluronidase (HYAL) originating from *Tityus serrulatus* with a N-terminal secretion signal and a C-terminal anchoring signal SEQ ID NO: 29 is a reencoded nucleic acid sequence of hyaluronidase (HYAL) originating from *Vespa magnifica* with a N-terminal secretion signal SEQ ID NO: 30 is a reencoded nucleic acid sequence of hyaluronidase (HYAL) originating from *Vespa magnifica* with a N-terminal secretion signal and a C-terminal anchoring signal SEQ ID NO: 31 is an amino acid sequence of hyaluronidase (HYAL) originating from *Bothrops atrox* with a N-terminal secretion signal SEQ ID NO: 32 is an amino acid sequence of hyaluronidase (HYAL) originating from *Bothrops atrox* with a N-terminal secretion signal and a C-terminal anchoring signal SEQ ID NO: 33 is an amino acid sequence of hyaluronidase (HYAL) originating from *Cupiennius salei* with a N-terminal secretion signal SEQ ID NO: 34 is an amino acid sequence of hyaluronidase (HYAL) originating from *Cupiennius salei* with a N-terminal secretion signal and a C-terminal anchoring signal SEQ ID NO: 35 is an amino acid sequence of hyaluronidase (HYAL) originating from *Hirudo nipponia* with a N-terminal secretion signal SEQ ID NO: 36 is an amino acid sequence of hyaluronidase (HYAL) originating from *Hirudo nipponia* with a N-terminal secretion signal and a C-terminal anchoring signal SEQ ID NO: 37 is an amino acid sequence of hyaluronidase (HYAL) originating from *Loxosceles intermedia* with a N-terminal secretion signal SEQ ID NO: 38 is an amino acid sequence of hyaluronidase (HYAL) originating from *Loxosceles intermedia* with a N-terminal secretion signal and a C-terminal anchoring signal SEQ ID NO: 39 is an amino acid sequence of hyaluronidase (HYAL) originating from *Tityus serrulatus* with a N-terminal secretion signal SEQ ID NO: 40 is an amino acid sequence of hyaluronidase (HYAL) originating from *Tityus serrulatus* with a N-terminal secretion signal and a C-terminal anchoring signal SEQ ID NO: 41 is an amino acid sequence of hyaluronidase (HYAL) originating from *Vespa magnifica* with a N-terminal secretion signal SEQ ID NO: 42 is an amino acid sequence of hyaluronidase (HYAL) originating from *Vespa magnifica* with a N-terminal secretion signal and a C-terminal anchoring signal SEQ ID NO: 43 is a nucleic acid sequence of the secretion sequence added in 5'

SEQ ID NO: 44 is an amino acid sequence of the secretion sequence added in N-ter SEQ ID NO: 45 is a nucleic acid sequence of the anchoring sequence added in 3'

SEQ ID NO: 46 is an amino acid sequence of the anchoring sequence added in C-ter SEQ ID NO: 47 is a nucleic acid sequence of glutamine-fructose-6-phosphate amidotransferase (GFA1) originating from *Saccharomyces cerevisiae*

SEQ ID NO: 48 is a reencoded nucleic acid sequence of glutamine-fructose-6-phosphate amidotransferase (GFA1) originating from *Chlorella* virus 1 (PBCV-1)

SEQ ID NO: 49 is a reencoded nucleic acid sequence of glutamine-fructose-6-phosphate amidotransferase (GFA1) originating from *Chlorella* virus 1 (PBCV-1)

SEQ ID NO: 50 is an amino acid sequence of glutamine-fructose-6-phosphate amidotransferase (GFA1) originating from *Saccharomyces cerevisiae*

SEQ ID NO: 51 is an amino acid sequence of glutamine-fructose-6-phosphate amidotransferase (GFA1) originating from *Chlorella* virus 1 (PBCV-1)

SEQ ID NO: 52 is a nucleic acid sequence of UDP-N-acetylglucosamine pyrophosphorylase (QRI1) originating from *Saccharomyces cerevisiae*

SEQ ID NO: 53 is an amino acid sequence of UDP-N-acetylglucosamine pyrophosphorylase (QRI1) originating from *Saccharomyces cerevisiae*

SEQ ID NO: 54 is a nucleic acid sequence of Phosphoglucomutase-1 (PGM1) originating from *Saccharomyces cerevisiae*

SEQ ID NO: 55 is an amino acid sequence Phosphoglucomutase-1 (PGM1) originating from *Saccharomyces cerevisiae*

SEQ ID NO: 56 is a nucleic acid sequence of UTP-glucose-1-phosphate uridylyltransferase (UGP1) originating from *Saccharomyces cerevisiae*

SEQ ID NO: 57 is an amino acid sequence of UTP-glucose-1-phosphate uridylyltransferase (UGP1) originating from *Saccharomyces cerevisiae*

SEQ ID NO: 58 is a nucleic acid sequence of Glucosamine 6-phosphate N-acetyltransferase (GNA1) originating from *Saccharomyces cerevisiae*

SEQ ID NO: 59 is an amino acid sequence of Glucosamine 6-phosphate N-acetyltransferase (GNA1) originating from *Saccharomyces cerevisiae*

SEQ ID NO: 60 is a nucleic acid sequence of phospho-acetylglucosamine mutase (PCM1) originating from *Saccharomyces cerevisiae*

SEQ ID NO: 61 is an amino acid sequence of phospho-acetylglucosamine mutase (PCM1) originating from *Saccharomyces cerevisiae*

SEQ ID NO: 62 is the nucleic acid sequence of promotor pTDH3

SEQ ID NO:63 is the nucleic acid sequence of promotor pTDH3.Sk

SEQ ID NO: 64 is the nucleic acid sequence of promotor pTDH3-1.sba

SEQ ID NO: 65 is the nucleic acid sequence of promotor pTDH3.Sar

SEQ ID NO: 66 is the nucleic acid sequence of promotor pENO2

SEQ ID NO: 67 is the nucleic acid sequence of promotor pTEF3

SEQ ID NO: 68 is the nucleic acid sequence of promotor pTEF1

SEQ ID NO: 69 is the nucleic acid sequence of promotor pTEF1.ago

SEQ ID NO: 70 is the nucleic acid sequence of promotor pTEF1.Sba

SEQ ID NO: 71 is the nucleic acid sequence of promotor pPDC1

SEQ ID NO: 72 is the nucleic acid sequence of promotor pCCW12

SEQ ID NO: 73 is the nucleic acid sequence of promotor pCCW12.Sm

SEQ ID NO: 74 is the nucleic acid sequence of promotor pCCW12.Sk

SEQ ID NO: 75 is the nucleic acid sequence of promotor pCCW12.Sba

SEQ ID NO: 76 is the nucleic acid sequence of promotor pCCW12.Sar

SEQ ID NO: 77 is the nucleic acid sequence of promotor pNUP57

SEQ ID NO: 78 is the nucleic acid sequence of promotor pCCW10.ago

SEQ ID NO: 79 is the nucleic acid sequence of promotor pCWP2

SEQ ID NO: 80 is the nucleic acid sequence of promotor pRPLA1

SEQ ID NO: 81 is the nucleic acid sequence of promotor pCUP1

SEQ ID NO: 82 is the nucleic acid sequence of promotor pMET6

SEQ ID NO: 83 is the nucleic acid sequence of promotor pMET25

SEQ ID NO: 84 is the nucleic acid sequence of promotor pSAM1

SEQ ID NO: 85 is the nucleic acid sequence of terminator tTPI1

SEQ ID NO: 86 is the nucleic acid sequence of terminator tMET25

SEQ ID NO: 87 is the nucleic acid sequence of terminator tDIT1

SEQ ID NO: 88 is the nucleic acid sequence of terminator tRPL3

SEQ ID NO: 89 is the nucleic acid sequence of terminator tRPL3.sm

SEQ ID NO: 90 is the nucleic acid sequence of terminator tRPL3.sba

SEQ ID NO: 91 is the nucleic acid sequence of terminator tRPL41B

SEQ ID NO: 92 is the nucleic acid sequence of terminator tRPL15A

SEQ ID NO: 93 is the nucleic acid sequence of terminator tRPL15A.sba

SEQ ID NO: 94 is the nucleic acid sequence of terminator tIDP1

SEQ ID NO: 95 is the nucleic acid sequence of terminator tTEF1.sba

SEQ ID NO: 96 is a nucleic acid sequence of Glutamine synthetase (GLN1) originating from *Saccharomyces cerevisiae*

SEQ ID NO: 97 is an amino acid sequence of Glutamine synthetase (GLN1) originating from *Saccharomyces cerevisiae*

SEQ ID NO: 98 is a nucleic acid sequence of Glutamate synthase (GLT1) originating from *Saccharomyces cerevisiae*

SEQ ID NO: 99 is an amino acid sequence of Glutamate synthase (GLT1) originating from *Saccharomyces cerevisiae*

SEQ ID NO: 100 is the nucleic acid sequence of terminator tTDH3.

SEQ ID NO: 101 is a reencoded nucleic acid sequence of hyaluronan synthase (HASA) originating from *Chlorella* virus CviK1

SEQ ID NO: 102 is a reencoded nucleic acid sequence of hyaluronan synthase (HASA) originating from *Chlorella* virus IL-5-2s1

SEQ ID NO: 103 is a reencoded nucleic acid sequence of hyaluronan synthase (HASA) originating from *Chlorella* virus CZ-2

SEQ ID NO: 104 is a reencoded nucleic acid sequence of hyaluronan synthase (HASA) originating from *Chlorella* virus CVG-1

SEQ ID NO: 105 is an amino acid sequence of hyaluronan synthase (HASA) originating from *Chlorella* virus CviK1

SEQ ID NO: 106 is an amino acid sequence of hyaluronan synthase (HASA) originating from *Chlorella* virus IL-5-2s1

SEQ ID NO: 107 is an amino acid sequence of hyaluronan synthase (HASA) originating from *Chlorella* virus CZ-2

SEQ ID NO: 108 is an amino acid sequence of hyaluronan synthase (HASA) originating from *Chlorella* virus CVG-1

DETAILED DESCRIPTION OF THE INVENTION

The inventors have conceived genetically modified cells, and especially genetically modified yeasts, having the ability to produce hyaluronic acid, as compared to the parent cells, and especially as compared to the parent yeasts which are not naturally capable of doing so.

These genetically modified cells are described throughout the present specification.

Definitions

The term "Hyaluronic acid" also known as hyaluronan or HA, is polysaccharide composed of D-glucuronic acid and N-acetyl-D-glucosamine, linked via alternating $\beta$-(1→4) and $\beta$-(1→3) glycosidic bonds and having the chemical formula $(C_{14}H_{21}NO_{11})n$.

Hyalyuronic acid may be produced in a recombinant cell.

As used herein, the term "recombinant", when used in reference to a cell, indicates that the cell has been modified by the introduction of an endogenous and/or heterologous nucleic acid or protein into the cell or the alteration of a native cell or that the cell is derived from a cell so modified. Thus, for example, recombinant cells express genes or nucleic acid that are not found within the native (non-recombinant) form of the cell or express native (eg endogenous) genes at a different level than their native level or express additional or supplementary copies of native (eg endogenous) at a different level than their native level.

As used herein, the term "recombinant", when used in reference to a nucleic acid or vector, are sequences formed/obtained by technics of genetic engineering well known to the man skilled in the art. The guidelines of the US National Institute for Health (NIH) accordingly indicate that:

"recombinant [ . . . ] nucleic acids are defined as:

i. molecules that (a) are constructed by joining nucleic acid molecules and (b) that can replicate in a living cell, i.e., recombinant nucleic acids;", which reflects the conventional use of the word "recombinant" attached to nucleic acid sequences to mean recombined following the insertion of, or joining together with, another nucleic acid.

Proteins that result from the expression of recombinant DNA or recombinant vector within living cells are also termed recombinant proteins.

The term "recombinant" is accordingly synonymous with the term "genetically modified". The term "gene" is synonymous with the term "nucleic acid" or "nucleotide sequence".

A recombinant nucleic acid sequence for use in a recombinant cell, and in particular a recombinant yeast, of the invention may be provided in the form of a nucleic acid construct. The term "nucleic acid construct" refers to as a nucleic acid molecule, either single- or double-stranded, which is isolated or derived from a native (eg endogenous) naturally occurring gene or is a heterologous nucleic acid or which has been modified to contain segments of nucleic acid which are combined and juxtaposed in a manner which would not otherwise exist in nature. The term "nucleic acid construct" is synonymous with the term "expression cassette" or "heterologous nucleic acid expression cassette" when the nucleic acid construct contains one or more regulatory elements required for expression of a coding sequence, wherein said control sequences are operably linked to said coding sequence. Non-limiting examples of regulatory elements include promoters, enhancers, silencers, terminators, and poly-A signals.

A recombinant nucleic acid sequence for use in a recombinant cell of the invention may be provided in the form of an expression vector, wherein the polynucleotide sequence is operably linked to at least one control sequence for the expression of the polynucleotide sequence in a recombinant cell.

The terms "obtained from" or "originate from" or "originating from" a microorganism or animal generally means that a substance (e.g., a nucleic acid molecule or polypeptide) originating from the microorganism or animal is native to that microorganism or animal.

The terms "derived from" a microorganism or animal generally means that a substance (e.g., a nucleic acid molecule or polypeptide) derived from the microorganism or animal is the result of modifications brought to the substance native to (i.e. present as such) in that microorganism or animal. For example, regarding a nucleic acid sequence derived from a microorganism or animal, said nucleic acid sequence can correspond to a reencoded and/or truncated version of the native nucleic acid sequence from this microorganism or animal. Other modifications well known to the man skilled in the art can be brought to the native substance of a microorganism or animal leading to the substance used being "derived from" said microorganism or animal.

As used herein, the term "polypeptide" refers to a molecule comprising amino acid residues linked by peptide bonds and containing more than five amino acid residues. The amino acids are identified by either the single-letter or three-letter designations. The term "protein" as used herein is synonymous with the term "polypeptide" and may also refer to two or more polypeptides. Thus, the terms "protein", "peptide" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity may be referred to as enzymes. It will be understood that, as a result of the degeneracy of the genetic code, a multitude of nucleotide sequences encoding a given polypeptide may be produced.

A polypeptide encoded by a recombinant nucleic acid for use in a recombinant cell, and in particular in a recombinant yeast, of the invention may comprise a signal peptide and/or a propeptide sequence. In the event that a polypeptide expressed by a recombinant cell, and in particular a recombinant yeast, of the invention comprises a signal peptide and/or a propeptide, sequence identity may be calculated over the mature polypeptide sequence.

The term "operably linked" as used herein refers to two or more nucleic acid sequence elements that are physically linked and are in a functional relationship with each other. For instance, a promoter is operably linked to a coding sequence if the promoter is able to initiate or regulate the transcription or expression of the coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

The term "native" or "endogenous" as used herein with reference to molecules, and in particular enzymes and nucleic acids, indicates molecules that are expressed in the organism in which they originated or are found in nature.

The term "endogenous gene" means that the gene was present in the cell before any genetic modification, in the wild-type strain. Endogenous genes may be overexpressed by introducing heterologous sequences in addition to, or to replace endogenous regulatory elements, or by introducing one or more additional or supplementary copies of the gene into the chromosome or a plasmid (said additional or supplementary copies being designated "exogenous or heterologous genes" or "heterologous nucleotide sequences" or "heterologous nucleic acids" as defined herein). Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, in the down-regulation and/or attenuation of the activity of the endogenous gene product. Another way to enhance expression of endogenous genes is to introduce one or more additional or supplementary copies of the gene onto the chromosome or a plasmid (said supplementary copies being designated "exogenous or heterologous genes" or "heterologous nucleotide sequences" or heterologous nucleic acids" as defined herein).

By "one or more additional or supplementary copies of a gene" according to the invention, it is for example understood in the present invention from 1 to 50 copies, in particular from 1 to 30 copies, more particularly from 1 to 20 copies, and preferably from 1 to 10 copies. Said copies may be inserted into the same locus or into different loci of a recombinant cell of the invention.

The term "exogenous gene" means that the gene was introduced into a cell, by means well known to the man skilled in the art, whereas this gene is or is not naturally occurring in the wild-type cell. Cells can express exogenous genes if these genes are introduced into the cell with all the elements allowing their expression in the cell. Transforming cells with exogenous DNA is a routine task for the man skilled in the art. Exogenous genes may be integrated into the host chromosome, or be expressed extra-chromosomally from plasmids or vectors. A variety of plasmids, which differ with respect to their origin of replication and their copy number in the cell, are all known in the art. The sequence of exogenous genes may be adapted for its expression in the cell. Indeed, the man skilled in the art knows the notion of codon usage bias and how to adapt nucleic sequences for a particular codon usage bias without modifying the deduced protein. In particular embodiments, codon optimized genes express native enzymes.

The term "heterologous gene" or heterologous nucleic acid sequence" refers to a gene or nucleic acid sequence not normally found in a given cell in nature. As such, a heterologous nucleic acid sequence may be: (a) foreign to its host cell (i.e. is "exogenous" to the cell); (b) naturally found in the host cell (i.e. "endogenous") but present at an unnatural quantity in the cell (i.e., greater or lesser quantity than naturally found in the host cell); or (c) be naturally found in the host cell but positioned outside of its natural locus.

In the present application, all genes are referenced with their common names and with references to their nucleotide sequences and, the case arising, to their amino acid sequences. Using the references given in accession number for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other cells and designing degenerated probes to clone the corresponding gene in another organism.

The man skilled in the art knows different means to modulate, and in particular up-regulate or down-regulate, the expression of endogenous genes. For example, a way to enhance expression of, or over express, endogenous genes is to introduce one or more additional or supplementary copies of the gene onto the chromosome or a plasmid.

Another way is to replace the endogenous promoter of a gene with a stronger promoter. These promoters may be homologous or heterologous. Promoters particularly interesting in the present invention are described in more detail elsewhere in the present specification.

The nucleic acid expression construct may further comprise 5' and/or 3' recognition sequences and/or selection markers.

The term "inducible promoter" is used to qualify a promoter whose activity is induced, i.e. increased:

in the presence of one or more particular metabolite(s). The higher the metabolite concentration in the medium, the stronger the promoter activity; or in the presence of a low concentration, or in the absence, of one or more metabolite(s). These metabolites are different from those whose increasing presence induces the activity of the promoter. The lower the metabolite concentration in the medium, the stronger the promoter activity.

The term "repressible promoter" is used to qualify a promoter whose activity is repressed, i.e. reduced:

in the presence of one or more particular metabolite(s). The higher the metabolite concentration in the medium, the weaker the promoter activity; or in the presence of a low concentration, or in the absence, of one or more metabolite(s). These metabolites are different from those whose increasing presence represses the activity of the promoter. The lower the metabolite concentration in the medium, the weaker the promoter activity.

As used herein, the term "anchoring signal" when used in conjunction with a protein or polypeptide such as an enzyme (such as, for example hyaluronidase) means for example a first nucleic acid encoding a protein that is operably linked to a second nucleic acid encoding a protein or a polypeptide, or a first protein or polypeptide that is operably linked to a second protein or polypeptide, such as an enzyme (such as, for example hyaluronidase to form, for example a fusion protein), and that enables the cellular transport machinery of a cell, in particular of a *S. cerevisiae* cell, to correctly anchor and/or position in the membrane of the cell the second protein operably linked to the first protein.

As used herein, the term "secretion signal" when used in conjunction with a protein or polypeptide such as an enzyme (such as, for example hyaluronidase) means for example a first nucleic acid encoding a peptide or protein that is operably linked to a second nucleic acid encoding a protein, or a first protein that is linked to a second protein, such as an enzyme (such as, for example hyaluronidase to form, for example a fusion protein), and that enables the cellular transport machinery of a cell, in particular of a *S. cerevisiae* cell, to locate at least the second protein to the membrane of the cell and to secrete the second protein outside of the cell, after the first protein has, for example, been cleaved from the second protein.

As used herein the terms "secretion signal" and "anchoring signal" when used in conjunction with a protein or polypeptide such as an enzyme (such as, for example, hyaluronidase), mean for example a first nucleic acid encoding a peptide or protein that is operably linked to a second nucleic acid encoding a protein, or a first protein that is operably linked to a second protein, such as an enzyme (such as, for example hyaluronidase), and that enables the cellular transport machinery of a cell, in particular of a *S. cerevisiae* cell, to locate at least the second protein to the membrane of the cell wherein if the second protein is also operably linked to an "anchoring signal" the second protein is not secreted but remains attached to the membrane of the cell. In some cases, a secretion-anchoring signal may provide a dual secretion signal and anchoring signal function.

Sequences of secretion and anchoring signals, methods for the expression, anchoring and/or secretion of heterologous proteins, such as enzymes (such as, for example, hyaluronidase) on the surface of a cell (such, as for example, a yeast cell) are well known in the art (see for example, Ast et al (2013) Cell 152:1134-1145, Ast and Schuldiner (2013) Crit Rev Biochem Mol Biol 48 (3) 273-288, Van der Vaart et al (1997) Applied Environmental Microbiology 63 (2) 615-620 and the entire contents of each of these publications are incorporated herein by reference).

The "activity" of an enzyme is used interchangeably with the term "function" and designates, in the context of the invention, the capacity of an enzyme to catalyze a desired reaction. The amount of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked.

Alternatively or in addition, the copy number of an enzyme in a host cell may be altered by modifying the level of translation of an mRNA that encodes the enzyme. This can be achieved for example by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed back or feed-forward regulation by another molecule in the pathway.

The terms "encoding" or "coding for" refer to the process by which a polynucleotide, through the mechanisms of transcription and translation, produces an amino-acid sequence.

The gene(s) encoding the enzyme(s) considered in the present invention can be exogenous or endogenous.

The methods implemented in the present invention preferably require the use of one or more chromosomal integration constructs for the stable introduction of a heterologous nucleotide sequence into a specific location on a chromosome or for the functional disruption of one or more target genes in a genetically modified cell. In some embodiments, disruption of a target gene prevents the expression of the related functional protein. In some embodiments, disruption of a target gene results in the expression of a non-functional protein from the disrupted gene.

Accordingly, a "disrupted endogeneous nucleic acid" in the present invention relates to an endogeneous nucleic acid, or gene, unable to encode the functional, or fully functional, protein or polypeptide it codes for before it was disrupted. The nucleic acid can for example be disrupted by the introduction of an integration construct into the nucleic acid, as illustrated in the examples. Said integration can for example prevent the expression of the related functional protein or polypeptide or result in the expression of a non-functional, or non-fully functional protein or polypeptide from the disrupted gene.

Parameters of chromosomal integration constructs that may be varied in the practice of the present invention include, but are not limited to, the lengths of the homologous sequences; the nucleotide sequence of the homologous sequences; the length of the integrating sequence; the nucleotide sequence of the integrating sequence; and the nucleotide sequence of the target locus. In some embodiments, an effective range for the length of each homologous sequence is 20 to 5,000 base pairs, preferentially 50 to 100 base pairs. In particular embodiments, the length of each homologous sequence is about 50 base pairs. For more information on the length of homology required for gene targeting, see D. Burke et al., Methods in yeast Genetics-A cold spring harbor laboratory course Manual (2000).

In some embodiments, (a) disrupted gene(s) in which the above-mentioned DNA construct(s) is/are intended to be inserted may advantageously comprises one or more selectable markers useful for the selection of transformed cells. Preferably, said selectable marker(s) are comprised in the DNA construct(s) according to the present invention.

In some embodiments, the selectable marker is an antibiotic resistance marker. Illustrative examples of antibiotic resistance markers include, but are not limited to the, NAT1, AUR1-C, HPH, DSDA, KAN<R>, and SH BLE gene products. The NAT 1 gene product from *S. noursei* confers resistance to nourseothricin; the AUR1-C gene product from *Saccharomyces cerevisiae* confers resistance to Auerobasidin A (AbA); the HPH gene product of *Klebsiella pneumoniae* confers resistance to Hygromycin B; the DSDA gene product of *E. coli* allows cells to grow on plates with D-serine as the sole nitrogen source; the KAN<R> gene of the Tn903 transposon confers resistance to G418; and the SH BLE gene product from *Streptoalloteichus hindustanus* confers resistance to Zeocin (bleomycin).

In some embodiments, the antibiotic resistance marker is deleted after the genetically modified cell of the invention is isolated. The man skilled in the art is able to choose suitable marker in specific genetic context.

In a particular embodiment, a recombinant cell according to the invention is devoid of any antibiotic resistance marker. This advantageously prevents the necessity to add antibiotics in the selection medium.

In some embodiments, the selectable marker rescues an auxotrophy (e.g., a nutritional auxotrophy) in the genetically modified cell. In such embodiments, a parent cell, and in particular a parent yeast, comprises a functional disruption in one or more gene products that function in an amino acid or nucleotide biosynthetic pathway, such as, for example, the HIS3, LEU2, LYS1, LYS2, MET15, TRP1, ADE2, and URA3 gene products in yeast, which renders the parent cell incapable of growing in media without supplementation with one or more nutrients (auxotrophic phenotype). The auxotrophic phenotype can then be rescued by transforming the parent cell with a chromosomal integration encoding a functional copy of the disrupted gene product (in some embodiments the functional copy of the gene may originate from close species, such as *Kluveromyces, Candida* etc.), and the genetically modified cell generated can be selected based on the loss of the auxotrophic phenotype of the parent microbial cell.

For each of the nucleic acid sequences comprising a promoter sequence, a coding sequence (e.g. an enzyme coding sequence), or a terminator sequence, reference sequences are described herein. The present description also encompasses nucleic acid sequences having specific percentages of nucleic acid identity with a reference nucleic acid sequence.

For each or the amino acid sequences of interest, reference sequences are described herein. The present description also encompasses amino acid sequences (e.g. enzyme amino acid sequences), having specific percentages of amino acid identity with a reference amino acid sequence.

For obvious reasons, in all the present description, a specific nucleic acid sequence or a specific amino acid sequence which complies with, respectively, the considered nucleotide or amino acid identity, should further lead to obtaining a protein (or enzyme) which displays the desired biological activity. As used herein, the "percentage of identity" between two nucleic acid sequences or between two amino acid sequences is determined by comparing both optimally aligned sequences through a comparison window.

The portion of the nucleotide or amino-acid sequence in the comparison window may thus include additions or deletions (for example "gaps") as compared to the reference sequence (which does not include these additions or these deletions) so as to obtain an optimal alignment between both sequences.

The terms "sequence homology" or "sequence identity" or "homology" or "identity" are used interchangeably herein. For the purpose of the invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley).

The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE.

For the purpose of the invention, the NEEDLE program from the EMBOSS package was used (version 2.8.0 or higher, EMBOSS: The European Molecular Biology Open Software Suite (2000) Rice, P. Longden J. and Bleasby, A. Trends in Genetics 16, (6) pp 276-277, http://emboss.bioinformatics.nl/). For protein sequences EBLOSUM62 is used for the substitution matrix. For nucleotide sequence, EDNAFULL is used. The optional parameters used are a gap opening penalty of 10 and a gap extension penalty of 0.5. No end gap penalty is added. In the Output section, Yes has been indicated in response to the question "Brief identity and similarity" and "SRS pairwise" indicated as Output alignment format.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The similarity of nucleotide and amino acid sequences, i.e. the percentage of sequence identity, can be determined via sequence alignments using several other art-known algorithms, preferably with the mathematical algorithm of Karlin and Altschul (Karlin & Altschul (1993) Proc. Natl. Acad. Sci. USA 90:5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) available e.g. on https://www.ebi.ac.uk/Tools/msa/clustalo/or the GAP program (mathematical algorithm of the University of Iowa) or the mathematical algorithm of Myers and Miller (1989-Cabios 4:11-17) or Clone Manager 9. Preferred parameters used are the default parameters as they are set on https://www.ebi.ac.uk/Tools/msa/clustalo/.

The grade of sequence identity (sequence matching) may be calculated using e.g. BLAST, BLAT or BlastZ (or BlastX). A similar algorithm is incorporated into the BLASTN and BLASTP programs of Altschul et al (1990) J. Mol. Biol. 215, 403-410. BLAST polynucleotide searches are performed with the BLASTN program, score=100, word length=12, to obtain polynucleotide sequences that are homologous to those nucleic acids which encode the relevant protein.

BLAST protein searches are performed with the BLASTP program, score=50, word length=3, to obtain amino acid sequences homologous to the SHC polypeptide. To obtain gapped alignments for comparative purposes, Gapped BLAST is utilized as described in Altschul et al (1997) Nucleic Acids Res. 25, 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

In particular embodiments, % identity between two sequences is determined using CLUSTAL O (version 1.2.4).

The "fermentation" or "culture" is generally conducted in fermenters with an appropriate culture medium adapted to the cell being cultivated, containing at least one simple carbon source, and if necessary co-substrates.

The term "fermentation composition" refers to a composition which comprises genetically modified host cells and products or metabolites produced by the genetically modified host cells. An example of a fermentation composition is a whole cell broth, which can be the entire contents of a vessel (e.g., a flasks, plate, or fermentor), including cells, aqueous phase, and compounds produced from the genetically modified host cells.

The term "medium" refers to a culture medium or cultivation medium or fermentation medium.

For maximal production of hyaluronic acid, the recombinant cells used as production hosts preferably have a high rate of carbohydrate utilization. These characteristics may be conferred by mutagenesis and selection, genetic engineering, or may be natural. Fermentation media, or "culture medium" or "cultivation medium", for the present cells may contain at least about 10 g/L of glucose and/or sucrose. Additional carbon substrates may include but are not limited to monosaccharides such as fructose, mannose, xylose and arabinose; oligosaccharides such as lactose, maltose, galactose, or sucrose; polysaccharides such as starch or cellulose or mixtures thereof and unpurified mixtures from renewable feedstocks such as cheese whey permeate cornsteep liquor, sugar beet molasses, and barley malt. Other carbon substrates may include glycerol, acetate and/or ethanol.

Hence, it is contemplated that the source of carbon utilized in the present invention may encompass a wide variety of carbon containing substrates and will only be limited by the choice of cell, and in particular of yeast.

Although it is contemplated that all of the above-mentioned carbon substrates and mixtures thereof are suitable in the present invention, preferred carbon substrates are glucose, fructose, and sucrose, or mixtures of these with C5 sugars such as xylose and/or arabinose for cells, and in particular yeasts, modified to use C5 sugars, and more particularly glucose.

Preferred carbon substrates are glucose or sucrose.

In addition to an appropriate carbon source, fermentation media may contain suitable minerals, salts, cofactors, buffers and other components, known to those skilled in the art, suitable for the growth of the cultures and promotion of the enzymatic pathway necessary for the production of the desired product.

Besides, additional genetic modifications suitable for the growth of recombinant cells according to the invention may be considered.

The terms "Aerobic conditions" refers to concentrations of oxygen in the culture medium that are sufficient for an aerobic or facultative anaerobic cell, and in particular yeast, to use di-oxygene as a terminal electron acceptor.

"Microaerobic condition" refers to a culture medium in which the concentration of oxygen is less than that in air, i.e. oxygen concentration up to 6% O2.

An "appropriate culture medium" designates a medium (e.g. a sterile, liquid medium) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids, vitamins, growth promoters, and the like. The term "carbon source" or "carbon substrate" or "source of carbon" according to the present invention denotes any source of carbon that can be used by those skilled in the art to support the normal growth of a cell, including hexoses (such as glucose, galactose or lactose), pentoses, monosaccharides, oligosaccharides, disaccharides (such as sucrose, cellobiose or maltose), molasses, starch or its derivatives, cellulose, hemicelluloses and combinations thereof.

Culture mediums that are particularly appropriate to produce recombinant cells of the invention, and in particular recombinant yeasts of the invention, are described in greater details further below in the text.

As used herein, the term "about" refers to a reasonable range about a value as determined by the practitioner of skill. In certain embodiments, the term about refers to ± one, two, or three standard deviations. In certain embodiments, the term about refers to ±5%, 10%, 20%, or 25%. In certain embodiments, the term about refers to ±0.1, 0.2, or 0.3 logarithmic units, e.g. pH units.

General Features of Genetic Modifications
Introduced According to the Invention

All the genome modifications are inserted in recombinant cells, and in particular recombinant yeasts, according to known genetic engineering techniques:

The successive nucleic acid sequences included in a gene construct that is introduced in the recombinant cell genome according to the invention are of the following structure:

$$\text{Prom}_1 - ORF_1 - \text{term}_1 - ORF_2 -$$

$$\text{gene}_2 - \text{term}_2 - \dots \: / \: \dots - \text{Prom}_n - ORF_n - \text{term}_n,$$

Prom1 is a sequence regulating the expression of the coding sequence ORF1,

ORF1 is a nucleic acid sequence encoding a desired protein PROT1, and especially a desired enzyme PROT1, Term1 is a transcription terminator sequence that mediates transcriptional termination by providing signals in the newly synthesized mRNA that trigger processes which release the mRNA from the transcriptional complex, and "1", "2", . . . / . . . "n" may or may not describe the same ORF (Open Reading Frame), promoter or terminator. The order of the nucleic acid sequences does not matter. "n" is an integer usually ranging from 5 and 20. These constructs are inserted in one of the recombinant cell chromosome at a controlled location. In some embodiments, the insertion site is neither essential for the functionality of the inserted construct, nor for the viability of the resulting genetically modified cell.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias." Codon optimization for other host cells can be readily determined using codon usage tables or can be performed using commercially available software, such as CodonOp (www.idtdna.com/CodonOptfrom) from Integrated DNA Technologies. Optimized coding sequences containing codons preferred by a particular prokaryotic or eukaryotic host (Murray et al, 1989, Nucl Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al, 1996, Nucl Acids Res. 24:216-8).

When the recombinant cell is a yeast cell, and in particular is *Saccharomyces cerevisiae* yeast cell, nucleic acid sequences introduced in the yeast genome and originating from other organisms than *Saccharomyces cerevisiae* are generally "transcoded" (generally "codon-optimized"), meaning that these nucleic acid sequences are synthesized with an optimal codon usage for expression in *S. cerevisiae*. The nucleotide sequence (and not the protein sequence) of some nucleic acid sequences from *S. cerevisiae* has also been modified ("transcoded") to minimize recombination with an endogenous copy of the said gene.

Genes may be deleted through standard procedures used in cell genetic engineering. In some embodiments, the genes targeted for deletion may be interrupted by insertion of one of the above-described gene constructs, or alternatively the genes targeted for deletion are replaced by a short stretch of nucleotide.

A nucleic acid sequences may be rendered "inducible or repressible" by deleting an endogenous copy of the nucleic acid sequences (if necessary) and placing a new copy of the ORF under the control of an inducible or repressible promoter. An inducible or repressible promoter is a promoter which activity is modulated or controlled, i.e. either increased or decreased, upon a change in the environmental conditions or external stimuli. Induction or repression may be artificially controlled, which encompasses induction or repression by abiotic factors such as chemical compounds not found naturally in the cell, and in particular yeast, of interest, light, oxygen levels, heat or cold. A list and sequences of inducible or repressible promoters are described elsewhere in the present specification.

Recombinant Cells According to the Invention

The inventors have conceived recombinant cells, in particular recombinant yeasts, having an ability of producing hyaluronic acid.

The present invention relates to recombinant cells, and in particular recombinant yeasts, having the ability to produce hyaluronic acid, and wherein this ability to produce hyaluronic acid is obtained through a plurality of alterations that have been introduced in the genome thereof, by genetic engineering methods.

The present invention pertains to a recombinant yeast cell producing hyaluronic acid (HA), wherein the recombinant cell comprises:

(a) one or more recombinant nucleic acids encoding a polypeptide having hyaluronan synthase activity;

(b) one or more recombinant nucleic acids encoding a polypeptide having UDP-Glucose dehydrogenase (UDP-GlcDH or HASB) activity;

(c) one or more recombinant nucleic acids encoding a polypeptide having hyaluronidase activity wherein the polypeptide having hyaluronidase activity comprises a secretion signal so that hyaluronic acid, in particular of a desired molecular weight (HAMW), is produced by the recombinant yeast cell, and (d) (i) one or more recombinant nucleic acids encoding a polypeptide having a glutamine synthetase (GLN1) activity; and/or (ii) one or more disrupted endogeneous nucleic acids encoding a glutamate synthase (GLT1);

wherein said recombinant yeast cell belongs to the *Saccharomyces* genus, or to the *Candida* genus, or to the *Kluyveromyces* genus, or to the *Ogataea* genus, or to the *Yarrowia* genus, or to the *Debaryomyces* genus, or to the *Ashbya* genus, and is in particular selected from the group consisting of *Saccharomyces cerevisiae*, *Saccharomyces boulardii*, *Saccharomyces bayanus*, *Saccharomyces paradoxus*, *Saccharomyces mikatae*, *Saccharomyces castelli*, *Candida albicans*, *Candida glabrata*, *Candida tropicalis*, *Kluyveromyces lactis*, *Kluyveromyces marxianus*, *Kluyveromyces polysporus*, *Kluyveromyces thermotolerens*, *Ogataea polymorpha*, *Yarrowia lypolytica*, *Debaryomyces hansenii*, and *Ashbya gossypii*, and is preferably *Saccharomyces cerevisiae*.

The present invention further relates to a recombinant host cell producing hyaluronic acid (HA) wherein the recombinant host cell comprises:

(a) one or more recombinant nucleic acids encoding a polypeptide having hyaluronan synthase activity;

(b) one or more recombinant nucleic acids encoding a polypeptide having UDP-Glucose dehydrogenase (UDP-GlcDH or HASB) activity;

(c) one or more recombinant nucleic acids encoding a polypeptide having hyaluronidase activity wherein the polypeptide having hyaluronidase activity comprises a secretion signal and an anchoring signal so that hyaluronic acid, in particular of a desired molecular weight (HAMW) is produced by the host cell; and (d) (i) one or more recombinant nucleic acids encoding a polypeptide having a glutamine synthetase (GLN1) activity; and/or (ii) one or more disrupted endogeneous nucleic acids encoding a glutamate synthase (GLT1).

The inventors have found that an ability to produce hyaluronic acid by cells, and in particular yeast cells, may be reached by introducing in the genome of these cells a plurality of genetic alterations.

The production of hyaluronic acid by cells of the invention, and in particular by yeast cells of the invention, has been achieved by optimizing the endogenous metabolism of UDP-Glucose, and optionally UDP-N-Acetyl-glucosamine, and direct the subsequent artificially modified metabolic pathway mainly towards hyaluronic acid production while in the same time maintaining an optimal viability of the resulting genetically modified cells.

It has been determined that a hyaluronic acid production by recombinant cells according to the invention may be increased by increasing the conversion of glucose-6-phosphate into the successive intermediate metabolites (i) glucose-1-phosphate, UDP-glucose, UDP-glucuronate and hyaluronic acid and (ii) fructose-6-phosphate, glucosamine-6-phosphate, N-acetyl-glucosamine-6-phosphate, N-acetyl-glucosamine-1-phosphate, UDP-N-acetyl-glucosamine and hyaluronic acid, while maintaining a metabolic balance allowing a good viability of the resulting recombinant cells.

Indeed, in order to obtain a viable recombinant cell of the invention, many different constructs were tested in order to obtain a viable and efficient recombinant cell, and in particular a viable recombinant yeast. In particular such recombinant yeast were difficult to obtain because the temporary accumulation of some intermediates appeared to be toxic for yeasts.

Unexpected technical difficulties were encountered in establishing the conditions suitable for the preparation of a recombinant cell able to produce hyaluronic acid, and in particular to produce hyaluronic acid with a controlled molecular weight.

By "controlled" molecular weight of a hyaluronic acid of the invention is intended to mean that at least 80%, in particular at least 85%, of the hyaluronic acid produced by a method of the invention has a molecular weight comprised within a certain molecular weight's range through the regulation of at least one parameter of the method and/or of the recombinant cell of the invention, such as for example:

the nature and origin of the nucleic acid encoding the hyaluronidase of the recombinant cell, the nature and origin of the promoter controlling the expression of the nucleic acid encoding the hyaluronidase(s) of the recombinant cell, the presence of an anchoring and/or of a secretion signal associated to the encoded hyaluronidase(s) of the recombinant cell, the pH of the culture medium during the step of culturing the recombinant cell, and/or the duration of the culturing of the recombinant cell.

Indeed, after much research and experimental trial, the inventors discovered that it was possible to cultivate a recombinant cell, and in particular a recombinant yeast cell, more particularly a recombinant Saccharomyces cerevisiae yeast cell, able to produce hyaluronic acid having a controlled molecular weight controlled using the following parameters:

the selection of the nature and origin of the nucleic acid sequences encoding the polypeptide having hyaluronidase activity of the recombinant cell, in particular the recombinant yeast, of the invention; and/or the nature and origin of the promoter controlling the expression of the nucleic acid sequences encoding the polypeptide having hyaluronidase activity of the recombinant cell, in particular the recombinant yeast, of the invention; and/or the optional presence of an anchoring signal, in addition to a secretion signal, associated to the encoded polypeptide having hyaluronidase activity of the recombinant cell, in particular the recombinant yeast, according to the invention; and/or the pH of the culture medium during the step of culturing the recombinant cell, in particular the recombinant yeast cell, according to the invention; and/or the duration of the culturing of the recombinant cell, in particular the recombinant yeast cell, according to the invention.

To the inventors' knowledge, this has never been achieved before.

The molecular weight of the hyaluronic acid (HA) can be in the range of less than 50 kDa, preferably in the range of about 20 kDa to about 50 kDa.

Alternatively, the molecular weight of the hyaluronic acid (HA) can be in the range of greater than 50 kDa, preferably in the range of about 50 kDa to about 250 kD.

In another alternative, the molecular weight of the HA can be in the range of greater than 100 kDa, preferably in the range of about 100 kDa to about 1500 kDa.

The nucleic acid encoding a polypeptide having a glutamine synthetase activity may be obtained or derived from Saccharomyces cerevisiae.

The nucleic acid encoding a polypeptide having hyaluronidase activity in a recombinant cell of the invention may be obtained or derived from at least one of Cupiennius salei, Loxosceles intermedia, Hirudo nipponia, Bothrops atrox or Tityus serrulatus.

The nucleic acid encoding a polypeptide having hyaluronan synthase activity in a recombinant cell of the invention may be obtained or derived from at least one of Streptococcus zooepidemicus, Chlorella virus PBCV1, Chlorella virus CviK1, Chlorella virus IL-5-2s1, Chlorella virus CZ-2, Chlorella virus CVG-1, Xenopus laevis or Pasteurella multocida, and is in particular obtained or derived from Streptococcus zooepidemicus, Chlorella virus PBCV1, Chlorella virus CviK1, Chlorella virus IL-5-2s1, Chlorella virus CZ-2, Chlorella virus CVG-1 or Xenopus laevis.

The nucleic acid encoding a polypeptide having UDP-Glucose dehydrogenase activity in a recombinant cell of the invention may be obtained or derived from at least one of Arabidopsis thaliana, Chlorella virus PBCV1 or Streptococcus zooepidemicus, and in particular from Arabidopsis thaliana or Chlorella virus PBCV1.

The recombinant cell according to the invention can comprise a recombinant nucleic acid encoding one or more of:

(i) a polypeptide having glutamine-fructose-6-phosphate amidotransferase (GFA1) activity; and/or (ii) a polypeptide having UDP-N-acetylglucosamine pyrophosphorylase (QRI1) activity.

The recombinant cell according to the invention can comprise at least one recombinant nucleic acid encoding one or more of:

(i) a polypeptide having Phosphoglucomutase-1 (PGM1) activity; and/or (ii) a polypeptide having UTP-glucose-1-phosphate uridylyltransferase (UGP1) activity; and/or (iii) a polypeptide having Glucosamine-6-phosphate N-acetyltransferase (GNA1) activity; and/or (iv) a polypeptide having phosphoacetylglucosamine mutase (PCM1) activity.

The recombinant yeast cell according to the invention can be in particular selected from the group consisting of *Saccharomyces cerevisiae, Saccharomyces boulardii, Saccharomyces bayanus, Saccharomyces paradoxus, Saccharomyces mikatae, Saccharomyces castelli, Candida albicans, Candida glabrata, Candida tropicalis, Kluyveromyces lactis, Kluyveromyces marxianus, Kluyveromyces polysporus, Kluyveromyces thermotolerens, Ogataea polymorpha, Yarrowia lypolytica, Debaryomyces hansenii,* and *Ashbya gossypii,* and is preferably *Saccharomyces cerevisiae.*

The recombinant host cell according to the invention can belong to the Saccharomycesales order and is in particular selected from the group consisting of *Saccharomyces cerevisiae, Saccharomyces boulardii, Saccharomyces bayanus, Saccharomyces paradoxus, Saccharomyces mikatae, Saccharomyces castelli, Candida albicans, Candida glabrata, Candida tropicalis, Kluyveromyces lactis, Kluyveromyces marxianus, Kluyveromyces polysporus, Kluyveromyces thermotolerens, Ogataea polymorpha, Yarrowia lypolytica, Debaryomyces hansenii,* and *Ashbya gossypii,* and is preferably *Saccharomyces cerevisiae.*

Another object of the invention relates to a method of producing hyaluronic acid (HA) of a desired molecular weight (HAMW) comprising:

(a) cultivating a recombinant cell as defined above, i.e. a recombinant yeast cell or a recombinant host cell of the invention, in a cultivation medium for a time sufficient to produce hyaluronic acid (HA) of the desired molecular weight; and (b) optionally isolating or recovering the hyaluronic acid (HA) from the recombinant cell and/or from the cultivation medium.

In the method of the invention, the HA may have a molecular weight of from about 20 kDa to about 50 kDA, and preferably from 20 kDa to 30 kDa.

In the method of the invention, the HA may alternatively have a molecular weight of from 30 kDa to 50 kDa.

In the method of the invention, the HA may alternatively have a molecular weight of from about 50 kDa to about 150 kDa.

In the method of the invention, the HA may alternatively have a molecular weight of from about 150 kDa to about 1500 kDa.

In a method of the invention, the nucleic acid encoding a polypeptide having hyaluronidase activity may be obtained or derived from *Cupiennius salei, Loxosceles intermedia, Hirudo nipponia, Bothrops atrox* or *Tityus serrulatus.*

In a method of the invention, the nucleic acid encoding a polypeptide having hyaluronan synthase activity may be obtained or derived from at least one of *Streptococcus zooepidemicus, Chlorella* virus PBCV1, *Chlorella* virus CviK1, *Chlorella* virus IL-5-2s1, *Chlorella* virus CZ-2, *Chlorella* virus CVG-1, *Xenopus laevis* or *Pasteurella multocida,* and is in particular obtained or derived from at least one of *Streptococcus zooepidemicus, Chlorella* virus PBCV1, *Chlorella* virus CviK1, *Chlorella* virus IL-5-2s1, *Chlorella* virus CZ-2, *Chlorella* virus CVG-1, or *Xenopus laevis.*

In a method of the invention, the nucleic acid encoding a polypeptide having UDP-Glucose dehydrogenase activity may be obtained or derived from at least one of *Arabidopsis*

*thaliana, Chlorella* virus PBCV1 or *Streptococcus zooepidemicus,* and in particular obtained or derived from *Arabidopsis thaliana* or *Chlorella* virus PBCV1.

In the method of the invention, the recombinant cell may comprise at least one recombinant nucleic acid encoding one or more of:

(i) a polypeptide having glutamine-fructose-6-phosphate amidotransferase (GFA1) activity; and/or (ii) a polypeptide having UDP-N-acetylglucosamine pyrophosphorylase (QRI1) activity.

In the method of the invention, the recombinant cell may comprise at least one recombinant nucleic acid encoding one or more of:

(i) a polypeptide having Phosphoglucomutase-1 (PGM1) activity;

(ii) a polypeptide having UTP-glucose-1-phosphate uridylyltransferase (UGP1) activity;

(iii) a polypeptide having Glucosamine-6-phosphate N-acetyltransferase (GNA1) activity; and/or (iv) a polypeptide having phosphoacetylglucosamine mutase (PCM1) activity.

In the method of the invention, the recombinant cell may be a member of the genus *Saccharomyces,* and in particular is *Saccharomyces cerevisiae.*

In the method of the invention, the molecular weight of the hyaluronic acid may be controlled by the fermentation time.

In the method of the invention, the time sufficient to produce hyaluronic acid (HA) of a desired molecular weight may be a period of from about 35 hours to about 50 hours, preferably from about 40 hours to about 50 hours, preferably about 48 hours.

In the method of the invention, the molecular weight of the hyaluronic acid may be controlled by the pH of the cultivation medium.

In the method of the invention, the molecular weight of the hyaluronic acid may be controlled by regulating the pH of the cultivation medium during the cultivation step (a) of a method of the invention.

In the method of the invention, the molecular weight of the hyaluronic acid may be controlled by removing the biomass from the cultivation medium.

The method of the invention can be carried out on an industrial scale, preferably where the cultivation medium is at least about 100 L, more preferably in the range of about 1000 L to about 3000 L, even more preferably about 10,000 L or even more preferably about 100,000 L, or even about 250,000 L.

Another object of the invention relates to hyaluronic acid (HA) obtained or obtainable from a recombinant cell of the invention or from the method of the invention.

A further object of the invention relates to a cultivation medium comprising the hyaluronic acid (HA) according to the invention.

The present invention further relates to a composition comprising the hyaluronic acid (HA) according to the invention.

The present invention moreover relates to an industrial product or a consumer product or a consumable comprising (i) the HA having a molecular weight in the range of greater than 100 kDa, preferably in the range of about 100 kDa to about 1500 kDa, (ii) the cultivation medium of the invention or (iii) the composition of the invention.

The present invention also relates to use of a recombinant cell according to the invention for the production of hyaluronic acid (HA) having a molecular weight in the range of from about 20 kDa to about 50 kDa or from about 50 kDa to about 1000 kDa.

Another object of the present invention relates to a method for producing hyaluronic acid comprising the steps of:

(a) culturing a recombinant yeast according to the invention in a culture medium; and (b) recovering the hyaluronic acid from said culture medium, wherein the hyaluronic acid recovered in step (b) has a molecular weight controlled through the selection of:

the nature and origin of the nucleic acid encoding the hyaluronidase of the recombinant yeast, the nature and origin of the promoter controlling the expression of the nucleic acid encoding the hyaluronidase(s) of the recombinant yeast, the presence of an anchoring and/or of a secretion signal associated to the encoded hyaluronidase(s) of the recombinant yeast, the pH of the culture medium during the step of culturing the recombinant yeast, and/or the duration of the culturing of the recombinant yeast.

More particularly, the invention pertains to a hyaluronic acid-producing recombinant yeast, wherein the recombinant yeast comprises:

(A) one or more recombinant nucleic acids encoding a polypeptide having glutamine-fructose-6-phosphate amidotransferase (GFA1) activity;

(B) one or more recombinant nucleic acids encoding a polypeptide having a UDP-N-acetylglucosamine pyrophosphorylase (QRI1) activity;

(C) one or more recombinant nucleic acids encoding a polypeptide having a UDP-Glucose dehydrogenase (UDP-GlcDH or HASB) activity;

(D) one or more recombinant nucleic acids encoding a polypeptide having a hyaluronan synthase (HASA) activity; and (E) one or more recombinant nucleic acids encoding a polypeptide having a hyaluronidase activity wherein the polypeptide having hyaluronidase activity comprises a secretion signal so that hyaluronic acid, in particular of a desired molecular weight (HAMW), is produced by the recombinant yeast cell, said recombinant yeast being *Saccharomyces cerevisiae.*

In a particular embodiment, the recombinant cell according to the invention, and in particular the recombinant yeast according to the invention, comprises one recombinant nucleic acid encoding a polypeptide having glutamine synthetase (GLN1) activity.

In a particular embodiment, the recombinant cell according to the invention, and in particular the recombinant yeast according to the invention, is such that at least one, and in particular all, its endogeneous nucleic acids encoding a glutamate synthase (GLT1) are disrupted.

In a particular embodiment, the recombinant cell according to the invention, and in particular the recombinant yeast according to the invention:

comprises one recombinant nucleic acid encoding a polypeptide having glutamine synthetase (GLN1) activity, and in particular a polypeptide having glutamine synthetase (GLN1) activity obtained or derived from *Saccharomyces cerevisiae*; and is such that at least one, and in particular all, its endogeneous nucleic acids encoding a glutamate synthase (GLT1) are disrupted.

In a particular embodiment, the recombinant cell according to the invention, and in particular the recombinant yeast according to the invention comprises only one recombinant nucleic acid encoding a polypeptide having glutamine-fructose-6-phosphate amidotransferase (GFA1) activity.

In a particular embodiment, the recombinant cell according to the invention, and in particular the recombinant yeast comprises between 5 and 10 recombinant nucleic acids encoding a polypeptide having UDP-N-acetylglucosamine pyrophosphorylase (QRI1) activity.

In a particular embodiment, the recombinant cell according to the invention, and in particular the recombinant yeast comprises between 3 and 7 recombinant nucleic acids encoding a polypeptide having UDP-Glucose dehydrogenase (UDP-GlcDH or HASB) activity.

In another embodiment, the one or more nucleic acids encoding a polypeptide having a UDP-Glucose dehydrogenase (UDP-GlcDH or HASB) activity is obtained or derived from at least one of *Arabidopsis thaliana, Chlorella* virus PBCV1 or *Streptococcus zooepidemicus,* and in particular obtained or derived from *Arabidopsis thaliana* or *Chlorella* virus PBCV1.

In a particular embodiment, the recombinant cell according to the invention, and in particular the recombinant yeast comprises between 4 and 8 recombinant nucleic acids encoding a polypeptide having hyaluronan synthase (HASA) activity.

In another embodiment, the one or more recombinant nucleic acids encoding a polypeptide having a hyaluronan synthase (HASA) activity is obtained or derived from at least one of *Streptococcus zooepidemicus, Chlorella* virus PBCV1, *Chlorella* virus CviK1, *Chlorella* virus IL-5-2s1, *Chlorella* virus CZ-2, *Chlorella* virus CVG-1, *Xenopus laevis* or *Pasteurella multocida,* and is in particular obtained or derived from *Streptococcus zooepidemicus, Chlorella* virus PBCV1, *Chlorella* virus CviK1, *Chlorella* virus IL-5-2s1, *Chlorella* virus CZ-2, *Chlorella* virus CVG-1 or *Xenopus laevis.*

In a particular embodiment, the recombinant cell according to the invention, and in particular the recombinant yeast of the invention only comprises one recombinant nucleic acid encoding a polypeptide having hyaluronidase activity.

In another embodiment, the one or more recombinant nucleic acids encoding a polypeptide having a hyaluronidase activity is obtained or derived from *Cupiennius salei, Loxosceles intermedia, Hirudo nipponia, Bothrops atrox* or *Tityus serrulatus.*

In another embodiment, the recombinant cell according to the invention, and in particular the recombinant yeast cell may comprise at least one recombinant nucleic acid encoding one or more of:

(A) a polypeptide having Phosphoglucomutase-1 (PGM1) activity; and/or (B) a polypeptide having UTP-glucose-1-phosphate uridylyltransferase
(UGP1) activity; and/or (C) a polypeptide having Glucosamine-6-phosphate N-acetyltransferase (GNA1) activity; and/or (D) a polypeptide having phosphoacetylglucosamine mutase (PCM1) activity.

In particular, the recombinant cell according to the invention, and in particular the recombinant yeast cell of the invention comprises at least two, in particular at least three, and more particularly all of the modifications indicated above.

In a particular embodiment, the nucleic acid encoding a polypeptide having Phosphoglucomutase-1 (PGM1) activity, the nucleic acid encoding a polypeptide having UTP-glucose-1-phosphate uridylyltransferase (UGP1) activity, the nucleic acid encoding a polypeptide having glutamine-fructose-6-phosphate amidotransferase (GFA1) activity, the nucleic acid encoding a polypeptide having Glucosamine-6-phosphate N-acetyltransferase (GNA1) activity, the nucleic acid encoding a polypeptide having phosphoacetyl-glucosamine mutase (PCM1) activity and the nucleic acid encoding a polypeptide having UDP-N-acetylglucosamine pyrophosphorylase (QRI1) activity are nucleic acids originating or derivating from a yeast, preferably from *Saccharomyces cerevisiae*.

In a particular embodiment, the one or more recombinant nucleic acids encoding a polypeptide defined above and comprised in a recombinant cell according to the invention, and in particular comprised in the recombinant yeast of the invention are under the control of a promoter selected from the group consisting of pPDC1, pTDH3, pCCW12, pCCW12.Sm, pCCW12.sk, pCCW12.sba, pCCW12.sar, pTEF1, pENO2, pRPLA1, pNUP57 and pTEF3.

In a particular embodiment, the inducible or repressible promoters mentioned in the present specification are selected from the group consisting of promoters inducible or repressible with copper or promoters inducible or repressible with methionine, in particular selected from the group consisting of pMET6, pMET25 and pSAM1.

The invention further relates to a method for producing hyaluronic acid as previously described, and comprising the steps of:

(a) culturing a recombinant cell according to the invention, and in particular a recombinant yeast as defined herein in a culture medium; and (b) recovering the hyaluronic acid from said culture medium, wherein the hyaluronic acid recovered in step (b) has a molecular weight controlled through the selection of:

the nature and origin of the nucleic acid encoding the hyaluronidase of the recombinant cell according to the invention, and in particular the recombinant yeast according to the invention, and/or the nature and origin of the promoter controlling the expression of the nucleic acid encoding the hyaluronidase(s) of the recombinant cell according to the invention, and in particular the recombinant yeast, and/or the presence of an anchoring and/or of a secretion signal associated to the encoded hyaluronidase(s) of the recombinant cell according to the invention, and in particular the recombinant yeast, and/or the pH of the culture medium during the step of culturing the recombinant cell according to the invention, and in particular the recombinant yeast; and/or the duration of the culturing of the recombinant cell according to the invention, and in particular the recombinant yeast.

Recombinant Nucleic Acids Encoding a Polypeptide Having Hyaluronan Synthase Activity A recombinant cell according to the invention, and in particular a recombinant yeast of the invention, comprises one or more recombinant nucleic acids encoding a polypeptide having hyaluronan synthase activity.

A polypeptide having hyaluronan synthase activity according to the invention means a polypeptide that converts the intermediate metabolites UDP-Glucoronate and UDP-N-acetylglucosamine (UDP-GlcNAc) into hyaluronic acid ((β-D-1,3-GlcNAc-β-D-1,4-GlcA)n).

In an embodiment, one or more of the recombinant nucleic acids encoding a polypeptide having hyaluronan synthase activity are under the control of an inducible or repressible promoter that is functional in the recombinant cells of the invention, such as for example the inducible or repressible promoters pCUP1 or pMET25.

One or more of the recombinant nucleic acids encoding a polypeptide having hyaluronan synthase activity may be under the control of a promoter selected from the group consisting of pCCW12, pCCW12.Sm, pTDH3-1.Sba and pTDH3.Sar.

The said one or more recombinant nucleic acids encoding a polypeptide having hyaluronan synthase activity may originate or be derived from at least one of *Streptococcus zooepidemicus* (sz), *Chlorella* virus PBCV1 (Vir), *Chlorella* virus CviK1 (Vir), *Chlorella* virus IL-5-2s1 (Vir), *Chlorella* virus CZ-2 (Vir), *Chlorella* virus CVG-1 (Vir), *Xenopus laevis* (xl) or *Pasteurella multocida* (pm), and may originate or derive in particular from *Streptococcus zooepidemicus, Chlorella* virus PBCV1, *Chlorella* virus CviK1, *Chlorella* virus IL-5-2s1, *Chlorella* virus CZ-2, *Chlorella* virus CVG-1 or *Xenopus laevis*, as shown in the examples herein.

A recombinant cell according to the invention, and in particular a recombinant yeast according to the invention, may comprise between 2 and 8, in particular between 4 and 8 recombinant nucleic acids encoding a polypeptide having hyaluronan synthase (HASA) activity. A recombinant cell according to the invention, and in particular a recombinant yeast according to the invention, may for example comprise 2 or 6, and in particular 6, recombinant nucleic acids encoding a polypeptide having hyaluronan synthase (HASA) activity.

Illustratively, the one or more recombinant nucleic acids encoding a polypeptide having hyaluronan synthase activity may be inserted within the JLP1 gene and/or within the SAM3 gene and/or within the TRP1 gene and/or within the LYP1 gene of the recombinant cell, and in particular of the recombinant yeast, as it is shown in the examples herein.

In an embodiment of the invention, a recombinant cell, and in particular a recombinant yeast, of the invention comprises:

between 2 and 8, in particular between 4 and 8 recombinant nucleic acids encoding a polypeptide having hyaluronan synthase (HASA) activity;

said one or more recombinant nucleic acids encoding a polypeptide having hyaluronan synthase activity originating or being derived from at least one of *Streptococcus zooepidemicus* (sz), *Chlorella* virus PBCV1 (Vir), *Xenopus laevis* (xl) or *Pasteurella multocida* (pm), and originating or being derived in particular from at least one of *Streptococcus zooepidemicus, Chlorella* virus PBCV1 or *Xenopus laevis*; and said one or more recombinant nucleic acids encoding a polypeptide having hyaluronan synthase activity being under the control of an inducible or repressible promoter that is functional in the recombinant cells of the invention, such as for example the inducible or repressible promoters pCUP or pMET25 and/or under the control of a promoter selected from the group consisting of pCCW12, pCCW12.Sm, pTDH3-1.Sba and pTDH3.Sar.

Recombinant Nucleic Acids Encoding a Polypeptide Having UDP-Glucose Dehydrogenase Activity A recombinant cell according to the invention, and in particular a recombinant yeast according to the invention, comprises one or more recombinant nucleic acids encoding a polypeptide having UDP-Glucose dehydrogenase (UDP-GlcDH or HASB) activity.

A polypeptide having UDP-Glucose dehydrogenase (UDP-GlcDH or HASB) activity according to the invention means a polypeptide that converts the intermediate metabolite Uridine-Diphosphate-Glucose (UDP-Glucose) into UDP-Glucuronate.

In an embodiment, one or more of the recombinant nucleic acids encoding a polypeptide having UDP-Glucose dehydrogenase (UDP-GlcDH or HASB) activity are under the control of an inducible or repressible promoter that is functional in recombinant cells of the invention, such as for example the inducible or repressible promoters pMET25 or pMET6.

One or more of the recombinant nucleic acids encoding a polypeptide having UDP-Glucose dehydrogenase activity may be under the control of a promoter selected from the group consisting of pCCW12, in particular the pCCW12.sk and the pCCW12.sba promoters; pTEF1.Sba and pTDH3.Sk.

The one or more recombinant nucleic acids encoding a polypeptide having UDP-Glucose dehydrogenase activity may originate or be derived from at least one of *Arabidopsis thaliana, Chlorella* virus PBCV1 or *Streptococcus zooepidemicus*, and in particular may originate or derive from *Arabidopsis thaliana* or *Chlorella* virus PBCV1.

A recombinant cell according to the invention, and in particular a recombinant yeast according to the invention, may comprise between 2 and 7, in particular between 3 and 7 recombinant nucleic acids encoding a polypeptide having UDP-Glucose dehydrogenase activity. A recombinant cell according to the invention, and in particular a recombinant yeast according to the invention, may for example comprise 2 or 5 recombinant nucleic acids encoding a polypeptide having UDP-Glucose dehydrogenase activity.

Illustratively, the one or more recombinant nucleic acids encoding a polypeptide having UDP-Glucose dehydrogenase activity may be inserted within the JLP1 gene and/or within the TRP1 gene, and/or within the LYP1 gene of the recombinant cell, and in particular of the recombinant yeast, as it is shown in the examples herein.

In an embodiment of the invention, a recombinant cell, and in particular a recombinant yeast, of the invention comprises:

between 2 and 7, and in particular between 3 and 7 recombinant nucleic acids encoding a polypeptide having UDP-Glucose dehydrogenase activity;

said one or more recombinant nucleic acids encoding a polypeptide having UDP-Glucose dehydrogenase activity originating or being derived from at least one of *Arabidopsis thaliana, Chlorella* virus PBCV1 or *Streptococcus zooepidemicus*, and originating or being derived in particular from *Arabidopsis thaliana* or *Chlorella* virus PBCV1; and said one or more recombinant nucleic acids encoding a polypeptide having UDP-Glucose dehydrogenase activity being under the control of an inducible or repressible promoter that is functional in the recombinant cells of the invention, such as for example the inducible or repressible promoters pMET25 or pMET6 and/or under the control of a promoter selected from the group consisting of pCCW12, in particular the pCCW12.sk and the pCCW12.sba promoters; pTEF1.Sba and pTDH3.Sk.

Recombinant Nucleic Acids Encoding a Polypeptide Having Hyaluronidase Activity

A recombinant cell according to the invention, and in particular a recombinant yeast according to the invention, comprises one or more recombinant nucleic acids encoding a polypeptide having hyaluronidase activity.

A polypeptide having hyaluronidase activity according to the invention means a polypeptide that degrades hyaluronic acid, i.e. that converts a hyaluronic acid of a given molecular weight into a hyaluronic acid of a lower molecular weight.

As previously indicated, polypeptides having hyaluronidase activity of the present invention comprise a secretion signal.

In an embodiment, polypeptide having hyaluronidase activity comprise both a secretion signal and an anchoring signal.

In an embodiment, the said one or more recombinant nucleic acids encoding a polypeptide having hyaluronidase activity are under the control of an inducible or repressible promoter that is functional in the recombinant cells of the invention.

One or more of the recombinant nucleic acids encoding a polypeptide having hyaluronidase activity may be under the control of a promoter selected from the group consisting of pTEF1, pCCW12, pCCW12.sba, pCCW12.Sar, pPDC1, pTEF3, pTDH3, pNUP57, pCWP2 and pCCW10.ago.

The said one or more recombinant nucleic acids encoding a polypeptide having hyaluronidase activity may originate or be derived from at least one of *Cupiennius salei* (Csa), *Loxosceles intermedia* (Li), *Hirudo nipponia* (Hn), *Bothrops atrox* (Ba) or *Tityus serrulatus* (Ts) as shown in the examples herein.

A recombinant cell according to the invention, and in particular a recombinant yeast according to the invention, may comprise only one recombinant nucleic acid encoding a polypeptide having hyaluronidase activity.

Illustratively, the one or more recombinant nucleic acids encoding a polypeptide having hyaluronidase activity may be inserted within the JLP1 gene and/or within the LYP1 gene, as it is shown in the examples herein.

In an embodiment of the invention, a recombinant cell, and in particular a recombinant yeast, of the invention comprises:

only one recombinant nucleic acid encoding a polypeptide having hyaluronidase activity;

said recombinant nucleic acid encoding a polypeptide having hyaluronidase activity originating or being derived from *Cupiennius salei* (Csa), *Loxosceles intermedia* (Li), *Hirudo nipponia* (Hn), *Bothrops atrox* (Ba) or *Tityus serrulatus* (Ts);

said recombinant nucleic acid encoding a polypeptide having hyaluronidase activity comprising either (i) a secretion signal and no anchoring signal or (ii) a secretion signal and an anchoring signal; and said recombinant nucleic acid encoding a polypeptide having hyaluronidase activity being under the control of a promoter selected from the group consisting of pTEF1, pCCW12, pCCW12.sba, pCCW12.Sar, pPDC1, pTEF3, pTDH3, pNUP57, pCWP2 and pCCW10.ago.

Recombinant Nucleic Acids Encoding a Polypeptide Having Glutamine Synthetase Activity A recombinant cell according to the invention, and in particular a recombinant yeast cell according to the invention, may comprise one or more recombinant nucleic acids encoding a polypeptide having glutamine synthetase activity.

A polypeptide having glutamine synthetase activity according to the invention means a polypeptide that converts glutamate into glutamine while consuming one ATP and one $NH_4^+$.

In an embodiment, one or more of the recombinant nucleic acids encoding a polypeptide having glutamine synthetase activity are under the control of an inducible or repressible promoter that is functional in the recombinant cells of the invention.

One or more of the recombinant nucleic acids encoding a polypeptide having glutamine synthetase activity may be under the control of a promoter selected from the group consisting of pTEF1 and pTEF1.Ago.

The said one or more recombinant nucleic acids encoding a polypeptide having glutamine synthetase activity can originate or be derived from *Saccharomyces cerevisiae*, as shown in the examples herein.

A recombinant cell according to the invention, and in particular a recombinant yeast cell according to the invention, may comprise only one recombinant nucleic acid encoding a polypeptide having glutamine synthetase activity.

Illustratively, the one or more recombinant nucleic acids encoding a polypeptide having glutamine synthetase activity may be inserted within the LYP1 or GLT1 gene of the recombinant cell, and in particular of the recombinant yeast cell, as it is shown in the examples herein.

In an embodiment of the invention, a recombinant cell, and in particular a recombinant yeast cell, of the invention comprises:

only one recombinant nucleic acid encoding a polypeptide having glutamine synthetase activity;

said recombinant nucleic acid encoding a polypeptide having glutamine synthetase activity originating or being derived from *Saccharomyces cerevisiae*; and said recombinant nucleic acid encoding a polypeptide having glutamine synthetase activity being under the control of a promoter selected from the group consisting of pTEF1 and pTEF1.Ago.

In a further embodiment of the invention, a recombinant cell, and in particular a recombinant yeast cell, of the invention comprises:

only one recombinant nucleic acid encoding a polypeptide having glutamine synthase activity;

said recombinant nucleic acid encoding a polypeptide having glutamine synthetase activity originating or being derived from *Saccharomyces cerevisiae;* said recombinant nucleic acid encoding a polypeptide having glutamine synthetase activity being under the control of a promoter selected from the group consisting of pTEF1 and pTEF1.Ago; and said recombinant nucleic acid encoding a polypeptide having glutamine synthetase activity being inserted within the LYP1 or GLT1 gene of the recombinant cell, and in particular of the recombinant yeast cell.

Recombinant Nucleic Acids Encoding a Polypeptide Having Glutamine-Fructose-6-Phosphate Amidotransferase Activity A recombinant cell according to the invention, and in particular a recombinant yeast cell according to the invention, may comprise one or more recombinant nucleic acids encoding a polypeptide having glutamine-fructose-6-phosphate amidotransferase activity.

A polypeptide having glutamine-fructose-6-phosphate amidotransferase activity according to the invention means a polypeptide that converts fructose-6-phosphate into glucosamine-6-phosphate.

In an embodiment, one or more of the recombinant nucleic acids encoding a polypeptide having glutamine-fructose-6-phosphate amidotransferase activity are under the control of an inducible or repressible promoter that is functional in the recombinant cells of the invention.

One or more of the recombinant nucleic acids encoding a polypeptide having glutamine-fructose-6-phosphate amidotransferase activity may be under the control of a promoter selected from the group consisting of pTEF1 and pTEF1.Ago.

The said one or more recombinant nucleic acids encoding a polypeptide having glutamine-fructose-6-phosphate amidotransferase activity can originate or be derived from *Saccharomyces cerevisiae*, as shown in the examples herein.

A recombinant cell according to the invention, and in particular a recombinant yeast cell according to the invention, may comprise only one recombinant nucleic acid encoding a polypeptide having glutamine-fructose-6-phosphate amidotransferase activity.

Illustratively, the one or more recombinant nucleic acids encoding a polypeptide having glutamine-fructose-6-phosphate amidotransferase activity may be inserted within the SAM3 gene of the recombinant cell, and in particular of the recombinant yeast cell, as it is shown in the examples herein.

In an embodiment of the invention, a recombinant cell, and in particular a recombinant yeast cell, of the invention comprises:

only one recombinant nucleic acid encoding a polypeptide having glutamine-fructose-6-phosphate amidotransferase activity;

said recombinant nucleic acid encoding a polypeptide having glutamine-fructose-6-phosphate amidotransferase activity originating or being derived from *Saccharomyces cerevisiae*; and said recombinant nucleic acid encoding a polypeptide having glutamine-fructose-6-phosphate amidotransferase activity being under the control of a promoter selected from the group consisting of pTEF1 and pTEF1.Ago.

Recombinant Nucleic Acids Encoding a Polypeptide Having UDP-N-Acetylglucosamine Pyrophosphorylase Activity A recombinant cell according to the invention, and in particular a recombinant yeast cell according to the invention, can comprise one or more recombinant nucleic acids encoding a polypeptide having UDP-N-acetylglucosamine pyrophosphorylase activity.

A polypeptide having UDP-N-acetylglucosamine pyrophosphorylase activity according to the invention means a polypeptide that can convert N-acetyl-glucosamine into UDP-N-acetyl-glucosamine.

In an embodiment, one or more of the recombinant nucleic acids encoding a polypeptide having UDP-N-acetylglucosamine pyrophosphorylase activity are under the control of an inducible or repressible promoter that is functional in the recombinant cells of the invention, such as for example the inducible or repressible promoters pMET6 or pCUP1.

One or more of the recombinant nucleic acids encoding a polypeptide having UDP-N-acetylglucosamine pyrophosphorylase activity may be under the control of the promoter pTDH3.

The said one or more recombinant nucleic acids encoding a polypeptide having UDP-N-acetylglucosamine pyrophosphorylase activity can originate or be derived from *Saccharomyces cerevisiae*, as shown in the examples herein.

A recombinant cell according to the invention, and in particular a recombinant yeast according to the invention, may comprise between 5 and 10 recombinant nucleic acids encoding a polypeptide having UDP-N-acetylglucosamine pyrophosphorylase activity. A recombinant cell according to the invention, and in particular a recombinant yeast cell according to the invention, may for example comprise 5, 7 or 8 recombinant nucleic acids encoding a polypeptide having UDP-N-acetylglucosamine pyrophosphorylase activity.

Illustratively, the one or more recombinant nucleic acids encoding a polypeptide having UDP-N-acetylglucosamine pyrophosphorylase activity may be inserted within the HIS3 gene and/or within the JLP1 gene and/or within the SAM3 gene of the recombinant cell, and in particular of the recombinant yeast, as it is shown in the examples herein.

In an embodiment of the invention, a recombinant cell, and in particular a recombinant yeast cell, of the invention comprises:

between 5 and 10 recombinant nucleic acids encoding a polypeptide having UDP-N-acetylglucosamine pyro-phosphorylase activity;

said one or more recombinant nucleic acids encoding a polypeptide having UDP-N-acetylglucosamine pyro-phosphorylase activity originating or being derived from *Saccharomyces cerevisiae*;

said one or more recombinant nucleic acids encoding a polypeptide having UDP-N-acetylglucosamine pyro-phosphorylase activity being under the control of an inducible or repressible promoter that is functional in the recombinant cells of the invention, such as for example the inducible or repressible promoters pMET6 or pCUP1 and/or under the control of the promoter pTDH3.

Recombinant Nucleic Acids Encoding a Polypeptide Having Phosphoglucomutase-1 Activity A recombinant cell according to the invention, and in particular a recombinant yeast cell according to the invention, may comprise one or more recombinant nucleic acids encoding a polypeptide having Phosphoglucomutase-1 (PGM1) activity.

A polypeptide having Phosphoglucomutase-1 (PGM1) activity according to the invention means a polypeptide that converts Glucose-6-phosphate into the intermediate metabolite Glucose-1-phosphate.

In an embodiment, one or more of the recombinant nucleic acids encoding a polypeptide having Phosphoglu-comutase-1 (PGM1) activity are under the control of an inducible or repressible promoter that is functional in recombinant cells of the invention, such as for example the inducible or repressible promoters.

One or more of the recombinant nucleic acids encoding a polypeptide having Phosphoglucomutase-1 (PGM1) activity may be under the control of the promoter pPDC1.

The one or more recombinant nucleic acids encoding a polypeptide having Phosphoglucomutase-1 (PGM1) activity may originate or be derived from *Saccharomyces cerevisiae*, as shown in the examples herein.

A recombinant cell according to the invention, and in particular a recombinant yeast cell according to the invention, may comprise only one recombinant nucleic acid encoding a polypeptide having Phosphoglucomutase-1 (PGM1) activity.

Illustratively, the one or more recombinant nucleic acids encoding a polypeptide having Phosphoglucomutase-1 activity may be inserted within the SAM3 gene of the recombinant cell, and in particular of the recombinant yeast, as it is shown in the examples herein.

In an embodiment of the invention, a recombinant cell, and in particular a recombinant yeast, of the invention comprises:

only one recombinant nucleic acid encoding a polypeptide having Phosphoglucomutase-1 activity;

said recombinant nucleic acid encoding a polypeptide having Phosphoglucomutase-1 activity originating or being derived from *Saccharomyces cerevisiae*; and said recombinant nucleic acid encoding a polypeptide having Phosphoglucomutase-1 activity being under the control of the promoter pPDC1.

Recombinant Nucleic Acids Encoding a Polypeptide Having UTP-Glucose-1-Phosphate Uridylyltransferase Activity A recombinant cell according to the invention, and in particular a recombinant yeast cell according to the invention, comprises one or more recombinant nucleic acids encoding a polypeptide having UTP-glucose-1-phosphate uridylyltransferase (UGP1) activity.

A polypeptide having UTP-glucose-1-phosphate uridylyl-transferase (UGP1) activity according to the invention means a polypeptide that converts the intermediate metabo-lite Glucose-1-Phosphate into the intermediate metabolite UDP-glucose.

In an embodiment, one or more of the recombinant nucleic acids encoding a polypeptide having UTP-glucose-1-phosphate uridylyltransferase activity are under the con-trol of an inducible or repressible promoter that is functional in recombinant cells of the invention, such as for example the inducible or repressible promoters pSAM1 or pCUP1.

One or more of the recombinant nucleic acids encoding a polypeptide having UTP-glucose-1-phosphate uridylyltrans-ferase activity may be under the control of a promoter selected from the group consisting of pPDC1 and pENO2.

The one or more recombinant nucleic acids encoding a polypeptide having UTP-glucose-1-phosphate uridylyltrans-ferase activity can originate or be derived from *Saccharo-myces cerevisiae*, as shown in the examples herein.

A recombinant cell according to the invention, and in particular a recombinant yeast cell according to the inven-tion, can comprise between 5 and 10 recombinant nucleic acids encoding a polypeptide having UTP-glucose-1-phos-phate uridylyltransferase activity. A recombinant cell according to the invention, and in particular a recombinant yeast cell according to the invention, may for example comprise 5, 7 or 8 recombinant nucleic acids encoding a polypeptide having UTP-glucose-1-phosphate uridylyltrans-ferase activity.

Illustratively, the one or more recombinant nucleic acids encoding a polypeptide having UTP-glucose-1-phosphate uridylyltransferase activity gene may be inserted within the HIS3 gene and/or within the JLP1 gene and/or within the SAM3 gene of the recombinant cell, and in particular of the recombinant yeast, as it is shown in the examples herein.

In an embodiment of the invention, a recombinant cell, and in particular a recombinant yeast cell, of the invention comprises:

between 5 and 10 recombinant nucleic acids encoding a polypeptide having UTP-glucose-1-phosphate uridy-lyltransferase activity;

said one or more recombinant nucleic acids encoding a polypeptide having UTP-glucose-1-phosphate uridy-lyltransferase activity originating or being derived from *Saccharomyces cerevisiae*; and said one or more recombinant nucleic acids encoding a polypeptide having being under the control of an induc-ible or repressible promoter that is functional in the recombinant cells of the invention, such as for example the inducible or repressible promoters pSAM1 or pCUP1 and/or under the control of a promoter selected from the group consisting of pPDC1 and pENO2.

Recombinant Nucleic Acids Encoding a Polypeptide Having Glucosamine-6-Phosphate N-Acetyltransferase Activity A recombinant cell according to the invention, and in particular a recombinant yeast cell according to the invention, can comprise one or more recombinant nucleic acids encoding a polypeptide having Glucosamine-6-phosphate N-acetyltransferase (GNA1) activity.

A polypeptide having Glucosamine-6-phosphate N-acetyltransferase (GNA1) activity according to the invention means a polypeptide that can convert Glucosamine-6-phosphate into N-acetyl-glucosamine-6-phosphate.

In an embodiment, one or more of the recombinant nucleic acids encoding a polypeptide having Glucosamine-6-phosphate N-acetyltransferase activity are under the control of an inducible or repressible promoter that is functional in the recombinant cells of the invention.

One or more of the recombinant nucleic acids encoding a polypeptide having Glucosamine-6-phosphate N-acetyltransferase activity may be under the control of the promoter pCWP2.

The said one or more recombinant nucleic acids encoding a polypeptide having Glucosamine-6-phosphate N-acetyltransferase activity may originate or be derived from *Saccharomyces cerevisiae*, as shown in the examples herein.

A recombinant cell according to the invention, and in particular a recombinant yeast cell according to the invention, can comprise only one recombinant nucleic acid encoding a polypeptide having Glucosamine-6-phosphate N-acetyltransferase activity.

Illustratively, the one or more recombinant nucleic acids encoding a polypeptide having Glucosamine-6-phosphate N-acetyltransferase activity may be inserted within the SAM3 gene of the recombinant cell, and in particular of the recombinant yeast, as it is shown in the examples herein.

In an embodiment of the invention, a recombinant cell, and in particular a recombinant yeast, of the invention comprises:

only one recombinant nucleic acid encoding a polypeptide having Glucosamine-6-phosphate N-acetyltransferase activity;

said recombinant nucleic acid encoding a polypeptide having Glucosamine-6-phosphate N-acetyltransferase activity originating or being derived from *Saccharomyces cerevisiae*; and said recombinant nucleic acid encoding a polypeptide having Glucosamine-6-phosphate N-acetyltransferase activity being under the control of the promoter pCWP2.

Recombinant Nucleic Acids Encoding a Polypeptide Having Phosphoacetylglucosamine Mutase Activity A recombinant cell according to the invention, and in particular a recombinant yeast cell according to the invention, can comprise one or more recombinant nucleic acids encoding a polypeptide having phosphoacetylglucosamine mutase (PCM1) activity.

A polypeptide having phosphoacetylglucosamine mutase (PCM1) activity according to the invention means a polypeptide that can convert N-acetyl-glucosamine-6-phosphate N-acetyl-glucosamine-1-phosphate.

In an embodiment, one or more of the recombinant nucleic acids encoding a polypeptide having phosphoacetylglucosamine mutase activity are under the control of an inducible or repressible promoter that is functional in the recombinant cells of the invention.

One or more of the recombinant nucleic acids encoding a polypeptide having phosphoacetylglucosamine mutase activity may be under the control a promoter selected from the group consisting of pTEF3 and pTEF1.

The said one or more recombinant nucleic acids encoding a polypeptide having phosphoacetylglucosamine mutase activity can originate or be derived from *Saccharomyces cerevisiae*, as shown in the examples herein.

A recombinant cell according to the invention, and in particular a recombinant yeast cell according to the invention, may comprise only one recombinant nucleic acid encoding a polypeptide having phosphoacetylglucosamine mutase activity.

Illustratively, the one or more recombinant nucleic acids encoding a polypeptide having phosphoacetylglucosamine mutase activity may be inserted within the SAM3 gene of the recombinant cell, and in particular of the recombinant yeast, as it is shown in the examples herein.

In an embodiment of the invention, a recombinant cell, and in particular a recombinant yeast cell, of the invention comprises:

only one recombinant nucleic acid encoding a polypeptide having phosphoacetylglucosamine mutase activity;

said recombinant nucleic acid encoding a polypeptide having phosphoacetylglucosamine mutase activity originating or being derived from *Saccharomyces cerevisiae*; and said recombinant acid encoding a polypeptide having phosphoacetylglucosamine mutase activity being under the control of the promoter a promoter selected from the group consisting of pTEF3 and pTEF1.

Hyaluronan Synthase (HASA)

The hyaluronan synthase enzyme is a protein which is described in the art for catalyzing the conversion of UDP-glucuronate or UDP-N-acetyl-glucose into hyaluronic acid. The hyaluronan synthase originating from *Streptococcus zooepidemicus, Chlorella* virus PBCV1, *Xenopus laevis* or *Pasteurella multocida* may be termed HASA.

A method implemented to measure the activity level of a polypeptide having hyaluronan synthase activity belongs to the general knowledge of the one skilled in the art.

In this regard, the one skilled in the art may advantageously refer to the method of colorimetric determination after treatment with concentrated sulfuric acid and carbazole described by Bitter and Muir (Analytical Biochemistry, 4, 330-334, 1962).

Preferred polypeptide having hyaluronan synthase activity in the present invention is an enzyme having an EC number of no 2.4.1.212.

According to a preferred embodiment, the one or more recombinant nucleic acids encoding a polypeptide having hyaluronan synthase activity may originate or be derived from organisms preferably selected in a group consisting of prokaryotic organisms and eukaryotic organisms. In some embodiments, the one or more recombinant nucleic acids encoding a polypeptide having hyaluronan synthase activity may originate or be derived from archaebacteria. In some embodiments, the one or more recombinant nucleic acids encoding a polypeptide having hyaluronan synthase activity may originate or be derived from bacteria, and especially from *Streptococcus zooepidemicus* (Sz) or from *Pasteurella multocida* (Pm), from *Chlorella* virus PBCV1 (Vir), *Chlorella* virus CviK1 (Vir), *Chlorella* virus IL-5-2s1 (Vir), *Chlorella* virus CZ-2 (Vir), *Chlorella* virus CVG-1 (Vir) or from *Xenopus laevis* (Xl).

According to a yet preferred embodiment, the one or more recombinant nucleic acids encoding a polypeptide having hyaluronan synthase activity may be selected from the group consisting of nucleic acid sequences having (i) at least 65%, advantageously at least 70%, preferably at least 80%, nucleic acid identity with a nucleic acid sequence as set forth as sequence SEQ ID NO: 1 (Vir), SEQ ID NO: 2 (Vir), SEQ ID NO: 3 (Pm), SEQ ID NO: 4 (Pm), SEQ ID NO: 5 (Pm), SEQ ID NO: 6 (X1), SEQ ID NO: 7 (sz), SEQ ID NO: 101 (Vir), SEQ ID NO: 102 (Vir), SEQ ID NO: 103 (Vir) or SEQ ID NO: 104 (Vir) and (ii) a biological activity of the same nature as the nucleic acid sequence having, respectively, the nucleic acid sequence as set forth as sequence SEQ ID NO: 1 (Vir), SEQ ID NO: 2 (Vir), SEQ ID NO: 3 (Pm), SEQ ID NO: 4 (Pm), SEQ ID NO: 5 (Pm), SEQ ID NO: 6 (X1), SEQ ID NO: 7 (sz), SEQ ID NO: 101 (Vir), SEQ ID NO: 102 (Vir), SEQ ID NO: 103 (Vir) or SEQ ID NO: 104 (Vir).

A biological activity of the same nature regarding this sequence is, as previously explained, the capacity to code for a polypeptide that converts UDP-glucuronate or UDP-N-acetyl-glucose into hyaluronic acid.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

As described herein, a nucleic acid sequence having at least 70% nucleotide identity with a reference nucleic acid sequence encompasses nucleic acid sequences having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

For the amino acid sequence of the polypeptide having hyaluronan synthase activity originating from *Streptococcus zooepidemicus, Chlorella* virus PBCV1, *Xenopus laevis* or *Pasteurella multocida*, the one skilled in the art may refer, respectively, to the accession numbers B4UOD4, Q84419, P13563, Q7BLV3, M1GZS8, M1H5V3, M1H2Q1 and M1HN86 in the UniProt database, or to SEQ ID NO: 8 (Vir), SEQ ID NO: 9 (Pm) SEQ ID NO: 10 (X1), SEQ ID NO:11 (Sz), SEQ ID NO: 105 (Vir), SEQ ID NO: 106 (Vir), SEQ ID NO: 107 (Vir) or SEQ ID NO: 108 (Vir) described herein, in particular to to SEQ ID NO: 8 (Vir), SEQ ID NO: 9 (Pm) SEQ ID NO: 10 (X1), SEQ ID NO:11 (Sz), SEQ ID NO: 105 (Vir), SEQ ID NO: 106 (Vir) or SEQ ID NO: 108 (Vir), and more particularly to SEQ ID NO: 8 (Vir), SEQ ID NO: 9 (Pm) SEQ ID NO: 10 (X1), SEQ ID NO:11 (Sz).

According to another particular embodiment, the one or more recombinant nucleic acids encoding a polypeptide having hyaluronan synthase activity may be nucleic acid(s) encoding polypeptide having an amino acid sequence selected from the group consisting of sequences having at least 50%, advantageously at least 65%, preferably at least 80%, amino acid identity with the amino acid sequence set forth as SEQ ID NO: 8 (Vir), SEQ ID NO: 9 (Pm) SEQ ID NO: 10 (X1), SEQ ID NO:11 (Sz), SEQ ID NO: 105 (Vir), SEQ ID NO: 106 (Vir), SEQ ID NO: 107 (Vir) or SEQ ID NO: 108 (Vir), and also a biological activity of the same nature as the amino acid sequence set forth as SEQ ID NO: 8 (Vir), SEQ ID NO: 9 (Pm) SEQ ID NO: 10 (X1), SEQ ID NO:11 (Sz), SEQ ID NO: 105 (Vir), SEQ ID NO: 106 (Vir), SEQ ID NO: 107 (Vir) or SEQ ID NO: 108 (Vir).

A biological activity of the same nature regarding this sequence is as described previously, i.e. the capacity to catalyze the conversion of UDP-glucuronate or UDP-N-acetyl-glucose into hyaluronic acid.

As described herein, an amino acid sequence having at least 50% amino acid identity with a reference amino acid sequence encompasses amino acid sequences having at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As above-mentioned, the expression level of the one or more recombinant nucleic acids encoding a polypeptide having hyaluronan synthase activity in the present invention is regulated by at least one promoter and at least one terminator, such as herein after defined more in details, which are present in 5' and 3' position respectively of the one or more recombinant nucleic acids encoding a polypeptide having hyaluronan synthase activity.

UDP-Glucose Dehydrogenase (UDP-GlcDH or HASB)

The UDP-Glucose dehydrogenase is a protein which is known in the art to catalyze the conversion of UDP-glucose into UDP-glucuronate. The UDP-Glucose dehydrogenase originating from the genome of *Arabidopsis thaliana, Chlorella* virus PBCV1 or *Streptococcus zooepidemicus* may be termed HASB.

A method implemented to measure the activity level of a polypeptide having UDP-Glucose dehydrogenase activity belongs to the general knowledge of the one skilled in the art.

In this regard, the one skilled in the art may advantageously refer to the method described by Oka and Jigami (FEBS Journal 273, 2645-2657, 2006).

Preferred polypeptide having UDP-Glucose dehydrogenase activity in the present specification is an enzyme having an EC number 1.1.1.22.

According to a preferred embodiment, the one or more recombinant nucleic acids encoding a polypeptide having UDP-Glucose dehydrogenase activity may originate or be derived from organisms preferably selected in a group comprising prokaryotic organisms and eukaryotic organisms. In some embodiments, the one or more recombinant nucleic acids encoding a polypeptide having UDP-Glucose dehydrogenase activity may originate or be derived from archaebacteria. In some preferred embodiments, the one or more recombinant nucleic acids encoding a polypeptide having UDP-Glucose dehydrogenase activity may originate or be derived from yeast, and especially from *Arabidopsis thaliana, Chlorella* virus PBCV1 or *Streptococcus zooepidemicus haromyces.*

According to a yet preferred embodiment, the one or more recombinant nucleic acids encoding a polypeptide having UDP-Glucose dehydrogenase activity may be selected from the group consisting of nucleic acid sequences having (i) at least 65%, advantageously at least 70%, preferably at least 80%, nucleic acid identity with a nucleic acid as set forth as sequence SEQ ID NO: 12 (At), SEQ ID NO. 13 (Vir), SEQ ID NO. 14 (Vir) or SEQ ID NO: 15 (Sz), and (ii) a biological activity of the same nature as the nucleic acid as set forth as sequence SEQ ID NO: 12 (At), SEQ ID NO. 13 (Vir), SEQ ID NO. 14 (Vir) or SEQ ID NO: 15 (Sz). The nucleic acids set forth as sequences SEQ ID NO: 12 (At), SEQ ID NO: 13 (Vir), SEQ ID NO. 14 (Vir) and SEQ ID NO: 15 (Sz) encode a polypeptide having UDP-Glucose dehydrogenase activity originating, respectively, from *Arabidopsis thaliana* (At), *Chlorella* virus PBCV1 (Vir) or *Streptococcus zooepidemicus* (Sz), that may herein also be collectively termed HASB.

A biological activity of the same nature regarding this sequence is, as previously explained, the capacity to code for a polypeptide that converts UDP-glucose into UDP-glucuronate.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

As described herein, a nucleic acid sequence having at least 70% nucleotide identity with a reference nucleic acid sequence encompasses nucleic acid sequences having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequences, and also a biological activity of the same nature as the said reference nucleic acid sequences.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequences.

For the amino acid sequence of the polypeptide having UDP-Glucose dehydrogenase activity from *Arabidopsis thaliana, Chlorella* virus PBCV1 or *Streptococcus zooepidemicus,* the one skilled in the art may refer to the accession numbers NP_173979.1, NP_048965 or KIS19289, respectively, in the UniProt database, or to the sequences as set forth in SEQ ID NO: 16 (At), SEQ ID NO. 17 (Vir) and SEQ ID NO: 18 (Sz) described herein.

According to another particular embodiment, the one or more recombinant nucleic acids encoding a polypeptide having UDP-Glucose dehydrogenase activity may be nucleic acid(s) encoding a polypeptide having an amino acid sequence selected from the group consisting of sequences having at least 55%, advantageously at least 65%, preferably at least 80%, amino acid identity with the amino acid sequence of SEQ ID NO: 16 (At), SEQ ID NO. 17 (Vir) and SEQ ID NO: 18 (Sz), and also a biological activity of the same nature as the amino acid sequence of SEQ ID NO: 16 (At), SEQ ID NO. 17 (Vir) and SEQ ID NO: 18 (Sz).

A biological activity of the same nature regarding this sequence is as described previously, i.e. the capacity to catalyze the conversion of UDP-glucose into UDP-glucuronate.

As described herein, an amino acid sequence having at least 55% amino acid identity with a reference amino acid sequence encompasses amino acid sequences having at least 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As above-mentioned, the expression level of the one or more recombinant nucleic acids encoding a polypeptide having UDP-Glucose dehydrogenase activity in the present invention is regulated by at least one promoter and at least one terminator, such as herein after defined more in details, which are present in 5' and 3' position respectively of the one or more recombinant nucleic acids encoding a polypeptide having UDP-Glucose dehydrogenase activity.

Hyaluronidase (HYAL)

The hyaluronidase enzyme is a protein which is described in the art for catalyzing the degradation of hyaluronic acid molecules into smaller hyaluronic acid molecules. The hyaluronidase originating from *Cupiennius salei, Loxosceles intermedia, Hirudo nipponia, Bothrops atrox, Tityus serrulatus* or *Vespa magnifica* may be termed HYAL.

The polypeptide having hyaluronidase activity of the invention may possess both a secretion signal and an anchoring signal or a secretion signal and no anchoring signal or a secretion-anchor signal with a dual secretion and anchoring function. When the encoded polypeptide having hyaluronidase activity possesses both a secretion signal and an anchoring signal, it may be termed HYAL-31 as represented in the examples. When the encoded polypeptide having hyaluronidase activity possesses a secretion signal and no anchoring signal, it may be termed HYAL-3 as represented in the examples.

A method implemented to measure the activity level of a polypeptide having hyaluronidase activity belongs to the general knowledge of the one skilled in the art.

In this regard, the one skilled in the art may advantageously monitor the molecular weight of the obtained hyaluronic acid on an agarose gel.

Preferred polypeptide having hyaluronidase activity in the present specification is an enzyme having an EC number of no EC 3.2.1.35.

According to a preferred embodiment, the one or more recombinant nucleic acids encoding a polypeptide having hyaluronidase activity may originate or be derived from organisms preferably selected in a group comprising pro- karyotic organisms and eukaryotic organisms. In some embodiments, the one or more recombinant nucleic acids encoding a polypeptide having hyaluronidase activity may originate or be derived from archaebacteria. In some embodiments, the one or more recombinant nucleic acids encoding a polypeptide having hyaluronidase activity may originate or be derived from organisms preferably selected from yeasts. In some other preferred embodiments, the one or more recombinant nucleic acids encoding a polypeptide having hyaluronidase activity may originate or be derived from *Cupiennius salei* (Csa), *Loxosceles intermedia* (Li), *Hirudo nipponia* (Hn), *Bothrops atrox* (Ba), *Tityus serrulatus* (Ts) or *Vespa magnifica* (Vm), and in particular from *Cupiennius salei* (Csa), *Loxosceles intermedia* (Li), *Hirudo nipponia* (Hn), *Bothrops atrox* (Ba) and *Tityus serrulatus* (Ts).

According to a yet preferred embodiment, the one or more recombinant nucleic acids encoding a polypeptide having hyaluronidase activity may be selected from the group consisting of nucleic acid sequences having at least 65%, advantageously at least 70%, preferably at least 80%, nucleic acid identity with a nucleic acid of SEQ ID NO: 19 (Ba), SEQ ID NO: 25 (Li), SEQ ID NO: 21 (Csa), SEQ ID NO: 27 (Ts), SEQ ID NO: 23 (Hn), or SEQ ID NO: 29 (Vm) and also a biological activity of the same nature as the nucleic acid of SEQ ID NO: 19 (Ba), SEQ ID NO: 25 (Li), SEQ ID NO: 21 (Csa), SEQ ID NO: 27 (Ts), SEQ ID NO: 23 (Hn), or SEQ ID NO: 29 (Vm). The nucleic acid of SEQ ID NO: 19 (Ba), SEQ ID NO: 25 (Li), SEQ ID NO: 21 (Csa), SEQ ID NO: 27 (Ts), SEQ ID NO: 23 (Hn) or SEQ ID NO: 29 (Vm) encode a polypeptide having hyluronidase activity, comprise a secretion signal and no anchoring signal, and originate or derive from *Bothrops atrox, Loxosceles intermedia, Cupiennius salei, Tityus serrulatus, Hirudo nipponia* or *Vespa magnifica*, respectively.

According to another preferred embodiment, the one or more recombinant nucleic acids encoding a polypeptide having hyaluronidase activity may be selected from the group consisting of nucleic acid sequences having at least 65%, advantageously at least 70%, preferably at least 80%, nucleic acid identity with a nucleic acid of SEQ ID NO: 22 (Csa), SEQ ID NO: 26 (Li), SEQ ID NO: 24 (Hn), SEQ ID NO: 20 (Ba), SEQ ID NO: 28 (Ts) or SEQ ID NO: 30 (Vm), and also a biological activity of the same nature as the nucleic acid of SEQ ID NO: 22 (Csa), SEQ ID NO: 26 (Li), SEQ ID NO: 24 (Hn), SEQ ID NO: 20 (Ba), SEQ ID NO: 28 (Ts) or SEQ ID NO: 30 (Vm). The nucleic acid of SEQ ID NO: 22 (Csa), SEQ ID NO: 26 (Li), SEQ ID NO: 24 (Hn), SEQ ID NO: 20 (Ba) SEQ ID NO: 28 (Ts) or SEQ ID NO: 30 (Vm) encode a polypeptide having hyluronidase activity, comprise a secretion signal and an anchoring signal, and originate or derive from *Cupiennius salei, Loxosceles intermedia, Hirudo nipponia, Bothrops atrox, Tityus serrulatus* or *Vespa magnifica*, respectively.

In a particular embodiment, the one or more recombinant nucleic acids encoding a polypeptide having hyaluronidase activity may be selected from the group consisting of nucleic acid sequences (i) having at least 65%, advantageously at least 70%, preferably at least 80%, nucleic acid identity with a nucleic acid of SEQ ID NO: 19 (Ba), SEQ ID NO: 25 (Li), SEQ ID NO: 21 (Csa), SEQ ID NO: 27 (Ts), or SEQ ID NO: 23 (Hn) and (ii) having a biological activity of the same nature as the nucleic acid of SEQ ID NO: 19 (Ba), SEQ ID NO: 25 (Li), SEQ ID NO: 21 (Csa), SEQ ID NO: 27 (Ts), or SEQ ID NO: 23 (Hn).

In a particular embodiment, the one or more recombinant nucleic acids encoding a polypeptide having hyaluronidase activity may be selected from the group consisting of nucleic acid sequences having (i) at least 65%, advantageously at least 70%, preferably at least 80%, nucleic acid identity with a nucleic acid of SEQ ID NO: 22 (Csa), SEQ ID NO: 26 (Li), SEQ ID NO: 24 (Hn), SEQ ID NO: 20 (Ba), or SEQ ID NO: 28 (Ts) and (ii) having a biological activity of the same nature as the nucleic acid of SEQ ID NO: 22 (Csa), SEQ ID NO: 26 (Li), SEQ ID NO: 24 (Hn), SEQ ID NO: 20 (Ba), or SEQ ID NO: 28 (Ts).

A biological activity of the same nature regarding this sequence is, as previously explained, the capacity to code for a polypeptide that catalyzes the degradation of hyaluronic acid molecules into smaller hyaluronic acid molecules.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

As described herein, a nucleic acid sequence having at least 70% nucleotide identity with a reference nucleic acid sequence encompasses nucleic acid sequences having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

For the amino acid sequence of the one or more recombinant nucleic acids encoding a polypeptide having hyaluronidase activity from *Cupiennius salei, Loxosceles intermedia, Hirudo nipponia, Bothrops atrox* or *Tityus serrulatus*, the one skilled in the art may refer to the accession numbers A0A0S4JYH2, R4J7Z9, X4Y2L4, A0A2H4Z8F4 or P85841, respectively in the UniProt database, or to SEQ ID NO: 33 (Csa), SEQ ID NO: 37 (Li), SEQ ID NO: 35 (Hn), SEQ ID NO: 31 (Ba) SEQ ID NO: 39 (Ts) or SEQ ID NO: 41 (Vm), described herein.

According to another particular embodiment, the one or more recombinant nucleic acids encoding a polypeptide having hyaluronidase activity may be nucleic acid(s) encoding polypeptide having an amino acid sequence selected from the group consisting of sequences having at least 50%, advantageously at least 65%, preferably at least 80%, amino acid identity with the amino acid sequence of SEQ ID NO: 33 (Csa), SEQ ID NO: 37 (Li), SEQ ID NO: 35 (Hn), SEQ ID NO: 31 (Ba), SEQ ID NO: 39 (Ts) or SEQ ID NO: 41 (Vm) which comprise a secretion signal and no anchoring signal, and also a biological activity of the same nature as the amino acid sequence SEQ ID NO: 33 (Csa), SEQ ID NO: 37 (Li), SEQ ID NO: 35 (Hn), SEQ ID NO: 31 (Ba), SEQ ID NO: 39 (Ts) or SEQ ID NO: 41 (Vm).

According to another particular embodiment, the one or more recombinant nucleic acids encoding a polypeptide having hyaluronidase activity may be nucleic acid(s) encoding polypeptide having an amino acid sequence selected from the group consisting of sequences having at least 55%, advantageously at least 65%, preferably at least 80%, amino acid identity with the amino acid sequence of SEQ ID NO: 34 (Csa), SEQ ID NO: 38 (Li), SEQ ID NO: 36 (Hn), SEQ ID NO: 32 (Ba), SEQ ID NO: 40 (Ts) or SEQ ID NO: 42 (Vm) which comprise a secretion signal and an anchoring signal, and also a biological activity of the same nature as the amino acid sequence of SEQ ID NO: 34 (Csa), SEQ ID NO: 38 (Li), SEQ ID NO: 36 (Hn), SEQ ID NO: 32 (Ba), SEQ ID NO: 40 (Ts) or SEQ ID NO: 42 (Vm).

In a particular embodiment, the one or more recombinant nucleic acids encoding a polypeptide having hyaluronidase activity may be nucleic acid(s) encoding a polypeptide having an amino acid sequence selected from the group consisting of sequences having at least 55%, advantageously at least 65%, preferably at least 80%, amino acid identity with the amino acid sequence of SEQ ID NO: 33 (Csa), SEQ ID NO: 37 (Li), SEQ ID NO: 35 (Hn), SEQ ID NO: 31 (Ba), or SEQ ID NO: 39 (Ts), and also a biological activity of the same nature as the amino acid sequence of SEQ ID NO: 33 (Csa), SEQ ID NO: 37 (Li), SEQ ID NO: 35 (Hn), SEQ ID NO: 31 (Ba), or SEQ ID NO: 39 (Ts).

In another particular embodiment, the one or more recombinant nucleic acids encoding a polypeptide having hyaluronidase activity may be nucleic acid(s) encoding a polypeptide having an amino acid sequence selected from the group consisting of sequences having at least 55%, advantageously at least 65%, preferably at least 80%, amino acid identity with the amino acid sequence of SEQ ID NO: 34 (Csa), SEQ ID NO: 38 (Li), SEQ ID NO: 36 (Hn), SEQ ID NO: 32 (Ba) or SEQ ID NO: 40 (Ts), and also a biological activity of the same nature as the amino acid sequence of SEQ ID NO: 34 (Csa), SEQ ID NO: 38 (Li), SEQ ID NO: 36 (Hn), SEQ ID NO: 32 (Ba) or SEQ ID NO: 40 (Ts).

A biological activity of the same nature regarding this sequence is as described previously, i.e. the capacity to catalyze the degradation of hyaluronic acid molecules into smaller hyaluronic acid molecules.

As described herein, an amino acid sequence having at least 55% amino acid identity with a reference amino acid sequence encompasses amino acid sequences having at least 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As above-mentioned, the expression level of the one or more recombinant nucleic acids encoding a polypeptide having hyaluronidase activity in the present invention is regulated by at least one promoter and at least one terminator, such as herein after defined more in details, which are present in 5' and 3' position respectively of the one or more recombinant nucleic acids encoding a polypeptide having hyaluronidase activity.

Glutamine Synthetase (GLN1)

The glutamine synthetase enzyme is a protein which is described in the art for catalyzing the conversion of glutamate into glutamine. The glutamine synthetase originating from *Saccharomyces cerevisiae* may be termed GLN1.

A method implemented to measure the activity level of a polypeptide having glutamine synthetase activity belongs to the general knowledge of the one skilled in the art.

In this regard, the one skilled in the art may advantageously refer to the method described by Legrain et al. (1982) European Journal of Biochemistry 123, 611-616.

Preferred polypeptide having glutamine synthetase activity in the present invention is an enzyme having an EC number of no EC 6.3.1.2.

According to a preferred embodiment, the one or more recombinant nucleic acids encoding a polypeptide having glutamine synthetase activity may originate or be derived from organisms preferably selected in a group comprising prokaryotic organisms and eukaryotic organisms. In some embodiments, the one or more recombinant nucleic acids encoding a polypeptide having glutamine synthetase activity may originate or be derived from archaebacteria. In some embodiments, the one or more recombinant nucleic acids encoding a polypeptide having glutamine synthetase activity may originate or be derived from a yeast, and especially from *Saccharomyces cerevisiae*.

According to a yet preferred embodiment, the one or more recombinant nucleic acids encoding a polypeptide having glutamine synthetase activity may be selected from the group consisting of nucleic acid sequences having (i) at least 65%, advantageously at least 70%, preferably at least 80%, nucleic acid identity with the nucleic acid sequence as set forth as sequence SEQ ID NO: 96 (Sc), and (ii) a biological activity of the same nature as the nucleic acid sequence as set forth as sequence SEQ ID NO: 96 (Sc). The nucleic acid as set forth as sequence SEQ ID NO: 96 encodes a polypeptide having glutamine synthetase activity originating from *Saccharomyces cerevisiae*, that may also be termed GLN1.

A biological activity of the same nature regarding this sequence is, as previously explained, the capacity to code for a polypeptide that converts glutamate into glutamine, in particular through the consumption of one ATP and one NH$_4^+$.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

As described herein, a nucleic acid sequence having at least 70% nucleotide identity with a reference nucleic acid sequence encompasses nucleic acid sequences having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

For the amino acid sequence of the polypeptide having glutamine synthetase activity originating from *Saccharomyces cerevisiae*, the one skilled in the art may refer to the accession number P32288 in the UniProt database, or to the sequence SEQ ID NO: 97 described herein.

According to another particular embodiment, the one or more recombinant nucleic acids encoding a polypeptide having glutamine synthetase activity may be nucleic acid(s) encoding polypeptide having an amino acid sequence selected from the group consisting of sequences having at least 35%, advantageously at least 65%, preferably at least 80%, amino acid identity with the amino acid sequence of SEQ ID NO: 97, and also a biological activity of the same nature as the amino acid sequence of SEQ ID NO: 97.

A biological activity of the same nature regarding this sequence is as described previously, i.e. the capacity to catalyze the conversion of glutamate into glutamine.

As described herein, an amino acid sequence having at least 35% amino acid identity with a reference amino acid sequence encompasses amino acid sequences having at least 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As above-mentioned, the expression level of the polypeptide having glutamine synthetase activity in the present invention is regulated by at least one promoter and at least one terminator, such as herein after defined more in details, which are present in 5' and 3' position respectively of one or more recombinant nucleic acids encoding a polypeptide having glutamine synthetase activity.

Glutamate Synthase (GLT1)

The glutamate synthase enzyme is a protein which is described in the art for catalyzing the conversion of glutamine into glutamate. The glutamate synthase originating from *Saccharomyces cerevisiae* may be termed GLT1.

A method implemented to measure the activity level of a polypeptide having glutamate synthase activity belongs to the general knowledge of the one skilled in the art.

In this regard, the one skilled in the art may advantageously refer to the method described by Roon et al. (1974) Journal of bacteriology 118, 89-95.

Preferred polypeptide having glutamate synthase activity in the present invention is an enzyme having an EC number of no EC 1.4.1.14 (SEQ ID NO: 98).

For the amino acid sequence of the polypeptide having glutamate synthase activity from *Saccharomyces cerevisiae*, the one skilled in the art may refer to the accession number Q12680 in the UniProt database, or to the sequence SEQ ID NO: 99 described herein.

As above-mentioned, the expression level of a polypeptide having glutamate synthase activity may be reduced in a recombinant cell, and in particular in a recombinant yeast according to the invention as compared to the said cell, and in particular yeast, in its non-recombined form, i.e. at least one endogeneous gene of the recombinant cell, and in particular of the recombinant yeast, is disrupted.

Glutamine-Fructose-6-Phosphate Amidotransferase (GFA1)

The glutamine-fructose-6-phosphate amidotransferase enzyme is a protein which is described in the art for catalyzing the conversion of fructose-6-phosphate into glucosamine-6-phosphate. The glutamine-fructose-6-phosphate amidotransferase originating from *Saccharomyces cerevisiae* may be termed GFA1.

A method implemented to measure the activity level of a polypeptide having glutamine-fructose-6-phosphate amidotransferase activity belongs to the general knowledge of the one skilled in the art.

In this regard, the one skilled in the art may advantageously refer to the method described by Shiga Shibatan and Hiroaki Kitazawa (Plant Biotechnology 26, 149-152, 2009).

Preferred polypeptide having glutamine-fructose-6-phosphate amidotransferase activity in the present invention is an enzyme having an EC number of no EC 2.6.1.16.

According to a preferred embodiment, the one or more recombinant nucleic acids encoding a polypeptide having glutamine-fructose-6-phosphate amidotransferase activity may originate or be derived from organisms preferably selected in a group comprising prokaryotic organisms and eukaryotic organisms. In some embodiments, the one or more recombinant nucleic acids encoding a polypeptide having glutamine-fructose-6-phosphate amidotransferase activity may originate or be derived from archaebacteria. In some embodiments, the one or more recombinant nucleic acids encoding a polypeptide having glutamine-fructose-6-phosphate amidotransferase activity may originate or be derived from organisms preferably selected from *Bacillus subtilis*, and yeasts. In some other preferred embodiments, the one or more recombinant nucleic acids encoding a polypeptide having glutamine-fructose-6-phosphate amidotransferase activity may originate or be derived from a yeast, and especially from *Saccharomyces cerevisiae*.

According to a yet preferred embodiment, the one or more recombinant nucleic acids encoding a polypeptide having glutamine-fructose-6-phosphate amidotransferase activity may be selected from the group consisting of nucleic acid sequences having (i) at least 65%, advantageously at least 70%, preferably at least 80%, nucleic acid identity with the nucleic acid sequence as set forth as sequence SEQ ID NO: 47 (Sc), and (ii) a biological activity of the same nature as the nucleic acid sequence as set forth as sequence SEQ ID NO: 47 (Sc). The nucleic acid as set forth as sequence SEQ ID NO: 47 encodes a polypeptide having glutamine-fructose-6-phosphate amidotransferase activity originating from *Saccharomyces cerevisiae*, that may also be termed GFA1.

According to yet another embodiment, the one or more recombinant nucleic acids encoding a polypeptide having glutamine-fructose-6-phosphate amidotransferase activity may be selected from the group consisting of nucleic acid sequences having (i) at least 65%, advantageously at least 70%, preferably at least 80%, nucleic acid identity with the nucleic acid sequence as set forth as sequence SEQ ID NO: 48 or SEQ ID NO: 49, and (ii) a biological activity of the same nature as the nucleic acid sequence as set forth as sequence SEQ ID NO: 48 or SEQ ID NO: 49. The nucleic acid sequence as set forth as sequence SEQ ID NO: 48 or SEQ ID NO: 49 encodes a polypeptide having glutamine-fructose-6-phosphate amidotransferase activity originating from *Chlorella* virus PBCV1.

A biological activity of the same nature regarding this sequence is, as previously explained, the capacity to code for a polypeptide that converts fructose-6-phosphate into glucosamine-6-phosphate.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

As described herein, a nucleic acid sequence having at least 70% nucleotide identity with a reference nucleic acid sequence encompasses nucleic acid sequences having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

For the amino acid sequence of the polypeptide having glutamine-fructose-6-phosphate amidotransferase activity originating from *Saccharomyces cerevisiae*, the one skilled in the art may refer to the accession number NP8012818 in the UniProt database, or to the sequence SEQ ID NO: 50 described herein.

For the amino acid sequence of the polypeptide having glutamine-fructose-6-phosphate amidotransferase activity originating from *Chlorella* virus PBCV1, the one skilled in the art may also refer to the accession number NP_048448 in the UniProt database, or to the sequence SEQ ID NO: 51 described herein.

According to another particular embodiment, the one or more recombinant nucleic acids encoding a polypeptide having glutamine-fructose-6-phosphate amidotransferase activity may be nucleic acid(s) encoding polypeptide having an amino acid sequence selected from the group consisting of sequences having at least 35%, advantageously at least 65%, preferably at least 80%, amino acid identity with the amino acid sequence of SEQ ID NO: 50 or with SEQ ID NO: 51, and also a biological activity of the same nature as the amino acid sequence of SEQ ID NO: 50 or with SEQ ID NO: 51.

A biological activity of the same nature regarding this sequence is as described previously, i.e. the capacity to catalyze the conversion of of fructose-6-phosphate into glucosamine-6-phosphate.

As described herein, an amino acid sequence having at least 35% amino acid identity with a reference amino acid sequence encompasses amino acid sequences having at least 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As above-mentioned, the expression level of the polypeptide having glutamine-fructose-6-phosphate amidotransferase activity in the present invention is regulated by at least one promoter and at least one terminator, such as herein after defined more in details, which are present in 5' and 3' position respectively of one or more recombinant nucleic acids encoding a polypeptide having glutamine-fructose-6-phosphate amidotransferase activity.

UDP-N-Acetylglucosamine Pyrophosphorylase (ORI1)

The UDP-N-acetylglucosamine pyrophosphorylase enzyme is a protein which is described in the art for catalyzing the conversion of N-acetyl-glucosmine-6-phosphate into UDP-N-acetyl-glucose. The UDP-N-acetylglucosamine pyrophosphorylase originating from *Saccharomyces cerevisiae* may be termed QRI1.

A method implemented to measure the activity level of a polypeptide having UDP-N-acetylglucosamine pyrophosphorylase activity belongs to the general knowledge of the one skilled in the art.

In this regard, the one skilled in the art may advantageously refer to the method described by Mio et al. (The Journal of Biological Chemistry, Col. 273, No 23, Jun. 5, 1998, 14392-14397) except that UDP-N-acetyl-glucosamine is detected by LC MS/MS using a Synergi RP Fusion column.

Preferred polypeptide having UDP-N-acetylglucosamine pyrophosphorylase activity in the present invention is an enzyme having an EC number of no EC 2.7.7.23

According to a preferred embodiment, the one or more recombinant nucleic acids encoding a polypeptide having UDP-N-acetylglucosamine pyrophosphorylase activity may originate or be derived from organisms preferably selected in a group consisting of prokaryotic organisms and eukaryotic organisms. In some embodiments, the one or more recombinant nucleic acids encoding a polypeptide having UDP-N-acetylglucosamine pyrophosphorylase activity may originate or be derived from archaebacteria. In some embodiments, the one or more recombinant nucleic acids encoding a polypeptide having UDP-N-acetylglucosamine pyrophosphorylase activity may originate or be derived from organisms preferably selected from *Bacillus subtilis*, and yeasts. In some other preferred embodiments, the one or more recombinant nucleic acids encoding a polypeptide having UDP-N-acetylglucosamine pyrophosphorylase activity may originate or be derived from yeasts, and especially from *Saccharomyces cerevisiae*.

According to a yet preferred embodiment, the one or more recombinant nucleic acids encoding a polypeptide having UDP-N-acetylglucosamine pyrophosphorylase activity may be selected from the group consisting of nucleic acid sequences having (i) at least 65%, advantageously at least 70%, preferably at least 80%, nucleic acid identity with a nucleic acid sequence as set forth as SEQ ID NO: 52, and (ii) a biological activity of the same nature as the nucleic acid sequence as set forth as SEQ ID NO: 52. The nucleic acid sequence set forth as SEQ ID NO: 52 encodes a polypeptide having UDP-N-acetylglucosamine pyrophosphorylase activity originating from *Saccharomyces cerevisiae*, that may also be termed QRI1.

A biological activity of the same nature regarding this sequence is, as previously explained, the capacity to code for a polypeptide that converts N-acetyl-glucosmine-6-phosphate into UDP-N-acetyl-glucose.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

As described herein, a nucleic acid sequence having at least 70% nucleotide identity with a reference nucleic acid sequence encompasses nucleic acid sequences having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

For the amino acid sequence of the polypeptide having UDP-N-acetylglucosamine pyrophosphorylase activity originating from *Saccharomyces cerevisiae*, the one skilled in the art may refer to the accession number NP_010180 in the UniProt database, or to SEQ ID NO. 53 described herein.

According to another particular embodiment, the one or more recombinant nucleic acids encoding a polypeptide having UDP-N-acetylglucosamine pyrophosphorylase activity may be nucleic acid(s) encoding polypeptide having an amino acid sequence selected from the group consisting of sequences having at least 35%, advantageously at least 45%, preferably at least 80%, amino acid identity with the amino acid sequence set forth as sequence SEQ ID NO. 53, and also a biological activity of the same nature as the amino acid sequence set forth as sequence SEQ ID NO. 53.

A biological activity of the same nature regarding this sequence is as described previously, i.e. the capacity to catalyze the conversion of of N-acetyl-glucosmine-6-phosphate into UDP-N-acetyl-glucose.

As described herein, an amino acid sequence having at least 35% amino acid identity with a reference amino acid sequence encompasses amino acid sequences having at least 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 45% amino acid identity with a reference amino acid sequence encompasses amino acid sequences having at least 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As above-mentioned, the expression level of the one or more recombinant nucleic acids encoding a polypeptide having UDP-N-acetylglucosamine pyrophosphorylase activity in the present invention is regulated by at least one promoter and at least one terminator, such as herein after defined more in details, which are present in 5' and 3' position respectively of the one or more recombinant nucleic acids encoding a polypeptide having UDP-N-acetylglucosamine pyrophosphorylase activity.

Phosphoglucomutase-1 (PGM1)

The Phosphoglucomutase-1 enzyme is a protein which is described in the art for catalyzing the conversion of Glucose-6-phosphate into Glucose-1-phosphate. The Phosphoglucomutase-1 originating from *Saccharomyces cerevisiae* may be termed PGM1.

A method implemented to measure the activity level of a polypeptide facing Phosphoglucomutase-1 activity belongs to the general knowledge of the one skilled in the art.

In this regard, the one skilled in the art may advantageously refer to the method described by Tiwari and Bhat (Biochemical and Biophysical Research Communications 366, 340-345, 2008).

Preferred polypeptide having Phosphoglucomutase-1 activity in the present invention is an enzyme having an EC number of no 5.4.2.2.

According to a preferred embodiment, the one or more recombinant nucleic acids encoding a polypeptide having Phosphoglucomutase-1 activity may originate from organisms preferably selected in a group consisting of prokaryotic organisms and eukaryotic organisms. In some embodiments, the one or more recombinant nucleic acids encoding a polypeptide having Phosphoglucomutase-1 activity may originate or be derived from archaebacteria. In some embodiments, the one or more recombinant nucleic acids encoding a polypeptide having Phosphoglucomutase-1 activity may originate or be derived from organisms preferably selected from bacteria. In a preferred embodiment, the one or more recombinant nucleic acids encoding a polypeptide having Phosphoglucomutase-1 activity may originate or be derived from *Saccharomyces cerevisiae*.

According to an embodiment, the one or more recombinant nucleic acids encoding a polypeptide having Phosphoglucomutase-1 activity may be selected from the group consisting of nucleic acid sequences having (i) at least 80% nucleic acid identity with the nucleic acid sequence set forth as sequence SEQ ID NO: 54, which originates from *Saccharomyces cerevisiae*, and (ii) a biological activity of the same nature as the nucleic acid sequence set forth as sequence SEQ ID NO: 54.

A biological activity of the same nature regarding this sequence is, as previously explained, the capacity to code for a polypeptide that converts Glucose-6-phosphate into Glucose-1-phosphate.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

For the amino acid sequence of the peptide having Phosphoglucomutase-1 activity from *Saccharomyces cerevisiae*, the one skilled in the art may refer to the accession number NP33401 in the UniProt database, or to SEQ ID NO: 55 described herein.

According to another particular embodiment, the one or more recombinant nucleic acids encoding a polypeptide having Phosphoglucomutase-1 activity may be nucleic acid(s) encoding polypeptide having an amino acid sequence selected from the group consisting of sequences having at least least 80% amino acid identity with the amino acid sequence set forth as sequence SEQ ID NO: 55, and also a biological activity of the same nature as the amino acid sequence set forth as sequence SEQ ID NO: 55.

A biological activity of the same nature regarding this sequence is as described previously, i.e. the capacity to catalyze the conversion of Glucose-6-phosphate into Glucose-1-phosphate.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As above-mentioned, the expression level of the one or more recombinant nucleic acids encoding a polypeptide having Phosphoglucomutase-1 activity in the present invention is regulated by at least one promoter and at least one terminator, such as herein after defined more in details, which are present in 5' and 3' position respectively of the one or more recombinant nucleic acids encoding a polypeptide having Phosphoglucomutase-1 activity.

UTP-Glucose-1-Phosphate Uridylyltransferase (UGP1)

The UTP-glucose-1-phosphate uridylyltransferase enzyme is a protein which is described in the art for catalyzing the conversion of Glucose-1-Phosphate into UDP-glucose. The UTP-glucose-1-phosphate uridylyltransferase originating from *Saccharomyces cerevisiae* may be termed UGP1.

A method implemented to measure the activity level of a polypeptide having UTP-glucose-1-phosphate uridylyltransferase activity belongs to the general knowledge of the one skilled in the art.

In this regard, the one skilled in the art may advantageously refer to the method described by Roeben (J. Mol. Biol 364, 551-560, 2006).

Preferred polypeptide having UTP-glucose-1-phosphate uridylyltransferase activity in the present invention is an enzyme having an EC number of no 2.7.7.9.

According to a preferred embodiment, the one or more recombinant nucleic acids encoding a polypeptide having UTP-glucose-1-phosphate uridylyltransferase activity may originate or be derived from organisms preferably selected in a group consisting of prokaryotic organisms and eukaryotic organisms. In some embodiments, the one or more recombinant nucleic acids encoding a polypeptide having UTP-glucose-1-phosphate uridylyltransferase activity may originate or be derived from archaebacteria. In some embodiments, the one or more recombinant nucleic acids encoding a polypeptide having UTP-glucose-1-phosphate uridylyltransferase activity may originate or be derived from organisms preferably selected from bacteria. In a preferred embodiment, the one or more recombinant nucleic acids encoding a polypeptide having UTP-glucose-1-phosphate uridylyltransferase activity may originate or be derived from *Saccharomyces cerevisiae*.

According to a particular embodiment, the one or more recombinant nucleic acids encoding a polypeptide having UTP-glucose-1-phosphate uridylyltransferase activity may be selected from the group consisting of nucleic acid sequences having (i) at least 80% nucleic acid identity with a nucleic acid as set forth as sequence SEQ ID NO: 56, originating from *Saccharomyces cerevisiae*, and (ii) a biological activity of the same nature as the nucleic acid as set forth as sequence SEQ ID NO: 56.

A biological activity of the same nature regarding this sequence is, as previously explained, the capacity to code for a polypeptide that converts Glucose-1-phosphate into UDP-glucose.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

For the amino acid sequence of the polypeptide having UTP-glucose-1-phosphate uridylyltransferase activity originating from *Saccharomyces cerevisiae*, the one skilled in the art may refer to the accession number NP_32861 in the UniProt database, or to the sequence set forth as sequence SEQ ID NO: 57 described herein.

According to another particular embodiment, the one or more recombinant nucleic acids encoding a polypeptide having UTP-glucose-1-phosphate uridylyltransferase activity may be nucleic acid(s) encoding polypeptide having an amino acid sequence selected from the group consisting of sequences having at least 80% amino acid identity with the amino acid sequence set forth as SEQ ID NO: 57, and also a biological activity of the same nature as the amino acid sequence set forth as SEQ ID NO: 57.

A biological activity of the same nature regarding this sequence is as described previously, i.e. the capacity to catalyze the conversion of Glucose-1-phosphate into UDP-glucose.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As above-mentioned, the expression level of the one or more recombinant nucleic acids encoding a polypeptide having UTP-glucose-1-phosphate uridylyltransferase activity in the present invention is regulated by at least one promoter and at least one terminator, such as herein after defined more in details, which are present in 5' and 3' position respectively of the one or more recombinant nucleic acids encoding a polypeptide having UTP-glucose-1-phosphate uridylyltransferase activity.

Glucosamine-6-Phosphate N-Acetyltransferase (GNA1)

The Glucosamine-6-phosphate N-acetyltransferase enzyme is a protein which is described in the art for catalyzing the conversion of Glucosamine-6-phosphate into N-acetyl-glucosamine-6-phosphate. The Glucosamine-6-phosphate N-acetyltransferase originating from *Saccharomyces cerevisiae* may be termed GNA1.

A method implemented to measure the activity level of a polypeptide having Glucosamine-6-phosphate N-acetyltransferase activity belongs to the general knowledge of the one skilled in the art.

In this regard, the one skilled in the art may advantageously refer to the method described by Li et al. (Anal. Biochem. 370, 142-146, 2007).

Preferred polypeptide having Glucosamine-6-phosphate N-acetyltransferase activity in the present invention is an enzyme having an EC number of no 2.3.1.4.

According to a preferred embodiment, the one or more recombinant nucleic acids encoding a polypeptide having Glucosamine-6-phosphate N-acetyltransferase activity may originate or be derived from organisms preferably selected in a group consisting of prokaryotic organisms and eukaryotic organisms. In some preferred embodiments, the one or more recombinant nucleic acids encoding a polypeptide having Glucosamine-6-phosphate N-acetyltransferase activity may originate or be derived from a yeast, and especially from *Saccharomyces cerevisiae*.

According to a particular embodiment, the one or more recombinant nucleic acids encoding a polypeptide having Glucosamine-6-phosphate N-acetyltransferase activity may be selected from the group consisting of nucleic acid sequences having (i) at least 80% nucleic acid identity with a nucleic acid sequence as set forth as sequence SEQ ID NO: 58, and (ii) a biological activity of the same nature as the nucleic acid sequence as set forth as sequence SEQ ID NO: 58. The nucleic acid sequence as set forth as sequence SEQ ID NO: 58 encodes a polypeptide having Glucosamine-6-phosphate N-acetyltransferase activity originating from *Saccharomyces cerevisiae*, that may also be termed GNA1.

A biological activity of the same nature regarding this sequence is, as previously explained, the capacity to code for a polypeptide that converts Glucosamine-6-phosphate into N-acetyl-glucosamine-6-phosphate.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

For the amino acid sequence of the polypeptide having Glucosamine-6-phosphate N-acetyltransferase activity originating from *Saccharomyces cerevisiae*, the one skilled in the art may refer to the accession number NP_116637 in the UniProt database, or to SEQ ID NO. 59 described herein.

According to another particular embodiment, the one or more recombinant nucleic acids encoding a polypeptide having Glucosamine-6-phosphate N-acetyltransferase activity may be nucleic acid(s) encoding polypeptide having an amino acid sequence selected from the group consisting of sequences having at least 80% amino acid identity with the amino acid sequence set forth as SEQ ID NO. 59, and also a biological activity of the same nature as the amino acid sequence set forth as SEQ ID NO. 59.

A biological activity of the same nature regarding this sequence is as described previously, i.e. the capacity to catalyze the conversion of Glucosamine-6-phosphate into N-acetyl-glucosamine-6-phosphate.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As above-mentioned, the expression level of the one or more recombinant nucleic acids encoding a polypeptide having Glucosamine-6-phosphate N-acetyltransferase activity in the present invention is regulated by at least one promoter and at least one terminator, such as herein after defined more in details, which are present in 5' and 3' position respectively of the one or more recombinant nucleic acids encoding a polypeptide having Glucosamine-6-phosphate N-acetyltransferase activity.

Phosphoacetylglucosamine Mutase (PCM1)

The phosphoacetylglucosamine mutase enzyme is a protein which is described in the art for catalyzing the conversion of N-acetyl-glucosamine-6-phosphate into N-acetyl-glucosamine-1-phosphate. The phosphoacetylglucosamine mutase originating from Saccharomyces cerevisiae may be termed PCM1.

A method implemented to measure the activity level of a polypeptide having phosphoacetylglucosamine mutase activity belongs to the general knowledge of the one skilled in the art.

In this regard, the one skilled in the art may advantageously refer to the method described by Bandini et al. (Molecular Microbiology 85 (3), 513-534, 2012).

Preferred polypeptide having phosphoacetylglucosamine mutase activity in the present invention is an enzyme having an EC number of no 5.4.2.3.

According to a preferred embodiment, the one or more recombinant nucleic acids encoding a polypeptide having phosphoacetylglucosamine mutase activity mayoriginate or be derived from organisms preferably selected in a group consisting of prokaryotic organisms and eukaryotic organisms. In some preferred embodiments, the one or more recombinant nucleic acids encoding a polypeptide having phosphoacetylglucosamine mutase activity may originate or be derived from a yeast, and especially from Saccharomyces cerevisiae.

According to a particular embodiment, the one or more recombinant nucleic acids encoding a polypeptide having phosphoacetylglucosamine mutase activity may be selected from the group consisting of nucleic acid sequences having (i) at least 80% nucleic acid identity with a nucleic acid sequence set forth as SEQ ID NO: 60, and (ii) a biological activity of the same nature as the nucleic acid sequence set forth as SEQ ID NO: 60. The nucleic acid set forth as SEQ ID NO: 60 encodes a polypeptide having phosphoacetylglucosamine mutase activity originating from Saccharomyces, that may also be termed PCM1.

A biological activity of the same nature regarding this sequence is, as previously explained, the capacity to code for a polypeptide that converts N-acetyl-glucosamine-6-phosphate into N-acetyl-glucosamine-1-phosphate.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature as the said reference nucleic acid sequence.

For the amino acid sequence of the polypeptide having phosphoacetylglucosamine mutase activity originating from Saccharomyces cerevisiae, the one skilled in the art may refer to the accession number NP_010856 in the UniProt database, or to SEQ ID NO. 61 described herein.

According to another particular embodiment, the one or more recombinant nucleic acids encoding a polypeptide having phosphoacetylglucosamine mutase activity may be nucleic acid(s) encoding polypeptide having an amino acid sequence selected from the group consisting of sequences having at least 80% amino acid identity with the amino acid sequence set forth as SEQ ID NO. 61, and also a biological activity of the same nature as the amino acid sequence set forth as SEQ ID NO. 61.

A biological activity of the same nature regarding this sequence is as described previously, i.e. the capacity to catalyze the conversion of N-acetyl-glucosamine-6-phosphate into N-acetyl-glucosamine-1-phosphate.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature as the said reference amino acid sequence.

As above-mentioned, the expression level of the one or more recombinant nucleic acids encoding a polypeptide having phosphoacetylglucosamine mutase activity in the present invention is regulated by at least one promoter and at least one terminator, such as herein after defined more in detail, which are present in 5' and 3' position respectively of the one or more recombinant nucleic acids encoding a polypeptide having phosphoacetylglucosamine mutase activity.

Promoters

As disclosed herein, the expression of the genes of interest that have been genetically engineered for obtaining a recombinant cell according to the invention comprise appropriate regulatory sequences that are functional in the recombinant cells of the invention, and in particular in recombinant yeast cells of the invention, including in particular Saccharomyces cerevisiae.

Various promoters may be used for the desired expression of the coding sequences of interest.

Promoters according to the invention can be selected from the group consisting of the following promoters:
pTDH3 (SEQ ID NO: 62),
pTDH3.sk (SEQ ID NO: 63),
pTDH3-1.Sba (SEQ ID NO: 64),
pTDH3.Sar (SEQ ID NO: 65),
pENO2 (SEQ ID NO: 66),
pTEF3 (SEQ ID NO: 67),
pTEF1 (SEQ ID NO: 68),
pTEF1.ago (SEQ ID NO: 69),
pTEF1.sba (SEQ ID NO: 70),
pPDC1 (SEQ ID NO: 71),
pCCW12 (SEQ ID NO: 72),
pCCW12.Sm (SEQ ID NO: 73),
pCCW12.sk (SEQ ID NO: 74),
pCCW12.sba (SEQ ID NO: 75),
pCCW12.sar (SEQ ID NO: 76),
pNUP57 (SEQ ID NO: 77),
pCCW10.ago (SEQ ID NO: 78),
pCWP2 (SEQ ID NO: 79), and
pRPLA1 (SEQ ID NO: 80).

Promoters more particularly interesting in the present invention may be selected from the group consisting of:

pTDH3 (SEQ ID NO: 62),
pTDH3.sk (SEQ ID NO: 63),
pTDH3-1.Sba (SEQ ID NO: 64),
pTDH3.Sar (SEQ ID NO: 65),
pENO2 (SEQ ID NO: 66),
pTEF3 (SEQ ID NO: 67),
pTEF1 (SEQ ID NO: 68),
pTEF1.ago (SEQ ID NO: 69),
pTEF1.sba (SEQ ID NO: 70),
pPDC1 (SEQ ID NO: 71),
pCCW12 (SEQ ID NO: 72),
pCCW12.Sm (SEQ ID NO: 73),
pCCW12.sk (SEQ ID NO: 74),
pCCW12.sba (SEQ ID NO: 75), and
pCCW12.sar (SEQ ID NO: 76), Said promoters can in particular be selected from the group consisting of pTDH3, pTDH3-1.Sba, pTDH3.Sar, pENO2, pTEF3, pTEF1, pPDC1, pCCW12, pCCW12.Sm, pCCW12.sk, pCCW12.sba, and pCCW12.sar.

Alternatively, promoters interesting in the present invention may be selected from the group consisting of:

pNUP57 (SEQ ID NO: 77), and
pCCW10.ago (SEQ ID NO: 78).

Other promoters of interest in the present invention may be:

pCWP2 (SEQ ID NO: 79); and
pRPLA1 (SEQ ID NO: 80).

As previously mentioned, inducible or repressible promoters are promoters whose activity is controlled by the presence or absence of biotic or abiotic factors and also by the quantity of said factor. Accordingly, for some promoters, their activity will in particular be induced and thus increased when the quantity of a given factor increases or is increased, and, accordingly, the activity of these same promoters can be repressed and thus reduced when the quantity of said factor diminishes or is reduced. The quantity of said factor(s) in the culture medium of a recombinant yeast cell of the invention comprising inducible or repressible promoters can be decided and thus controlled by the man skilled in the art.

For example, increasing the quantity of copper in a culture medium of a recombinant yeast cell according to the invention comprising a pCUP-1 promoter will induce and thus increase transcription of the gene under the control of this promoter. On the contrary, reducing the quantity of copper in said culture medium will lead to a repression, and thus a reduced, transcription of the gene under the control of this promoter.

In another example, increasing the quantity of methionine in a culture medium of a recombinant yeast cell according to the invention comprising a pMET6 promoter will repress and thus decrease transcription of the gene under the control of this promoter. On the contrary, reducing the quantity of methionine in said culture medium will lead to an induced, and thus an increased, transcription of the gene under the control of this promoter.

For this reason, the following promoters are referred to in the present text as being inducible or repressible promoters.

According to a first embodiment, inducible or repressible promoters according to the invention may be selected from the group comprising promoters inducible or repressible with copper, promoters inducible or repressible with methionine and promoters inducible or repressible with threonine, and are in particular is CUP1-copper inducible or repressible (SEQ ID NO: 81).

According to this embodiment, the inducible or repressible promoter according to the invention can in particular be pCUP1.

The activity of these promoters is thus induced by the increasing presence of methionine, copper or threonine as indicated above, and their activity diminishes, i.e. is repressed, when the quantity of methionine, copper or threonine is reduced.

According to a second embodiment, inducible or repressible promoters according to the invention may be selected from the group comprising promoters inducible or repressible with copper, promoters inducible or repressible with lysine and promoters inducible or repressible with methionine, and in particular selected from the group consisting of:

pMET6-methionine inducible or repressible (SEQ ID NO: 82),
pMET25-methionine inducible or repressible (SEQ ID NO: 83), and
pSAM1-methionine inducible or repressible (SEQ ID NO: 84), According to this particular embodiment, the inducible or repressible promoter according to the invention may, be selected from the group consisting of pMET6, pMET25 and pSAM1.

The activity of these promoters is thus repressed by the increasing presence of methionine, copper, lysine or glucose as indicated above, and their activity increases, i.e. is induced, when the quantity of methionine, copper, lysine or glucose is reduced.

In a particular embodiment, inducible or repressible promoters according to the invention may be selected from the group comprising promoters inducible or repressible with copper, promoters inducible or repressible with glucose, promoters inducible or repressible with lysine, promoters inducible or repressible with methionine and promoters inducible or repressible with threonine.

In a more particular embodiment, the inducible or repressible promoter according to the invention may be selected from the group consisting of pCUP1, pMET6, pSAM1, and pMET25.

Synthetic promoters as described in Blazeck & Alper (2013) Biotechnol. J. 8 46-58 can also be used.

The promoters of the invention can originate from any organism from the *Saccharomyces* class and can in particular originate from an organism selected from the group consisting of at least one of *Saccharomyces cerevisiae, Saccharomyces boulardii, Saccharomyces castelii, Saccharomyces bayanus, Saccharomyces arboricola, Saccharomyces kudriavzevii, Saccharomyces mikatae, Ashbya gossypii, Kluveromyces lactis, Pichia pastoris, Candida glabrata, Candida tropicalis, Debaryomyces castelii, Yarrowia lipolitica*, and *Cyberlindnera jadinii*.

The promoters of the invention can preferably originate from an organism selected from the group consisting of *Saccharomyces cerevisiae* (sc), *Saccharomyces mikatae* (Sm), *Saccharomyces kudriavzevii* (sk), *Saccharomyces bayanus* (sba), and *Saccharomyces arboricola* (Sar).

Terminators

As it is disclosed herein, the expression of the genes of interest that have been genetically engineered for obtaining a recombinant cell according to the invention, and in particular a recombinant yeast according to the invention, comprise appropriate transcription terminator sequences that are functional in recombinant cells of the invention, and in particular in recombinant yeast cells of the invention, in particular in *Saccharomyces cerevisiae*.

Said transcription terminators, identical or different, may be found in literature Yamanishi et al., (2013) ACS synthetic biology 2, 337-347.

Terminators more particularly interesting in the present invention may be selected from the group comprising:

tTPI1 from the gene encoding for the Triose Phosphate Isomerase (SEQ ID NO: 85), tMET25 from the gene encoding for the O-acetyl homo-serine-O-acetyl serine sulfhydrylase (SEQ ID NO: 86), tDIT1 (SEQ ID NO: 87), tRPL3 (SEQ ID NO: 88), tRPL3.sm (SEQ ID NO: 89), tRPL3.sba (SEQ ID NO: 90), tRPL41B (SEQ ID NO: 91), tRPL15A (SEQ ID NO: 92), tRPL15A.sba (SEQ ID NO: 93), tIDP1 (SEQ ID NO: 94), tTEF1.sba (SEQ ID NO: 95), and tTDH3 (SEQ ID NO: 100).

In particular, said terminator may be selected from the group consisting of tTPI1, tMET25, tDIT1, tRPL3, tRPL3.sm, tRPL3.sba, tRPL41B, tRPL15A, tRPL15A.sba, tIDP1, tTEF1.sba and tTDH3.

The terminators of the invention can originate from any organism from the Saccharomyceses class and can in particular originate from an organism selected from the group consisting of *Saccharomyces cerevisiae* and *Saccharomyces Bayanus*.

Recombinant Cells

Recombinant cells of the invention can be selected from the group consisting of yeasts and bacteria.

Recombinant cells of the invention, such as a recombinant host cell of the invention, are preferably recombinant yeast cells.

Generally, yeast can grow rapidly and can be cultivated at higher density as compared with bacteria, and does not require an aseptic environment in the industrial setting. Furthermore, yeast cells can be more easily separated from the culture medium compared to bacterial cells, greatly simplifying the process for product extraction and purification.

A recombinant cell of the invention, and in particular a recombinant yeast cell of the invention is preferably a *Saccharomyces* cell.

A recombinant cell of the invention, and in particular a recombinant yeast of the invention can in particular belong to the *Saccharomyces* genus, or to the *Candida* genus, or to the *Kluyveromyces* genus, or to the *Ogataea* genus, or to the *Yarrowia* genus, or to the *Debaryomyces* genus, or to the *Ashbya* genus.

A recombinant cell of the invention belonging to the *Saccharomyces* genus can be selected from the group consisting of *Saccharomyces cerevisiae, Saccharomyces boulardii, Saccharomyces bayanus, Saccharomyces paradoxus, Saccharomyces mikatae, Saccharomyces castelli, Saccharomyces cariocanus, Saccharomyces kudriavzevii, Saccharomyces arboricolus, Saccharomyces pastorianus, Saccharomyces uvarum* and *Saccharomyces delbrueckii*.

A recombinant cell of the invention belonging to the *Candida* genus can be selected from the group consisting of *Candida albicans, Candida glabrata, Candida tropicalis, Candida dubliniensis, Candida parapsilosis, Candida lusitaniae* and *Candida guilliermondii*.

A recombinant cell of the invention belonging to the *Kluyveromyces* genus can be selected from the group consisting of *Kluyveromyces lactis, Kluyveromyces marxianus,*

*Kluyveromyces polysporus, Kluyveromyces thermotoleren, Kluyveromyces dobzhanskii* and *Kluyveromyces wickerhamii*.

A recombinant cell of the invention belonging to the *Ogataea* genus can be selected from the group consisting of *Ogataea polymorpha, Ogataea histrianica, Ogataea deakii, Ogataea kolombanensis, Ogataea philodendra, Ogataea siamensis, Ogataea angusta, Ogataea parapolymorpha, Ogataea minuta, Ogataea nonfermentans* and *Ogataea kodamae*.

A recombinant cell of the invention belonging to the *Yarrowia* genus can be selected from the group consisting of *Yarrowia lypolytica, Yarrowia parophonii, Yarrowia galli, Yarrowia oslonensis, Yarrowia alimentaria, Yarrowia hollandica* and *Yarrowia yakushimensis*.

A recombinant cell of the invention belonging to the *Debaryomyces* genus can be selected from the group consisting of *Debaryomyces hansenii, Debaryomyces carsonii, Debaryomyces castellii, Debaryomyces marama, Debaryomyces occidentalis, Debaryomyces oviformis, Debaryomyces nepalensis, Debaryomyces coudertii, Debaryomyces udenii, Debaryomyces psychrosporus* and *Debaryomyces yamadae*.

A recombinant cell of the invention belonging to the *Ashbya* genus can be selected from the group consisting of *Ashbya gossypii* and *Ashbya aceri*.

A recombinant cell of the invention, and in particular a recombinant yeast cell of the invention, can in particular be selected from the group consisting of *Saccharomyces cerevisiae, Saccharomyces boulardii, Saccharomyces bayanus, Saccharomyces paradoxus, Saccharomyces mikatae, Saccharomyces castelli, Candida albicans, Candida glabrata, Candida tropicalis, Kluyveromyces lactis, Kluyveromyces marxianus, Kluyveromyces polysporus, Kluyveromyces thermotolerens, Ogataea polymorpha, Yarrowia lypolytica, Debaryomyces hansenii*, and *Ashbya gossypii*, and is preferably *Saccharomyces cerevisiae*.

In a particular embodiment, the recombinant yeast cell according to the invention is of the genus *Saccharomyces, Kluyveromyces*, or *Eremothecium*, more particularly is of the species selected from the group consisting of *Saccharomyces cerevisiae, Kluyveromyces Marxianus, Ogataea polymorpha* and *Ashbya gossypii*.

In an embodiment, a recombinant host cell of the invention is a yeast selected belonging to the *Saccharomyces* order, in particular to the Saccharomycesaceae family, and is in particular selected from the group consisting of *Yarrowia lipolitica, Kluyveromyces Marxianus, Ogataea polymorpha, Ashbya gossypii* and *Saccharomyces cerevisiae*.

A recombinant cell of the invention can most preferably be a *Saccharomyces cerevisiae* cell.

As above-mentioned, a recombinant cell according to the invention has the ability to produce hyaluronic acid by insertion of the one or more recombinant nucleic acids according to the present invention. In certain embodiments, a recombinant yeast according to the invention has the ability to produce hyaluronic acid having a controlled size (controlled molecular weight) by insertion of the one or more recombinant nucleic acids according to the present invention.

Methods implemented to insert a specific DNA construct within a gene belong to the general knowledge of a man skilled in the art. A related method is described in more details in the herein after examples.

However, unexpected technical difficulties were encountered because the consequences of the insertion of DNA constructs within the genome of a cell, and in particular within the genome of a yeast, such as for example in the genome of *Saccharomyces cerevisiae*, are unpredictable. In particular, the survival rate of the cells, and in particular of the yeasts, and their ability to grow and produce the desired hyaluronic acid is also unpredictable.

In order to obtain a recombinant cell, and in particular a recombinant yeast, of the invention, many different constructs were tested by the inventors in order to obtain a viable and efficient recombinant cell, and in particular yeast.

Culture Conditions

The present invention also relates to the use of a recombinant cell of the invention, for the production of hyaluronic acid, in particular of hyaluronic acid of controlled molecular weight.

The present invention further relates to a method of producing hyaluronic acid (HA) of a desired molecular weight (HAMW) comprising:

(a) cultivating a recombinant cell of the present invention in a cultivation medium for a time sufficient to produce hyaluronic acid (HA) of the desired molecular weight; and (b) optionally isolating or recovering the hyaluronic acid (HA) from the recombinant cell and/or from the cultivation medium.

Typically, cells of the invention, and in particular yeasts of the invention, are grown at a temperature in the range of about 20° C. to about 37° C., preferably at a temperature ranging from 27 to 34° C., in an appropriate culture medium.

Suitable growth media for cells of the invention, and in particular for yeasts of the invention, are common commercially prepared media such as broth that includes yeast nitrogen base, ammonium sulfate, and dextrose as the carbon/energy source or YPD Medium, a blend of peptone, yeast extract, and dextrose in optimal proportions for growing most. Other defined or synthetic growth media may also be used and the appropriate medium for growth of the particular cell, and in particular yeast, will be known by one skilled in the art of microbiology or fermentation science.

A particular medium that is suitable herein is the SY medium which comprises the following elements:

KH2PO4: 100 mM; MgSO4 7H2O: 2.8 mM; K2SO4: 11.5 mM; Na2SO4: 1.1 mM; NaCl: 2.6 mM; CaCl2 2H2O: 0.7 mM; CuSO4 5H2O: 15 µM; KI: 6 µM; FeCl3: 30 µM; ZnSO4 7H2O: 61 µM; MnSO4 H2O: 25 µM; H2SO4: 110 µM; Panthotenic Acids hemicalcium salt: 42 µM; Thiamin hydrochloride: 59 µM; Pyridoxin hydrochloride: 49 µM; Myo-Inositol (C6H12O6): 555 µM; Nicotinic acid (C6H5NO2): 29 µM; D-Biotine: 0.82 µM; Ammonium citrate tribasic: 33 mM; and glucose or sucrose 2-30%.

Carbon sources that may be used in the culture medium include fructose, mannose, xylose and arabinose; oligosaccharides such as lactose, maltose, galactose, or sucrose; polysaccharides such as starch or cellulose or mixtures thereof; and unpurified mixtures from renewable feedstocks such as cheese whey permeate cornsteep liquor, sugar beet molasses, and barley malt.

Nitrogen sources that may be included in the culture medium include peptone, yeast extracts, meat extracts, malt extracts, urea, ammonium sulfate, ammonium chloride, ammonium nitrate, ammonium phosphate, ammonium citrate and combinations thereof.

The culture medium may further comprise trace elements (e.g., metal salts), for example magnesium salts, cobalt salts and/or manganese salts; as well as growth factors such as amino acids, vitamins, growth promoters, and the like.

Examples of vitamins that may be included are Panthotenic Acids hemicalcium, Thiamin hydrochloride; Pyridoxin hydrochloride; Myo-Inositol; Nicotinic acid; D-Biotine, folic acid, p-aminobenzoïque acid, riboflavin.

A culture medium of the invention may further include rare elements, such as CuSO4·5H2O, KI, FeCl3, ZnSO4.7H2O, MnSO4·H2O, or H2SO4, MgCl2, CaCl2, NaCl, K2HPO4, KH2PO4, ZnCl, H3BO3, MnSO4, Na2MoO4.

The term "appropriate culture medium" is above-defined.

Examples of known culture media for a recombinant cell according to the present invention are known to the person skilled in the art, and are presented in the following publication D. Burke et al., Methods in yeast Genetics-A cold spring harbor laboratory course Manual (2000).

Suitable pH ranges for the fermentation may be between pH 3.0 to pH 7.5, where pH 4 to pH 6 is preferred as the initial condition.

As mentioned elsewhere in this specification, the pH value of the culture medium can be regulated during the cultivation step of a method of the invention in order to modulate the activity of the polypeptide facing hyaluronidase activity, which will impact the molecular weight of the hyaluronic acid molecules produced by the recombinant cell of the invention, and in particular by the recombinant yeast of the invention.

In particular, the pH of the culture medium can be modified according to the hyaluronic acid that is meant to be produced by the recombinant yeast. For example, the pH of the culture medium may remain at a pH of 4, of 5.5 or of 6 during the culture time.

In a particular embodiment, the pH of the culture medium may change or be changed during the time length of the culture of the recombinant cell of the invention, in particular of the recombinant yeast of the invention. As previously mentioned, *Saccharomyces cerevisiae* acidifies the medium in which it is cultivated and thus reduces the pH of its culture medium. For example, the pH of the culture medium may begin at 6, may be taken down to 4 and then brought back up to 6. In another example, the pH of the culture medium may begin at 6, remain or be maintained at 6, and then may be lowered to 4.

In a particular embodiment, the pH of the culture medium may be modulated during the cultivating step (a) of a method of the invention so that at the end of the cultivating step of a method of the invention, the pH of the cultivation medium is the same as the pH at the beginning of said cultivation step (a).

In another embodiment, the pH of the culture medium may remain the same during the time length of the culture of the recombinant cell of the invention, and in particular the recombinant yeast cell of the invention.

Said time length of the culture of a recombinant cell according to the invention, and in particular of the recombinant yeast of the invention, can vary depending on the molecular weight of the hyaluronic acid of interest. The longer said time length, the lower the molecular weight of hyaluronic acid in a given culture medium of a recombinant cell of the invention, and in particular a recombinant yeast cell of the invention.

The time length of the culture time of a recombinant cell of the invention, and in particular a recombinant yeast cell in the present invention can be a period of from about 35 hours to about 50 hours, preferably from about 40 hours to about 50 hours, and is in particular about 48 hours.

Fermentations may be performed under aerobic conditions or micro-aerobic conditions.

The amount of hyaluronic acid product in the fermentation medium can be determined using a number of methods known in the art, for example, high performance liquid chromatography (HPLC) or gas chromatography (GC).

The present process may employ a batch method of fermentation. A classical batch fermentation is a closed system where the composition of the medium is set at the beginning of the fermentation and not subject to artificial alterations during the fermentation. Thus, at the beginning of the fermentation, the medium is inoculated with the desired organism or organisms, and fermentation is permitted to occur without adding anything to the system. Typically, however, a "batch" fermentation method or system is batch with respect to the addition of carbon source and attempts are often made at controlling factors such as temperature, pH and oxygen concentration. In batch systems, the metabolite and biomass compositions of the system change constantly up to the time when the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

A Fed-Batch system may also be used in the present invention. A Fed-Batch system is similar to a typical batch system with the exception that the carbon source substrate is added in increments as the fermentation progresses. Fed-Batch systems are useful when catabolite repression (e.g. glucose repression) is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$.

Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, MA, or Deshpande, Mukund V., Appl. Biochem. Biotechnol., 36, 227, (1992). Although the present invention is performed in batch mode it is contemplated that the method would be adaptable to continuous fermentation.

Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for production.

In order to still improve the hyaluronic acid production, a particular embodiment may consist of culturing the recombinant cells of the invention, in particular the recombinant yeast cells of the invention, in an appropriate culture medium, such as above-mentioned, wherein the said culture medium comprises an optimal amount of carbon source, especially glucose or sucrose.

In preferred embodiments, the carbon source comprised in said optimal culture medium consists of glucose and/or sucrose. In preferred embodiments, the said optimal culture medium comprises 1% w/w or more glucose and/or sucrose, in particular comprises 5% w/w or more glucose and/or sucrose, in particular comprises 10% w/w or more glucose and/or sucrose, in particular comprises 15% w/w or more glucose and/or sucrose. In preferred embodiments, the said optimal culture medium comprises at most 40% w/w glucose, which includes at most 35% w/w glucose.

In a preferred embodiment, the method of the invention is carried out on an industrial scale.

More particularly, the cultivation medium of the method according to the invention can be at least about 100 L, more preferably in the range of about 1000 L to about 3000 L, even more preferably about 10,000 L, even more preferably 100,000 L, or even about 250,000 L.

The invention further relates to a method for producing hyaluronic acid as previously described, and comprising the steps of:

(a) culturing a recombinant cell of the invention in a culture medium; and (b) recovering the hyaluronic acid from said culture medium, wherein the hyaluronic acid recovered in step (b) has a molecular weight controlled through the selection of:

the nature and origin of the one or more recombinant nucleic acids encoding a polypeptide having hyaluronidase activity of the recombinant cell of the invention, and in particular of the recombinant yeast of the invention, the nature and origin of the promoter controlling the expression of the one or more recombinant nucleic acids encoding a polypeptide having hyaluronidase activity of the recombinant cell of the invention, and in particular of the recombinant yeast of the invention, the presence or absence of an anchoring signal associated to the one or more recombinant nucleic acids encoding a polypeptide having hyaluronidase activity of the recombinant cell of the invention, and in particular of the recombinant yeast of the invention, the pH of the culture medium during the step of culturing the recombinant cell of the invention, and in particular of the recombinant yeast of the invention, and/or the duration of the culturing of the recombinant cell of the invention, and in particular of the recombinant yeast of the invention.

The molecular weight of the hyaluronic acid can be a particular molecular weight or more preferably a specific range of molecular weights such as, for example, less than 50 kDa, in the range of about 20 kDa to about 50 kDa, greater than or equal to 50 kDa, in the range of about 50 kDa to about 150 kDa, in the range of about 50 kDa to about 250 kDa, greater than or equal to 100 kDa, in the range of about 100 kDa to about 1500 kDa, in the range of about 150 kDa to about 1500 kDa, greater than 1000 kDa or greater than 1500 kDa.

The present invention also relates to the use of a recombinant cell according to the invention, and in particular a recombinant yeast cell of the invention, for the production of hyaluronic acid (HA) having a molecular weight in the range of from about 20 kDa to about 50 kDa or from about 50 kDa to about 1000 kDa.

The one or more recombinant nucleic acids encoding a polypeptide having hyaluronidase activity of a recombinant cell of the invention can for example be selected from those originating or being derived from at least one of *Cupiennius salei* (Csa), *Loxosceles intermedia* (Li), *Hirudo nipponia* (Hn), *Bothrops atrox* (Ba), *Tityus serrulatus* (Ts) or *Vespa magnifica* (Vm), in particular from at least one of *Cupiennius salei* (Csa), *Loxosceles intermedia* (Li), *Hirudo nipponia* (Hn), *Bothrops atrox* (Ba) or *Tityus serrulatus* (Ts), more particularly from those of sequences set forth as sequences SEQ ID NO: 19 (Ba), SEQ ID NO: 25 (Li), SEQ ID NO: 21 (Csa), SEQ ID NO: 27 (Ts) or SEQ ID NO: 23 (Hn) (in the presence of a secretion signal and in the absence of an anchoring signal).

The one or more recombinant nucleic acids encoding a polypeptide having hyaluronidase activity of a recombinant cell of the invention can for example be selected from those originating or being derived from at least one of *Cupiennius salei* (Csa), *Loxosceles intermedia* (Li), *Hirudo nipponia* (Hn), *Bothrops atrox* (Ba), *Tityus serrulatus* (Ts) or *Vespa magnifica* (Vm), in particular from *Cupiennius salei* (Csa), *Loxosceles intermedia* (Li), *Hirudo nipponia* (Hn), *Bothrops atrox* (Ba) or *Tityus serrulatus* (Ts), in particular from those of sequences set forth as sequences SEQ ID NO: 22 (Csa), SEQ ID NO: 26 (Li), SEQ ID NO: 24 (Hn), SEQ ID NO: 20 (Ba) or SEQ ID NO: 28 (Ts) (in the presence of both a secretion signal and an anchoring signal).

The one or more recombinant nucleic acids encoding a polypeptide having hyaluronidase activity of a recombinant cell of the invention can for example be placed under the control of a promoter selected from the group consisting of pTEF1, pCCW12, pCCW12.sba, pCCW12.Sar, pPDC1, pTEF3, pTDH3, pNUP57 and pCCW10.ago.

In particular, the promoters of the one or more recombinant nucleic acids encoding a polypeptide having hyaluronidase activity of a recombinant cell of the invention, and in particular of a recombinant yeast of the invention, may originate or be derived from *Saccharomyces Bayanus, Saccharomyces kudriavzevii, Saccharomyces mikatae, Saccharomyces arboricola* or other saccharomycesles, or *Abishia gossypii*.

The secretion signal of the present invention may for example have:

the nucleic acid sequence set forth as SEQ ID NO: 43; and/or the amino acid sequence set forth as SEQ ID NO: 44.

The anchoring signal of the present invention may for example have:

the nucleic acid sequence set forth as SEQ ID NO: 45; and/or the amino acid sequence set forth SEQ ID NO: 46.

The secretion signal may be fused to the polypeptide having hyluronidase activity by creating a chimeric nucleic acid starting by a nucleic acid sequence encoding the signal peptide followed by a recombinant nucleic acid encoding a polypeptide having hyaluronidase activity as previously defined.

The secretion signal and anchoring signal may be fused to the polypeptide having hyluronidase activity by creating a chimeric nucleic acid starting by a nucleic acid sequence encoding the signal peptide followed by a recombinant nucleic acid encoding a polypeptide having hyaluronidase activity as previously defined, followed by a nucleic acid sequence encoding for the anchoring signal.

Such chimeric nucleic acid sequences may be obtained by techniques known by the man skilled in the art such as chemical synthesis of nucleic acids or any recombination techniques such as cloning or PCR.

The invention further relates to a method as previously described, for producing hyaluronic acid having a molecular weight less than or equal to about 50 kDa, and in particular less than 50 kDa and greater than or equal to about 20 kDa, wherein:

(a) the pH of the medium is superior to 4, and is in particular in the range of from about 5 to about 7;

(b) the one or more recombinant nucleic acids encoding a polypeptide having hyaluronidase activity integrated in the genome of the recombinant cell of the invention originates or is derived:

(i) from *Tityus serrulatus*, possesses a secretion signal but is devoid of an anchoring signal, and is under the control of a promoter selected from the group consisting of pTDH3, pENO2, pTEF3, pTEF1, pPDC1, pCCW12, pCCW12.Sm, pCCW12.sk, pCCW12.sba, pCCW12.sar, pTDH3-1.Sba and pTDH3.Sar;

(ii) from *Cupiennius salei*, possesses a secretion signal but is devoid of an anchoring signal, and is under the control of a promoter selected from the group consisting of pNUP57 and pCCW10.ago;

(iii) from *Cupiennius salei*, possesses a secretion signal and an anchoring signal, and is under the control of the promoter pCWP2;

(iv) from *Loxosceles intermedia* possesses a secretion signal but is devoid of an anchoring signal, and is under the control of a promoter selected from the group consisting of pTDH3, pENO2, pTEF3, pTEF1, pPDC1, pCCW12, pCCW12.Sm, pCCW12.sk, pCCW12.sba, pCCW12.sar, pTDH3-1.Sba and pTDH3.Sar; or (v) from *Hirudo nipponia*, possesses a secretion signal but is devoid of an anchoring signal, and is under the control of a promoter selected from the group consisting of pNUP57 and pCCW10.ago; or (vi) from *Hirudo nipponia*, possesses both a secretion signal and an anchoring signal, and is under the control of a promoter selected from the group consisting of pTDH3, pENO2, pTEF3, pTEF1, pPDC1, pCCW12, pCCW12.Sm, pCCW12.sk, pCCW12.sba, pCCW12.sar, pTDH3-1.Sba and pTDH3.Sar; and (c) the step of recovering the hyaluronic acid from the culture medium is performed about 48 hours after the beginning of the culturing of the recombinant cell of the invention, in particular the recombinant yeast cell of the invention;

the recombinant cell being in particular a recombinant yeast cell, and more particularly a *Saccharomyces cerevisiae* cell.

The invention further relates to a method as previously described, for producing hyaluronic acid having a molecular weight greater than or equal to about 50 kDa and less than or equal to about 1000 kDa, wherein:

(a) the pH of the medium is between about 4 and about 6 and is optionally varied from about 6 to about 4 during the culturing step of the recombinant cell, in particular the recombinant yeast cell, of the invention;

(b) the one or more recombinant nucleic acids encoding a polypeptide having hyaluronidase activity integrated in the genome of the recombinant cell of the invention originates or is derived:

(i) from *Tityus serrulatus*, possesses a secretion signal but is devoid of an anchoring signal, and is under the control of a promoter selected from the group consisting of pTDH3, pENO2, pTEF3, pTEF1, pPDC1, pCCW12, pCCW12.Sm, pCCW12.sk, pCCW12.sba, pCCW12.sar, pTDH3-1.Sba and pTDH3.Sar;

(ii) from *Tityus serrulatus*, possesses both a secretion signal and an anchoring signal, and is under the control of a promoter selected from the group consisting of pTDH3, pENO2, pTEF3, pTEF1, pPDC1, pCCW12, pCCW12.Sm, pCCW12.sk, pCCW12.sba, pCCW12.sar, pTDH3-1.Sba and pTDH3.Sar;

(iii) from *Loxosceles intermedia*, possesses both a secretion signal and an anchoring signal, and is under the control of a promoter selected from the group consisting of pNUP57 and pCCW10.ago;

(iv) from *Loxosceles intermedia*, possesses a secretion signal but is devoid of an anchoring signal, and is under the control of a promoter selected from the group consisting of pTDH3, pENO2, pTEF3, pTEF1, pPDC1, pCCW12, pCCW12.Sm, pCCW12.sk, pCCW12.sba, pCCW12.sar, pTDH3-1.Sba and pTDH3.Sar, (v) from *Cupiennius salei*, possesses both a secretion signal and an anchoring signal, and is under the control of a promoter selected from the group consisting of pNUP57 and pCCW10.ago, (vi) from *Cupiennius salei*, possesses a secretion signal but is devoid of an anchoring signal, and is under the control of a promoter selected from the group consisting of pNUP57 and pCCW10.ago, or (vii) from *Hirudo nipponia*, possesses both a secretion signal and an anchoring signal, and is under the control of a promoter selected from the group consisting of pTDH3, pENO2, pTEF3, pTEF1, pPDC1, pCCW12, pCCW12.Sm, pCCW12.sk, pCCW12.sba, pCCW12.sar, pTDH3-1.Sba and pTDH3.Sar; and (c) the step of recovering the hyaluronic acid from the culture medium is performed about 48 hours after the beginning of the culturing of the recombinant cell of the invention, in particular the recombinant yeast cell of the invention;

the recombinant cell being in particular a recombinant yeast cell, and more particularly a *Saccharomyces cerevisiae* cell.

The invention further relates to a method as previously described, for producing hyaluronic acid having a molecular weight greater than about 1000 kDa, and in particular having a molecular weight from about 1000 kDa to about 1.5 Million Da, wherein:

(a) the pH of the medium is from about 4 to about 6 and is optionally varied from about 6 to about 4 during the culturing step of the recombinant cell, in particular recombinant yeast, of the invention;

(b) the one or more recombinant nucleic acids encoding a polypeptide having hyaluronidase activity integrated in the genome of the recombinant cell of the invention originates or is derived:

(i) from *Tityus serrulatus*, possesses a secretion signal but is devoid of an anchoring signal, and is under the control of a promoter selected from the group consisting of pNUP57 and pCCW10.ago;

(ii) from *Loxosceles intermedia*, possesses a secretion signal but is devoid of an anchoring signal, and is under the control of a promoter selected from the group consisting of pNUP57 and pCCW10.ago;

(iii) from *Bothrops atrox*, possesses a secretion signal but is devoid of an anchoring signal, and is under the control of a promoter selected from the group consisting of pTDH3, pENO2, pTEF3, pTEF1, pPDC1, pCCW12, pCCW12.Sm, pCCW12.sk, pCCW12.sba, pCCW12.sar, pTDH3-1.Sba and pTDH3.Sar; or (iv) from *Bothrops atrox*, possesses both a secretion signal and an anchoring signal, and is under the control of a promoter selected from the group consisting of pTDH3, pENO2, pTEF3, pTEF1, pPDC1, pCCW12, pCCW12.Sm, pCCW12.sk, pCCW12.sba, pCCW12.sar, pTDH3-1.Sba and pTDH3.Sar;

and (c) the step of recovering the hyaluronic acid from the culture medium is performed about 48 hours after the beginning of the culturing of the recombinant cell of the invention, in particular the recombinant yeast cell of the invention;

the recombinant cell being in particular a recombinant yeast, and more particularly a *Saccharomyces cerevisiae* cell.

Another aspect of the present invention relates to hyaluronic acid (HA) obtained or obtainable from a recombinant cell of the invention or from a method according to the invention.

A further aspect of the invention is a cultivation medium comprising the hyaluronic acid of the invention.

The invention further relates to a composition comprising the hyaluronic acid according to the invention.

The invention also relates to an industrial product or a consumer product or a consumable comprising (i) the hyaluronic acid of the invention, (ii) the cultivation medium comprising hyaluronic acid of the invention or (iii) the composition comprising hyaluronic acid of the invention.

In particular, said industrial product or consumer product or consumable according to the invention can be a cosmetic product, a flavour product, a fragrance product, a food product, a food, a beverage, a texturant, a pharmaceutical composition, a dietary supplement, a nutraceutical, a cleaning product and/or a dental and/or an oral hygiene composition.

Purification of Hyaluronic Acid

According to a specific aspect of the invention, the fermentative production of hyaluronic acid preferably comprises a step of isolation of the hyaluronic acid produced from the culture medium. Recovering the hyaluronic acid from the culture medium is a routine task for a man skilled in the art. It may be achieved by a number of techniques well known in the art including but not limiting to pervaporation, selective precipitation, filtration, centrifugation, spray drying, lyophylisation or liquid extraction. The expert in the field knows how to adapt parameters of each technique dependent on the characteristics of the material to be separated.

The yeast as model of a cell in the present invention is preferred in that the synthesized hyaluronic acid is/are entirely exported outside the cells, thus simplifying the purification process.

Gas stripping is achieved with a stripping gas chosen among helium, argon, carbon dioxide, hydrogen, nitrogen or mixture thereof.

Liquid extraction is achieved with organic solvent as the hydrophobic phase such as pentane, hexane, heptane or dodecane. Renewal solvents may also be used.

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

Described herein are specific genes and proteins useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes Techniques known to those skilled in the art may be suitable to identify additional homologous genes and homologous enzymes. Generally, analogous genes and/or analogous enzymes can be identified by functional analysis and will have functional similarities.

Techniques known to those skilled in the art may be suitable to identify analogous genes and analogous enzymes or any biosynthetic pathway genes, proteins, or enzymes, techniques may include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., Branched-Chain Amino Acids Methods Enzymology, 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein.

Derivatives

The term "Hyaluronic acid (HA)", as used herein, is also intended to cover derivatives of Hyaluronic acid, such as but not limited to acetylated or sulfated Hyaluronic acid useful for applications in a cosmetic product, flavor product a fragrance product, a food product, a food, a beverage, a texturant, a pharmaceutical composition, a dietary supplement, a nutraceutical, a cleaning product and/or a dental and/or an oral hygiene composition or combinations thereof.

Hyaluronic acid may be prepared as a composition.

Formulations and Products

A composition of the invention may be incorporated into a formulation/product, such as a nutraceutical, pharmaceutical, veterinary, oenological or cosmetic formulation/product.

Thus, the present invention provides a formulation comprising a composition of the invention. For example, the present invention may provide a cosmetic formulation comprising the composition of the invention.

The present invention also provides a product comprising a composition of the invention. For example, the present invention may provide a cosmetic product comprising the composition of the invention.

A "cosmetic product" is intended to mean any substance or mixture intended to be placed in contact with the external parts of the human body (epidermis, hair system, nails, lips and external genital organs) or with the teeth and the mucous membranes of the oral cavity with a view exclusively or mainly to cleaning them, perfuming them, changing their appearance, protecting them, keeping them in good condition, correcting body odours and/or combinations thereof.

A "substance" is intended to mean a chemical element and its compounds in the natural state or obtained by any manufacturing process, including any additive necessary to preserve its stability and any impurity deriving from the process used but excluding any solvent which may be separated without affecting the stability of the substance or changing its composition.

A "mixture" is intended to mean a mixture or solution composed of two or more substances.

The present invention also provides the use of a composition of the invention in a nutraceutical, pharmaceutical, veterinary, oenological or cosmetic formulation/product.

Such formulations or products are hereinafter referred to as the "formulations or products of the invention".

The nutraceutical, pharmaceutical, veterinary, oenological or cosmetic formulation/product may optionally further comprise pharmaceutically/veterinary/cosmetic (including cosmetic active) ingredients, such as excipients, carriers and mixtures thereof as appropriate.

"Cosmetic" or "Cosmetic Active Ingredients" means any and all natural, naturally occurring, nature identical, synthetic synthetically produced, biosynthetically produced, sustainable, renewable and/or biodegradable compounds, ingredients, intermediates, molecules, substances, raw materials or products individually or as part of a mixture of compounds, ingredients, intermediates, molecules, substances, raw materials or products, blends, compositions, formulations (including but not limited to skin moisturizers, creams, balms, serums, oils, eye, facial makeup, wash off hair products, leave-on hair products, hair colorants (including but not limited to natural hair colorants) and/or combinations thereof), finished products and related technologies including, but not limited to components, incorporated, for example, into a cosmetic formulation (such as but not limited to natural colorants, preservatives, emulsifiers, antioxidants and the like which do not, for example, have an activity on the skin, hair, scalp and the like but play a role in the formulation of the finished product), delivery systems, marketing aids (such as, for example, coloured unispheres applied to translucent formulations) and methods of making anything related thereto useful in/used for/intended for:

application by rubbing, pouring, sprinkling, spraying or otherwise directly on or to a human or animal body and/or by placing in contact with the various external and/or on surface parts of a human or animal body (including but not limited to the skin, hair, body hair, the hair system, scalp, nails, lips, external genitalia, teeth, oral and/or nasal mucosa and the like); and/or application indirectly on or to a human or animal body such as for example, application as part of a textile or application to a textile as part of a delivery device (such as a capsule) or a delivery system (such as blends or formulations) applied to a textile; and/or cleansing, caring, cooling, beautifying, conditioning, treating, soothing, texturizing, promoting attractiveness, protecting, maintaining, improving, enhancing, altering and/or changing an external part and/or surface of a human or animal body (such as, but not limited to the scalp) or the aesthetic appearance of a human or animal body; and/or with a view to mainly cleaning or perfuming, or protecting or maintaining in good condition or combating body odour or changing the appearance of or correcting or repairing a state of imbalance in skin, oral mucosa, scalp or hair by providing a calming, healing, repairing, or revitalization, hydration of the skin or in order to provide relief to, lubricate, moisten, tone, heal, sterilize, relieve, correct and/or remedy states of dryness, irritation, injury or fatigue, and/or with a view to correcting pigmentation disorders or providing a non-pharmaceutical prevention and/or treatment of dandruff, acne, irritation and/or inflammation and the like and/or rebalancing the bacterial flora (such as, for example, the microbiome) on the surface of the skin (such as, for example, by promoting the level of beneficial bacterial flora on the skin surface) and/or for the purposes of keeping a human or animal body in good condition for health and/or wellbeing purposes and/or for improving the appearance of a human or animal body by, for example, improving the appearance of a product applied to a human or body; and/or providing a cosmetic and/or dermatological function and/or benefit with a biological activity benefit (but without affecting a body's structure or function. For the avoidance of doubt, a Cosmetic or Cosmetic Active Ingredient or any part thereof may also qualify as a Functional Ingredient and/or Nutraceutical.

"Functional Ingredient" means a food ingredient or part of a food that provides medicinal or health benefits, including any of the following: a carotenoid, dietary fiber, fatty acid, saponin, antioxidant, flavonoid, isothiocyanate, phenol, polyphenol (such as resveratrol), plant sterol or stanol (phytosterols and phytostanols), a polyol, a prebiotic, a phytoestrogen, soy protein, sulfides/thiol, a vitamin, glucosamine, preservatives, hydration agents, edible gelling ingredients, edible gel mixes and gel compositions, long chain primary aliphatic saturated alcohols, colour agents, texturizing agents, emulsifiers and combinations thereof.

"Nutraceutical" means any and all natural, naturally occurring, sustainable, synthetically-produced and bio-synthetically-produced compounds, mixtures of compounds, Functional Ingredients, molecules, compositions, raw materials, and intermediates (including components and delivery devices (such as capsules) related thereto, delivery systems thereof (such as blends or formulations) and methods of making the foregoing) that are associated with health and/or cosmetic benefits, as well as improving or maintaining the appearance of the human body. For the avoidance of doubt, Nutraceuticals includes compounds that can be used as supplements to food or beverage, whether a solid formulation, capsule, tablet, liquid formulation, solution or suspension.

Alternatively, the nutraceutical, pharmaceutical, veterinary, oenological or cosmetic formulation/product may consist or consist essentially of the composition of the invention.

The cosmetic formulation/product may be an anti-aging formulation.

As used herein, references to pharmaceutically, veterinary or cosmetically acceptable excipients may refer to pharmaceutically, veterinary or cosmetically acceptable adjuvants, diluents and/or carriers as known to those skilled in the art.

By "pharmaceutically/veterinary/cosmetically acceptable" we mean that the additional components of the composition are generally safe, non-toxic, and neither biologically nor otherwise undesirable. For example, the additional components may be generally sterile and pyrogen free. Such components must be "acceptable" in the sense of being compatible with the composition of the invention and not deleterious to the recipients thereof. Thus, "pharmaceutically acceptable excipients" includes any compound(s) used in forming a part of the formulation that is intended to act merely as an excipient, i.e. not intended to have biological activity itself.

The nutraceutical, pharmaceutical, veterinary, oenological or cosmetic formulation/product may be in the form of a liquid or a solid.

Liquid dosage formulations/products for oral administration include solutions, emulsions, aqueous or oily suspensions, syrups and elixirs.

Formulations and products (e.g. pharmaceutical, veterinary or cosmetic formulations/products) described herein, such as those intended for oral administration, may be prepared according to methods known to those skilled in the art, such as by mixing the components of the formulation/product together.

The formulation or product (e.g. pharmaceutical, veterinary or cosmetic formulation/product) may contain one or more additional ingredients, such as pharmaceutical ingredients and excipients, such as sweetening agents, flavouring agents, colouring agents and preserving agents.

The formulation or product (e.g. pharmaceutical, veterinary or cosmetic formulation/product) may also contain one or more additional active ingredients, such as cosmetic or pharmaceutical active ingredients, such as hyaluronic acid, centella *asiatica* extract, peptides such as Matrixyl® and Argireline®, and mixtures thereof.

The formulation or product of the invention may contain the active ingredient(s) in admixture with non-toxic pharmaceutically acceptable excipients (or ingredients). These excipients (or ingredients) may, for example, be: inert diluents, such as calcium carbonate, sodium carbonate, lactose, calcium phosphate or sodium phosphate; granulating and disintegrating agents, for example, corn starch, maltodextrin or alginic acid; binding agents, for example, starch, gelatine or acacia; or lubricating agents, for example magnesium stea-rate, stearic acid, talc and mixtures thereof.

Liquid formulations or products (e.g. pharmaceutical, veterinary or cosmetic formulations/products) may be contained within a capsule, which may be uncoated or coated as defined above.

Suitable pharmaceutical or veterinary carriers include inert solid diluents or fillers, sterile aqueous solutions and various organic solvents. Examples of liquid carriers are syrup, peanut oil, olive oil, phospholipids, fatty acids, fatty acid amines, polyoxyethylene and water.

Moreover, the carrier or diluent may include any sustained release material known in the art, such as glyceryl monostearate or glyceryl distearate, alone or mixed with a wax.

Suitable pharmaceutical carriers include inert sterile aqueous solutions and various organic solvents. Examples of liquid carriers are syrup, vegetables oils, phospholipids, fatty acids, fatty acid amines, polyoxyethylene and water. Moreover, the carrier or diluent may include any sustained release material known in the art, such as glyceryl monostearate or glyceryl distearate, alone or mixed with a wax.

Suitable cosmetic carriers are typically those that are suitable for topical administration to the outer surface of the human body, such as the skin and/or hair and/or scalp.

Typically, such carriers are dermatologically acceptable. The phrase "dermatologically acceptable carrier" means that the carrier is suitable for topical application to the keratinous tissue, has good aesthetic properties, is compatible with the actives in the composition, and will not cause any unreasonable safety or toxicity concerns.

The carrier can be in a wide variety of forms. In some instances, the solubility or dispersibility of the components (e.g. extracts, sunscreen active, additional components) may dictate the form and character of the carrier. Non-limiting examples include simple solutions (e.g. aqueous or anhydrous), dispersions, emulsions, and solid forms (e.g. gels, sticks, flowable solids, or amorphous materials).

The dermatologically acceptable carrier may be in the form of an emulsion. An emulsion may be generally classified as having a continuous aqueous phase (e.g. oil-in-water and water-in-oil-in-water) or a continuous oil phase (e.g. water-in-oil or oil-in-water). The oil phase of the present invention may comprise silicone oils, non-silicone oils such as hydrocarbon oils, esters, ethers, and the like, and mixtures thereof. The aqueous phase typically comprises water and water-soluble ingredients (e.g. water-soluble moisturizing agents, conditioning agents, anti-microbials, humectants and/or other skin care actives). However, in some instances, the aqueous phase may comprise components other than water, including but not limited to water-soluble moisturizing agents, conditioning agents, antimicrobials, humectants and/or other watersoluble skin care actives. In some instances, the non-water component of the composition comprises a humectant, such as glycerin and/or other polyol(s). Emulsions may also contain an emulsifier. Emulsifiers may be non-ionic, anionic or cationic.

The carrier may contain one or more dermatologically acceptable, hydrophilic diluents. As used herein, "diluent" includes materials in which the composition of the invention can be dispersed, dissolved, or otherwise incorporated. Hydrophilic diluents include water, organic hydrophilic diluents, such as lower monovalent alcohols (e.g., C1-C4), and low molecular weight glycols and polyols, including propylene glycol, polyethylene glycol, polypropylene glycol, glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

The cosmetic formulation/product may optionally include one or more additional ingredients commonly used in cosmetic compositions (e.g., colorants, skin tone agents, skin anti-aging agents, anti-inflammatory agents, sunscreen agents, combinations of these and the like), provided that the additional ingredients do not undesirably alter the anti-glycation benefits provided by the composition.

In some instances, it may be desirable to select skin tone agents that function via different biological pathways so that the actives do not interfere with one another, which could reduce the efficacy of both agents. The additional ingredients, when incorporated into the composition, should be suitable for use in contact with human skin tissue without undue toxicity, incompatibility, instability, allergic response, and the like.

The term "carrier" as used herein, may also refer to a natural product or a product originating from nature that has been transformed or modified so that it is distinct from the natural product from which it originated, such as maltodextrin.

The amount of the composition of the invention present in nutraceutical, pharmaceutical, veterinary, oenological or cosmetic formulations or products will vary depending on the application.

Typically, the amount of composition of the invention that may be present in nutraceutical, pharmaceutical, veterinary, oenological or cosmetic formulations or products will be from about 0.001 to about 50% by weight, such as from about 0.01% to about 30% or from about 1% to about 20% of the nutraceutical, pharmaceutical, veterinary, oenological or cosmetic formulations or products, such as from about 0.01 to about 20%, or from about 0.1 to 10% or from about 1 to about 5% by weight of the formulation or product.

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

Described herein are specific genes and proteins useful in the methods, compositions and organisms of the disclosure;

however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

Techniques known to those skilled in the art may be suitable to identify additional homologous genes and homologous enzymes. Generally, analogous genes and/or analogous enzymes can be identified by functional analysis and will have functional similarities.

Techniques known to those skilled in the art may be suitable to identify analogous genes and analogous enzymes or any biosynthetic pathway genes, proteins, or enzymes, techniques may include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., Branched-Chain Amino Acids Methods Enzymology, 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above-mentioned databases in accordance with the teachings herein.

The terms "between . . . and . . . " and "ranging from . . . to . . . " should be understood as being inclusive of the limits, unless otherwise specified. Throughout this specification and the claims which follow, unless the context requires otherwise, the word "comprise", and variations such as "comprises", "comprising" and "possesses", will be understood to imply the inclusion of a stated integer or step or group of integers or steps but not the exclusion of any other integer or step or group of integer or step. The term "comprising" also means "including" as well as "consisting" e.g. a composition "comprising" X may consist exclusively of X or may include something additional e.g. X+Y. It must be noted also that, as used in this specification and the appended claims, the singular forms "a", "an" and "the" include plural referents unless the content clearly dictates otherwise. By way of example, a reference to "a gene" or "an enzyme" is a reference to "one or more genes" or "one or more enzymes".

It is to be understood that this disclosure is not limited to the particular methodology, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by the person skilled in the art. In accordance with the present disclosure there may be conventional molecular biology, microbiology, and recombinant DNA techniques employed which are within the skill of the art.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety.

The examples and figures which follow are presented by way of illustration and without implied limitation of the invention.

EXAMPLES

Example 1: Protocol for Making a Recombinant *Saccharomyces cerevisiae* Strain According to the Invention All the hereinafter implemented recombinant *Saccharomyces cerevisiae* strains were constructed from standard strains using standard yeast molecular genetics procedure (Methods in yeast Genetics-A cold spring harbor laboratory course Manual (2000) by D. Burke, D. Dawson, T. Stearns CSHL Press).

Cluster of the following-mentioned genes were integrated in recombinant yeast at once using the ability of yeast to efficiently recombine free DNA ends which have sequence homology.

In addition, for a better comprehension of following genotypes:

jlp1, lyp1, sam3, his3, leu2, trp1 and ura3 are insertion sites.

Lowercase letters mean that the considered gene is inactive, uppercase letters reflect an active gene.

"::": following a gene name means that the gene is interrupted by what follows (if more than one gene are inserted, they are noted in brackets [ ]). The interruption of the gene is concomitant with an entire deletion of the coding sequence but preserves the promoter. In consequence the gene followed by "::" is inactive and is noted in lowercase. If not specified the transcription of the gene inserted is controlled by the promoter of the disrupted gene.

"gene.K1" means that the gene originates from *Kluyveromyces lactis*.

More particularly, the coding sequences to be cloned were artificially synthetized. For heterologous sequences (non-yeast), the nucleic sequences were modified in order to obtain a synonymous coding sequence using the yeast codon usage. Using restriction enzyme and classical cloning technology, each synthetic sequence was cloned in between a transcription promoter and a transcription terminator. Each promoter sequence is preceded by a 50 to 200 nucleotide sequence homologous to the sequence of the terminator of the upstream gene. Similarly, the terminator of each gene (a gene comprising the promoter-coding sequence-terminator) is followed by sequences homologous to the gene immediately following. So that each of the unit to be integrated have a 50-200 nucleotide overlap with both the unit upstream and the unit downstream. For the first unit, the promoter is preceded by 50-200 nucleotides homologous to the yeast chromosome nucleotide for the locus in which it will be integrated. Similarly, for the last unit, the terminator is followed by 50-200 nucleotides homologous to the yeast chromosome nucleotide for the locus in which it will be integrated.

Each unit is then PCR amplified from the plasmids constructs, yielding X unit of linear DNA having overlapping sequences. At least one of this gene is an auxotrophic marker, in order to select for recombination event. All the linear fragments are transformed in the yeast at once, and a recombinant yeast cell is selected for the auxotrophy related to the marker used. The integrity of the sequence is then verified by PCR and sequencing.

Example 2: Comparative examples for the production of Hyaluronic acid

1. Production of Hyaluronic Acid of Less than 50 kDa
    A. Firstly, three recombinant strains are obtained: YA5234-1, YA5235-1 and YA5302-2.
    Accordingly, these three strains are as follows:
    YA5234-1: MAT-α, can1-100, his3::[pSAM1-UGP1-tRPL3-pMET6-QRI1-tIDP1-HIS3]×5, jlp1::[LEU2.K1, pCUP1-HASA2.Sz-tRPL41B, pCUP1-UGP1-tTPI1, pTDH3-QRI1-tMET25, pCCW12-HASB.At-tRPL15A], leu2, lyp1::[pCCW12.sba-HYAL-pCCW12.Sk-HASB-A.Vir-tTEF1.Sba, pCCW12-HASA-1.Vir-tDIT1, 3.Ts-tRPL15A, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2
    YA5235-1: MAT-α, can1-100, his3::[pSAM1-UGP1-tRPL3-pMET6-QRI1-tIDP1-HIS3]×5, jlp1::[LEU2.K1, pCUP1-HASA2.Sz-tRPL41B, pCUP1-UGP1-tTPI1, pTDH3-QRI1-tMET25, pCCW12-HASB.At-tRPL15A], leu2, lyp1::[pNUP57-HYAL-3.Csa-tRPL15A, pCCW12.Sk-HASB-A.Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2
    YA5302-2: MAT-α, can1-100, his3::[pSAM1-UGP1-tRPL3-pMET6-QRI1-tIDP1-HIS3]×5, jlp1::[LEU2.K1, pCUP1-HASA2.Sz-tRPL41B, pCUP1-UGP1-tRPL3, pCUP1-QRI1-tIDP1, pPDC1-UGP1-tTPI1, pTDH3-QRI1-tMET25, pCCW12-HASB.At-tRPL15A], leu2, lyp1::[pCCW12.Sba-HYAL-3.Li-tRPL15A, pCCW12.Sk-HASB-A. Vir-tTEF1.Sba, pCCW12-HASA-1.Vir-tDIT1, pCCW12.Sba-HASB.vir-tRPL3, pCCW12.Sm-HASA-A.Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

HYAL-3 represents a nucleic acid sequence encoding a polypeptide having hyaluronidase activity associated with a secretion signal but no anchoring signal.

HASA, HASA-1, HASA-A, HASA2 and XHASA2 all represent a nucleic acid encoding a polypeptide having hyaluronan synthase activity. They differ from one another in that they are different reencoded versions of a nucleic acid sequence encoding the hyaluronan synthase enzymes. HASA-1 has the sequence SEQ ID NO: 1, HASA-A has the sequence SEQ ID NO: 2, HASA2 has the sequence SEQ ID NO: 7 and XHASA2 has the sequence SEQ ID NO: 6.

HASB and HASB-A represent a nucleic acid sequence encoding a polypeptide having UDP-glucose 6-dehydrogenase activity. They differ from one another in that they are different reencoded versions of a nucleic acid sequence encoding the enzyme. HASB.At has the sequence SEQ ID NO: 12, HASB. Vir has the sequence SEQ ID NO: 13 and HASB-A. Vir has the sequence SEQ ID NO: 14.

All these strains were incubated in 25 ml of SY medium buffered with MES 0.1 M ph 5.5 in a baffled erlenmeyer for 48 hours at 28° C. under vigourous agitation.

SY medium comprises the following elements:
KH2PO4: 100 mM; MgSO4 7H2O: 2.8 mM; K2SO4: 11.5 mM; Na2SO4: 1.1 mM; NaCl: 2.6 mM; CaCl2 2H2O: 0.7 mM; CuSO4 5H2O: 15 µM; K1: 6 µM; FeCl3: 30 µM; ZnSO4 7H2O: 61 µM; MnSO4 H2O: 25 µM; H2SO4: 110 µM; Panthotenic Acids hemicalcium salt: 42 µM; Thiamin hydrochloride: 59 µM; Pyridoxin hydrochloride: 49 µM; Myo-Inositol (C6H12O6): 555 µM; Nicotinic acid (C6H5NO2): 29 µM; D-Biotine: 0.82 µM; Ammonium citrate tribasic: 33 mM; and glucose or sucrose 2-30%.

Growth medium was recovered at 48h hours and assayed for hyaluronic acid content and quality. An aliquot of the medium was loaded and ran on a 0.5% agarose gel subsequently colored with "stains all" (sigma Aldrich CAS Number 7423-31-6).

The amount of hyaluronic acid present in the medium was evaluated by a colorimetric determination after treatment with concentrated sulfuric acid and carbazole (Bitter and Muir (1962) analytical biochemistry 4, 330-334).

Figure 2A:
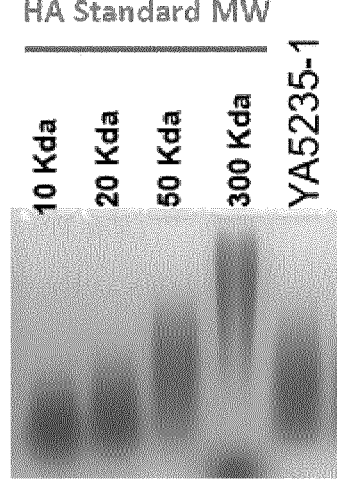
FIGS. 2A and 2B show agarose gels used to determine the molecular weight of the hyaluronic acid produced by strains according to the invention, (for example strain YA5235-1 (FIG. 2A) and strain YA5359-10 (FIG. 2B)). The agarose gels are obtained after running an aliquot of the supernatant of the considered strain and staining it with "stains all" (CAS Number 7423-31-6). HA molecular weight standards are present in each gel for reference.

For illustrative purposes, the agarose gel obtained after running an aliquot of the supernatant of strain YA5235-1 and staining it with "stains all" (CAS Number 7423-31-6) is provided as FIG. 2A. It is classically run into the gel side-by-side with HA molecular weight (MW) standards (from left to right MW of 10 kDa, 20 kDa, 50 kDa and 300 kDa).

The amounts obtained with these different strains are respectively:
YA5234-1:2.4 g·L-1.
YA5235-1:4.5 g·L-1.
YA5302-2:3.7 g·L-1.
In comparison, a native yeast strain, as for example the CC788-2D strain (Chérest et al. (2000) J Biol. Chem. 275:14056-14063), does not produce hyaluronic acid.

It results from this experiment that a recombinant strain comprising the modifications according to the invention produces a greater amount of hyarluronic acid when cultured in the same conditions as compared with other recombinant strains not comprising all the genetic modifications according to the invention.

Moreover, these three strains led to the production, after 48 hours, of hyarluronic acid having a molecular weight comprised between 20 kDa and 50 kDa.

B. Three other recombinant strains have also been obtained: YA5110-13 and YA5260-4.

These three strains are as follows:

YA5110-13: MAT-α, can1-100, his3: [pSAM1-UGP1-tRPL3, pMET6-QRI1-tIDP1-HIS3]×5, jlp1:: [LEU2.K1, pCUP1-HASA2.Sz-tRPL41B, pCUP1-UGP1-tTPI1, pTDH3-QRI1-tMET25, pCCW12-HASB.At-tRPL15A], leu2, lyp1::[pNUP57-HYAL-3.Hn-tRPL15A, pCCW12.Sk-HASB-A.Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5260-4: MAT-α, can1-100, his3::[pSAM1-UGP1-tRPL3-pMET6-QRI1-tIDP1-HIS3]×5, jlp1:: [LEU2.K1, pCUP1-HASA2.Sz-tRPL41B, pCUP1-UGP1-tRPL3, pCUP1-QRI1-tIDP1, pPDC1-UGP1-tTPI1, pTDH3-QRI1-tMET25, pCCW12-HASB.At-tRPL15A], leu2, lyp1::[pTEF3-HYAL-31.Hn-tRPL15A, pCCW12.Sk-HASB-A. Vir-tTEF1.Sba, pCCW12-HASA-1.Vir-tDIT1, pCCW12.Sba-HASB. vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5569: MAT-α, his3::[pSAM1-UGP1-tRPL3, pMET6-QRI1-tIDP1, HIS3]×5, jlp1::[LEU2.K1, pCUP1-HASA-1.Sz-tRPL41B, pCUP1-UGP1-tRPL3, pCUP1-QRI1-tIDP1, pPDC1-UGP1-tTPI1, pTDH3-QRI1-tMET25, pCCW12-HASB.At-tRPL15A], leu2, lyp1:: [pCWP2-HYAL-31.Csa-tRPL15A, pCCW12.Sba-HASB.vir-tRPL3, pCCW12.Sk-HASB-A. Vir-tTEF1.Sba, pCCW12-HASA-1.Vir-tRPL41B, pCCW12.Sm-HASA-A. Vir-tRPL15A.Sba], sam3:: [LEU2.K1, pPDC1-PGM1-tIDP1, pTEF1.Ago-GFA1-tRPL15A, pENO2-UGP1-tRPL3, pCWP2-GNA1-tTPI1, pTEF1-PCM1-tIDP1, pCCW12-XHASA2.X1-tRPL3, pTDH3-QRI1-tIDP1], trp1::[tRPL3-HASB. Vir-pMET6, pMET25-HASA-1. Vir-tIDP1, TRP1]×2

HYAL-31 represents a nucleic acid sequence encoding a polypeptide having hyaluronidase activity associated with both a secretion signal and an anchoring signal.

HASA-1, HASA-A, HASA2 and XHASA2 all represent a nucleic acid sequence encoding a polypeptide having hyaluronan synthase activity. They differ from one another in that they are different reencoded versions of a nucleic acid sequence encoding the hyaluronan synthase enzyme. HASA-1 has the sequence SEQ ID NO: 1, HASA-A has the sequence SEQ ID NO: 2, HASA2 has the sequence SEQ ID NO: 7 and XHASA2 has the sequence SEQ ID NO: 6.

HASB and HASB-A represent a nucleic acid sequence encoding a polypeptide having UDP-glucose 6-dehydrogenase activity. They differ from one another in that they are different reencoded versions of a nucleic acid sequence encoding the enzyme. HASB.At has the sequence SEQ ID NO: 12, HASB. Vir has the sequence SEQ ID NO: 13 and HASB-A. Vir has the sequence SEQ ID NO: 14.

The strains were inoculated in 2 liters of the above defined SY medium at ph 6 in 2% sucrose and 500 μM CuSO4 in a bioreactor. They were then grown in fed-batch adding 500 μM CuSO4 at 7 h, 24 h, 31h and between 130 and 175 g·L-1 of sucrose from 10 to 48 h.

For YA5110-13, pH was maintained between 5.8 and 6.2 using 15% H2SO4 and 10% NH4OH from t=31 h.

For YA5260-4, pH maintained between 5.8 and 6.2 using 15% H2SO4 and 10% NH4OH all along the fermentation.

For YA5569, pH maintained between 5.8 and 6.2 using 15% H2SO4 and 10% NH4OH all along the fermentation.

Growth medium was recovered at 48h hours and assayed for hyaluronic acid content and quality as described above.

The hyaluronic acid amounts obtained with these two strains are respectively:

YA5110-13:23 g·L-1.

YA5260-4:16 g·L-1.

YA5569: 32 g·L-1

In comparison, a native strain does not produce hyaluronic acid.

It results from this experiment that a recombinant strain comprising the modifications according to the invention produces a greater amount of hyaluronic acid when cultured in the same conditions as compared with other recombinant strains not comprising all the genetic modifications according to the invention.

Moreover, the hyaluronic acid produced by YA5110-13 and YA5260 strains had a molecular weight of about 20 kDa while the hyaluronic acid produced by YA5569 had a molecular weight of about 20 kDa to 50 kDa.

The exact same experiment was performed using these three recombinant strains while replacing sucrose by glucose. The hyaluronic acid obtained had the same molecular weight of about 20 kDa or of about 20 kDa to about 50 kDa after 48h.

C. Another recombinant strain has been obtained 5672-29A, as follows:

5672-29A: MAT-α, his3::[pSAM1-UGP1-tRPL3, pMET6-QRI1-tIDP1, HIS3]×5, jlp1::[LEU2.Sba, pTEF1.Sba-HASB. Vir-tRPL3.Sm, pTDH3.Sk-HASB.Vir-tTEF1.Sba, pTDH3-1.Sba-HASA-1.Vir-tRPL3.Sba, pTDH3.Sar-HASA-1.Vir-tRPL15A.Sba, pTEF1-HYAL-31.Hn-tRPL15A], leu2, sam3::[LEU2.K1, pPDC1-PGM1-tIDP1, pTEF1.Ago-GFA1-tRPL15A, pENO2-UGP1-tRPL3, pCWP2-GNA1-tTPI1, pTEF1-PCM1-tRPL41B, TRP1.Sba-loxP], trp1

HYAL-31 represents a hyaluronidase associated with an anchoring signal.

1 HASA-1 represents a nucleic acid sequence encoding a polypeptide having hyaluronan synthase activity. HASA-1 has the sequence SEQ ID NO: 1.

The strain was inoculated in 25 ml of the above defined SY medium at ph 5.5 buffered with MES 0.1 M in a baffled erlenmeyer at 28° C. under vigourous agitation.

Growth medium was recovered at 48h hours and assayed for hyaluronic acid content and quality as described above.

The hyaluronic acid amount obtained with the strain was 3.7 g·L-1.

2. Production of Hyaluronic Acid Having a Molecular Weight Comprised Between 50 kDa and 1000 kDa A. Firstly, three recombinant strains are obtained: YA5233-1, YA5359-10 and YA5381-1.

Accordingly, these three strains are as follows:

YA5233-1: MAT-α, can1-100, his3::[pSAM1-UGP1-tRPL3-pMET6-QRI1-tIDP1-HIS3]×5, jlp1::[LEU2.K1, pCUP1-HASA2.Sz-tRPL41B, pCUP1-UGP1-tTPI1, pTDH3-QRI1-tMET25, pCCW12-HASB.At-tRPL15A], leu2, lyp1::[pTEF1-HYAL-3.Ts-tRPL15A, pCCW12.Sk-HASB-A.Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5359-10: MAT-α, can1-100, his3::[pSAM1-UGP1-tRPL3-pMET6-QRI1-tIDP1-HIS3]×5, jlp1::[LEU2.K1, pCUP1-HASA2.Sz-tRPL41B, pCUP1-UGP1-tTPI1, pTDH3-QRI1-tMET25, pCCW12-HASB.At-tRPL15A], leu2, lyp1::[pCCW12.sba-HYAL-31.Ts-tRPL15A, pCCW12.Sk-HASB-A. Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5381-1: MAT-α, can1-100, his3::[pSAM1-UGP1-tRPL3-pMET6-QRI1-tIDP1-HIS3]×5, jlp1::[LEU2.K1, pCUP1-HASA2.Sz-tRPL41B, pCUP1-UGP1-tTPI1, pTDH3-QRI1-tMET25, pCCW12-HASB.At-tRPL15A], leu2, lyp1::[pCCW12.Sar-HYAL2-31.Ts-tRPL15A, pCCW12.Sk-HASB-A. Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

HASA-1, HASA-A, HASA2 and XHASA2 are previously defined.

HASB and HASB-A are previously defined.

All these strains were incubated in 25 ml of the above-defined SY medium buffered with MES 0.1 M ph 5.5 baffled erlenmeyer for 48 hours at 28° C. under vigourous agitation.

Growth medium was recovered at 48h hours and assayed for hyaluronic acid content and quality as defined above.

Figure 2B:
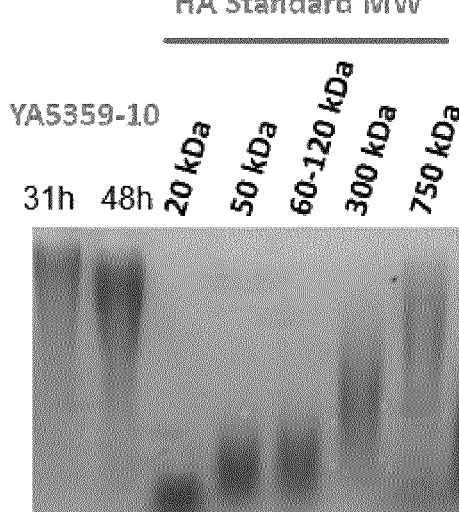

For illustrative purposes, the agarose gel obtained after running an aliquot of the supernatant of strain YA5359-10, after 31h and after 48h, and staining it with "stains all" (CAS Number 7423-31-6) is provided as FIG. 2B. It is classically run into the gel side-by-side with HA molecular weight (MW) standards (from left to right MW of 20 kDa, 50 kDa, 60-120 kDa, 300 kDa and 750 kDa).

The amounts obtained with these different strains are respectively:

YA5233-1:3.1 g·L-1.
YA5359-10:3.4 g·L-1.
YA5381-1:3.0 g·L-1.

In comparison, a native strain does not produce hyaluronic acid.

It results from this experiment that a recombinant strain comprising the modifications according to the invention produces a greater amount of hyarluronic acid when cultured in the same conditions as compared with other recombinant strains not comprising all the genetic modifications according to the invention.

Moreover, these three strains led to the production, after 48 hours, of hyaluronic acid having a molecular weight comprised:

for YA5233-1: between 50 kDa and 500 kDa;
for YA5359-10: between 100 kDa and 750 kDa; and
for YA5381-1: between 50 kDa and 250 kDa.

B. Six other recombinant strains have also been obtained: YA5262-16, YA5326-3, YA5300-15, YA5358-4, YA5264-1 and YA5331-6.

These six strains are as follows:

YA5262-16: MAT-α, can1-100, his3::[pSAM1-UGP1-tRPL3-pMET6-QRI1-tIDP1-HIS3]×5, jlp1::[LEU2.K1, pCUP1-HASA2.Sz-tRPL41B, pCUP1-UGP1-tRPL3, pCUP1-QRI1-tIDP1, pPDC1-UGP1-tTPI1, pTDH3-QRI1-tMET25, pCCW12-HASB.At-tRPL15A], leu2, lyp1::[pCCW10.ago-HYAL-31.Hn-tRPL15A, pCCW12.Sk-HASB-A. Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5326-3: MAT-α, can1-100, his3::[pSAM1-UGP1-tRPL3-pMET6-QRI1-tIDP1-HIS3]×5, jlp1::[LEU2.K1, pCUP1-HASA2.Sz-tRPL41B, pCUP1-UGP1-tTPI1, pTDH3-QRI1-tMET25, pCCW12-HASB.At-tRPL15A], leu2, lyp1::[pCCW10.ago-HYAL-31.Csa-tRPL15A, pCCW12.Sk-HASB-A. Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5300-15: MAT-α, can1-100, his3::[pSAM1-UGP1-tRPL3-pMET6-QRI1-tIDP1-HIS3]×5, jlp1::[LEU2.K1, pCUP1-HASA2.Sz-tRPL41B, pCUP1-UGP1-tRPL3, pCUP1-QRI1-tIDP1, pPDC1-UGP1-tTPI1, pTDH3-QRI1-tMET25, pCCW12-HASB.At-tRPL15A], leu2, lyp1::[pTDH3-HYAL-3.Ts-tRPL15A, pCCW12.Sk-HASB-A. Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5358-4: MAT-α, can1-100, his3::[pSAM1-UGP1-tRPL3-pMET6-QRI1-tIDP1-HIS3]×5, jlp1::[LEU2.K1, pCUP1-HASA2.Sz-tRPL41B, pCUP1-UGP1-tRPL3, pCUP1-QRI1-tMET25, pCCW12-HASB.At-tRPL15A], leu2, lyp1::[pCCW12.Sar-HYAL-31.Li-tRPL15A, pCCW12.Sk-HASB-A. VirtTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5264-1: MAT-α, can1-100, his3::[pSAM1-UGP1-tRPL3-pMET6-QRI1-tIDP1-HIS3]×5, jlp1:: [LEU2.K1, pCUP1-HASA2.Sz-tRPL41B, pCUP1-UGP1-tTPI1, pTDH3-QRI1-tMET25, pCCW12-HASB.At-tRPL15A], leu2, lyp1::[pTDH3-HYAL-31.Ts-tRPL15A, pCCW12.Sk-HASB-A.Vir-tTEF1.Sba, pCCW12-HASA-1.Vir-tDIT1, sam3:: [LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5331-6: MAT-α, can1-100, his3::[pSAM1-UGP1-tRPL3-pMET6-QRI1-tIDP1-HIS3]×5, jlp1:: [LEU2.K1, pCUP1-HASA2.Sz-tRPL41B, pCUP1-UGP1-tRPL3, pCUP1-QRI1-tIDP1, pPDC1-UGP1-tTPI1, pTDH3-QRI1-tMET25, pCCW12-HASB.At-(RPL15A], leu2, lyp1::[pTEF3-HYAL-31.Li-tRPL15A, pCCW12.Sk-HASB-A. Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1.Vir-tIDP1-TRP1]×2

HASA-1, HASA-A, HASA2 and XHASA2 are previously defined.

HASB and HASB-A are previously defined.

YA5262-16 was inoculated in 2 liters of the above defined SY medium at ph 4 in 2% glucose in a bioreactor and ph was maintained at 4 all along the fermentation using 15% H2SO4 and 10% NH4OH.

YA5326-3 was:

inoculated in 2 liters of the above defined SY medium at ph 6 in 2% glucose in a bioreactor and ph was maintained at 6 all along the fermentation using 15% H2SO4 and 10% NH4OH; or inoculated in 2 liters of the above defined SY medium at ph 6 in 2% sucrose in a bioreactor and ph was maintained at 6 until 34h and at ph 4 from 34h to 48h with 15% H2SO4 and 10% NH4OH.

YA5300-15 was inoculated in 2 liters of the above defined SY medium at ph 6 in 2% sucrose in a bioreactor and ph was maintained at 6 all along the fermentation using 15% H2SO4 and 10% NH4OH.

YA5358-4 was inoculated in 2 liters of the above defined SY medium at ph 6 in 2% glucose in a bioreactor and ph was maintained at 6 all along the fermentation using 15% H2SO4 and 10% NH4OH.

YA5264-1 was inoculated in 2 liters of the above defined SY medium at ph 6 in 2% sucrose in a bioreactor and ph was maintained at 6 all along the fermentation using 15% H2SO4 and 10% NH4OH.

YA5331-6 was inoculated in 2 liters of the above defined SY medium at ph 6 in 2% glucose in a bioreactor and ph was maintained at 6 all along the fermentation using 15% H2SO4 and 10% NH4OH.

Growth medium was recovered at 48h hours and assayed for hyaluronic acid content and quality as described above.

The hyaluronic acid amounts obtained with these two strains are respectively:

YA5262-16:19 g·L-1;

YA5326-3: respectively 13 g·L-1 and 15 g·L-1;

YA5300-15:9 g·L-1;

YA5358-4:14 g·L-1;

YA5264-1:6 g·L-1; and

YA5331-6:9 g·L-1.

In comparison, a native strain does not produce hyaluronic acid.

It results from this experiment that a recombinant strain comprising the modifications according to the invention produces a greater amount of hyaluronic acid when cultured in the same conditions as compared with other recombinant strains not comprising all the genetic modifications according to the invention.

Moreover, the hyaluronic acid produced by these strains after 48 hours had a molecular weight:

YA5262-16: of 50 kDa;

YA5326-3: of respectively 50 kDa or comprised between 50 kDa and 250 kDa;

YA5300-15: comprised between 100 kDa and 1000 kDa;

YA5358-4: comprised between 100 kDa and 1000 kDa;

YA5264-1: comprised between 100 kDa and 1000 kDa; and

YA5331-6: comprised between 100 kDa and 1000 kDa.

Furthermore, previously described recombinant strain YA5235-1 was inoculated in a bioreactor at ph 6 in 2% sucrose and ph was maintained at 6 until 34h and at 4 from 34h to 48h with 15% H2SO4 and 10% NH4OH.

After 48 h the medium contains 18 g·L-1 of 100-1000 kDa Hyaluronic acid.

The same experiment was performed using YA5235-1 while using glucose instead of sucrose. The obtained hyaluronic acid also has a molecular weight comprised between 100 and 1000 kDa.

These results show that, in particular, pH regulation along the fermentation process as well as the production of a hyaluronidase coupled to a secretion signal or a secretion signal and an anchoring signal influences, or even allows controlling, the size of the hyaluronic acid polymer produced.

3. Production of Hyaluronic Acid Having a Molecular Weight Superior to 1000 kDa

Four recombinant strains are obtained: YA5232-1, YA5303-3, YA5374-4 and YA5382-1.

Accordingly, these four strains are as follows:

YA5232-1: MAT-α, can1-100, his3::[pSAM1-UGP1-tRPL3-pMET6-QRI1-tIDP1-HIS3]×5, jlp1:: [LEU2.K1, pCUP1-HASA2.Sz-tRPL41B, pCUP1-UGP1-tTPI1, pTDH3-QRI1-tMET25, pCCW12-HASB.At-tRPL15A], leu2, lyp1::[pNUP57-HYAL-3.Ts-tRPL15A, pCCW12.Sk-HASB-A.Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5303-2: MAT-α, can1-100, his3::[pSAM1-UGP1-tRPL3-pMET6-QRI1-tIDP1-HIS3]×5, jlp1:: [LEU2.K1, pCUP1-HASA2.Sz-tRPL41B, pCUP1-UGP1-tTPI1, pTDH3-QRI1-tMET25, pCCW12-

HASB.At-tRPL15A], leu2, lyp1::[pNUP57-HYAL-3.Li-tRPL15A, pCCW12.Sk-HASB-A.Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5374-3: MAT-α, can1-100, his3::[pSAM1-UGP1-tRPL3-pMET6-QRI1-tIDP1-HIS3]×5, jlp1:: [LEU2.K1, pCUP1-HASA2.Sz-tRPL41B, pCUP1-UGP1-tTPI1, pTDH3-QRI1-tMET25, pCCW12-HASB.At-tRPL15A], leu2, lyp1::[pCCW12.Sar-HYAL-3.Ba-tRPL15A, pCCW12.Sk-HASB-A.Vir-tTEF1.Sba, pCCW12-HASA-1.Vir-tDIT1, sam3:: [LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

YA5382-1: MAT-α, can1-100, his3::[pSAM1-UGP1-tRPL3-pMET6-QRI1-tIDP1-HIS3]×5, jlp1:: [LEU2.K1, pCUP1-HASA2.Sz-tRPL41B, pCUP1-UGP1-tTPI1, pTDH3-QRI1-tMET25, pCCW12-HASB.At-tRPL15A], leu2, lyp1::[pTEF1-HYAL2-31.Ba-tRPL15A, pCCW12.Sk-HASB-A.Vir-tTEF1.Sba, pCCW12-HASA-1.Vir-tDIT1, pCCW12.Sba-HASB.vir-tRPL3, pCCW12.Sm-HASA-A. Vir-tRPL15A.Sba], sam3::[LEU2.K1, pPDC1-PGM1-tIDP1, pTEF1-GFA1-tRPL15A, pENO2-UGP1-tRPL3, pCWP2-GNA1-tTPI1, pTEF3-PCM1-tIDP1, pCCW12-XHASA2.X1-tRPL3, pTDH3-QRI1-tIDP1], trp1::[pMET6-HASB. Vir-tRPL3, pMET25-HASA-1. Vir-tIDP1-TRP1]×2

HASA-1, HASA-A, HASA2 and XHASA2 are previously defined.

HASB and HASB-A are previously defined.

All these strains were incubated in 25 ml of the above-defined SY medium buffered with MES 0.1 M ph 5.5 in a baffled erlenmeyer for 48 hours at 28° C. under vigourous agitation.

Growth medium was recovered at 48h hours and assayed for hyaluronic acid content and quality as defined above.

The amounts obtained with these different strains are respectively:

YA5232-1:4 g·L-1.

YA5303-3:2.7 g·L-1.

YA5374-3:2.5 g·L-1.

YA5382-1:3.0 g·L-1.

In comparison, a native strain does not produce hyaluronic acid.

It results from this experiment that a recombinant strain comprising the modifications according to the invention produces a greater amount of hyarluronic acid when cultured in the same conditions as compared with other recombinant strains not comprising all the genetic modifications according to the invention.

Moreover, these four strains led to the production, after 48 hours, of hyaluronic acid having a molecular weight:

for YA5232-1: greater than about 1000 kDa;

for YA5303-3: of about 1000 kDa;

for YA5374-3: greater than about 1000 kDa; and for YA5382-1: greater than about 1000 kDa.

Example 3: Comparative Examples for the Production of Hyaluronic Acid

A. The five following recombinant strains are obtained:

YA5509: MAT-α, can1-100, his3::[tRPL3-UGP1-pSAM1, pMET6-QRI1-tIDP1, HIS3]×5, jlp1:: [LEU2.K1-RS, pCUP1-HASA.Sz-tRPL41B, pCUP1-UGP1-tTPI1, pTDH3-QRI1-tMET25, pCCW12-UGD1.At-tRPL15A], leu2, lyp1: [pCCW10.Ago-HYAL-31.Hn-tRPL15A, pCCW12.Sba-HASB.vir-tRPL3, pCCW12.Sk-HASB-A. Vir-tTEF1.Sba, pCCW12-HASA-1.Vir-tRPL41B, pCCW12.Sm-HASA-A. Vir-tRPL15A.Sba], sam3::[LEU2.K1-RS, pPDC1-PGM1-tIDP1, pTEF1.Ago-GFA1-tRPL15A, pENO2-UGP1-tRPL3, pCWP2-GNA1-tTPI1, pTEF1-PCM1-tIDP1, pCCW12-XHASA2.X1-tRPL3, pTDH3-QRI1-tIDP1], trp1::[tRPL3-HASB. Vir-pMET6, pMET25-HASA. Vir-tIDP1, TRP1]×2, ura3:: [tRPL3-MHPF.Ec-pPDC1, pTDH3-GDH-21.Eca-tIDP1, URA3]×2

YA5789: MAT-α, can1-100, his3::[tRPL3-UGP1-pSAM1, pMET6-QRI1-tIDP1, HIS3]×5, jlp1:: [LEU2.K1-RS, pCUP1-HASA.Sz-tRPL41B, pCUP1-UGP1-tRPL3, pCUP1-QRI1-tIDP1, pPDC1-UGP1-tTPI1, pTDH3-QRI1-tMET25, pCCW12-UGD1.At-tRPL15A], leu2, lyp1::[tMET3.Sba-MET3.Sba-RS-pMET3.Sba, pCCW10.Ago-HYAL-31.Hn-tRPL15A, pTEF1.Ago-GLN1-tTDH3, pCCW12.Sba-HASB.vir-tRPL3, pCCW12.Sk-HASB-A. Vir-tTEF1.Sba, pCCW12-HASA-1.Vir-tRPL41B, pCCW12.Sm-HASA-A.Vir-tRPL15A.Sba], met3::, sam3:: [LEU2.K1-RS, pPDC1-PGM1-tIDP1, pTEF1.Ago-GFA1-tRPL15A, pENO2-UGP1-tRPL3, pCWP2-GNA1-tTPI1, pTEF1-PCM1-tIDP1, pCCW12-XHASA2.X1-tRPL3, pTDH3-QRI1-tIDP1], trp1:: [tRPL3-HASB. Vir-pMET6, pMET25-HASA. Vir-tIDP1, TRP1]×2, ura3::[tRPL3-MHPF.Ec-pPDC1, pTDH3-GDH-21.Eca-tIDP1, URA3]×2

YA5790: MAT-α, can1-100, glt1::[MET3.Sba-RS, pCCW10.Ago-HYAL-31.Hn-tRPL15A, pCCW12.Sba-HASB.vir-tRPL3, pCCW12.Sk-HASB-A. Vir-tTEF1.Sba, pCCW12-HASA-1.Vir-tRPL41B, pCCW12.Sm-HASA-A. Vir-tRPL15A.Sba, pTEF1.Ago-GLN1-[TDH3], his3::[tRPL3-UGP1-pSAM1, pMET6-QRI1-tIDP1, HIS3]×5, jlp1:: [LEU2.K1-RS, pCUP1-HASA.Sz-tRPL41B, pCUP1-UGP1-tRPL3, pCUP1-QRI1-tIDP1, pPDC1-UGP1-[TPI1, pTDH3-QRI1-tMET25, pCCW12-UGD1.At-tRPL15A], leu2, met3::, sam3::[LEU2.K1-RS, pPDC1-PGM1-tIDP1, pTEF1.Ago-GFA1-tRPL15A, pENO2-UGP1-tRPL3, pCWP2-GNA1-tTPI1, pTEF1-PCM1-tIDP1, pCCW12-XHASA2.X1-tRPL3, pTDH3-QRI1-tIDP1], trp1::[tRPL3-HASB. Vir-pMET6, pMET25-HASA. Vir-tIDP1, TRP1]×2, ura3::[tRPL3-MHPF.Ec-pPDC1, pTDH3-GDH-21.Eca-tIDP1, URA3]×2

YA5806: MAT-α, can1-100, glt1::[MET3.Sba-RS, pCCW10.Ago-HYAL-31.Hn-tRPL15A, pCCW12.Sba-HASB.vir-tRPL3, pCCW12.Sk-HASB-A. Vir-tTEF1.Sba, pCCW12-HASA-1.Vir-tRPL41B, pCCW12.Sm-HASA-A. Vir-tRPL15A.Sba], his3: [tRPL3-UGP1-pSAM1, pMET6-QRI1-tIDP1, HIS3]× 5, jlp1::[LEU2.K1-RS, pCUP1-HASA.Sz-tRPL41B, pCUP1-UGP1-tRPL3, pCUP1-QRI1-tIDP1, pPDC1-UGP1-tTPI1, pTDH3-QRI1-tMET25, pCCW12-UGD1.At-tRPL15A], leu2, met3::, sam3::[LEU2.K1-

RS, pPDC1-PGM1-tIDP1, pTEF1.Ago-GFA1-tRPL15A, pENO2-UGP1-tRPL3, pCWP2-GNA1-tTPI1, pTEF1-PCM1-tIDP1, pCCW12-XHASA2.X1-tRPL3, pTDH3-QRI1-tIDP1], trp1::[tRPL3-HASB.Vir-pMET6, pMET25-HASA. Vir-tIDP1, TRP1]×2, ura3::[tRPL3-MHPF.Ec-pPDC1, pTDH3-GDH-21.Eca-tIDP1, URA3]×2

YA5658: MAT-α, can1-100, his3::[tRPL3-UGP1-pSAM1, pMET6-QRI1-tIDP1, HIS3]×5, jlp1::[LEU2.K1-RS, pCUP1-HASA.Sz-tRPL41B, pCUP1-UGP1-tRPL3, pCUP1-QRI1-tIDP1, pPDC1-UGP1-tTPI1, pTDH3-QRI1-tMET25, pCCW12-UGD1.At-tRPL15A], leu2, lyp1::[pCCW10.Ago-HYAL-31.Hn-tRPL15A, pTEF1.Ago-GLN1-tTDH3, pCCW12.Sba-HASB.vir-tRPL3, pCCW12.Sk-HASB-A.Vir-tTEF1.Sba, pCCW12-HASA-1. Vir-tRPL41B, pCCW12.Sm-HASA-A. Vir-tRPL15A.Sba], sam3::[LEU2.K1-RS, pPDC1-PGM1-tIDP1, pTEF1.Ago-GFA1-tRPL15A, pENO2-UGP1-tRPL3, pCWP2-GNA1-tTPI1, pTEF1-PCM1-tIDP1, pCCW12-XHASA2.X1-tRPL3, pTDH3-QRI1-tIDP1], trp1::[tRPL3-HASB. Vir-pMET6, pMET25-HASA. Vir-tIDP1, TRP1]×2, ura3::[tRPL3-MHPF.Ec-pPDC1, pTDH3-GDH-21.Eca-tIDP1, URA3]×2

HASA-1, HASA-A and XHASA2 are previously defined. HASB and HASB-A are previously defined.

All these strains were incubated in 25 mL of the above-defined SY medium buffered with MES 0.1 M ph 5.5 in a baffled erlenmeyer for 48 hours at 28° C. under vigorous agitation.

Growth medium was recovered at 48h hours and assayed for hyaluronic acid content and quality as defined above.

The amounts obtained with these different strains are respectively:

YA5509: 3.5 g·L-1.

YA5789 (GLN1 overexpression): 5 g·L-1.

YA5658 (GNL1 overexpression): 4.5 g·L-1.

YA5806 (AGLT1): 4.5 g·L-1.

YA5790 (GNL1 overexpression; AGLT1): 6.7 g·L-1

In comparison, a native strain does not produce hyaluronic acid.

It results from this experiment, under similar conditions, a recombinant strain according to the invention produces significantly more hyaluronic acid when either GLN1 is overexpressed or GLT1 is disrupted as compared with other recombinant strains according to the invention devoid of any of these two modifications (a respect increased yield of production by 27-32% and 27%).

Moreover, a recombinant strain according to the invention produces even more hyaluronic acid when both GLN1 is overexpressed and GLT1 is disrupted as compared with other recombinant strains according to the invention comprising only one of these two modifications or devoid of both (an increased yield of production by 48% compared to the one comprising none of these two modifications).

B. The four following recombinant strains are obtained:

YA6178: MAT-α, glt1::[MET3.Sba, pTDH3-HYAL-31.Csa-tRPL15A, pTEF1.Ago-GLN1-tTDH3, pCCW12.Sba-HASB.vir-tRPL3, pCCW12.Sm-HASA-A. Vir-tRPL15A.Sba], his3::[pSAM1-UGP1-tRPL3, pMET6-QRI1-tIDP1, HIS3]×3, jlp1::[LEU2.Sba-loxP, pTEF1.Sba-HASB.Vir-tRPL3.Sm, pTDH3.Sk-HASB-A. Vir-TEF1.Sba, pTDH3-1.Sba-HASA-1.Vir-tRPL3.Sba, pTDH3.Sar-HASA-A. Vir-tRPL15A.Sba], leu2, met3A1, sam3::[LEU2.K1, pPDC1-PGM1-tIDP1, pTEF1.Ago-GFA1-tRPL15A, pENO2-UGP1-tRPL3, pCWP2-GNA1-tTPI1, pTEF1-

PCM1-tRPL41B, TRP1.Sba-loxP], trp1, ura3::[pPDC1-MHPF.Ec-tRPL3, pTDH3-GDH-21.Eca-tIDP1, URA3]×2

YA6179: MAT-α, glt1::[MET3.Sba, pTDH3-HYAL-31.Csa-tRPL15A, pTEF1.Ago-GLN1-tTDH3, pCCW12.Sba-HASB.vir-tRPL3, pCCW12.Sm-HASA-2.Vir-tRPL15A.Sba], his3::[pSAM1-UGP1-tRPL3, pMET6-QRI1-tIDP1, HIS3]×3, jlp1::[LEU2.Sba-loxP, pTEF1.Sba-HASB.Vir-tRPL3.Sm, pTDH3.Sk-HASB-A. Vir-tTEF1.Sba, pTDH3-1.Sba-HASA-1. Vir-tRPL3.Sba, pTDH3.Sar-HASA-A. Vir-tRPL15A.Sba], leu2, met3A1, sam3::[LEU2.K1, pPDC1-PGM1-tIDP1, pTEF1.Ago-GFA1-tRPL15A, pENO2-UGP1-tRPL3, pCWP2-GNA1-tTPI1, pTEF1-PCM1-tRPL41B, TRP1.Sba-loxP], trp1, ura3::[pPDC1-MHPF.Ec-tRPL3, pTDH3-GDH-21.Eca-tIDP1, URA3]×2

YA6180: MAT-α, glt1::[MET3.Sba, pTDH3-HYAL-31.Csa-tRPL15A, pTEF1.Ago-GLN1-tTDH3, pCCW12.Sba-HASB.vir-tRPL3, pCCW12.Sm-HASA-3.Vir-tRPL15A.Sba], his3::[pSAM1-UGP1-tRPL3, pMET6-QRI1-tIDP1, HIS3]×3, jlp1::[LEU2.Sba-loxP, pTEF1.Sba-HASB. Vir-tRPL3.Sm, pTDH3.Sk-HASB-A. Vir-tTEF1.Sba, pTDH3-1.Sba-HASA-1.Vir-tRPL3.Sba, pTDH3.Sar-HASA-A. Vir-tRPL15A.Sba], leu2, met3A1, sam3::[LEU2.K1, pPDC1-PGM1-tIDP1, pTEF1.Ago-GFA1-tRPL15A, pENO2-UGP1-tRPL3, pCWP2-GNA1-tTPI1, pTEF1-PCM1-tRPL41B, TRP1.Sba-loxP], trp1, ura3::[pPDC1-MHPF.Ec-tRPL3, pTDH3-GDH-21.Eca-tIDP1, URA3]×2

YA6181: MAT-α, glt1::[MET3.Sba, pTDH3-HYAL-31.Csa-tRPL15A, pTEF1.Ago-GLN1-tTDH3, pCCW12.Sba-HASB.vir-tRPL3, pCCW12.Sm-HASA-5.Vir-RPL15A.Sba], his3::[pSAM1-UGP1-tRPL3, pMET6-QRI1-tIDP1, HIS3]×3, jlp1::[LEU2.Sba-loxP, pTEF1.Sba-HASB. Vir-tRPL3.Sm, pTDH3.Sk-HASB-A. Vir-tTEF1.Sba, pTDH3-1.Sba-HASA-1.Vir-tRPL3.Sba, pTDH3.Sar-HASA-A. Vir-tRPL15A.Sba], leu2, met3A1, sam3::[LEU2.K1, pPDC1-PGM1-tIDP1, pTEF1.Ago-GFA1-tRPL15A, pENO2-UGP1-tRPL3, pCWP2-GNA1-tTPI1, pTEF1-PCM1-tRPL41B, TRP1.Sba-loxP], trp1, ura3::[pPDC1-MHPF.Ec-tRPL3, pTDH3-GDH-21.Eca-tIDP1, URA3]×2

HASA-1 and HASA-A are previously defined.

HASB and HASB-A are previously defined.

HASA-2, HASA-3 and HASA5 all represent a nucleic acid sequence encoding a polypeptide having hyaluronan synthase activity. They differ from one another in that they are different reencoded versions of a nucleic acid sequence encoding the hyaluronan synthase enzyme. HASA-2 has the sequence SEQ ID NO: 101, HASA-3 has the sequence SEQ ID NO: 102 and HASA-5 has the sequence SEQ ID NO: 104.

All these strains were incubated in 25 mL of the above-defined SY medium buffered with MES 0.1 M ph 5.5 in a baffled erlenmeyer for 48 hours at 28° C. under vigorous agitation.

Growth medium was recovered at 48h hours and assayed for hyaluronic acid content and quality as defined above.

The amounts obtained with these different strains are respectively:

YA6178: 6.3 g·L-1.

YA6179: 5.9 g·L-1

YA6180: 5.2 g·L-1.

YA6181: 6.4 g·L-1

In comparison, a native strain does not produce hyaluronic acid.

Moreover, these four strains led to the production, after 48 hours, of hyaluronic acid having a molecular weight of about 20 kDa.

SEQUENCES

SEQ ID NO: 1 is a reencoded nucleic acid sequence of hyaluronan synthase (HASA)
originating from *Chlorella* virus PBCV-1
ATGGGTAAGAACATCATTATTATGGTTTCTTGGTACACTATTATTACATCCAATCTCATCGCAGTGGGTGGCGCC
TCACTCATACTAGCCCCAGCTATTACGGGCTATGTCCTTCACTGGAACATTGCCCTTTCAACAATTTGGGGAGTG
TCGGCCTACGGAATTTTCGTGTTTGGTTTCTTTCTTGCCCAGGTATTATTTAGTGAACTCAACCGGAAAAGGCTC
CGGAAGTGGATTTCCCTCCGACCCAAAGGGTGGAATGATGTTAGGTTGGCTGTAATTATTGCCGGCTACCGTGAG
GACCCGTATATGTTCCAAAAGTGTCTTGAAAGTGTGCGTGACTCAGACTATGGGAATGTAGCTAGACTAATATGC
GTTATTGACGGCGATGAAGACGACGACATGAGGATGGCTGCAGTGTACAAGGCTATCTATAACGACAACATCAAG
AAACCTGAGTTTGTCCTCTGTGAGAGTGACGATAAGGAGGGTGAGAGAATAGATAGCGATTTCAGCCGTGATATC
TGCGTGCTGCAACCGCATCGCGGAAAGCGTGAATGTTTGTACACAGGGTTCCAATTGGCAAAGATGGACCCCTCA
GTTAATGCCGTCGTCCTAATCGACAGTGACACTGTGTTAGAAAAGGACGCGATTCTCGAaGTAGTATACCCGCTG
GCATGCGATCCAGAAATACAGGCTGTAGCAGGCGAATGCAAAATATGGAATACTGACACACTGTTGAGTTTGCTG
GTAGCCTGGCGATATTACAGCGCCATTTTGCGTAGAGCGTAGCGCCCAATCATTCTTCAGGACAGTACAATGCGTC
GGAGGACCTCTCGGCGCCTACAAGATTGATATAATTAAGGAAATCAAGGACCCATGGATCAGCCAACGTTTCCTT
GGCCAAAAGTGCACATACGGCGACGATAGACGACTCACTAATGAAATACTAATGAGGGGTAAGAAAGTAGTTTTC
ACCCCATTCGCTGTTGGCTGGTCCGACAGCCCGACGAACGTCTTCCGTTACATTGTACAGCAAACACGGTGGTCC
AAGTCGTGGTGTAGGGAGATATGGTATACACTGTTTGCAGCATGGAAGCATGGACTTTCGGGCATTTGGCTCGCA
TTCGAGTGCTTATACCAGATTACTTATTTCTTCCTGGTGATTTACCTATTCTCCCGTTTGGCTGTTGAGGCTGAC
CCACGGGCGCAAACGGCCACCGTCATTGTTTCGACCACAGTTGCGCTTATTAAGTGCGGTTACTTTAGCTTCAGA
GCTAAAGACATTAGGGCCTTCTATTTCGTCCTCTACACGTTCGTTTACTTCTTCTGCATGATTCCGGCACGAATA
ACTGCGATGATGACCCTGTGGGACATAGGTTGGGGAACCAGGGGAGGAAATGAGAAGCCTTCCGTAGGCACCAGA
GTTGCTTTGTGGGCCAAGCAATATTTGATTGCTTACATGTGGTGGGCCGCTGTCGTCGGTGCTGGCGTGTACTCC
ATCGTTCATAATTGGATGTTTGACTGGAATTCACTTTCCTACAGGTTCGCACTGGTAGGCATCTGTTCGTATATA
GTTTTCATTGTAATAGTGCTGGTAGTCTACTTTACAGGAAAGATCACGACCTGGAACTTCACGAAGCTACAGAAA
GAATTGATCGAGGACCGCGTACTGTACGACGCAACGACCAATGCCCAGTCGGTATAA SEQ ID NO: 2 is a reencoded nucleic acid sequence of hyaluronan synthase (HASA)
originating from *Chlorella* virus PBCV-1
ATGGGCAAGAATATTATTATCATGGTCAGTTGGTATACCATTATTACATCAAACCTAATTGCTGTCGGTGGAGCC
TCACTAATCTTAGCTCCCGCGATTACGGGTTATGTGCTTCATTGGAATATTGCTTTATCCACTATTTGGGGTGTT
AGCGCTTACGGCATCTTTGTGTTCGGTTTCTTCTTGGCTCAGGTGTTATTCTCTGAGCTAAACAGAAAGAGACTC
AGAAAGTGGATTTCGCTGCGGCCGAAGGGATGGAACGATGTTCGGTTAGCGGTGATCATTGCCGGTTATCGTGAA
GATCCTTATATGTTTCAGAAGTGTTTGGAATCTGTTCGAGACTCAGACTACGGTAACGTTGCTAGGCTGATCTGC
GTAATCGATGGAGACGAAGATGACGATATGAGAATGGCCGCGGTTTATAAAGCCATCTATAACGATAACATTAAG
AAGCCAGAGTTTGTTTTATGCGAATCGGATGACAAGGAGGGTGAGAGGATTGATTCTGACTTCTCGCGTGACATC
TGTGTCCTGCAGCCCCACAGGGGAAAGCGAGAGTGCCTCTATACAGGATTCCAATTAGCTAAAATGGACCCAAGC
GTTAATGCTGTCGTCCTTATCGATAGCGACACGGTGTTGGAAAAGGACGCAATATTGGAAGTAGTCTATCCACTC
GCTTGTGATCCAGAGATCCAGGCCGTGGCTGGCGAGTGCAAGATTTGGAATACAGATACGCTTCTGTCATTACTG
GTGGCGTGGCGTTATTATTCAGCATTCTGTGTGGAGAGGAGCGCACAATCGTTCTTTCGGACTGTACAATGCGTA
GGCGGTCCACTAGGAGCATATAAAATTGACATAATCAAAGAGATAAAAGATCCTTGGATTTCGCAGAGATTCCTC
GGTCAAAAGTGTACCTATGGGGACGACAGGCGGTTGACTAACGAGATTCTAATGAGAGGTAAGAAGGTGGTGTTC
ACTCCTTTTGCGGTAGGTTGGAGCGATTCGCCCACAAATGTATTCAGATACATTGTTCAACAAACAAGGTGGTCG
AAATCGTGGTGCCGAGAAATATGGTACACGTTGTTCGCCGCATGGAAACACGGCTTGTCGGGTATATGGCTCGCT
TTCGAGTGCCTTTATCAGATCACTTACTTCTTCCTGGTTATTTACTTGTTTTCAAGACTGGCAGTGGAAGCTGAT
CCAAGGGCTCAGACTGCTACTGTCATCGTTTCAACAACAGTGGCGCTAATAAAGTGTGGTTACTTCAGCTTTCGC
GCGAAGGACATAAGAGCGTTTTACTTTGTTCTTTATACCTTTGTATATTTCTTCTGTATGATCCCGGCCCGGATA
ACAGCTATGATGACATTATGGGACATTGGTTGGGGCACCAGGGGTGGGAATGAGAAGCCGTCCGTAGGAACGAGA
GTAGCGCTGTGGGCCAAGCAGTATCTTATCGCATACATGTGGTGGGCAGCTGTCGTCGGGGCAGGTGTATACAGC
ATAGTACATAACTGGATGTTTGACTGGAACTCACTCTCTATCGATTCGCATTGGTCGGGATCTGCTCTTACATC
GTGTTTATTGTTATAGTCTTAGTAGTATATTTCACTGGAAAGATAACAACATGGAATTTCACTAAGCTTCAAAAG
GAATTGATTGAAGACAGGGTGCTCTACGATGCGACAACTAATGCACAAAGCGTATAA SEQ ID NO: 3 is a reencoded nucleic acid sequence of hyaluronan synthase (HASA)
originating from *Pasteurella multocida*
ATGAACACCCTTTCCCAGGCAATTAAGGCTTATAATAGTAATGATTATCAACTAGCCCTCAAGCTGTTCGAAAAG
TCGGCAGAAATCTACGGCAGAAAGATAGTTGAgTTCCAAATTACGAAGTGCAAGGAGAAACTTTCTGCGCACCCA
TCCGTTAACAGTGCGCATCTCTCGGTTAACAAAGAAGAGAAGGTGAATGTTTGCGACAGTCCATTAGACATAGCC
ACTCAATTATTGTTATCGAATGTGAAAAAACTCGTTCCTTAGTGATAGCGAGAAAAATACACTAAAGAATAAATGG
AAGTTGTTGACTGAAAAGAAGTCTGAGAACGCAGAGGTCCGGGCCGTAGCTTTAGTTCCCAAGGACTTTCCGAAA
GATTTAGTGCTTGCGCCGTTACCAGACCATGTGAACGATTTTACGTGGTATAAGAAGCGGAAGAAACGCCTAGGA
ATCAAACCAGAACACCAACACGTTGGCCTCTCCATTATTGTGACAACGTTCAACCGTCCTGCCATCCTCAGCATC
ACCCTGGCTTGCCTCGTCGTCAATCAAAAGACCCATTATCCTTTTGAGGTGATCGGTGGTTCTCAAGAG
GATTTATCGCCTATAATCCGTCAATATGAGAACAAGCTAGACATCCGTTATGTTCGGCAAAAGGACAACGGTTTT
CAGGCATCGGCCGCACGTAATATGGGCCTACGTCTAGCCAAATATGACTTCATTGGGCTCCTTGATTGTGATATG
GCTCCCAACCCTTTGTGGGTACACTCATACGTTGCGGAACTATTAGAGGACGATGATTTGACCATAATAGGCCCC
AGGAAGTACATTGACACGCAACACATAGATCCCAAGGATTTCCTTAATAACGCCTCTCTGTTAGAGTCGTTGGACA
GAGGTTAAGACCAATAATTCCGTCGCGGCTAAGGGCGAGGGGACCGTATCTTTAGACTGGCGTTTGGAACAATTT
GAGAAGACCGAGAACTTGAGGCTATCCGATAGCCCTTTCCGATTCTTCGCAGCTGGGAATGTGGCTTTCGCCAAG
AAGTGGCTTAACAAGTCAGGATTCTTCGACGAGGAATTCAATCACTGGGGAGGTGAAGATGTAGAGTTCGGTTAT
CGTCTGTTTCGGTACGGTTCGTTCTTCAAAACTATAGACGGCATCATGGCCTATCATCAGGAACCGCCAGGTAACA
GAAAACGAAACTGACAGAGAAGCGGGCAAGAACATTACCCTCGATATAATGAGGGAGAAGGTGCCTTACATCTAC
CGTAAACTCCTGCCTATAGAAGACAGTCATATCAACCGAGTACCATTGGTATCAATTTACATCCCGGCCTACAAC
TGTGCTAACTATATTCAAAGATGTGTTGATTCAGCTTTGAATCAAACGGTAGTTGATCTCGAAGTGTGCATTTGC
AACGACGTAGTACTGACAACACGCTGGAAGTTATTAACAAGCTGTATGGTAATAATCCGCGTGTGACGTAATAATTG
TCTAAACCCAATGGCGGCATTGCGAGTGCATCCAACGCAGCGGTCAGCTTCGCAAAGGGTTATTACATAGGACAG
TTGGACAGCGACGATTACTTAGAACCCGACGCAGTGGAGTTATGTCTCAAGGAATTTCTTAAGGATAAGACCCTT
GCGTGCGTTTACACCACTAATCGTAACGTCAACCCAGATGGCTCTTTAATAGCCAATGGCTATAACTGGCCAGAG
TTCAGTCGTGAGAAGTTGACTACGGCCATGATTGCTCATCACTTCCGGATGTTTACCATTCGTCTTGGCATCTG
ACGGATGGGTTCAATGAGAAGATTGAGAACGCTGTTGACTACGACATGTTTCTCAAGCTCAGTGAAGTTGGTAAA -continued

SEQUENCES

```
TTTAAGCATCTGAACAAAATATGTTATAATCGGGTGTTACACGGCGATAACACCTCAATCAAGAAgCTTGGCATA
CAAAAGAAGAATCATTTCGTAGTTGTCAATCAGTCTCTAAACCGCCAAGGTATAACTTATTATAACTACGATGAA
TTTGATGATCTCGATGAGAGTCGGAAATACATTTTCAACAAGACTGCAGAGTATCAAGAAGAGATAGATATTCTT
AAAGATATTAAGATCATTCAGAACAAAGACGCCAAAATAGCTGTCTCCATTTTCTATCCGAACACTCTAAACGGG
TTGGTGAAGAAGCTAAATAATATTATAGAGTATAATAAGAATATCTTCGTTATTGTACTTCATGTCGATAAGAAT
CACTTAACCCCAGACATCAAGAAGGAGATATTAGCCTTCTACCATAAGCATCAGGTGAACATCTTATTGAACAAT
GACATCTCCTACTATACATCAAATCGTCTGATTAAGACAGAAGCCCATTTGAGTAACATTAACAAGCTaAGTCAA
TTAAATCTTAACTGCGAATACATTATATTCGACAATCACGATTCCTTATTTGTGAAGAACGATTCCTATGCATAC
ATGAAGAAGTATGATGTTGGAATGAACTTCTCTGCATTGACTCATGATTGGATTGAAAAGATAAACGCTCACCCG
CCATTTAAGAAGCTgATCAAAACTTACTTCAATGACAATGATCTTAAGTCGATGAATGTAAAGGGTGCCTCCCAG
GGAATGTTTATGACATACGCATTAGCCCACGAGTTATTGACGATCATCAAGGAGGTGATAACCTCTTGTCAATCC
ATTGACTCCGTCCCCGAATACAACACAGAAGATATTTGGTTTCAGTTTGCACTTTTAATTCTGGAAAAGAAGACC
GGCCACGTATTCAACAAGACAAGCACTCTCACGTATATGCCATGGGAACGTAAACTGCAGTGGACGAATGAACAA
ATAGAGTCCGCAAAGAGGGGCGAAAACATTCCGGTAAACAAGTTCATCATTAACAGCATTACCCTTTAA
```

SEQ ID NO: 4 is a reencoded nucleic acid sequence of hyaluronan synthase (HASA)
originating from *Pasteurella multocida*

```
ATGAACACCCTTTCCCAGGCAATTAAGGCTTATAATAGTAATGATTATCAACTAGCCCTCAAGCTGTTCGAAAAG
TCGGCAGAAATCTACGGCAGAAAGATAGTTGAgTTCCAAATTACGAAGTGCAAGGAGAAACTTTCTGCGCACCCA
TCCGTTAACAGTGCGCATCTCTCGGTTAACAAAGAAGAGAAGGTGAATGTTTGCGACAGTCCATTAGACATAGCC
ACTCAATTATTGTTATCGAATGTGAAAAAACTCGTCCTTAGTGATAGCGAGAAAAATACACTAAAGAATAAATGG
AAGTTGTTGACTGAAAAGAAGTCTGAGAACGCAGAGGTCCGGGCCGTAGCTTTAGTTCCCAAGGACTTTCCGAAA
GATTTAGTGCTTGCGCCGTTACCAGACCATGTGAACGATTTTACGTGGTATAAGAAGCGGAAGAAACGCCTAGGA
ATCAAACCAGAACACCAACACGTTGGCCTCTCCATTATTGTGACAACGTTCAACCGTCCTGCCATCCTCAGCATC
ACCCTGGCTTGCCTCGTCAATCAAAAGACCCATTATCCTTTTGAGGTGATCGTGACCGACGATGGTTCTCAAGAG
GATTTATCGCCTATAATCCGTCAATATGAGAACAAGCTAGACATCCGTTATGTTCGGCAAAAGGACAACGGTTTT
CAGGCATCGGCCGCACGTAATATGGGCCTACGTCTAGCCAAATATGACTTCATTGGGCTCCTTGATTGTGATATG
GCTCCCAACCCTTTGTGGGTACACTCATACGTTGCGGAACTATTAGAGGACGATGATTTGACCATAATAGGCCCC
AGGAAGTACATTGACACGCAACACATAGATCCCAAGGATTTCCTTAATAACGCCTCTCTGTTAGAGTCGTTGCCA
GAGGTTAAGACCAATAATTCCGTCGCGGCTAAGGGCGAGGGGACCGTATCTTTAGACTGGCGTTTGGAACAATTT
GAGAAGACCGAGAACTTGAGGCTATCCGATAGCCCTTTCCGATTCTTCGCAGCTGGGAATGTGGCTTTCGCCAAG
AAGTGGCTTAACAAGTCAGGATTCTTCGACGAGGAATTCAATCACTGGGGAGGTGAAGATGTAGAGTTCGGTTAT
CGTCTGTTTCGGTACGGTTCGTTCTTCAAAACTATAGACGGCATCATGGCCTATCATCAGGAACCGCCAGGTAAA
GAAAACGAAACTGACAGAGAAGCGGGCAAGAACATTACCCTCGATATAATGAGGGAGAAGGTGCCTTACATCTAC
CGTAAACTCCTGCCTATAGAAGACAGTCATATCAACCGAGTACCATTGGTATCAATTTACATCCCGGCCTACAAC
TGTGCTAACTATATTCAAAGATGTGTTGATTCAGCTTTGAATCAAACGGTAGTTGATCTCGAAGTGTGCATTTGC
AACGACGGTAGTACTGACAACACGCTGGAAGTTATTAACAAGCTGTATGGTAATAATCCGCGTGTGCGTATAATG
TCTAAACCCAATGGCGGCATTGCGAGTGCATCCAACGCAGCGGTCAGCTTCGCAAAGGGTTATTACATAGGACAG
TTGGACAGCGACGATTACTTAGAACCCGACGCAGTGGAGTTATGTCTCAAGGAATTTCTTAAGGATAAGACCCTT
GCGTGCGTTTACACCACTAATCGTAACGTCAACCCAGATGGCTCTTTAATAGCCAATGGCTATAACTGGCCAGAG
TTCAGTCGTGAGAAGTTGACTACGGCCATGATTGCTCATCACTTCCGGATGTTTACCATTCGTGCTTGGCATCTG
ACGGATGGGTTCAATGAGAAGATTGAGAACGCTGTTGACTACGACATGTTTCTCAAGCTCAGTGAAGTTGGTAAA
TTTAAGCATCTGAACAAAATATGTTATAATCGGGTGTTACACGGCGATAACACCTCAATCAAGAAgCTTGGCATA
CAAAAGAAGAATCATTTCGTAGTTGTCAATCAGTCTCTAAACCGCCAAGGTATAACTTATTATAACTACGATGAA
TTTGATGATCTCGATGAGAGTCGGAAATACATTTTCAACAAGACTGCAGAGTATCAAGAAGAGATAGATATTCTT
AAAGATATTTAA
```

SEQ ID NO: 5 is a reencoded nucleic acid sequence of hyaluronan synthase (HASA)
originating from *Pasteurella multocida*

```
ATGAACACCCTTTCCCAGGCAATTAAGGCTTATAATAGTAATGATTATCAACTAGCCCTCAAGCTGTTCGAAAAG
TCGGCAGAAATCTACGGCAGAAAGATAGTTGAgTTCCAAATTACGAAGTGCAAGGAGAAACTTTCTGCGCACCCA
TCCGTTAACAGTGCGCATCTCTCGGTTAACAAAGAAGAGAAGGTGAATGTTTGCGACAGTCCATTAGACATAGCC
ACTCAATTATTGTTATCGAATGTGAAAAAACTCGTCCTTAGTGATAGCGAGAAAAATACACTAAAGAATAAATGG
AAGTTGTTGACTGAAAAGAAGTCTGAGAACGCAGAGGTCCGGGCCGTAGCTTTAGTTCCCAAGGACTTTCCGAAA
GATTTAGTGCTTGCGCCGTTACCAGACCATGTGAACGATTTTACGTGGTATAAGAAGCGGAAGAAACGCCTAGGA
ATCAAACCAGAACACCAACACGTTGGCCTCTCCATTATTGTGACAACGTTCAACCGTCCTGCCATCCTCAGCATC
ACCCTGGCTTGCCTCGTCAATCAAAAGACCCATTATCCTTTTGAGGTGATCGTGACCGACGATGGTTCTCAAGAG
GATTTATCGCCTATAATCCGTCAATATGAGAACAAGCTAGACATCCGTTATGTTCGGCAAAAGGACAACGGTTTT
CAGGCATCGGCCGCACGTAATATGGGCCTACGTCTAGCCAAATATGACTTCATTGGGCTCCTTGATTGTGATATG
GCTCCCAACCCTTTGTGGGTACACTCATACGTTGCGGAACTATTAGAGGACGATGATTTGACCATAATAGGCCCC
AGGAAGTACATTGACACGCAACACATAGATCCCAAGGATTTCCTTAATAACGCCTCTCTGTTAGAGTCGTTGCCA
GAGGTTAAGACCAATAATTCCGTCGCGGCTAAGGGCGAGGGGACCGTATCTTTAGACTGGCGTTTGGAACAATTT
GAGAAGACCGAGAACTTGAGGCTATCCGATAGCCCTTTCCGATTCTTCGCAGCTGGGAATGTGGCTTTCGCCAAG
AAGTGGCTTAACAAGTCAGGATTCTTCGACGAGGAATTCAATCACTGGGGAGGTGAAGATGTAGAGTTCGGTTAT
CGTCTGTTTCGGTACGGTTCGTTCTTCAAAACTATAGACGGCATCATGGCCTATCATCAGGAACCGCCAGGTAAA
GAAAACGAAACTGACAGAGAAGCGGGCAAGAACATTACCCTCGATATAATGAGGGAGAAGGTGCCTTACATCTAC
CGTAAACTCCTGCCTATAGAAGACAGTCATATCAACCGAGTACCATTGGTATCAATTTACATCCCGGCCTACAAC
TGTGCTAACTATATTCAAAGATGTGTTGATTCAGCTTTGAATCAAACGGTAGTTGATCTCGAAGTGTGCATTTGC
AACGACGGTAGTACTGACAACACGCTGGAAGTTATTAACAAGCTGTATGGTAATAATCCGCGTGTGCGTATAATG
TCTAAACCCAATGGCGGCATTGCGAGTGCATCCAACGCAGCGGTCAGCTTCGCAAAGGGTTATTACATAGGACAG
TTGGACAGCGACGATTACTTAGAACCCGACGCAGTGGAGTTATGTCTCAAGGAATTTCTTAAGGATAAGACCCTT
GCGTGCGTTTACACCACTAATCGTAACGTCAACCCAGATGGCTCTTTAATAGCCAATGGCTATAACTGGCCAGAG
TTCAGTCGTGAGAAGTTGACTACGGCCATGATTGCTCATCACTTCCGGATGTTTACCATTCGTGCTTGGCATCTG
ACGGATGGGTTCAATGAGAAGATTGAGAACGCTGTTGACTACGACATGTTTCTCAAGCTCAGTGAAGTTGGTAAA
TTTAAGCATCTGAACAAAATATGTTATAATCGGGTGTTACACGGCGATAACACCTCAATCAAGAAGCTTGGCATA
CAAAAGAAGAATCATTTCGTAGTTGTCAATCAGTCTCTAAACCGCCAAGGTATAACTTATTATAACTACGATGAA
TTTGATGATCTCGATGAGAGTCGGAAATACATTTTCAACAAGACTGCAGAGTATCAAGAAGAGATAGATATTCTT
```

---

SEQUENCES

---

AAAGATATTGGATCCGCCATTTCTCAAATCACTGACGGTCAAATCCAAGCTACTACCACTGCTACCACCGAAGCT
ACCACCACTGCTGCCCCATCTTCCACCGTTGAAACTGTTTCTCCATCCAGCACCGAAACTATCTCTCAACAAACT
GAAAATGGTGCTGCTAAGGCCGCTGTCGGTATGGGTGCCGGTGCTCTAGCTGCTGCTGCTATGTTGTTATAA

SEQ ID NO: 6 is a reencoded nucleic acid sequence of hyaluronan synthase (HASA)
originating from *Xenopus laevis*
ATGCACTGTGAACGATTTATTTGTATATTACGAATAATTGGTACGACTTTGTTCGGAGTAAGTCTGCTACTAGGG
ATATCCGCCGCTTATATCGTGGGATACCAATTCATTCAGACGGATAATTACTACTTTTCCTTCGGTCTCTACGGT
GCTATTTTAGCTTTACATTTAATCATTCAGTCTCTCTTCGCATTCCTGGAGCATCGTAAGATGAAGCGGTCACTT
GAAACCCCTATAAAATTAAACAAGAGCGTAGCATTGTGTATCGCTGCATACCAGGAAGACGAAGATTATCTTAGA
AAATGTTTGCTTTCTGTGAAACGGCTCACATACCCCGGTATGAAGGTAATCATGGTGATAGATGGTAACTCTGAT
GACGATCTATACATGATGAACATATTCAGAGAGATCATGGGAAATGATAGCTGCGCCACCTATGTATGGAAGAAT
AATTTTCACATGAAGGGACCAAACGAGACCGACGAGACTCACCGCGAGTCCATGCAGCATGTAACACAGATGGTG
CTTTCTAACAGAAATGTCTGTATCATGCAAAAGTGGAACGGGAAACGCGAGGTGATGTATACTGCATTCAAAGCG
CTGGGTCGGTCGGTTGATTACGTCCAAGTGTGCGACTCAGATACAGTCCTTGATCCAGCAAGCTCGGTGGAGATG
GTCAAGGTGTTGGAGGAAGACATTATGGTCGGAGGTGTAGGCGGAGACGTGCAGATACTCAATAAGTACGACTCC
TGGATCAGTTTCTTGAGTTCGGTTCGTTATTGGATGGCTTTCAATATAGAACGAGCATGCCAATCATACTTTGGC
TGTGTGCAGTGTATATCGGGGCCTCTGGGCATGTACAGAAACTCACTCTTACATGAGTTCATTGAAGACTGGTAC
AATCAAGAATTCCTCGGTTCCCAATGCTCTTTCGGTGATGATCGGCATTTGACTAATCGAGTACTATCATTGGGC
TATGCTACTAAATACACTGCGCGCAGTAAGTGTCTGACAGAAACCCCCACAGATATCTTAGATGGTTGAACCAA
CAAACCAGGTGGAGTAAGTCCTATTTCCGCGAGTGGTTGTACAACTCTTTGTGGTTCCACAAACACCATTTATGG
ATGACTTATGAAGCCGTAATTACGGGTTTCTTCCCCTTCTTCTTAATAGCGACGGTGATTCAGCTCTTCTATCGT
GGTCGAATTTGGAATATCTTACTCTTTCTACTCACAGTTCAATTAGTTGGTCTAATAAAGTCGTCGTTTGCAAGT
GCGTTGCGTGGAAACATCGTTATGGTCTTTATGAGTTTCTACAGTGTTTTATACATGAGTAGCTTGCTGCCAGCA
AAGATGTTTGCAATCGCCACGATAAACAAGGCTGGATGGGGTACTAGTGGTAGAAAGACCATAGTTGTTAATTTT
ATTGGTTTAATCCCTATTACGGTATGGTTCACAATTTTACTAGGGGGAGTATGCTACACTATATGGCGGGAAACC
AAGAAGCCGTTTAGCGAGTCTGAGAAGATCGTTCTTGCGGTCGGTGCTATATTGTATGCTTGTTATTGGGTCATG
TTGCTTACAATGTATGTCAGTCTTGTCATGAAGTGCGGGCGCCGTAGGAAGGAACCACAGCACGACCTTGTTTTA
GCATAA SEQ ID NO: 7 is a reencoded nucleic acid sequence of hyaluronan synthase (HASA)
originating from *Streptococcus zooepidemicus*
ATGAGGACGTTAAAGAATCTTATCACTGTTGTAGCGTTCAGTATATTCTGGGTTTTGCTGATCTATGTAAATGTC
TATCTTTTCGGTGCGAAGGGGTCTCTATCAATATATGGATTCTTGCTAATTGCGTATTTGCTTGTGAAGATGAGT
CTTTCATTCTTCTATAAACCATTCAAAGGTCGAGCTGGTCAGTATAAAGTCGCAGCGATTATCCCTTCATACAAC
GAGGATGCAGAATCGCTGTTGGAAACCTTAAAATCTGTTCAACAACAAACCTATCCCCTTGCTGAAATTTATGTA
GTTGATGATGGTTCCGCAGATGAAACCGGTATCAAGCGGATCGAGGATTATGTCAGGGATACAGGCGACTTAAGT
TCAAATGTGATTGTGCATCGATCAGAAAAGAATCAAGGCAAGAGACACGCCCAAGCATGGGCATTTGAAAGATCT
GATGCAGATGTATTTCTAACAGTCGATAGTGATACTTACATTTATCCGGACGCCCTTGAAGAGTTATTGAAAACC
TTCAATGATCCGACAGTATTTGCCGCAACTGGCCACTTGAACGTTCGTAACAGGCAGACTAATCTATTGACCAGA
CTCACTGATATAAGATACGACAATGCTTTTGGCGTCGAACGTGCTGCTCAAAGTGTAACTGGTAATATACTGGTG
TGTTCCGGGCCACTGTCCGTCTATCGCAGAGAAGTAGTAGTCCCGAACATTGACAGGTATATTAATCAGACTTTT
CTGGGTATCCCCGTGTCAATTGGGGACGACCGGTGTTTAACGAACTACGCTACTGATTTGGGCAAGACTGTATAT
CAGTCGACGGCTAAATGTATTACAGACGTCCCAGATAAGATGTCGACTTACCTTAAACAGCAGAATAGATGGAAT
AAGTCATTCTTTAGAGAATCTATCATCAGCGTGAAGAAGATCATGAATAATCCATTCGTGGCGCTTTGGACCATT
TTGGAGGTTTCCATGTTTATGATGCTTGTCTACTCTGTCGTTGATTTCTTTGTAGGTAACGTTCGAGAATTTGAT
TGGCTCAGAGTTCTTGCTTTCTTAGTTATCATCTTCATCGTTGCGCTATGCAGGAATATTCATTACATGCTAAAA
CATCCGCTTAGCTTCTTACTCAGCCCTTTCTACGGCGTTTTGCATCTCTTCGTTTTGCAGCCATTGAAGCTCTAC
TCCTTATTTACCATTCGAAACGCTGATTGGGGTACGCGCAAGAAACTATTAtaa SEQ ID NO: 8 is an amino acid sequence of hyaluronan synthase (HASA) originating from
*Chlorella* virus PBCV-1
MGKNIIIMVSWYTIITSNLIAVGGASLILAPAITGYVLHWNIALSTIWGVSAYGIFVFGFFLAQVLFSELNRKRL
RKWISLRPKGWNDVRLAVIIAGYREDPYMFQKCLESVRDSDYGNVARLICVIDGDEDDDMRMAAVYKAIYNDNIK
KPEFVLCESDDKEGERIDSDFSRDICVLQPHRGKRECLYTGFQLAKMDPSVNAVVLIDSDTVLEKDAILEVVYPL
ACDPEIQAVAGECKIWNTDTLLSLLVAWRYYSAFCVERSAQSFFRTVQCVGGPLGAYKIDIIKEIKDPWISQRFL
GQKCTYGDDRRLTNEILMRGKKVVFTPFAVGWSDSPTNVFRYIVQQTRWSKSWCREIWYTLFAAWKHGLSGIWLA
FECLYQITYFFLVIYLFSRLAVEADPRAQTATVIVSTIVALIKCGYFSFRAKDIRAFYFVLYTFVYFFCMIPARI
TAMMTLWDIGWGTRGGNEKPSVGTRVALWAKQYLIAYMWWAAVVGAGVYSIVHNWMFDWNSLSYRFALVGICSYI
VFIVIVLVVYFTGKITTWNFTKLQKELIEDRVLYDATTNAQSV SEQ ID NO: 9 is an amino acid sequence of hyaluronan synthase (HASA) originating from
*Pasteurella multocida*
MNTLSQAIKAYNSNDYQLALKLFEKSAEIYGRKIVEFQITKCKEKLSAHPSVNSAHLSVNKEEKVNVCDSPLDIA
TQLLLSNVKKLVLSDSEKNTLKNKWKLLTEKKSENAEVRAVALVPKDFPKDLVLAPLPDHVNDFTWYKKRKKRLG
IKPEHQHVGLSIIVTTFNRPAILSITLACLVNQKTHYPFEVIVIDDGSQEDLSPIIRQYENKLDIRYVRQKDNGF
QASAARNMGLRLAKYDFIGLLDCMAPNPLWVHSYVAELLEDDDLTIIGPRKYIDTQHIDPKDFLNNASLLESLP
EVKTNNSVAAKGEGTVSLDWRLEQFEKTENLRLSDSPFRFFAAGNVAFAKKWINKSGFFDEEFNHWGGEDVEFGY
RLFRYGSFFKTIDGIMAYHQEPPGKENETDREAGKNITLDIMREKVPYIYRKLLPIEDSHINRVPLVSIYIPAYN
CANYIQRCVDSALNQTVVDLEVCICNDGSTDNILEVINKLYGNNPRVRIMSKPNGGIASASNAAVSFAKGYYIGQ
LDSDDYLEPDAVELCLKEFLKDKTLACVYTTNRNVNPDGSLIANGYNWPEFSREKLITAMIAHHFRMFTIRAWHL
TDGFNEKIENAVDYDMFLKLSEVGKFKHLNKICYNRVLHGDNTSIKKLGIQKKNHFVVVNQSLNRQGITYYNYDE
FDDLDESRKYIFNKTAEYQEEIDILKDIKIIQNKDAKIAVSIFYPNTLNGLVKKLNNIIEYNKNIFVIVLHVDKN
HLTPDIKKEILAFYHKHQVNILLNNDISYYTSNRLIKTEAHLSNINKLSQLNLNCEYIIFDNHDSLFVKNDSYAY
MKKYDVGMNFSALTHDWIEKINAHPPFKKLIKTYFNDNDLKSMNVKGASQGMFMTYALAHELLTIIKEVITSCQS
IDSVPEYNTEDIWFQFALLILEKKTGHVFNKTSTLTYMPWERKLQWTNEQIESAKRGENIPVNKFIINSITL -continued

SEQUENCES

SEQ ID NO: 10 is an amino acid sequence of hyaluronan synthase (HASA) originating from
*Xenopus laevis*
MHCERFICILRIIGTTLFGVSLLLGISAAYIVGYQFIQTDNYYFSFGLYGAILALHLIIQSLFAFLEHRKMKRSL
ETPIKLNKSVALCIAAYQEDEDYLRKCLLSVKRLTYPGMKVIMVIDGNSDDDLYMMNIFREIMGNDSCATYVWKN
NFHMKGPNETDETHRESMQHVTQMVLSNRNVCIMQKWNGKREVMYTAFKALGRSVDYVQVCDSDTVLDPASSVEM
VKVLEEDIMVGGVGGDVQILNKYDSWISFLSSVRYWMAFNIERACQSYFGCVQCISGPLGMYRNSLLHEFIEDWY
NQEFLGSQCSFGDDRHLTNRVLSLGYATKYTARSKCLTETPTEYLRWLNQQTRWSKSYFREWLYNSLWFHKHHLW
MTYEAVITGFFPPFFLIATVIQLFYRGRIWNILLFLLTVQLVGLIKSSFASALRGNIVMVFMSFYSVLYMSSLLPA
KMFAIATINKAGWGTSGRKTIVVNFIGLIPITVWFTILLGGVCYTIWRETKKPFSESEKIVLAVGAILYACYWVM
LLTMYVSLVMKCGRRRKEPQHDLVLA SEQ ID NO: 11 is an amino acid sequence of hyaluronan synthase (HASA) originating from
*Streptococcus zooepidemicus*
MRTLKNLITVVAFSIFWVLLIYVNVYLFGAKGSLSIYGFLLIAYLLVKMSLSFFYKPFKGRAGQYKVAAIIPSYN
EDAESLLETLKSVQQQTYPLAEIYVVDDGSADETGIKRIEDYVRDTGDLSSNVIVHRSEKNQGKRHAQAWAFERS
DADVFLTVDSDTYIYPDALEELLKTFNDPTVFAATGHLNVRNRQTNLLTRLTDIRYDNAFGVERAAQSVTGNILV
CSGPLSVYRREVVVPNIDRYINQTFLGIPVSIGDDRCLTNYATDLGKTVYQSTAKCITDVPDKMSTYLKQQNRWN
KSFFRESIISVKKIMNNPFVALWTILEVSMFMMLVYSVVDFFVGNVREFDWLRVLAFLVIIFIVALCRNIHYMLK
HPLSFLLSPFYGVLHLFVLQPLKLYSLFTIRNADWGTRKKLL SEQ ID NO: 12 is a nucleic acid sequence of UDP-Glucose dehydrogenase (HASB)
originating from *Arabidopsis thaliana*
ATGGTCAAAATATGCTGTATCGGGGCTGGATATGTCGGTGGGCCTACAATGGCCGTTATGGCCCTAAAGTGTCCA
GAGATTGAAGTCGTGGTAGTTGATATATCGGAGCCACGAATTAACGCATGGAACTCAGACCGTCTACCAATTTAT
GAGCCAGGGTTAGAGGATGTCGTCAAACAGTGTAGAGGGAAGAATTTGTTCTTCTCTACAGATGTAGAGAAGCAT
GTATTTGAGTCAGATATAGTGTTTGTTTCGGTAAACACTCCTACGAAAACGCAGGGTCTGGGTGCAGGTAAAGCA
GCAGATTTGACATATTGGGAGTCCGCTGCTCGCATGATAGCTGATGTGAGCAAATCGTCGAAAATCGTCGTTGAA
AAGAGTACAGTACCAGTTCGTACAGCCGAGGCTATAGAAAAGATTTTAACGCACAATTCGAAGGGTATCGAATTC
CAGATCTTATCAAATCCAGAATTCTTGGCCGAAGGGACGGCGATTAAAGACTTATATAACCCTGATAGAGTTCTA
ATCGGTGGCAGGGACACCGCTGCGGGACAAAAGGCCATTAAGGCGTTGCGTGACGTGTATGCCCACTGGGTTCCT
GTTGAGCAAATAATCTGTACTAATTTATGGAGTGCCGAGCTATCAAAGTTGGCTGCGAACGCATTTCTAGCTCAA
AGGATAAGTTCAGTAAACGCAATGTCAGCGCTTTGTGAGGCAACTGGTGCTGACGTAACCCAAGTCGCTCACGCC
GTTGGAACCGACACTAGAATTGGACCGAAGTTTCTTAACGCATCCGTAGGCTTCGGCGGATCTTGCTTTCAGAAA
GACATCCTGAATCTTATTTACATCTGCGAATGCAATGGTCTTCCAGAAGCAGCCAATTATTGGAAACAGGTAGTC
AAGGTAAATGACTACCAAAAGATTAGGTTTGCTAATCGAGTCGTATCTTCTATGTTCAACACCGTCTCCGGTAAG
AAAATTGCTATTTTGGGATTTGCGTTCAAGAAGGACACCGGCGACACGCGTGAAACTCCTGCCATAGATGTGTGT
AATCGCCTCGTGGCTGATAAAGCAAAGCTGTCGATCTATGATCCGCAAGTATTAGAAGAGCAGATCCGCCGTGAT
CTGTCCATGGCCCGATTCGATTGGGACCATCCAGTCCCACTCCAGCAGATCAAAGCTGAAGGTATCTCCGAACAG
GTTAACGTTGTGTCCGACGCCTACGAGGCTACGAAGGATGCTCATGGTTTATGTGTTTTAACCGAATGGGACGAA
TTCAAGTCACTTGATTTTAAGAAGATCTTTGATAATATGCAGAAACCCGCTTTCGTTTTCGACGGAAGAAACGTG
GTCGACGCTGTGAAATTGAGAGAAATTGGATTCATAGTATATTCCATAGGTAAACCTCTGGATAGTTGGCTCAAG
GATATGCCGGCTGTTGCATAA SEQ ID NO: 13 is a reencoded nucleic acid sequence of UDP-Glucose dehydrogenase (HASB)
originating from *Chlorella* virus PBCV-1
ATGAGTAGAATTGCTGTCGTTGGATGCGGTTACGTGGGTACGGCCTGCGCCGTACTTTTGGCGCAGAAGAACGAA
GTTATCGTTTTGGATATCTCGGAGGACCGGGTACAACTGATTAAGAATAAGAAGTCACCTATAGAAGATAAGGAA
ATCGAAGAATTCCTGGAGACGAAAGATTTGAATCTAACAGCGACGACGGATAAGGTGCTCGCCTATGAGAATGCT
GAATTCGTTATAATAGCTACACCGACCGATTACGATGTCGTCACTAGGATATTTCAACACTAAGTCTGTTGAAAAT
GTGATAGGCGATGTCATTAAGAACACTCAGACACACCCTACTATAGTGATCAAGAGTACTATTCCAATCGGTTTC
GTGGATAAAGTTAGAGAACAGTTCGATTATCAAAATATTATCTTCTCGCCGGAATTCTTGAGAGAAGGACGAGCA
TTATATGATAATCTTTACCCCTCCCGTATCATCGTCGGTGATGACTCCCCAATTGCCTTAAAATTCGCGAATCTC
TTGGTCGAGGGTAGCAAAACTCCACTAGCTCCCGTATTAACTATGGGTACGCGAGAGGCCGAAGCTGTAAAACTA
TTTTCAAATACATATTTGGCTATGAGAGTAGCATACTTCAATGAGCTAGACACATTTGCAATGTCCCATGGTATG
AACGCAAAAGAGATTATCGACGGAGTCACACTAGAACCAAGGATAGGGCAGGGTTATTCGAATCCTTCATTTGGG
TATGGAGCCTATTGTTTCCCAAAAGATACAAAGCAATTGTTGGCTAATTTTGAAGGGGTTCCACAAGATATTATT
GGCGCAATCGTAGAGTCTAACGAAACTAGAAAGGAGGTTATTGTTTCTGAGGTCGAGAACAGATTTCCGACCACA
GTTGGCGTATATAAGTTGGCTGCTAAAGCTGGTTCGGATAATTTCAGGTCTAGTGCGATAGTCGATATCATGGAA
AGGTTGGCTAATAAGGGCTACCACATCAAAATATTTGAACCTACCGTTGAACAATTTGAGAATTTTGAGGTAGAT
AATAATCTCACAACTTTTGCAACCGAGTCTGATGTAATAATTGCGAACAGAGTTCCAGTCGAACATCGCATTCTG
TTTGGGAAGAAGTTAATAACACGGGATGTCTATGGGATAA SEQ ID NO: 14 is a reencoded nucleic acid sequence of UDP-Glucose dehydrogenase (HASB)
originating from *Chlorella* virus PBCV-1
ATGTCACGAATCGCAGTAGTTGGCTGTGGGTACGTGGGAACCGCATGCGCTGTACTGCTGGCGCAAAAGAATGAG
GTAATCGTTCTTGATATTAGTGAGGATAGGGTCCAACTAATCAAGAACAAGAAATCCCCGATCGAAGATAAGGAG
ATTGAAGAATTCTTGGAAACAAAAGACCTAAACTTAACTGCAACAACTGACAAAGTTTTAGCCTACGAAAACGCT
GAGTTTGTGATTATAGCGACACCCACAGATTATGACGTAGTTACCAGATACTTTAACACGAAGTCCGTAGAGAAC
GTCATTGGAGATGTTATAAAGAATACTCAGACTCATCCTACGATAGTAATAAAGTCAACCATTCCCATAGGTTTC
GTAGATAAGGTTAGGGAGCAATTCGATTACCAGAACATTATATTTTCGCCAGAATTTCTGAGAGAGGGTCGCGCC
CTGTATGATAATCTATATCCATCACGGATTATAGTGGGCGATGACTCTCCCAATTGCACTTAAGTTTGCTAATCTT
TTAGTTGAGGGCTCCAAAACTCCGCTCGCCCCAGTACTTACGATGGGTACACGTGAGGCTGAAGCTGTCAAGCTG
TTTTCAAACACATACCTTGCTATGCGAGTCGCATACTTTAACGAACTAGATACCTTTGCTATGTCGCACGGTATG
AATGCTAAAGAAATCATAGATGGCGTAACGTTGGAGCCTCGGATAGGTCAAGGATATTCCAATCCATCTTTTGGC
TACGGTGCGATTGTTTCCCAAAGGACACGAAGCAATTATTAGCTAACTTTGAGGGTGTTCCGCAAGATATAATT
GGGGCGATAGTAGAAAGCAATGAAACACGGAAGGAGGTAATCGTGAGTGAAGTGGAAAACCGATTCCCCACTACG
GTCGGCGTTTACAAATTAGCCGCCAAGGCTGGTTCCGACAATTTCCGATCCAGCGCAATAGTAGATATTATGGAA

SEQUENCES

```
AGATTAGCTAATAAGGGATACCACATTAAAATCTTTGAACCTACTGTCGAACAGTTCGAGAACTTCGAGGTTGAT
AATAACTTGACGACTTTCGCAACGGAGAGCGATGTAATTATTGCAAACCGCGTACCTGTGGAACATCGAATTTTG
TTCGGAAAGAAGCTGATTACACGCGATGTATATGGCGATAACTAA
```

SEQ ID NO: 15 is a reencoded nucleic acid sequence of UDP-Glucose dehydrogenase (HASB)
originating from *Streptococcus zooepidemicus*
```
ATGAAGATATCGGTAGCGGGTTCGGGGTACGTGGGGTTATCCTTGTCAATCTTGCTTGCCCAACATAACGATGTG
ACTGTTGTAGATATAATCGACGAAAAGGTACGGCTAATTAACCAGGGCATATCTCCGATTAAGGATGCGGACATT
GAGGAATATCTGAAGAATGCACCGTTGAATCTTACGGCTACACTAGACGGAGCTTCGGCTTATAGTAATGCTGAT
CTGATTATAATCGCAACGCCAACTAATTACGATTCAGAACGCAATTATTTCGACACCAGACACGTTGAAGAAGTA
ATTGAGCAAGTATTGGATTTAAATGCCTCCGCTACTATAATCATCAAGAGTACCATACCCTTGGGTTTTATTAAA
CACGTAAGAGAGAAATACCAAACAGACAGAATCATCTTTTCTCCAGAGTTCTTAAGAGAGTCAAAGGCATTGTAC
GATAACTTATACCCCTCTCGTATAATAGTCAGTTATGAGAAGGATGACTCTCCAAGAGTTATACAAGCAGCTAAG
GCGTTCGCGGGTTTATTAAAAGAGGGGGCAAAGAGCAAGGATACCCCAGTTCTGTTTATGGGCTCTCAAGAAGCT
GAAGCTGTCAAGCTGTTTGCTAATACTTTTCTCGCCATGAGGGTCAGTTACTTCAACGAGCTTGACACTTATAGC
GAATCAAAAGGACTAGACGCCCAAAGAGTTATAGAAGGCGTCTGCCATGATCAAAGGATAGGTAATCATTACAAT
AATCCATCCTTCGGATATGGCGGTTATTGTTTACCCAAAGACTCAAAGCAACTTTTGGCTAATTATAGAGGCATA
CCTCAGTCTCTAATGTCTGCCATCGTTGAATCGAACAAGATCCGTAAGTCGTATTTAGCTGAACAAATATTAGAT
AGGGCTTCTTCACAAAAGCAGGCTGGTGTACCTTTAACCATAGGATTTTACCGTTTGATTATGAAGTCCAACTCC
GATAACTTTAGAGAATCAGCCATTAAAGATATTATTGACATCATTAATGACTACGGTGTCAATATTGTCATTTAT
GAACCTATGTTGGGAGAAGACATTGGTTATAGAGTCGTTAAAGATTTGGAACAGTTTAAGAACGAAAGTACAATT
ATTGTTAGTAACAGGTTTGAAGATGATTTAGGTGATGTTATTGATAAAGTTTATACACGTGACGTCTTTGGTAG
```

SEQ ID NO: 16 is an amino acid sequence of UDP-Glucose dehydrogenase (HASB)
originating from *Arabidopsis thaliana*
```
MVKICCIGAGYVGGPTMAVMALKCPEIEVVVVDISEPRINAWNSDRLPIYEPGLEDVVKQCRGKNLFFSTDVEKH
VFESDIVFVSVNTPTKTQGLGAGKAADLTYWESAARMIADVSKSSKIVVEKSTVPVRTAEAIEKILTHNSKGIEF
QILSNPEFLAEGTAIKDLYNPDRVLIGGRDTAAGQKAIKALRDVYAHVVPVEQIICTNLWSAELSKLAANAFLAQ
RISSVNAMSALCEATGADVTQVAHAVGTDTRIGPKFLNASVGFGGSCFQKDILNLIYICECNGLPEAANYWKQVV
KVNDYQKIRFANRVVSSMFNTVSGKKIAILGPAFKKDTGDTRETPAIDVCNRLVADKAKLSIYDPQVLEEQIRRD
LSMARFDWDHPVPLQQIKAEGISEQVNVVSDAYEATKDAHGLCVLTEWDEFKSLDFKKIFDNMQKPAFVFDGRNV
VDAVKLREIGFIVYSIGKPLDSWLKDMPAVA
```

SEQ ID NO: 17 is an amino acid sequence of UDP-Glucose dehydrogenase (HASB)
originating from *Chlorella* virus PBCV1
```
MSRIAVVGCGYVGTACAVLLAQKNEVIVLDISEDRVQLIKNKKSPIEDKEIEEFLETKDLNLTATTDKVLAYENA
EFVIIATPTDYDVVTRYFNTKSVENVIGDVIKNTQTHPTIVIKSTIPIGFVDKVREQFDYQNIIFSPEFLREGRA
LYDNLYPSRIIVGDDSPIALKFANLLVEGSKTPLAPVLTMGTREAEAVKLFSNTYLAMRVAYFNELDTFAMSHGM
NAKEIIDGVTLEPRIGQGYSNPSFGYGAYCFPKDTKQLLANFEGVPQDIIGAIVESNETRKEVIVSEVENRFPTT
VGVYKLAAKAGSDNFRSSAIVDIMERLANKGYHIKIFEPTVEQFENFEVDNNLITFATESDVIIANRVPVEHRIL
FGKKLITRDVYGDN
```

SEQ ID NO: 18 is an amino acid sequence of UDP-Glucose dehydrogenase (HASB)
originating from *Streptococcus zooepidemicus*
```
MKISVAGSGYVGLSLSILLAQHNDVTVVDIIDEKVRLINQGISPIKDADIEEYLKNAPLNLTATLDGASAYSNAD
LIIIATPTNYDSERNYFDTRHVEEVIEQVLDLNASATIIKSTIPLGFIKHVREKYQTDRIIFSPEFLRESKALY
DNLYPSRIIVSYEKDDSPRVIQAAKAFAGLLKEGAKSKDTPVLFMGSQEAEAVKLFANTFLAMRVSYFNELDTYS
ESKGLDAQRVIEGVCHDQRIGNHYNNPSFGYGGYCLPKDSKQLLANYRGIPQSLMSAIVESNKIRKSYLAEQILD
RASSQKQAGVPLTIGFYRLIMKSNSDNFRESAIKDIIDIINDYGVNIVIYEPMLGEDIGYRVVKDLEQFKNESTI
IVSNRFEDDLGDVIDKVYTRDVFGRD
```

SEQ ID NO: 19 is a reencoded nucleic acid sequence of hyaluronidase (HYAL) originating
from *Bothrops atrox* with a N-terminal secretion signal
```
ATGCAATTTAGCACAGTCGCATCAGTAGCCTTCGTTGCCTTGGCCAACTTCGTGGCAGCACCGATGTATCCGAAC
GAACCGTTCTTAGTCTTTTGGAACGCGCCTACAACTCAGTGTAGACTTCGATATAAGGTTGACCTTGATCTGAAG
ACATTCCATATCGTGACAAATGCTAATGACTCGCTGTCAGGATCGGCTGTCACGATTTTCTATCCCACGCACTTA
GGGGTTTACCCACATATTGATGACAGGGGGCACTTCTTCAATGGCATCATACCCCAAAATGAATCCCTGGTAAAG
CATTTAAACAAATCTAAATCAGATATTAATCGAATGATTCCCTTAAGAACATTCCACGGGCTGGGAGTCATAGAC
TGGGAAAACTGGCGGCCACAGTGGGATAGGAATTGGGGAAGTAAGAACGTTTATAGGAATAGATCAATCCAATTC
GCGCGTGATCTCCACCCAGAGCTTAGTGAGGACAAGATTAAACGCTTGGCAAAACAGGAATTCGAGAAAGCTGCA
AAGAGTTTTATGAGGGATACACTATTATTAGCCGAGGAGATGCGACCCAGACGGCTACTGGGGATACTATCTGTAC
CCCGATTGTCACAATTACAATTATAAGACTAAGCCAGATCAGTACACAGGAGAGTGCCCTGACATCGAGATGTCA
CGTAACAATCAACTCTTGTGGCTTTGGCGGGATAGCACTGCCCTTTTCCCCAATATCTACTTAGAGACTATACTA
AGAAGCTCTGACAATGCCCTGAAGTTTGTGCACCATAGGCTCAAGGAGGCAATGAGGATAGCCTCAATGGCTCGA
AATGACTACGCGTTGCCTTTCTTTGTTTATGCTCGACCATTCTATGCCTATACCTTCGAACCATTGACTCAGGAA
GACCTTGTGACTACGGTCGGAGAGACCGCGGACATGGGCGCCTGGGATCGTATTTTGGGGGAGTATGCAGTAC
GCAAGCACGGTTGAATCTTGCGGCAAAGTCAAGGACTACATGAATGGCCCACTGGGGCGTTACATTGTGAATGTT
ACAACTGCCGCCAAAATTTGCTCACGATTCTTGTGCAAACGTCATGGTAGGTGTGTAAGAAAGCACTCAGACTCC
AATGCATTCCTTCACCTATTTCCCGATTCGTTTCGCATAATGGTGCACGGGAATGCAACCGAGAAGAAAGTTATA
GTAAAGGGGAAGCTGGAATTAAAGAATCTTATATTCTTACGTAATAACTTTATGTGCCAGTGTTATCAAGGCTGG
AAAGGTCTATATTGCGAGAAGCATTCGATAAAGGAAATTCGGAAAATCTAA
```

SEQ ID NO: 20 is a reencoded nucleic acid sequence of hyaluronidase (HYAL) originating
from *Bothrops atrox* with a N-terminal secretion signal and a C-terminal anchoring signal
```
ATGCAATTTAGCACAGTCGCATCAGTAGCCTTCGTTGCCTTGGCCAACTTCGTGGCAGCACCGATGTATCCGAAC
GAACCGTTCTTAGTCTTTTGGAACGCGCCTACAACTCAGTGTAGACTTCGATATAAGGTTGACCTTGATCTGAAG
ACATTCCATATCGTGACAAATGCTAATGACTCGCTGTCAGGATCGGCTGTCACGATTTTCTATCCCACGCACTTA
```

SEQUENCES

```
GGGGTTTACCCACATATTGATGACAGGGGGCACTTCTTCAATGGCATCATACCCCAAAATGAATCCCTGGTAAAG
CATTTAAACAAATCTAAATCAGATATTAATCGAATGATTCCCTTAAGAACATTCCACGGGCTGGGAGTCATAGAC
TGGGAAAACTGGCGGCCACAGTGGGATAGGAATTGGGGAAGTAAGAACGTTTATAGGAATAGATCAATCCAATTC
GCGCGTGATCTCCACCCAGAGCTTAGTGAGGACAAGATTAAACGCTTGGCAAACAGGAATTCGAGAAAGCTGCA
AAGAGTTTTATGAGGGATACACTATTATTAGCCGAGGAGATGCGACCAGACGGCTACTGGGGATACTATCTGTAC
CCCGATTGTCACAATTACAATTATAAGACTAAGCCAGATCAGTACACAGGAGAGTGCCCTGACATCGAGATGTCA
CGTAACAATCAACTCTTGTGGCTTTGGCGGGATAGCACTGCCCTTTTCCCCAATATCTACTTAGAGACTATACTA
AGAAGCTCTGACAATGCCCTGAAGTTTGTGCACCATAGGCTCAAGGAGGCAATGAGGATAGCCTCAATGGCTCGA
AATGACTACGCGTTGCCTTTCTTTGTTTATGCTCGACCATTCTATGCCTATACCTTCGAACCATTGACTCAGGAA
GACCTTGTGACTACGGTCGGAGAGACCGCGGACATGGGCGCCGCTGGGATCGTATTTTGGGGGAGTATGCAGTAC
GCAAGCACGGTTGAATCTTGCGGCAAAGTCAAGGACTACATGAATGGCCCACTGGGGCGTTACATTGTGAATGTT
ACAACTGCCGCCAAAATTTGCTCACGATTCTTGTGCAAACGTCATGGTAGGTGTGTAAGAAAGCACTCAGACTCC
AATGCATTCCTTCACCTATTTCCCGATTCGTTTCGCATAATGGTGCACGGGAATGCAACCGAGAAGAAAGTTATA
GTAAAGGGGAAGCTGGAATTAAAGAATCTTATATTCTTACGTAATAACTTTATGTGCCAGTGTTATCAAGGCTGG
AAAGGTCTATATTGCGAGAAGCATTCGATAAAGGAAATTCGGAAAATCGGATCCGCCATTTCTCAAATCACTGAC
GGTCAAATCCAAGCTACTACCACTGCTACCACCGAAGCTACCACCACTGCTGCCCCATCTTCCACCGTTGAAACT
GTTTCTCCATCCAGCACCGAAACTATCTCTCAACAAACTGAAAATGGTGCTGCTAAGGCCGCTGTCGGTATGGGT
GCCGGTGCTCTAGCTGCTGCTGCTATGTTGTTATAA
```

SEQ ID NO: 21 is a reencoded nucleic acid sequence of hyaluronidase (HYAL) originating from *Cupiennius salei* with a N-terminal secretion signal

```
ATGCAATTCAGCACTGTTGCATCAGTTGCATTTGTCGCCCTGGCGAATTTTGTAGCCGCGTTCAAGATTTACTGG
AACGTCCCAACTTTTCAGTGCACGCATAACTACAAAATCGATTATGTCAAATTGTTGTCCACTTACGGGATACAG
GTCAATGATGGCGGTAAGTTTCAAGGAAACCAAGTGACTATCTTTTATGAAACCCAGTTGGGTTTGTATCCACGA
ATCCTAAAATCTGGTAAAATGGAAAACGGCGGAATCCCTCAACGCGGTAACTTTGAGAAACACCTAGAAAAGGCA
AGCACGGACCTCCAGAAAGTGATCCCTTGGAAAGAGTTTAGCGGATTAGGTGTGATAGATTGGGAGGCTTGGAGA
CCCACATGGGAATTTAACTGGGAACCGTTGAGGATATATCAAACCGAATCAATTAAGAGAGCTAAAGAACTACAC
CCTACCGCAAACGATTCCGCAGTAAAAGAAATTGCAGAGCGGCAATGGGAAGATTCAGCCAAGTTATACATGTTA
GAAACACTGCGGCTGGCAAAGAAACTTCGACCTCAAGCGCCTTGGTGTTACTACTTATTTCCTGATTGCTATAAT
TACGTCGGAAAGAAACCAAAAGATTTCCAATGTAGTGCCTCGATACGTAAAGGTAACGATAAGCTAAGCTGGTTG
TGGAAAGATTCTACGGCATTGTGTCCATCGATATACGTATATGAATCACAATTAGACAGGTATTCTTTTGAACAA
AGGACATGGCGCGACAATGAGAAACTTCGGGAAGCGTTGCGTGTAGCCACGAGAACCTCTAAAATATACCCATAC
GTTAACTATTTCGATAAGGAGCTTATACCGGAGCAAGAAGTATGGAGAATGCTTGCGCAGGCAGCTGCTGTCGGT
GGCAGTGGTGCGGTAATTTGGGGCTCATCTGCTGCAGTTGCATCTGAAGAGTTATGTAAATCTTTAAAACAGTAT
ATTATTGAAACGCTTGGGCCGGCGGCAGAGAAGGTGGCTTGGCGTAGTGACTTATGCAGCAAAGAAATTTGTAAT
AATCAGGGTCGCTGCACATTCCCGGACGATGATTATGCAAACGCATGGAAATTATTTACAGATGATACTGTTAAG
TTTTATGCTGGTAATATTACATGTAGGTGCTCCGAGAATTATTCTGGTCGTTTCTGCGAAAGAAGAATTAA
```

SEQ ID NO: 22 is a reencoded nucleic acid sequence of hyaluronidase (HYAL) originating from *Cupiennius salei* with a N-terminal secretion signal and a C-terminal anchoring signal

```
ATGCAATTCAGCACTGTTGCATCAGTTGCATTTGTCGCCCTGGCGAATTTTGTAGCCGCGTTCAAGATTTACTGG
AACGTCCCAACTTTTCAGTGCACGCATAACTACAAAATCGATTATGTCAAATTGTTGTCCACTTACGGGATACAG
GTCAATGATGGCGGTAAGTTTCAAGGAAACCAAGTGACTATCTTTTATGAAACCCAGTTGGGTTTGTATCCACGA
ATCCTAAAATCTGGTAAAATGGAAAACGGCGGAATCCCTCAACGCGGTAACTTTGAGAAACACCTAGAAAAGGCA
AGCACGGACCTCCAGAAAGTGATCCCTTGGAAAGAGTTTAGCGGATTAGGTGTGATAGATTGGGAGGCTTGGAGA
CCCACATGGGAATTTAACTGGGAACCGTTGAGGATATATCAAACCGAATCAATTAAGAGAGCTAAAGAACTACAC
CCTACCGCAAACGATTCCGCAGTAAAAGAAATTGCAGAGCGGCAATGGGAAGATTCAGCCAAGTTATACATGTTA
GAAACACTGCGGCTGGCAAAGAAACTTCGACCTCAAGCGCCTTGGTGTTACTACTTATTTCCTGATTGCTATAAT
TACGTCGGAAAGAAACCAAAAGATTTCCAATGTAGTGCCTCGATACGTAAAGGTAACGATAAGCTAAGCTGGTTG
TGGAAAGATTCTACGGCATTGTGTCCATCGATATACGTATATGAATCACAATTAGACAGGTATTCTTTTGAACAA
AGGACATGGCGCGACAATGAGAAACTTCGGGAAGCGTTGCGTGTAGCCACGAGAACCTCTAAAATATACCCATAC
GTTAACTATTTCGATAAGGAGCTTATACCGGAGCAAGAAGTATGGAGAATGCTTGCGCAGGCAGCTGCTGTCGGT
GGCAGTGGTGCGGTAATTTGGGGCTCATCTGCTGCAGTTGCATCTGAAGAGTTATGTAAATCTTTAAAACAGTAT
ATTATTGAAACGCTTGGGCCGGCGGCAGAGAAGGTGGCTTGGCGTAGTGACTTATGCAGCAAAGAAATTTGTAAT
AATCAGGGTCGCTGCACATTCCCGGACGATGATTATGCAAACGCATGGAAATTATTTACAGATGATACTGTTAAG
TTTTATGCTGGTAATATTACATGTAGGTGCTCCGAGAATTATTCTGGTCGTTTCTGCGAAAGAAGAATGGATCC
GCCATTTCTCAAATCACTGACGGTCAAATCCAAGCTACTACCACTGCTGCC
CCATCTTCCACCGTTGAAACTGTTTCTCCATCCAGCACCGAAACTATCTCTCAACAAACTGAAAATGGTGCTGCT
AAGGCCGCTGTCGGTATGGGTGCCGGTGCTCTAGCTGCTGCTGCTATGTTGTTATAA
```

SEQ ID NO: 23 is a reencoded nucleic acid sequence of hyaluronidase (HYAL) originating from *Hirudo Nipponia* with a N-terminal secretion signal

```
ATGCAATTCTCTACTGTCGCTTCCGTTGCTTTCGTCGCTTTGGCTAACTTTGTTGCCGCTATGAAGGAGATAGCA
GTTACCATCGATGATAAGAATGTTATAGCGTCTGTCAGTGAAAGCTTCCATGGTGTGGCTTTCGACGCAAGCCTA
TTCTCACCTAAAGGGCTATGGTCGTTTGTTGACATTACTTCACCCAAGTTATTCAAGCTTCTGGAGGGACTCTCC
CCTGGTTATTTCCGTGTCGGCGGCACATTTGCGAACTGGTTATTCTTCGACCTCGATGAAAACAACAAGTGGAAG
GATTACTGGGCTTTTAAGGACAAGACTCCAGAGACCGCCACGATTACCCGACGGTGGCTCTTCAGGAAGCAAAAC
AACCTCAAGAAGGAAACCTTTGATGATTTGGTAAAGCTTACAAAGGGGTCCAAGATGCGGCTGCTATTTGATCTA
AACGCAGAGGTCCGTACAGGATATGAGATAGGCAAGAAGATGACATCAACTTGGGACTCAAGCGAGGCAGAAAAG
TTGTTCAAATATTGCGTTAGCAAGGGATATGGAGATAATATCGATTGGGAGTTAGGCAACGAACCTGATCACACG
TCAGCACACAATTTGACAGAGAAGCAAGTAGGTGAAGATTTTAAGGCCCTACACACAAGGTGTTGGAAAAGTATCCA
ACACTTAATAAAGGTAGCTTGGTTGGTCCAGACGTTGGGTGGATGGGAGTGTCGTACGTCAAGGGTCTGGCTGAC
GGGGCTGGAGATCATGTGACCGCTTTTACTCTACATCAGTATTATTTCGATGGAAATACGAGTGATGTTAGTACC
TACTTGGATGCGACGTACTTTAAGAAGTTGCAACAGTTATTCGATAAGGTAAAAGACGTACTCAAGAATTCTCCA
CATAAGGACAAACCCTTGTGGCTAGGGGAAACCTCTTCCGGCTACAACAGTGGGACTAAAGATGTATCCGATAGA
TACGTGTCGGGGTTCTTGACGCTGGACAAGTTGGGGCTTTCGGCGGCAAATAACGTCAAGGTGGTCATCAGACAA
ACGATTTATAATGGTTACTATGGTTTGCTTGACAAGAATACTTTGGAGCCCAATCCGGACTACTGGCTGATGCAC
```

SEQUENCES

```
GTCCACAATTCCTTAGTTGGTAATACCGTTTTCAAGGTCGATGTCAGCGATCCCACAAACAAAGCCCGTGTTTAC
GCTCAGTGTACGAAGACCAATAGTAAACATACCCAGTCACGTTATTATAAGGGGTCCCTAACCATTTTCGCGTTG
AATGTAGGTGATGAAGATGTTACACTCAAGATTGATCAATACAGTGGTAAGAAAATATACTCATATATTCTGACG
CCTGAAGGCGGCCAGTTAACCTCTCAAAAGGTACTGCTTAACGGTAAAGAATTGAAGTTAGTGTCAGATCAACTT
CCAGAACTTAACGCGGACGAAAGTAAAACATCCTTCACATTGTCTCCCAAAACTTTTGGATTCTTTGTGGTCTCG
GATGCCAACGTTGAAGCTTGCAAGAAATAA

SEQ ID NO: 24 is a reencoded nucleic acid sequence of hyaluronidase (HYAL) originating
from Hirudo Nipponia with a N-terminal secretion signal and a C-terminal anchoring signal
ATGCAATTCTCTACTGTCGCTTCCGTTGCTTTCGTCGCTTTGGCTAACTTTGTTGCCGCTATGAAGGAGATAGCA
GTTACCATCGATGATAAGAATGTTATAGCGTCTGTCAGTGAAAGCTTCCATGGTGTGGCTTTCGACGCAAGCCTA
TTCTCACCTAAAGGGCTATGGTCGTTTGTTGACATTACTTCACCCAAGTTATTCAAGCTTCTGGAGGGACTCTCC
CCTGGTTATTTCCGTGTCGGCGGCACATTTGCGAACTGGTTATTCTTCGACCTCGATGAAAACAACAAGTGGAAG
GATTACTGGGCTTTTAAGGACAAGACTCCAGAGACCGCCACGATTACCCGACGGTGGCTCTTCAGGAAGCAAAAC
AACCTCAAGAAGGAAACCTTTGATGATTTGGTAAAGCTTACAAAGGGGTCCAAGATGCGGCTGCTATTTGATCTA
AACGCAGAGGTCCGTACAGGATATGAGATAGGCAAGAAGATGACATCAACTTGGGACTCAAGCGAGGCAGAAAG
TTGTTCAAATATTGCGTTAGCAAGGGATATGGAGATAATATCGATTGGGAGTTAGGCAACGAACCTGATCACACG
TCAGCACACAATTTGACAGAGAAGCAAGTAGGTGAAGATTTTAAGGCCCTACACAAGGTGTTGGAAAAGTATCCA
ACACTTAATAAAGGTAGCTTGGTTGGTCCAGACGTTGGGTGGATGGGAGTGTCGTACGTCAAGGGTCTGGCTGAC
GGGGCTGGAGATCATGTGACCGCTTTTACTCTACATCAGTATTATTTCGATGGAAATACGAGTGATGTTAGTACC
TACTTGGATGCGACGTACTTTAAGAAGTTGCAACAGTTATTCGATAAGGTAAAAGACGTACTCAAGAATTCTCCA
CATAAGGACAAACCCTTGTGGCTAGGGGAAACCTCTTCCGGCTACAACAGTGGGACTAAAGATGTATCCGATAGA
TACGTGTCGGGGTTCTTGACGCTGGACAAGTTGGGGCTTTCGGCGGCAAATAACGTCAAGGTGGTCATCAGACAA
ACGATTTATAATGGTTACTATGGTTTGCTTGACAAGAATACTTTGGAGCCCAATCCGGACTACTGGCTGATGCAC
GTCCACAATTCCTTAGTTGGTAATACCGTTTTCAAGGTCGATGTCAGCGATCCCACAAACAAAGCCCGTGTTTAC
GCTCAGTGTACGAAGACCAATAGTAAACATACCCAGTCACGTTATTATAAGGGGTCCCTAACCATTTTCGCGTTG
AATGTAGGTGATGAAGATGTTACACTCAAGATTGATCAATACAGTGGTAAGAAAATATACTCATATATTCTGACG
CCTGAAGGCGGCCAGTTAACCTCTCAAAAGGTACTGCTTAACGGTAAAGAATTGAAGTTAGTGTCAGATCAACTT
CCAGAACTTAACGCGGACGAAAGTAAAACATCCTTCACATTGTCTCCCAAAACTTTTGGATTCTTTGTGGTCTCG
GATGCCAACGTTGAAGCTTGCAAGAAAGGATCCGCCATTTCTCAAATCACTGACGGTCAAATCCAAGCTACTACC
ACTGCTACCACCGAAGCTACCACCACTGCTGCCCCATCTTCCACCGTTGAAACTGTTTCTCCATCCAGCACCGAA
ACTATCTCTCAACAAACTGAAAATGGTGCTGCTAAGGCCGCTGTCGGTATGGGTGCCGGTGCTCTAGCTGCTGCT
GCTATGTTGTTATAA SEQ ID NO: 25 is a reencoded nucleic acid sequence of hyaluronidase (HYAL) originating
from Loxosceles intermedia with a N-terminal secretion signal
ATGCAGTTTTCAACCGTTGCGAGCGTCGCTTTTGTGGCTCTTGCTAATTTCGTTGCCGCCTTCGATGTCTTCTGG
AATGTTCCGTCGCAGCAATGCAAGAAATATGGTATGAAATTCGTTCCGCTCTTAGAGCAATACTCTATCCTAGTC
AACAAAGAAGACAATTTCAAGGGCGACAAAATAACGATCTTTTATGAGTCACAGCTCGGGCTTTACCCACATATT
GGTGCAAACGACGAGTCGTTTAATGGCGGGATACCACAATTAGGTGACCTGAAAGCACACTTAGAAAAGTCAGCG
GTTGATATACGACGTGATATTTTGGATAAGTCGGCGACTGGTCTAAGAATTATAGACTGGGAAGCATGGAGACCA
ATATGGGAATTCAACTGGTCTAGCCTACGAAAGTACCAAGATAAAATGAAGAAAGTCGTCCGCCAGTTTAACCCG
ACTGCTCATGAATCCACAGTGGCCAAACTAGCACATAATGAGTGGGAAAATAGTAGTAAGTCTTGGATGCTTTCT
ACATTGCAGTTGGGTAAGCAACTTCGTCCAAACTCTGTATGGTGCTATTATTTATTTCCCGACTGTTATAACTAT
GATGGCAACTCAGTCCAAGAATTTCAGTGTTCTGAAGCTATCCGTAAGGGGAACGATAGGTTGAAATGGTTGTGG
GAAGAATCGACAGCTGTATGCCCATCTATCTACATAAAAGAAGGCCAACTGACCAATTATACCTTGCAAAAGAGA
ATCTGGTTTACCAATGGGAGATTACAGGAAGCCTTGAGAGTAGCTCAACCTAAAGCGCGTATTTATCCATACATA
AATTACTCCATCAAACCCGGAATGATGGTGCCTGAAGTTGAGTTTTGGCGGTTAATCGCTCAGATAGCCTCGCTG
GGTATGGATGGAGCAGTGATTTGGGGATCAAGTGCGAGTGTAGGCAGTAAGAATCATTGTGCGCAATTAATGAAG
TACATTGCAGACGTATTGGGTCCTGCAACTTTGCGCATAAAAGAAAATGTAGCACGGTGCAGTAAACAGGCGTGC
TCTGGTAGGGGTAGATGTACCTGGCCTAAAGATACCTCTGTTATTGCTTGGAAGTTCCTCGTTGAAAAGGAAGAC
TATGACTTTTATCTGGGTGATATAGAGTGTAAATGTGTTGAAGGCTACGAAGGTAGGTACTGTGAACAAAAGACT
AAGTAA SEQ ID NO: 26 is a reencoded nucleic acid sequence of hyaluronidase (HYAL) originating
from Loxosceles intermedia with a N-terminal secretion signal and a C-terminal anchoring
signal
ATGCAGTTTTCAACCGTTGCGAGCGTCGCTTTTGTGGCTCTTGCTAATTTCGTTGCCGCCTTCGATGTCTTCTGG
AATGTTCCGTCGCAGCAATGCAAGAAATATGGTATGAAATTCGTTCCGCTCTTAGAGCAATACTCTATCCTAGTC
AACAAAGAAGACAATTTCAAGGGCGACAAAATAACGATCTTTTATGAGTCACAGCTCGGGCTTTACCCACATATT
GGTGCAAACGACGAGTCGTTTAATGGCGGGATACCACAATTAGGTGACCTGAAAGCACACTTAGAAAAGTCAGCG
GTTGATATACGACGTGATATTTTGGATAAGTCGGCGACTGGTCTAAGAATTATAGACTGGGAAGCATGGAGACCA
ATATGGGAATTCAACTGGTCTAGCCTACGAAAGTACCAAGATAAAATGAAGAAAGTCGTCCGCCAGTTTAACCCG
ACTGCTCATGAATCCACAGTGGCCAAACTAGCACATAATGAGTGGGAAAATAGTAGTAAGTCTTGGATGCTTTCT
ACATTGCAGTTGGGTAAGCAACTTCGTCCAAACTCTGTATGGTGCTATTATTTATTTCCCGACTGTTATAACTAT
GATGGCAACTCAGTCCAAGAATTTCAGTGTTCTGAAGCTATCCGTAAGGGGAACGATAGGTTGAAATGGTTGTGG
GAAGAATCGACAGCTGTATGCCCATCTATCTACATAAAAGAAGGCCAACTGACCAATTATACCTTGCAAAAGAGA
ATCTGGTTTACCAATGGGAGATTACAGGAAGCCTTGAGAGTAGCTCAACCTAAAGCGCGTATTTATCCATACATA
AATTACTCCATCAAACCCGGAATGATGGTGCCTGAAGTTGAGTTTTGGCGGTTAATCGCTCAGATAGCCTCGCTG
GGTATGGATGGAGCAGTGATTTGGGGATCAAGTGCGAGTGTAGGCAGTAAGAATCATTGTGCGCAATTAATGAAG
TACATTGCAGACGTATTGGGTCCTGCAACTTTGCGCATAAAAGAAAATGTAGCACGGTGCAGTAAACAGGCGTGC
TCTGGTAGGGGTAGATGTACCTGGCCTAAAGATACCTCTGTTATTGCTTGGAAGTTCCTCGTTGAAAAGGAAGAC
TATGACTTTTATCTGGGTGATATAGAGTGTAAATGTGTTGAAGGCTACGAAGGTAGGTACTGTGAACAAAAGACT
AAGGGATCCGCCATTTCTCAAATCACTGACGGTCAAATCCAAGCTACTACCACTGCTACCACCGAAGCTACCACC
ACTGCTGCCCCATCTTCCACCGTTGAAACTGTTTCTCCATCCAGCACCGAAACTATCTCTCAACAAACTGAAAAT
GGTGCTGCTAAGGCCGCTGTCGGTATGGGTGCCGGTGCTCTAGCTGCTGCTGCTATGTTGTTATAA
```

SEQUENCES

SEQ ID NO: 27 is a reencoded nucleic acid sequence of hyaluronidase (HYAL) originating
from *Tityus serrulatus* with a N-terminal secretion signal
ATGCAATTCTCTACTGTCGCTTCCGTTGCTTTCGTCGCTTGGCTAACTTTGTTGCCGCTGCTGATTTTAAAGTT
TACTGGGAAGTGCCTTCCTTCCTTTGTTCTAAACGTTTTAAAATTAATGTAACGGAAGTTTTAACAAGTCACGAG
ATTCTTGTCAATCAGGGTGAGAGTTTCAACGGTGACAAGATAGTAATCTTTTACGAAAACCAATTGGGGAAGTAC
CCGCATATTGACTCAAACAATGTGGAGATCAATGGAGGAATACTTCAAGTAGCCGATTTGGCGAAGCATTTGAAA
GTAGCCAAGGATAATATCACTAAATTCGTCCCGAATCCTAATTTCAACGGTGTCGGAGTGATCGACTGGGAAGCT
TGGCGGCCATCATGGGAATTTAACTGGGGTAAGTTAAAAGTATATAAAGAAAAGAGCATTGACTTGGTCAAGTCG
AAACATCCGGAGTGGCCCTCCGACAGGGTTGAAAAGGTTGCTAAAGAGGAGTGGGAGGAGAGTGCCAAAGAATGG
ATGGTGAAGACCCTGAAGTTAGCACAGGAAATGCGACCGAACGCAGTTTGGTGCTATTATCTATTCCCTGACTGC
TACAATTATTTCGGTAAGGATCAACCCTCTCAATTCAGCTGCTCGTCTCGAATTCAGAAGGAAAATTCTCGTCTT
TCTTGGCTCTGGAATCAATCAACAGCCATTTGCCTAAGCATTTATATCCAGGAATCCCATGTTACCAAATATAAT
ATGTCCCAGCGGACATGGTGGATCGATGCGAGATTAAGAGAAGCAATTCGAGTCAGCGAACACAGACCAAACATA
CCCATCTACCCTTACATTAATTATATTCTACCTGGAACTAATCAAACTGTACCAGCAATGGACTTTAAAAGGACA
CTGGGTCAAATAGCTAGCCTCGGCCTAGATGGTGCTTTGTTATGGGGATCTAGCTATCATGTTTTAACAGAATCT
CAATGCAAAATCACTTCTGATTATGTGAAATCAGTGATTGCTCCTACCGTGGCTACTGTCGTTCTCAATACAAAC
AGATGCTCACAGATAATTTGTAAGGGTCGCGGCAACTGTGTTTGGCCTGAAGAACCATTTAGTTCTTGGAAATAC
TTAGTTGACCCCAAAATGCCAGTGTTCAAGCCAACCAACATCCACTGTAAATGTAAAGGTTACCTAGGTAGATAC
TGTGAGATCCCAAAGTAA SEQ ID NO: 28 is a reencoded nucleic acid sequence of hyaluronidase (HYAL) originating
from *Tityus serrulatus* with a N-terminal secretion signal and a C-terminal anchoring signal
ATGCAATTCTCTACTGTCGCTTCCGTTGCTTTCGTCGCTTTGGCTAACTTTGTTGCCGCTGCTGATTTTAAAGTT
TACTGGGAAGTGCCTTCCTTCCTTTGTTCTAAACGTTTTAAAATTAATGTAACGGAAGTTTTAACAAGTCACGAG
ATTCTTGTCAATCAGGGTGAGAGTTTCAACGGTGACAAGATAGTAATCTTTTACGAAAACCAATTGGGGAAGTAC
CCGCATATTGACTCAAACAATGTGGAGATCAATGGAGGAATACTTCAAGTAGCCGATTTGGCGAAGCATTTGAAA
GTAGCCAAGGATAATATCACTAAATTCGTCCCGAATCCTAATTTCAACGGTGTCGGAGTGATCGACTGGGAAGCT
TGGCGGCCATCATGGGAATTTAACTGGGGTAAGTTAAAAGTATATAAAGAAAAGAGCATTGACTTGGTCAAGTCG
AAACATCCGGAGTGGCCCTCCGACAGGGTTGAAAAGGTTGCTAAAGAGGAGTGGGAGGAGAGTGCCAAAGAATGG
ATGGTGAAGACCCTGAAGTTAGCACAGGAAATGCGACCGAACGCAGTTTGGTGCTATTATCTATTCCCTGACTGC
TACAATTATTTCGGTAAGGATCAACCCTCTCAATTCAGCTGCTCGTCTCGAATTCAGAAGGAAAATTCTCGTCTT
TCTTGGCTCTGGAATCAATCAACAGCCATTTGCCTAAGCATTTATATCCAGGAATCCCATGTTACCAAATATAAT
ATGTCCCAGCGGACATGGTGGATCGATGCGAGATTAAGAGAAGCAATTCGAGTCAGCGAACACAGACCAAACATA
CCCATCTACCCTTACATTAATTATATTCTACCTGGAACTAATCAAACTGTACCAGCAATGGACTTTAAAAGGACA
CTGGGTCAAATAGCTAGCCTCGGCCTAGATGGTGCTTTGTTATGGGGATCTAGCTATCATGTTTTAACAGAATCT
CAATGCAAAATCACTTCTGATTATGTGAAATCAGTGATTGCTCCTACCGTGGCTACTGTCGTTCTCAATACAAAC
AGATGCTCACAGATAATTTGTAAGGGTCGCGGCAACTGTGTTTGGCCTGAAGAACCATTTAGTTCTTGGAAATAC
TTAGTTGACCCCAAAATGCCAGTGTTCAAGCCAACCAACATCCACTGTAAATGTAAAGGTTACCTAGGTAGATAC
TGTGAGATCCCAAAGGGATCCGCCATTTCTCAAATCACTGACGGTCAAATCCAAGCTACTACCACTGCTACCACC
GAAGCTACCACCACTGCTGCCCCATCTTCCACCGTTGAAACTGTTTCTCCATCCAGCACCGAAACTATCTCTCAA
CAAACTGAAAATGGTGCTGCTAAGGCCGCTGTCGGTATGGGTGCCGGTGCTCTAGCTGCTGCTGCTATGTTGTTA
TAA SEQ ID NO: 29 is a reencoded nucleic acid sequence of hyaluronidase (HYAL) originating
from *Vespa magnifica* with a N-terminal secretion signal
ATGCAATTTTCTACAGTGGCAAGTGTTGCATTCGTTGCACTAGCCAACTTTGTGGCGGCAGATAGCTGTGGGTCA
AACTGCGAAAAGAGTGAGAGACCGAAAAGGGTCTTCAACATTTACTGGAACGTACCTACATTCATGTGTCACCAG
TACGGACTATACTTTGACGAGGTCACGAATTTTAATATAAAGCACAACAGCAAAGACAATTTTCAAGGGGACAAG
ATCGCGATCTTTTATGACCCCGGGGAGTTTCCCGCTCTGCTGCCACTAAACTATGGTAAGTACAAGATCAGGAAT
GGTGGTGTTCCACAAGAGGGTAACATCACCATCCATCTGCAGAGATTCATAGAGTACCTAGATAAGACCTATCCG
AACCGTAACTTTTCAGGCATCGGTGTGATCGATTTCGAGAGGTGGAGACCAATTTTCAGACAGAATTGGGGTAAT
ATGAAGATTTACAAGAACTTCTCCATCGATCTTGTGCGTAAAGAGCATCCTTTCTGGAATAAGAAAATGATCGAG
TTGGAAGCTTCTAAAAGATTCGAGAAATACGCCCGTCTGTTCAACGGAGAAACATTAAAGTTGGCTAAGAAAACT
AGAAAACAGGCCGATTGGGGCTACTACGGTTACCCCTATTGCTTCAACATGTCTCCTACTAATTTCGTTCCTGAC
TGCGATGTCACAGCTAGGGATGAGAACAACGAGATGTCTTGGTTGTTTAACAACCAGAATGTCCTATTACCAAGT
GTATACATTAGGAGAGAGCTAACTCCTGACCAGAGGATTGGGCTTGTACAGGGGAGAGTGAAGGAAGCTGTGAGA
ATTTCAAATAAACTGAAGCACTCACCTAAAGTCTTCAGCTATTGGTGGTATGTTTACCAAGACGAGACCAACACC
TTCTTAACGGAGACCGACGTCAAGAAGACGTTTCAGGAGATTGTGATCAACGGTGGAGATGGGATTATAATCTGG
GGTTCGTCCTCTGATGTAAACAGCTTGTCCAAGTGTACGAGGTTAAGGGAGTACCTATTGACAGTCTTGGGACCA
ATTGCTGTTAACGTGACTGAAGCAGTAAACTAA SEQ ID NO: 30 is a reencoded nucleic acid sequence of hyaluronidase (HYAL) originating
from *Vespa magnifica* with a N-terminal secretion signal and a C-terminal anchoring signal
ATGCAATTTTCTACAGTGGCAAGTGTTGCATTCGTTGCACTAGCCAACTTTGTGGCGGCAGATAGCTGTGGGTCA
AACTGCGAAAAGAGTGAGAGACCGAAAAGGGTCTTCAACATTTACTGGAACGTACCTACATTCATGTGTCACCAG
TACGGACTATACTTTGACGAGGTCACGAATTTTAATATAAAGCACAACAGCAAAGACAATTTTCAAGGGGACAAG
ATCGCGATCTTTTATGACCCCGGGGAGTTTCCCGCTCTGCTGCCACTAAACTATGGTAAGTACAAGATCAGGAAT
GGTGGTGTTCCACAAGAGGGTAACATCACCATCCATCTGCAGAGATTCATAGAGTACCTAGATAAGACCTATCCG
AACCGTAACTTTTCAGGCATCGGTGTGATCGATTTCGAGAGGTGGAGACCAATTTTCAGACAGAATTGGGGTAAT
ATGAAGATTTACAAGAACTTCTCCATCGATCTTGTGCGTAAAGAGCATCCTTTCTGGAATAAGAAAATGATCGAG
TTGGAAGCTTCTAAAAGATTCGAGAAATACGCCCGTCTGTTCAACGGAGAAACATTAAAGTTGGCTAAGAAAACT
AGAAAACAGGCCGATTGGGGCTACTACGGTTACCCCTATTGCTTCAACATGTCTCCTACTAATTTCGTTCCTGAC
TGCGATGTCACAGCTAGGGATGAGAACAACGAGATGTCTTGGTTGTTTAACAACCAGAATGTCCTATTACCAAGT
GTATACATTAGGAGAGAGCTAACTCCTGACCAGAGGATTGGGCTTGTACAGGGGAGAGTGAAGGAAGCTGTGAGA
ATTTCAAATAAACTGAAGCACTCACCTAAAGTCTTCAGCTATTGGTGGTATGTTTACCAAGACGAGACCAACACC
TTCTTAACGGAGACCGACGTCAAGAAGACGTTTCAGGAGATTGTGATCAACGGTGGAGATGGGATTATAATCTGG
GGTTCGTCCTCTGATGTAAACAGCTTGTCCAAGTGTACGAGGTTAAGGGAGTACCTATTGACAGTCTTGGGACCA -continued

---

SEQUENCES

---

ATTGCTGTTAACGTGACTGAAGCAGTAAACGGATCCGCCATTTCTCAAATCACTGACGGTCAAATCCAAGCTACT
ACCACTGCTACCACCGAAGCTACCACCACTGCTGCCCCATCTTCCACCGTTGAAACTGTTTCTCCATCCAGCACC
GAAACTATCTCTCAACAAACTGAAAATGGTGCTGCTAAGGCCGCTGTCGGTATGGGTGCCGGTGCTCTAGCTGCT
GCTGCTATGTTGTTATAA

SEQ ID NO: 31 is an amino acid sequence of hyaluronidase (HYAL) originating from
*Bothrops atrox* with a N-terminal secretion signal
MQFSTVASVAFVALANFVAAPMYPNEPFLVFWNAPTTQCRLRYKVDLDLKTFHIVTNANDSLSGSAVTIFYPTHL
GVYPHIDDRGHFFNGIIPQNESLVKHLNKSKSDINRMIPLRTFHGLGVIDWENWRPQWDRNWGSKNVYRNRSIQF
ARDLHPELSEDKIKRLAKQEFEKAAKSFMRDILLLAEEMRPDGYWGYYLYPDCHNYNYKTKPDQYTGECPDIEMS
RNNQLLWLWRDSTALFPNIYLETILRSSDNALKFVHHRLKEAMRIASMARNDYALPFFVYARPFYAYTFEPLTQE
DLVTTVGETADMGAAGIVFWGSMQYASTVESCGKVKDYMNGPLGRYIVNVTTAAKICSRFLCKRHGRCVRKHSDS
NAFLHLFPDSFRIMVHGNATEKKVIVKGKLELKNLIFLRNNFMCQCYQGWKGLYCEKHSIKEIRKI SEQ ID NO: 32 is an amino acid sequence of hyaluronidase (HYAL) originating from
*Bothrops atrox* with a N-terminal secretion signal and a C-terminal anchoring signal
MQFSTVASVAFVALANFVAAPMYPNEPFLVFWNAPTTQCRLRYKVDLDLKTFHIVTNANDSLSGSAVTIFYPTHL
GVYPHIDDRGHFFNGIIPQNESLVKHLNKSKSDINRMIPLRTFHGLGVIDWENWRPQWDRNWGSKNVYRNRSIQF
ARDLHPELSEDKIKRLAKQEFEKAAKSFMRDILLLAEEMRPDGYWGYYLYPDCHNYNYKTKPDQYTGECPDIEMS
RNNQLLWLWRDSTALFPNIYLETILRSSDNALKFVHHRLKEAMRIASMARNDYALPFFVYARPFYAYTFEPLTQE
DLVTTVGETADMGAAGIVFWGSMQYASTVESCGKVKDYMNGPLGRYIVNVTTAAKICSRFLCKRHGRCVRKHSDS
NAFLHLFPDSFRIMVHGNATEKKVIVKGKLELKNLIFLRNNFMCQCYQGWKGLYCEKHSIKEIRKIGSAISQITD
GQIQATTTATTEATTTAAPSSTVETVSPSSTETISQQTENGAAKAAVGMGAGALAAAMLL SEQ ID NO: 33 is an amino acid sequence of hyaluronidase (HYAL) originating from
*Cupiennius salei* with a N-terminal secretion signal
MQFSTVASVAFVALANFVAAFKIYWNVPTFQCTHNYKIDYVKLLSTYGIQVNDGGKFQGNQVTIFYETQLGLYPR
ILKSGKMENGGIPQRGNFEKHLEKASTDLQKVIPWKEFSGLGVIDWEAWRPTWEENWEPLRIYQTESIKRAKELH
PTANDSAVKEIAERQWEDSAKLYMLETLRLAKKLRPQAPWCYYLFPDCYNYVGKKPKDFQCSASIRKGNDKLSWL
WKDSTALCPSIYVYESQLDRYSFEQRTWRDNEKLREALRVATRISKIYPYVNYFDKELIPEQEVWRMLAQAAAVG
GSGAVIWGSSAAVASEELCKSLKQYIIETLGPAAEKVAWRSDLCSKEICNNQGRCTFPDDDYANAWKLFTDDTVK
FYAGNITCRCSENYSGRFCEKKN SEQ ID NO: 34 is an amino acid sequence of hyaluronidase (HYAL) originating from
*Cupiennius salei* with a N-terminal secretion signal and a C-terminal anchoring signal
MQFSTVASVAFVALANFVAAFKIYWNVPTFQCTHNYKIDYVKLLSTYGIQVNDGGKFQGNQVTIFYETQLGLYPR
ILKSGKMENGGIPQRGNFEKHLEKASTDLQKVIPWKEFSGLGVIDWEAWRPTWEFNWEPLRIYQTESIKRAKELH
PTANDSAVKEIAERQWEDSAKLYMLETLRLAKKLRPQAPWCYYLFPDCYNYVGKKPKDFQCSASIRKGNDKLSWL
WKDSTALCPSIYVYESQLDRYSFEQRTWRDNEKLREALRVATRISKIYPYVNYFDKELIPEQEVWRMLAQAAAVG
GSGAVIWGSSAAVASEELCKSLKQYIIETLGPAAEKVAWRSDLCSKEICNNQGRCTFPDDDYANAWKLFTDDTVK
FYAGNITCRCSENYSGRFCEKKNGSAISQITDGQIQATTTATTEATTTAAPSSTVETVSPSSTETISQQTENGAA
KAAVGMGAGALAAAMLL SEQ ID NO: 35 is an amino acid sequence of hyaluronidase (HYAL) originating from *Hirudo
Nipponia* with a N-terminal secretion signal
MQFSTVASVAFVALANFVAA~MKEIAVTIDDKNVIASVSESFHGVAFDASLFSPKGLWSFVDITSPKLFKLLEGL
SPGYFRVGGTFANWLFFDLDENNKWKDYWAFKDKTPETATITRRWLFRKQNNLKKETFDDLVKLTKGSKMRLLFD
LNAEVRTGYEIGKKMTSTWDSSEAEKLFKYCVSKGYGDNIDWELGNEPDHISAHNLTEKQVGEDFKALHKVLEKY
PTLNKGSLVGPDVGWMGVSYVKGLADGAGDHVTAFTLHQYYFDGNTSDVSTYLDATYFKKLQQLFDKVKDVLKNS
PHKDKPLWLGETSSGYNSGTKDVSDRYVSGFLTLDKLGLSAANNVKVVIRQTIYNGYYGLLDKNTLEPNPDYWLM
HVHNSLVGNTVFKVDVSDPTNKARVYAQCTKTNSKHTQSRYYKGSLTIFALNVGDEDVTLKIDQYSGKKIYSYIL
TPEGGQLTSQKVLLNGKELKLVSDQLPELNADESKTSFTLSPKTFGFFVVSDANVEACKKGSAISQITDGQIQAT
TTATTEATTTAAPSSTVETVSPSSTETISQQTENGAAKAAVGMGAGALAAAMLL SEQ ID NO: 36 is an amino acid sequence of hyaluronidase (HYAL) originating from *Hirudo
Nipponia* with a N-terminal secretion signal and a C-terminal anchoring signal
MQFSTVASVAFVALANFVAA~MKEIAVTIDDKNVIASVSESFHGVAFDASLFSPKGLWSFVDITSPKLFKLLEGL
SPGYFRVGGTFANWLFFDLDENNKWKDYWAFKDKTPETATITRRWLFRKQNNLKKETFDDLVKLTKGSKMRLLFD
LNAEVRIGYEIGKKMTSTWDSSEAEKLFKYCVSKGYGDNIDWELGNEPDHTSAHNLTEKQVGEDFKALHKVLEKY
PTLNKGSLVGPDVGWMGVSYVKGLADGAGDHVTAFTLHQYYFDGNTSDVSTYLDATYFKKLQQLFDKVKDVLKNS
PHKDKPLWLGETSSGYNSGTKDVSDRYVSGFLTLDKLGLSAANNVKVVIRQTIYNGYYGLLDKNTLEPNPDYWLM
HVHNSLVGNTVFKVDVSDPTNKARVYAQCTKTNSKHTQSRYYKGSLTIFALNVGDEDVTLKIDQYSGKKIYSYIL
TPEGGQLTSQKVLLNGKELKLVSDQLPELNADESKTSFTLSPKTFGFFVVSDANVEACKK SEQ ID NO: 37 is an amino acid sequence of hyaluronidase (HYAL) originating from
*Loxosceles intermedia* with a N-terminal secretion signal
MQFSTVASVAFVALANFVAAFDVFWNVPSQQCKKYGMKFVPLLEQYSILVNKEDNEKGDKITIFYESQLGLYPHI
GANDESFNGGIPQLGDLKAHLEKSAVDIRRDILDKSATGLRIIDWEAWRPIWEFNWSSLRKYQDKMKKVVRQFNP
TAHESTVAKLAHNEWENSSKSWMLSTLQLGKQLRPNSVWCYYLFPDCYNYDGNSVQEFQCSEAIRKGNDRLKWLW
EESTAVCPSIYIKEGQLTNYTLQKRIWFTNGRLQEALRVAQPKARIYPYINYSIKPGMMVPEVEFWRLIAQIASL
GMDGAVIWGSSASVGSKNHCAQLMKYIADVLGPATLRIKENVARCSKQACSGRGCTWPKDTSVIAWKFLVEKED
YDFYLGDIECKCVEGYEGRYCEQKTK SEQ ID NO: 38 is an amino acid sequence of hyaluronidase (HYAL) originating from
*Loxosceles intermedia* with a N-terminal secretion signal and a C-terminal anchoring signal
MQFSTVASVAFVALANFVAAFDVFWNVPSQQCKKYGMKFVPLLEQYSILVNKEDNEKGDKITIFYESQLGLYPHI
GANDESFNGGIPQLGDLKAHLEKSAVDIRRDILDKSATGLRIIDWEAWRPIWEFNWSSLRKYQDKMKKVVRQFNP -continued

| SEQUENCES |
|---|

TAHESTVAKLAHNEWENSSKSWMLSTLQLGKQLRPNSVWCYYLFPDCYNYDGNSVQEFQCSEAIRKGNDRLKWLW
EESTAVCPSIYIKEGQLTNYTLQKRIWFTNGRLQEALRVAQPKARIYPYINYSIKPGMMVPEVEFWRLIAQIASL
GMDGAVIWGSSASVGSKNHCAQLMKYIADVLGPATLRIKENVARCSKQACSGRGRCTWPKDTSVIAWKFLVEKED
YDFYLGDIECKCVEGYEGRYCEQKTKGSAISQITDGQIQATTTATTTEATTTAAPSSTVETVSPSSTETISQQTEN
GAAKAAVGMGAGALAAAMLL

SEQ ID NO: 39 is an amino acid sequence of hyaluronidase (HYAL) originating from *Tityus*
*serrulatus* with a N-terminal secretion signal
MQFSTVASVAFVALANFVAAADFKVYWEVPSFLCSKRFKINVTEVLTSHEILVNQGESENGDKIVIFYENQLGKY
PHIDSNNVEINGGILQVADLAKHLKVAKDNITKFVPNPNFNGVGVIDWEAWRPSWEFNWGKLKVYKEKSIDLVKS
KHPEWPSDRVEKVAKEEWEESAKEWMVKTLKLAQEMRPNAVWCYYLFPDCYNYFGKDQPSQFSCSSRIQKENSRL
SWLWNQSTAICLSIYIQESHVTKYNMSQRTWWIDARLREAIRVSEHRPNIPIYPYINYILPGTNQTVPAMDFKRT
LGQIASLGLDGALLWGSSYHVLTESQCKITSDYVKSVIAPTVATVVLNTNRCSQIICKGRGNCVWPEEPFSSWKY
LVDPKMPVFKPTNIHCKCKGYLGRYCEIPK SEQ ID NO: 40 is an amino acid sequence of hyaluronidase (HYAL) originating from *Tityus*
*serrulatus* with a N-terminal secretion signal and a C-terminal anchoring signal
MQFSTVASVAFVALANFVAAADFKVYWEVPSFLCSKRFKINVTEVLTSHEILVNQGESFNGDKIVIFYENQLGKY
PHIDSNNVEINGGILQVADLAKHLKVAKDNITKFVPNPNFNGVGVIDWEAWRPSWEFNWGKLKVYKEKSIDLVKS
KHPEWPSDRVEKVAKEEWEESAKEWMVKILKLAQEMRPNAVWCYYLFPDCYNYFGKDQPSQFSCSSRIQKENSRL
SWLWNQSTAICLSIYIQESHVTKYNMSQRTWWIDARLREAIRVSEHRPNIPIYPYINYILPGTNQTVPAMDFKRT
LGQIASLGLDGALLWGSSYHVLTESQCKITSDYVKSVIAPTVATVVLNITNRCSQIICKGRGNCVWPEEPFSSWKY
LVDPKMPVFKPTNIHCKCKGYLGRYCEIPKGSAISQITDGQIQATTTATTTEATTTAAPSSTVETVSPSSTETISQ
QTENGAAKAAVGMGAGALAAAMLL SEQ ID NO: 41 is an amino acid sequence of hyaluronidase (HYAL) originating from *Vespa*
*magnifica* with a N-terminal secretion signal
MQFSTVASVAFVALANFVAADSCGSNCEKSERPKRVFNIYWNVPTFMCHQYGLYFDEVTNFNIKHNSKDNFQGDK
IAIFYDPGEFPALLPLNYGKYKIRNGGVPQEGNITIHLQRFIEYLDKTYPNRNFSGIGVIDFERWRPIFRQNWGN
MKIYKNFSIDLVRKEHPFWNKKMIELEASKRFEKYARLFMEETLKLAKKTRKQADWGYYGYPYCFNMSPTNFVPD
CDVTARDENNEMSWLENNQNVLLPSVYIRRELTPDQRIGLVQGRVKEAVRISNKLKHSPKVFSYWWYVYQDETNT
FLTETDVKKTFQEIVINGGDGIIIWGSSSDVNSLSKCTRLREYLLTVLGPIAVNVTEAVN SEQ ID NO: 42 is an amino acid sequence of hyaluronidase (HYAL) originating from *Vespa*
*magnifica* with a N-terminal secretion signal and a C-terminal anchoring signal
MQFSTVASVAFVALANFVAADSCGSNCEKSERPKRVFNIYWNVPTFMCHQYGLYFDEVTNFNIKHNSKDNFQGDK
IAIFYDPGEFPALLPLNYGKYKIRNGGVPQEGNITIHLQRFIEYLDKTYPNRNFSGIGVIDFERWRPIFRQNWGN
MKIYKNFSIDLVRKEHPFWNKKMIELEASKRFEKYARLFMEETLKLAKKTRKQADWGYYGYPYCFNMSPTNFVPD
CDVTARDENNEMSWLENNQNVLLPSVYIRRELTPDQRIGLVQGRVKEAVRISNKLKHSPKVFSYWWYVYQDETNT
FLTETDVKKTFQEIVINGGDGIIIWGSSSDVNSLSKCTRLREYLLTVLGPIAVNVTEAVNAISQITDGQIQATTT
ATTEATTTAAPSSTVETVSPSSTETISQQTENGAAKAAVGMGAGALAAAMLL SEQ ID NO: 43 is a nucleic acid sequence of the secretion sequence added in 5'
ATGCAATTTAGCACAGTCGCATCAGTAGCCTTCGTTGCCTTGGCCAACTTCGTGGCAGCA SEQ ID NO: 44 is an amino acid sequence of the secretion sequence added in N-ter
MQFSTVASVAFVALANFVAA SEQ ID NO: 45 is a nucleic acid sequence of the anchoring sequence added in 3'
GGATCCGCCATTTCTCAAATCACTGACGGTCAAATCCAAGCTACTACCACTGCTACCACCGAAGCTACCACCACT
GCTGCCCCATCTTCCACCGTTGAAACTGTTTCTCCATCCAGCACCGAAACTATCTCTCAACAAACTGAAAATGGT
GCTGCTAAGGCCGCTGTCGGTATGGGTGCCGGTGCTCTAGCTGCTGCTGCTATGTTGTTATAA SEQ ID NO: 46 is an amino acid sequence of the anchoring sequence added in C-ter
AISQITDGQIQATTTATTTEATTTAAPSSTVETVSPSSTETISQQTENGAAKAAVGMGAGALAAAMLL SEQ ID NO: 47 is a nucleic acid sequence of glutamine-fructose-6-phosphate amidotransferase
(GFA1) originating from *Saccharomyces cerevisiae*
ATGTGTGGTATCTTTGGTTACTGCAATTATCTAGTGGAAAGATCCAGAGGAGAAATTATCGACACCTTAGTGGAT
GGTTTACAAAGATTAGAATATAGAGGCTATGATTCCACCGGTATTGCTATCGATGGTGACGAAGCTGATTCTACT
TTCATCTATAAGCAAATCGGTAAAGTGAGTGCTTTGAAAGAGGAGATTACTAAGCAAAATCCGAACAGAGACGTT
ACTTTTGTCTCTCATTGTGGTATTGCGCATACTAGATGGGCTACTCACGGTCGACCAGAACAAGTTAACTGTCAC
CCTCAAAGATCTGACCCAGAAGACCAATTTGTGGTCGTTCATAATGGTATCATCACAAATTTTAGAGAACTGAAG
ACTCTTTTAATTAACAAAGGTTATAAATTCGAAAGTGATACCGATACCGAGTGTATTGCTAAACTATATTTGCAT
TTATACAATACAAATTTACAAAATGGGCATGACTTAGATTTCCACGAATTAACCAAGCTAGTTCTTTTAGAACTA
GAAGGTTCATACGGGTTATTATGTAAATCTTGTCACTATCCTAATGAGGTTATCGCCACTAGAAAAGGGTCCCCT
TTACTGATTGGTGTCAAATCTGAAAAAAAACTAAAAGTCGACTTCGTGGATGTGGAATTTCCCGAAGAAAACGCT
GGTCAACCGGAAATTCCATTGAAATCTAACAACAAATCATTTGGCTTGGGCCCAAAGAAAGCTCGTGAATTTGAA
GCTGGTTCCCAAAATGCCAATTTACTACCAATTGCCGCCAATGAATTTAACTTGAGACATTCTCAATCCAGGGCT
TTCCTATCAGAAGATGGATCTCCAACACCGGTGGAATTTTTTGTTCTTCGGATGCGGCATCTGTTGTTAAACAT
ACCAAGAAGGTGCTATTTTTAGAAGATGACGATTTGGCTCATATTTACGATGGTGAGTTACATATTCATAGATCT
AGAAGAGAAGTAGGCGCATCAATGACAAGGTCCATTCAAACTTTAGGATGGAGTTAGCTCAGATCATGAAGGGC
CCTTACGACCATTTTATGCAAAAGGAAATCTATGAGCAACCAGAATCTACTTTCAATACTATGAGAGGTAGAATC
GACTATGAAATAATAAAGTGATATTGGGTGGTTTAAAGGCATGGTTACCAGTTGTCAGAAGAGCACGGAGACTG
ATCATGATCGCATGCGGTACTTCTTATCATTCATGTTTGGCTACTCGTGCTATCTTCGAAGAATTATCAGATATC
CCAGTTAGTGTGGAATTAGCGTCTGACTTTCTGGACAGAAATGCCCCTGTCTTCAGAGACGATGTATGCGTGTTT
GTTTCACAAAGTGGTGAAACTGCGGATACCATGCTGGCTCTAAATTATTGTTTAGAAAGAGGAGCCTTAACTGTC -continued

---
SEQUENCES
---

```
GGAATTGTTAACAGTGTTGGTTCTTCTATCTCTCGTGTCACCCACTGTGGTGTTCATATTAACGCTGGTCCTGAA
ATTGGTGTTGCCTCTACAAAAGCTTATACTTCCCAGTATATTGCCTTAGTGATGTTTGCTCTATCGCTGTCAGAT
GACCGTGTATCGAAAATAGACAGAAGAATTGAAATCATTCAAGGCTTGAAGTTAATCCCGGGCCAAATTAAGCAG
GTATTAAAGCTGGAACCAAGAATAAAAAAGCTCTGTGCGACTGAATTAAAGGATCAAAAATCTCTATTGTTATTG
GGTAGAGGTTACCAATTTGCTGCTGCTCTGGAAGGTGCTTTGAAGATCAAAGAAATTTCTTATATGCATTCTGAA
GGTGTTTTGGCAGGTGAGTTGAAGCACGGTGTCTTGGCCTTGGTGGACGAAAACTTGCCAATCATTGCTTTTGGT
ACCAGAGACTCTCTATTCCCTAAAGTAGTTTCCTCTATTGAGCAAGTTACTGTAAGAAAGGGCCATCCAATTATT
ATTTGTAACGAAAATGATGAAGTGTGGGCGCAAAAATCTAAATCAATCGACCTGCAAACCTTAGAAGTTCCACAA
ACTGTTGATTGTTTACAAGGTCTAATTAATATTATTCCATTACAACTAATGTCATATTGGTTGGCTGTTAATAAA
GGGATTGATGTTGATTTTCCAAGAAACTTGGCTAAATCTGTTACCGTCGAATAA
```

SEQ ID NO: 48 is a reencoded nucleic acid sequence of glutamine-fructose-6-phosphate
amidotransferase (GFA1) originating from *Chlorella* virus 1 (PBCV-1)
```
ATGTGCGGGATCTTCGGTGCTGTGTCGAACAATAATAGCATAGAAGTTTCCATCAAGGGTATACAGAAGCTAGAG
TACCGCGGGTACGATTCGTGTGGAATAGCCTATACAGACGGAGGCGCCATTGAACGGATCAGGTCAATAGATGGG
ATCGACGACTTAAGGAAGAAAACAATAACAGAGTCTTCCCCGGTAGCTATCGCTCATTCAAGGTGGAGTACCACT
GGGATTCCAAGTGTTGTGAACGCCCACCCGCACATCTCTCGGGGCACGTCTGGATGCGAGTCGCGCATTGCAGTC
GTACACAATGGCATTATTGAAAATTACCAGCAGATCCGCAAGTACTTGATAAATCTTGGGTATACTTTCGATTCA
CAGACCGACACGGAAGTCATTGCTCATCTAATAGACTCGCAGTATAACGGGAACATCCTGCACACCGTCCAAATG
GCAGTTAAGCACCTCAAAGGAAGCTACGCCATAGCAGTCATTGTGCCATAAGGAGTCCGGGAAGATCGTGGTGGCA
AAACAGAAGAGTCCGTTGGTATTGGGTATAGGAAGCGACGGAGCTTATTATATCGCATCGGACGTATTGGCTCTT
CCCACTAACAAAGTGGTCTACATAAGTGACGGATTCTCTGCTGAGTTAAGTCCTGGATCGATGACTATCTATGAT
CTGGATGGCAATAAGGTAGAATACGAGGTGGAAGACGTTGAAATGGAGCAGACGTCGATGTCTTTAGATAACTTT
GATCACTACATGATCAAAGAGATCAATGAACAGCCGATATCAATTCTCAATACTATTAAGAACAAAGGATTCTAT
GCAGAGATATTTGGTGATCTAGCACATGAAATATTTCAGAAGATCGACAATATATTGATTCTAGCCTGCGGAACT
TCGTATCATGCAGGTCTCGTCGGGAAGCAATGGATAGAGACCATCTCACGCATCCCGGTGGATGTTCATATTGCA
AGCGAGTATGAGCCGACAATTCCACGAGCCAATACACTTGTGATAACGATTAGTCAAAGCGGCGAGACTGCGGAT
ACAATCGCAGCCCTTCAACGAGCGCAAAACGCAGGAATGATATACACTTTGTGTATCTGCAACAGCCCCAAGTCA
ACTCTAGTGCGCGAGTCGATAATGAAATACATAACCAAATGCGGTTCAGAAGTTTCTGTTGCCAGTACTAAAGCA
TTTACGTCGCAACTTGTGGTGTTGTATATGCTTGCGAACGTTCTTGCGAACAAAACTGATGATCTGCTAGGGGAT
CTTCCTCAAGCTATCGAGAGAGTAATCTGTCTTACTAATGACGAAATGAAGCGTTGGGCGGATGAAATTTGTACT
GCCAAAAGTGCCATCTTCTTAGGGAGAGGACTGAACGCACCTGTAGCATTTGAGGGGCGCGCTAAAGTTGAAGGAA
ATCTCATATATCCATGCCGAGGGTTTCCTCGGTGGAGAGTTGAAGCATGGGCGCTGGCTTTGTTGGACGATAAG
ATCCCTGTAATCGTGACTGTTGCTGACCACGCTTATTTGGATCACATTAAGGCTAACATCGACGAGGTATTGGCA
CGAAACGTTACCGTATACGCGATCGTCGATCAGTATGTTAATATTGAACCACAGGAGCGACTGCATGTAGTAAAA
GTGCCGTTTGTGAGTAAAGAGTTTTCTCCCATCATCCACACAATTCCGATGCAATTGTTATCGTATTATGTCGCG
ATCAAGCTGGGCAAGAACGTTGACAAGCCACGTAACCTGGCGAAAAGTGTTACAACATTCtaa
```

SEQ ID NO: 49 is a reencoded nucleic acid sequence of glutamine-fructose-6-phosphate
amidotransferase (GFA1) originating from *Chlorella* virus 1 (PBCV-1)
```
ATGTGTGGCATCTTTGGAGCAGTGTCAAACAACAACTCTATCGAGGTGTCAATCAAGGGTATTCAGAAGCTAGAA
TATCGTGGGTATGATTCGTGCGGTATTGCGTATACAGATGGGGGTGCGATTGAGCGTATACGTTCTATTGACGGC
ATTGACGATCTGCGTAAGAAAACAATCACAGAATCATCACCAGTGGCCATTGCTCACTCGCGGTGGAGCACCACT
GGAATTCCATCAGTGGTGAACGCACATCCTCATATTTCTCGCGGAACCAGTGGGTGTGAGTCTCGTATCGCGGTA
GTCCACAACGGTATCATTGAAAACTATCAGCAGATCCGAAAATATCTCATCAATCTTGGTTATACGTTTGATAGT
CAAACGGACACAGAGGTCATTGCGCATTTGATTGATTCTCAGTACAATGGGAATATCTTGCACACCGTCCAAATG
GCTGTCAAGCACCTGAAGGGCTCTTATGCCATTGCAGTTATGTGTCATAAAGAGTCTGGTAAAATAGTCGTGGCG
AAACAGAAGTCACCCCTCGTACTTGGAATCGGCTCAGATGGTGCTTACTACATCGCTTCGGACGTGCTGGCGCTG
CCGACAAATAAAGTTGTTTATATTTCAGACGGTTTCTCCGCAGAACTATCTCCAGGGAGTGATGTCCACCATTACGAT
CTTGATGGAAATAAAGTAGAATATGAAGTAGAGGACGTTGAAATGGAACAAACTAGTATGTCTCTCGATAACTTT
GATCATTACATGATTAAGGAAATTAATGAGCAACCAATCAGTATTCTAAACACTATAAAAAATAAAGGGTTCTAT
GCAGAAATATTCGGTGATTTGGCTCATGAAATCTTCCAAAAAATAGACAACATCCTGATACTGGCTTGTGGTACA
AGTTATCACGCCGGTCTTGTAGGAAAACAGTGGATAGAGACCATCTCtAGAATCCCCGTGGATGTTCACATCGCG
AGTGAATACGAACCTACTATTCCGAGAGCGAACACATTGGTAATCACTATTTCACAGTCGGGTGAAACTGCGGAC
ACGATAGCGGCTTTGCAACGGGCCCAAAACGCCGGGATGATTTATACATTGTGTATTTGCAATTCACCCAAAGAGC
ACTCTTGTTCGTGAGAGCATTATGAAGTACATCACGAAATGTGGTTCTGAGGTGTCAGTGGCATCAACGAAGGCG
TTTACTTCTCAGCTCGTAGTACTGTACATGCTGGCAAACGTATTGGCAAATAAAACCGATGATTTGCTGGGGAGAC
CTCCCACAGGCAATAGAACGGGTAATTTGTTTGACAAATGACGAAATGAAACGATGGGCCGACGAAATTTGCACT
GCGAAATCCGCGATCTTCCTGGGAAGAGGACTAAACGCACCAGTTGCCTTTGAGGGAGCGTTGAAGCTCAAAGAA
ATCTCTTACATTCATGCAGAGGGCTTCCTGGGAGGTGAGTTGAAACACGGCCCCCTCGCACTCCTTGATGACAAG
ATTCCTGTTATCGTAACCGTAGCAGATCATGCTTATTTGGACCATATCAAAGCAAATATCGACGAAGTGCTTCAG
AGGAACGTTACGGTATACGCCATAGTAGACCAGTATGTGAACATCGAGCCCCAGGAACGCCTTCACGTCGTCAAG
GTTCCGTTTGTATCCAAAGAATTTTCTCCGATAATTCACACTATCCCGATGCAACTGCTTTCGTATTACGTGGCA
ATTAAGCTTGGAAAGAACGTTGACAAACCAAGGAATCTTGCAAAATCCGTGACTACCTTTTAA
```

SEQ ID NO: 50 is an amino acid sequence of glutamine-fructose-6-phosphate
amidotransferase (GFA1) originating from *Saccharomyces cerevisiae*
```
MCGIFGYCNYLVERSRGEIIDTLVDGLQRLEYRGYDSTGIAIDGDEADSTFIYKQIGKVSALKEEITKQNPNRDV
TFVSHCGIAHTRWATHGRPEQVNCHPQRSDPEDQFVVVHNGIITNFRELKTLLINKGYKFESDTDTECIAKLYLH
LYNTNLQNGHDLDFHELTKLVLLELEGSYGLLCKSCHYPNEVIATRKGSPLLIGVKSEKKLKVDFVDVEFPEENA
GQPEIPLKSNNKSFGLGPKKAREFEAGSQNANLLPIAANEFNLRHSQSRAFLSEDGSPTPVEFFVSSDAASVVKH
TKKVLFLEDDDLAHIYDGELHIHRSRREVGASMTRSIQTLEMELAQIMKGPYDHFMQKEIYEQPESTENTMRGRI
DYENNKVILGGLKAWLPVVRRARRLIMIACGTSYHSCLATRAIFEELSDIPVSVELASDFLDRKCPVFRDDVCVF
VSQSGETADTMLALNYCLERGALTVGIVNSVGSSISRVTHCGVHINAGPEIGVASTKAYTSQYIALVMFALSLSD
DRVSKIDRRIEIIQGLKLIPGQIKQVLKLEPRIKKLCATELKDQKSLLLLGRGYQFAAALEGALKIKEISYMHSE
GVLAGELKHGVLALVDENLPIIAFGTRDSLFPKVVSSIEQVTARKGHPIIICNENDEVWAQKSKSIDLQTLEVPQ
TVDCLQGLINIIPLQLMSYWLAVNKGIDVDFPRNLAKSVTVE
```

-continued

SEQUENCES

SEQ ID NO: 51 is an amino acid sequence of glutamine-fructose-6-phosphate
amidotransferase (GFA1) originating from *Chlorella* virus 1 (PBCV-1)
MCGIFGAVSNNNSIEVSIKGIQKLEYRGYDSCGIAYTDGGAIERIRSIDGIDDLRKKTITESSPVAIAHSRWSTT
GIPSVVNAHPHISRGTSGCESRIAVVHNGIIENYQQIRKYLINLGYTFDSQTDTEVIAHLIDSQYNGNILHTVQM
AVKHLKGSYAIAVMCHKESGKIVVAKQKSPLVLGIGSDGAYYIASDVLALPINKVVYISDGFSAELSPGSMTIYD
LDGNKVEYEVEDVEMEQTSMSLDNFDHYMIKEINEQPISILNTIKNKGFYAEIFGDLAHEIFQKIDNILILACGT
SYHAGLVGKQWIETISRIPVDVHIASEYEPTIPRANTLVITISQSGETADTIAALQRAQNAGMIYTLCICNSPKS
TLVRESIMKYITKCGSEVSVASTKAFTSQLVVLYMLANVLANKTDDLLGDLPQAIERVICLINDEMKRWADEICT
AKSAIFLGRGLNAPVAFEGALKLKEISYIHAEGFLGGELKHGPLALLDDKIPVIVTVADHAYLDHIKANIDEVLA
RNVTVYAIVDQYVNIEPQERLHVVKVPFVSKEFSPIIHTIPMQLLSYYVAIKLGKNVDKPRNLAKSVTTF SEQ ID NO: 52 is a nucleic acid sequence of UDP-N-acetylglucosamine pyrophosphorylase
(QRI1) originating from *Saccharomyces cerevisiae*
ATGACTGACACAAAACAGCTATTCATTGAAGCCGGACAAAGTCAACTTTTCCACAATTGGGAAAGCTTGTCTCGC
AAAGACCAAGAAGAATTGCTTTCAAACCTGGAGCAAATATCTTCCAAGAGGTCCCCTGCAAAACTACTGGAAGAC
TGTCAAAATGCTATTAAATTCTCACTAGCTAACTCTTCTAAGGATACTGGCGTCGAAATTTCACCATTGCCCCCT
ACTTCGTACGAGTCGCTTATTGGCAACAGTAAGAAAGAAAATGAATACTGGCGTTTAGGCCTTGAAGCTATTGGC
AAGGGTGAAGTCGCAGTGATTTTAATGGCTGGCGGACAAGGTACGCGGTTAGGATCCTCTCAACCAAAGGGCTGT
TACGACATTGGATTGCCTTCTAAGAAATCTCTTTTTCAAATTCAAGCTGAAAAGTTGATCAGGTTGCAAGATATG
GTAAAGGACAAAAAGGTAGAAATTCCTTGGTATATTATGACATCAGGCCCCACTAGAGCGGCTACTGAGGCATAC
TTTCAAGAACACAATTATTTTGGCTTGAATAAAGAACAAATTACGTTCTTCAACCAGGGAACCCTGCCTGCCTTT
GATTTAACCGGGAAGCATTTCCTAATGAAAGACCCAGTAAACCTATCTCAATCACCAGATGGAAATGGTGGACTC
TACCGTGCCATCAAGGAAAACAAGTTGAACGAAGACTTTGATAGGAGAGGAATCAAGCATGTTTACATGTACTGT
GTCGATAATGTCCTATCTAAAATCGCAGACCCTGTATTTATTGGTTTTGCCATCAAGCATGGCTTCGAACTGGCC
ACCAAAGCCGTTAGAAAGAGAGATGCGCATGAATCAGTTGGGTTAATTGCTACTAAAAACGAGAAACCATGTGTC
ATAGAATATTCTGAAATTTCCAATGAATTGGCTGAAGCAAAGGATAAAGATGGCTTATTAAAACTACGCGCAGGC
AACATTGTAAATCATTATTACCTAGTGGATTTACTAAAACGTGATTTGGATCAGTGGTGTGAGAATATGCCATAT
CACATTGCGAAGAAGAAAATTCCAGCTTATGATAGTGTTACCGGCAAGTACACTAAGCCTACCGAACCAAACGGT
ATAAAATTAGAGCAATTCATATTTGATGTCTTTGACACTGTACCACTGAACAAGTTTGGGTGCTTAGAAGTAGAT
AGATGCAAAGAATTTTCACCTTTAAAAAACGGTCCTGGTTCTAAGAACGATAATCCTGAGACCAGCAGACTAGCA
TATTTGAAACTAGGAACCTCGTGGTTGGAAGATGCAGGCGCTATTGTAAAAGATGGGGTACTAGTCGAAGTTTCC
AGCAAATTGAGTTATGCAGGTGAAAATCTATCCCAGTTCAAAGGTAAAGTCTTTGACAGAAGTGGTATAGTATTA
GAAAAATAA SEQ ID NO: 53 is an amino acid sequence of UDP-N-acetylglucosamine pyrophosphorylase
(QRI1) originating from *Saccharomyces cerevisiae*
MTDTKQLFIEAGQSQLFHNWESLSRKDQEELLSNLEQISSKRSPAKLLEDCQNAIKFSLANSSKDTGVEISPLPP
TSYESLIGNSKKENEYWRLGLEAIGKGEVAVILMAGGQGTRLGSSQPKGCYDIGLPSKKSLFQIQAEKLIRLQDM
VKDKKVEIPWYIMISGPTRAATEAYFQEHNYFGLNKEQITFFNQGTLPAFDLTGKIHFLMKDPVNLSQSPDGNGGL
YRAIKENKLNEDFDRRGIKHVYMYCVDNVLSKIADPVFIGFAIKHGFELATKAVRKRDAHESVGLIATKNEKPCV
IEYSEISNELAEAKDKDGLLKLRAGNIVNHYYLVDLLKRDLDQWCENMPYHIAKKKIPAYDSVTGKYTKPTEPNG
IKLEQFIFDVFDTVPLNKFGCLEVDRCKEFSPLKNGPGSKNDNPETSRLAYLKLGTSWLEDAGAIVKDGVLVEVS
SKLSYAGENLSQFKGKVFDRSGIVLEK SEQ ID NO: 54 is a nucleic acid sequence of Phosphoglucomutase-1 (PGM1) originating from
*Saccharomyces cerevisiae*
ATGTCACTTCTAATAGATTCTGTACCAACAGTTGCTTATAAGGACCAAAAACCGGGTACTTCAGGTTTACGTAAG
AAGACCAAGGTTTTCATGGATGAGCCTCATTATACTGAGAACTTCATTCAAGCAACAATGCAATCTATCCCTAAT
GGCTCAGAGGGAACCACTTTAGTTGTTGGAGGAGATGGTCGTTTCTACAACGATGTTATCATGAACAAGATTGCC
GCAGTAGGTGCTGCAAACGGTGTCAGAAAGTTAGTCATTGGTCAAGGCGGTTTACTTTCAACACCAGCTGCTTCT
CATATAATTAGAACATACGAGGAAAAGTGTACCGGTGGTGGTATCATATTAACTGCCTCACACAACCCAGGCGGT
CCAGAGAATGATTTAGGTATCAAGTATAATTTACCTAATGGTGGGCCAGCTCCAGAGAGTGTCACTAACGCTATC
TGGGAAGCGTCTAAAAAATTAACTCACTATAAAATTATAAAGAACTTCCCCAAGTTGAATTTGAACAAGCTTGGT
AAAAACCAAAAATATGGCCCATTGTTAGTGGACATAATTGATCCTGCCAAAGCATACGTTCAATTTCTGAAGGAA
ATTTTTGATTTTGACTTAATTAAAAGCTTCTTAGCGAAACAGCGCAAAGACAAAGGGTGGAAGTTGTTGTTTGAC
TCCTTAAATGGTATTACAGGACCATATGGTAAGGCTATATTTGTTGATGAATTTGGTTTACCGGCAGAGGAAGTT
CTTCAAAATTGGCACCCTTTACCTGATTTCGGCGGTTTACATCCCGATCCGAATCTAACCTATGCACGAACTCTT
GTTGACAGGGTTGACCGCGAAAAAATTGCCTTTGGAGCAGCCTCCGATGGTGATGGTGATAGGAATATGATTTAC
GGTTATGGCCCTGCTTTCGTTTCGCCAGGTGATTCTGTTGCCATTATTGCCGAATATGCACCCGAAATTCCATAC
TTCGCCAAACAAGGTATTTATGGCTTGGCACGTTCATTTCCTACATCCTGACATTGATCGTGTTGCAGCAAAA
AAGGGATTAAGATGTTACGAAGTTCCAACCGGCTGGAAATTCTTCTGTGCCTTATTTGATGCTAAAAAGCTATCA
ATCTGTGGTGAAGAATCCTTCGGTACAGGTTCCAATCATATCAGAGAAAAGGACGGTCTATGGGCCATTATTGCT
TGGTTAAATATCTTGGCTATCTACCATAGGCGTAACCCTGAAAAGGAAGCTTCGATCAAAACTATTCAGGACGAA
TTTTGGAACGAGTATGGCCGTACTTTCTTCACAAGATACGATTACGAACATATCGAATGCGAGCAGGCCGAAAAA
GTTGTAGCTCTTTTGAGTGAATTTGTATCAAGGCCAAACGTTTGTGCTCCCACTTCCCAGCTGATGAGTCTTTA
ACCGTTATCGATTGTGGTGATTTTTCGTATAGAGATCTAGATGGCTCCATCTCTGAAAATCAAGGCCTTTTCGTA
AAGTTTTCGAATGGGACTAAATTTGTTTTGAGGTTATCCGGCACAGGCAGTTCTGGTGCAACAATAAGATTATAC
GTAGAAAAGTATACTGATAAAAAGGAGAACTATGGCCAAACAGCTGACGTCTTCTTGAAACCCGTCATCAACTCC
ATTGTAAAATTCTTAAGATTTAAAGAAATTTTAGGAACAGACGAACCAACAGTCCGCACATAG SEQ ID NO: 55 is an amino acid sequence Phosphoglucomutase-1 (PGM1) originating from
*Saccharomyces cerevisiae*
MSLLIDSVPTVAYKDQKPGTSGLRKKTKVFMDEPHYTENFIQATMQSIPNGSEGTTLVVGGDGRFYNDVIMNKIA
AVGAANGVRKLVIGQGGLLSTPAASHIIRTYEEKCTGGGIILTASHNPGGPENDLGIKYNLPNGGPAPESVTNAI
WEASKKLTHYKIIKNFPKLNLNKLGKNQKYGPLLVDIIDPAKAYVQFLKEIFDFDLIKSFLAKQRKDKGWKLLFD
SLNGITGPYGKAIFVDEFGLPAEEVLQNWHPLPDFGGLHPDPNLTYARTLVDRVDREKIAFGAASDGDGDRNMIY -continued

---

SEQUENCES

---

GYGPAFVSPGDSVAIIAEYAPEIPYFAKQGIYGLARSFPTSSAIDRVAAKKGLRCYEVPTGWKFFCALFDAKKLS
ICGEESFGTGSNHIREKDGLWAIIAWLNILAIYHRRNPEKEASIKTIQDEFWNEYGRIFFTRYDYEHIECEQAEK
VVALLSEFVSRPNVCGSHFPADESLTVIDCGDFSYRDLDGSISENQGLFVKFSNGTKFVLRLSGTGSSGATIRLY
VEKYTDKKENYGQTADVFLKPVINSIVKFLRFKEILGTDEPTVRT

SEQ ID NO: 56 is a nucleic acid sequence of UTP--glucose-1-phosphate uridylyltransferase
(UGP1) originating from *Saccharomyces cerevisiae*
ATGTCCACTAAGAAGCACACCAAAACACATTCCACTTATGCATTCGAGAGCAACACAAACAGCGTTGCTGCCTCA
CAAATGAGAAACGCCTTAAACAAGTTGGCGGACTCTAGTAAACTTGACGATGCTGCTCGCGCTAAGTTTGAGAAC
GAACTGGATTCGTTTTTCACGCTTTTCAGGAGATATTTGGTAGAGAAGTCTTCTAGAACCACCTTGGAATGGGAC
AAGATCAAGTCTCCCAACCCGATGAAGTGGTTAAGTATGAAATTATTTCTCAGCAGCCCGAGAATGTCTCAAAC
CTTTCCAAATTGGCTGTTTTGAAGTTGAACGGTGGGCTGGGTACCTCCATGGGCTGCGTTGGCCCTAAATCTGTT
ATTGAAGTGAGAGAGGGAAACACCTTTTTGGATTTGTCTGTTCGTCAAATTGAATACTTGAACAGACAGTACGAT
AGCGACGTGCCATTGTTATTGATGAATTCTTTCAACACTGACAAGGATACGGAACACTTGATTAAGAAGTATTCC
GCTAACAGAATCAGAATCAGATCTTTCAATCAATCCAGGTTCCCAAGAGTCTACAAGGATTCTTTATTGCCTGTC
CCCACCGAATACGATTCTCCACTGGATGCTTGGTATCCACCAGGTCACGGTGATTTGTTTGAATCTTTACACGTA
TCTGGTGAACTGGATGCCTTAATTGCCCAAGGAAGAGAAATATTATTTGTTTCTAACGGTGACAACTTGGGTGCT
ACCGTCGACTTAAAAATTTTAAACCACATGATCGAGACTGGTGCCGAATATATAATGGAATTGACTGATAAGACC
AGAGCCGATGTTAAAGGTGGTACTTTGATTTCTTACGATGGTCAAGTCCGTTTATTGGAAGTCGCCCAAGTTCCA
AAAGAACACATTGACGAATTCAAAAATATCAGAAAGTTTACCAACTTCAACAGCGAATAACTTATGGATCAATCTG
AAAGCAGTAAAGAGGTTGATCGAATCGAGCAATTTGGAGATGGAAATCATTCCAAACCAAAAAACTATAACAAGA
GACGGTCATGAAATTAATGTCTTACAATTAGAAACCGCTTGTGGTGCTGCTATCAGGCATTTTGATGGTGCTCAC
GGTGTTGTCGTTCCAAGATCAAGATTCTTGCCTGTCAAGACCTGTTCCGATTTGTTGCTGGTTAAATCAGATCTA
TTCCGTCTGGAACACGGTTCTTTGAAGTTAGACCCATCCCGTTTTGGTCCAAACCCATTAATCAAGTTGGGCTCG
CATTTCAAAAAGGTTTCTGGTTTTAACGCAAGAATCCCTCACATCCCAAAAATCGTCGAGCTAGATCATTTGACC
ATCACTGGTAACGTCTTTTTAGGTAAAGATGTCACTTTGAGGGGTACTGTCATCATCGTTTGCTCCGACGGTCAT
AAAATCGATATTCCAAACGGCTCCATATTGGAAAATGTTGTCGTTACTGGTAATTTGCAAATCTTGGAACATTGA SEQ ID NO: 57 is an amino acid sequence of UTP--glucose-1-phosphate uridylyltransferase
(UGP1) originating from *Saccharomyces cerevisiae*
MSTKKHTKTHSTYAFESNTNSVAASQMRNALNKLADSSKLDDAARAKFENELDSFFTLFRRYLVEKSSRITLEWD
KIKSPNPDEVVKYEIISQQPENVSNLSKLAVLKLNGGLGTSMGCVGPKSVIEVREGNTFLDLSVRQIEYLNRQYD
SDVPLLLMNSENTDKDTEHLIKKYSANRIRIRSFNQSRFPRVYKDSLLPVPTEYDSPLDAWYPPGHGDLFESLHV
SGELDALIAQGREILFVSNGDNLGATVDLKILNHMIETGAEYIMELTDKTRADVKGGTLISYDGQVRLLEVAQVP
KEHIDEFKNIRKFTNFNINNLWINLKAVKRLIESSNLEMEIIPNQKTITRDGHEINVLQLETACGAAIRHFDGAH
GVVVPRSRFLPVKTCSDLLLVKSDLFRLEHGSLKLDPSRFGPNPLIKLGSHFKKVSGFNARIPHIPKIVELDHLT
ITGNVFLGKDVTLRGTVIIVCSDGHKIDIPNGSILENVVVTGNLQILEH SEQ ID NO: 58 is a nucleic acid sequence of Glucosamine 6-phosphate N-acetyltransferase
(GNA1) originating from *Saccharomyces cerevisiae*
ATGAGCTTACCCGATGGATTTTATATAAGGCGAATGGAAGAGGGGGATTTGGAACAGGTCACTGAGACGCTAAAG
GTTTTGACCACCGTGGGCACTATTACCCCCGAATCCTTCAGCAAACTCATAAAATACTGGAATGAAGCCACAGTA
TGGAATGATAACGAAGATAAAAAAATAATGCAATATAACCCCATGGTGATTGTGGACAAGCGCACCGAGACGGTT
GCCGCTACGGGGAATATCATCATCGAAAGAAAGATCATTCATGAACTGGGGCTATGTGGCCACATCGAGGACATT
GCAGTAAACTCCAAGTATCAGGGCCAAGGTTTGGGCAAGCTCTTGATTGATCAATTGGTAACTATCGGCTTTGAC
TACGGTTGTTATAAGATTATTTTAGATTGCGATGAGAAAAATGTCAAATTCTATGAAAAATGTGGGTTTAGCAAC
GCAGGCGTGGAAATGCAAATTAGAAAATAG SEQ ID NO: 59 is an amino acid sequence of Glucosamine 6-phosphate N-acetyltransferase
(GNA1) originating from *Saccharomyces cerevisiae*
MSLPDGFYIRRMEEGDLEQVTETLKVLTTVGTITPESFSKLIKYWNEATVWNDNEDKKIMQYNPMVIVDKRTETV
AATGNIIIERKIIHELGLCGHIEDIAVNSKYQGQGLGKLLIDQLVTIGFDYGCYKIILDCDEKNVKFYEKCGFSN
AGVEMQIRK SEQ ID NO: 60 is a nucleic acid sequence of phosphoacetylglucosamine mutase (PCM1)
originating from *Saccharomyces cerevisiae*
ATGAAGGTTGATTACGAGCAATTGTGCAAACTCTACGATGACACGTGCCGCACAAAGAATGTGCAGTTCAGTTAC
GGTACGGCCGGATTCAGAACGCTGGCCAAGAATTTGGATACGGTGATGTTCAGTACTGGTATACTGGCGGTTCTC
AGGTCGCTGAAGCTTCAGGGTCAGTATGTGGGGGTGATGATCACGGCGTCGCACAACCCATACCAGGACAACGGG
GTCAAGATCGTGGAACCAGACGGATCGATGCTTTTGGCCACATGGGAGCCATATGCCATGCAGTTGGCCAATGCG
GCCTCTTTTGCCACTAATTTTGAAGAATTTCGTGTTGAGTTGGTCCAAGCTGATTGAACACGAAAAGATTGATTTG
AATACAACCGTCGTGCCTCACATCGTGGTTGGGAGAGACTCTAGGGAAAGTAGTCCATACTTGCTGCGCTGCTTG
ACTTCCTCCATGGCCAGCGTCTTCCACGCGCAAGTTTTGGACCTAGGCTGTGTCACTACGCCTCAATTGCATTAC
ATTACTGATTTGTCCAACAGGCGGAAACTGGAAGGAGACACAGCGCCAGTTGCCACAGAACAGGACTACTATTCG
TTCTTTATAGGAGCCTTCAACGAGCTCTTCGCCACGTATCAGCTGGAGAAGAGGCGTGTCGTCCCAAAATTGTTC
ATAGACACAGCCAATGGTATCGGTGGTCCACAGTTGAAAAAACTACTGGCCTCCGAAGATTGGGACGTGCCAGCG
GAGCAAGTTGAGGTAATCAACGACAGGTCCGATGTTCCAGAACTGTTGAATTTTGAATGCGGTGCGGATTATGTG
AAGACTAACCAGAGATTACCCAAGGGTCTTTCTCCATCCTCGTTTGATTCGCTATATTGCTCCTTTGATGGTGAC
GCAGACAGGGTTGTGTTCTACTATGTCGACTCAGGATCAAAATTTCATTTGTTGGATGGTGACAAAATTTCCACT
TTGTTTGCAAAGTTCTTGTCTAAACAACTAGAATTGGCACACCTAGAACATTCTTTGAAGATTGGTGTTGTGCAA
ACTGCCTATGCAAACGGCAGTTCCACCGCTTACATAAAAAAATACTGGTAGCCCGTGTCTTGCACTAAGACA
GGTGTTAAACACTTGCATCATGAAGCTGCCACTCAGTACGATATTGGCATTTATTTCGAAGCAAATGGACATGGT
ACGATTATATTCAGCGAAAAATTTCATCGAACTATCAAATCTGAATTATCCAAGTCCAAGTTAAATGGTGATACG
TTAGCTTTGAGAACTTTGAAGTGTTTCTCTGAATTGATTAATCAGACCGTGGGAGATGCTATTTCAGACATGCTT
GCTGTCCTTGCTACTTTGGCGATTTTGAAAATGTCGCCAATGGATTGGGATGAAGAGTATACTGATTTGCCCAAC
AAGCTGGTTAAGTGCATCGTTCCTGATAGGTCAATTTTCCAAACCACGGACCAGGAAAGAAAATTGCTCAATCCA
GTGGGGGTTGCAAGACAAGATAGATCTTGTGGTAGCCAAGTATCCCATGGGAAGAAGCTTTGTCAGAGCCAGTGGT

SEQUENCES

ACGGAGGATGCGGTGAGGGTTTATGCGGAATGTAAGGACTCCTCTAAGTTAGGTCAATTTTGTGACGAAGTGGTG
GAGCACGTTAAGGCATCTGCTTGA

SEQ ID NO: 61 is an amino acid sequence of phosphoacetylglucosamine mutase (PCM1)
originating from *Saccharomyces cerevisiae*
MKVDYEQLCKLYDDTCRTKNVQFSYGTAGFRTLAKNLDTVMFSTGILAVLRSLKLQGQYVGVMITASHNPYQDNG
VKIVEPDGSMLLATWEPYAMQLANAASFATNFEEFRVELAKLIEHEKIDLNTTVVPHIVVGRDSRESSPYLLRCL
TSSMASVFHAQVLDLGCVTTPQLHYITDLSNRRKLEGDTAPVATEQDYYSFFIGAFNELFATYQLEKRLSVPKLF
IDTANGIGGPQLKKLLASEDWDVPAEQVEVINDRSDVPELLNFECGADYVKTNQRLPKGLSPSSFDSLYCSFDGD
ADRVVFYYVDSGSKFHLLDGDKISTLFAKFLSKQLELAHLEHSLKIGVVQTAYANGSSTAYIKNTLHCPVSCTKT
GVKHLHHEAATQYDIGIYFEANGHGTIIFSEKFHRTIKSELSKSKLNGDTLALRTLKCFSELINQTVGDAISDML
AVLATLAILKMSPMDWDEEYTDLPNKLVKCIVPDRSIFQTTDQERKLLNPVGLQDKIDLVVAKYPMGRSFVRASG
TEDAVRVYAECKDSSKLGQFCDEVVEHVKASA SEQ ID NO: 62 is the nucleic acid sequence of promotor pTDH3
CTGCTGTAACCCGTACATGCCCAAAATAGGGGGGGGGTTACACAGAATATATAACATCGTAGGTGTCTGGGTGAA
CAGTTTATTCCTGGCATCCACTAAATATAATGGAGCCCGCTTTTTAAGCTGGCATCCAGAAAAAAAAAGAATCCC
AGCACCAAAATATTGTTTTCTTCACCAACCATCAGTTCATAGGTCCATTCTCTTAGCGCAACTACAGAGAACAGG
GGCACAAACAGGCAAAAAACGGGCACAACCTCAATGGAGTGATGCAACCTGCCTGGAGTAAATGATGACACAAGG
CAATTGACCCACGCATGTATCTATCTCATTTTCTTACACCTTCTATTACCTTCTGCTCTCTCTGATTTGGAAAAA
GCTGAAAAAAAAGGTTGAAACCAGTTCCCTGAAATTATTCCCCTACTTGACTAATAAGTATATAAAGACGGTAGG
TATTGATTGTAATTCTGTAAATCTATTTCTTAAACTTCTTAAATTCTACTTTTATAGTTAGTCTTTTTTTTAGTT
TTAAAACACCAAGAACTTAGTTTCGAATAAACACACATAAACAAACAAA SEQ ID NO: 63 is the nucleic acid sequence of promotor pTDH3.Sk
CAATTCATCGGCCCTTTTAGCGGCTACCCGCGCCATCTAAATGATAGGGCGGGTGACACTATGGTAAATCCCATA
ATTAGGTGTCTGGGTGAGTGGTTCTGATGCCGGCATCCACTAAATATATTGGAGCCCATTTTTTACGCGGGCTTC
CAGAAAAAAAGAGAATCCCAGCACCAAAAGGTGGTTCTCTTCACCAACCATCAGATCATAGGTCCACAACCACAC
ATAACAGGGGCACAAAAAGGCAAAAAACGGACATAACCTCAATGGAGTGATGCAAATTGACTGGAGCAAAAGCTG
ACACAAGGCATTGATTGACCTACGCATGTATCTGTATTCTTTTCTTACACCTTCTATTACCTTCTAACTCTTTGG
GTTGGAAAAAACTGAAAAAAAAGGTTGGGACCTGGTTCCCCCAAGTTGTCCCCCTACTTGGTTATTAAATATATA
AAGACAGCAAGTGTTGATTATAATCTTGTAAATCTATAGTTCTTAATCTATACTTCTATTTATATTTTAAATTAG
TCTTTTTATTTCCAAGTCCCCAAGAACTTAGTTTCGAATAAACACACACAAATAAACACA SEQ ID NO: 64 is the nucleic acid sequence of promotor pTDH3-1.sba
GCAGCGCTTCTTCCGCTCTAGTTTTTATAGTTATTATTACTACCACCTTAAAAATACGTAAATACTCAAAATAGT
AGTGATATTCCCAACCTTATTCATCCAAGGCACATCATCATCATCAGCCATTCATCTTTCACCTGCCATTAGTAA
CCCGTCTTCTCATTGAGCGGGTTACGGCAGCCACAGGCCACATTCCGAATGCTGGGTGAGCGGTCCCTTTTCCA
GCATCCACTAAATATCTCCGATCCCGCTTTTTAATCTGGCTTCCTGAAAAAAAGAGAATCCCAGCACCAAAAAAT
GGCTCTCTTCACCAACCATCAGATCATAGGTCCCATTCTCTTACCGCAACCGTACAGAACAGGGGAAAACGGGTA
CAACCTCAATGGAGTGATGCAAACTGACTGGAGCAAAAAGCTGACACAAGGCAATCGACCTACGTGTCTGTCTAT
TTTCTCACACCTTCTATTACCTTCTAACTCTCTGGGTTGGAAAAAACTGAAAAAAAGGTTGAGACCAGTTTCCAC
AAATCATCCCCCTGTTTGATTAATAAATATATAAAGACGACAACTATCGATCATAAACTCATAAAACTATAACTC
CTTTACACTTCTTATTTTATAGTTATTCTATTTTAATTCTTATTGATTTTAAAACCCCAAGAACTTAGTTTCGAA
AACACACACACACAAACAATTAAAA SEQ ID NO: 65 is the nucleic acid sequence of promotor pTDH3.Sar
GAGCTAAATATCAGCCCTTCGGGTCCTGCCTGCTACCCGGTCCTGTTCGAATAAAAACGCGGGTAACACGACCCA
GTAACACCTGTCGTTGGGTGTCTGGGTCAGAAGTTCTGATACCGGCTTCCACTAAATAGATTGGGTTCCGCTCTT
TACGCTGGCTTCCTGAAAAAAGAGATTCCGGGCACCAAAAAATTGGTCTCTTTGCCAACCATCAGATCATAGGTC
CATTCTCTTACCATAACCACACAGGATAGGGGCACCACAGGCGAAATGGGCACAAAATCTCAATGGAGTGATGC
AAATTAGCTGGAACAAAAGCTGACACAAGGCAATTAACCTGCGCATGTATCCATCTCCTTTTCTTACACCTTCTC
TTACGTTCTAACTGTTTGGGTTGGAAAAAATTAAAAAAAAAAAGGTTGAGACCAGTTTCCCCAAATCGTCCCCCTAC
TTGATTCATAAATATATAAAGACGACAACTATTGATTATAATCTTGTAAATCTATAACTCTTTACTTTCTCCTAT
TTATAATTTAACTTAATCTTTTTAGATTTAAAACCCCAAGAACTTAGTTTCGAACAAACACACACAAATAAACAA
AA SEQ ID NO: 66 is the nucleic acid sequence of promotor pENO2
CGCTCAGCATCTGCTTCTTCCCAAAGATGAACGCGGCGTTATGTCACTAACGACGTGCACCAACTTGCGGAAAGT
GGAATCCCGTTCCAAAACTGGCATCCACTAATTGATACATCTACACACCGCACGCCTTTTTTCTGAAGCCCACTT
TCGTGGACTTTGCCATATGCAAAATTCATGAAGTGTGATACCAAGTCAGCATACACCTTCACCTAGGGTAGTTTCCA
TGGTTGTATTGATCATTTGGTTCATCGTGGTTCATTAATTTTTTTTCTCCATTGCTTTCTGGCTTTGATCTTACT
ATCATTTGGATTTTTGTCGAAGGTTGTAGAATTGTATGTGACAAGTGGCACCAAGCATATATAAAAAAAAAAAGC
ATTATCTTCCTACCAGAGTTGATTGTTAAAAACGTATTTATAGCAAACGCAATTGTAATTAATTCTTATTTTGTA
TCTTTTCTTCCCTTGTCTCAATCTTTTATTTTTATTTTATTTTTCTTTTCTTAGTTTCTTTCATAACACCAAGCA
ACTAATACTATAACATACAATAATA SEQ ID NO: 67 is the nucleic acid sequence of promotor pTEF3
GGCTGATAATAGCGTATAAACAATGCATACTTTGTACGTTCAAAATACAATGCAGTAGATATATTTATGCATATT
ACATATAATACATATCACATAGGAAGCAACAGGCGCGTTGGACTTTTAATTTTCGAGGACCGCGAATCCTTACAT
CACACCCAATCCCCCACAAGTGATCCCCCACACACCATAGCTTCAAAATGTTTCTACTCCTTTTTTACTCTTCCA
GATTTTCTCGGCATCCGCGCATCGCCGTACCACTTCAAAACACCCAAGCACAGCATACTAAATTTCCCCTCTTTC
TTCCTCTAGGGTGTCGTTAATTACCCGTACTAAAGGTTTGGAAAAGAAAAAAGAGACCGCCTCGTTTCTTTTTCT
TCGTCGAAAAAGGCAATAAAAATTTTTATCACGTTTCTTTTTCTTGAAATTTTTTTTTTTGATTTTTTTCTCTT
TCGATGACCTCCCATTGATATTTAAGTTAATAAACGGTCTTCAATTTCTCAAGTTTCAGTTTCATTTTTCTTGTT
CTATTACAACTTTTTTTACTTCTTGCTCATTAGAAAGAAAGCATAGCAATCTAATCTAAGTTTTAATTACAAA

SEQUENCES

SEQ ID NO: 68 is the nucleic acid sequence of promotor pTEF1
GTTTAGCTTGCCTCGTCCCCGCCGGGTCACCCGGCCAGCGACATGGAGGCCCAGAATACCCTCCTTGACAGTCTT
GACGTGCGCAGCTCAGGGGCATGATGTGACTGTCGCCCGTACATTTAGCCCATACATCCCCATGTATAATCATTT
GCATCCATACATTTTGATGGCCGCACGGCGCGAAGCAAAAATTACGGCTCCTCGCTGCAGACCTGCGAGCAGGGA
AACGCTCCCCTCACAGACGCGTTGAATTGTCCCCACGCCGCGCCCCTGTAGAGAAATATAAAAGGTTAGGATTTG
CCACTGAGGTTCTTCTTTCATATACTTCCTTTTAAAATCTTGCTACGATACAGTTCTCACATCACATCCGAACAT
AAACAACC SEQ ID NO: 69 is the nucleic acid sequence of promotor pTEF1.ago
GTTTAGCTTGCCTCGTCCCCGCCGGGTCACCCGGCCAGCGACATGGAGGCCCAGAATACCCTCCTTGACAGTCTT
GACGTGCGCAGCTCAGGGGCATGATGTGACTGTCGCCCGTACATTTAGCCCATACATCCCCATGTATAATCATTT
GCATCCATACATTTTGATGGCCGCACGGCGCGAAGCAAAAATTACGGCTCCTCGCTGCAGACCTGCGAGCAGGGA
AACGCTCCCCTCACAGACGCGTTGAATTGTCCCCACGCCGCGCCCCTGTAGAGAAATATAAAAGGTTAGGATTTG
CCACTGAGGTTCTTCTTTCATATACTTCCTTTTAAAATCTTGCTACGATACAGTTCTCACATCACATCCGAACAT
AAACAACC SEQ ID NO: 70 is the nucleic acid sequence of promotor pTEF1.Sba
CGCCAACAAACCTTCGAACACTTTAATTTTCGAGGACCGCAGATCCTCACATCACACCCACACCCAAGACTGCTT
CCCCCACACACCCTGCATCTGTACACTTTCTTCTGCTCTGTTTTTCTCTCCGGCGTTCTCTCGGGTCGCCCGCAT
CGCCGCGCCGGCTGGAACCGCCCACGCACCGCATATTGCAAATCGCCTGCCCCCTCTTGCTCCTTTTTGAGGGCG
CGCCGTTACCCGCGCCCAGGGTCCGGAAAAAGAAACAAGGCTCTACCGCGTTTCTTTTTCCTTGTCGAAAAAGGC
AAAAATGAAAATTTTTATCACGTTTCTTTTTTTTTGAAAAATTTTTTTTTTGGTTTTTTTTCTTTCGATGGCCTC
CCATTGATATTTAAGTTAATAAATGGTTTTCAGTTTTCAAGTTTCAGTTTGTGTTCTTCTTTGCTAACTTTCACT
TACACCTCGAAAGAAAGTATAGCAATCTAATCTTAGTTTTAATTACAA SEQ ID NO: 71 is the nucleic acid sequence of promotor pPDC1
TTATTTACCTATCTCTAAACTTCAACACCTTATATCATAACTAATATTTCTTGAGATAAGCACACTGCACCCATA
CCTTCCTTAAAAACGTAGCTTCCAGTTTTTGGTGGTTCCGGCTTCCTTTCCCGATTCCGCCCGCTAAACGCATATT
TTTGTTGCCTGGTGGCATTTGCAAAATGCATAACCTATGCATTTAAAAGATTATGTATGCTCTTCTGACTTTTCG
TGTGATGAGGCTCGTGGAAAAAATGAATAATTTATGAATTTGAGAACAATTTTGTGTTGTTACGGTATTTTACTA
TGGAATAATCAATCAATTGAGGATTTTATGCAAATATCGTTTGAATATTTTTCCGACCCTTTGAGTACTTTTCTT
CATAATTGCATAATATTGTCCGCTGCCCCTTTTTCTGTTAGACGGTGTCTTGATCTACTTGCTATCGTTCAACAC
CACCTTATTTTCTAACTATTTTTTTTTTAGCTCATTTGAATCAGCTTATGGTGATGGCACATTTTTGCATAAACC
TAGCTGTCCTCGTTGAACATAGGAAAAAAAAATATATAAACAAGGCTCTTTCACTCTCCTTGCAATCAGATTTGG
GTTTGTTCCCTTTATTTTCATATTTCTTGTCATATTCCTTTCTCAATTATTATTTTCTACTCATAACCTCACGCA
AAATAACACAGTCAAATCAATCAAA SEQ ID NO: 72 is the nucleic acid sequence of promotor pCCW12
aaccagggcaaagcaaaataaaagAAACTTAATACGTTATGCCGTAATGAAGGGCTACCAAAAACGATAATCTCA
ACTGTAAACAGGTACAATGCGGACCCTTTTGCCACAAAACATACATCATTCATTGCCGGAAAAAGAAAGAAGTGA
AGACAGCAGTGCAGCCAGCCATGTTGCGCCAATCTAATTATAGATGCTGGTGCCCTGAGGATGTATCTGGAGCCA
GCCATGGCATCATGCGCTACCGCCGGATGTAAAATCCGACACGCAAAAGAAAACCTTCGAGGTTGCGCACTTCGC
CCACCCATGAACCACACGGTTAGTCCAAAAGGGGCAGTTCAGATTCCAGATGCGGGAATTAGCTTGCTGCCACCC
TCACCTCACTAACGCTGCGGTGTGCGGATACTTCATGCTATTTATAGACGCGCGTGTCGGAATCAGCACGCGCAA
GAACCAAATGGGAAAATCGGAATGGGTCCAGAACTGCTTTGAGTGCTTTGGCGTCTGATTTCCGTTTTGG
GAATCCTTTGCCGCGCGCCCCTCTCAAAACTCCGCACAAGTCCCAGAAAGCGGGAAAGAAATAAAACGCCACCAA
AAAAAAAAATAAAAGCCAATCCTCGAAGCGTGGGTGGTAGGCCCTGGATTATCCCGTACAAGTATTTCTCAGGAG
TAAAAAAACCGTTTGTTTTGGAATTCCCCATTTCGCGGCCACCTACGCCGCTATCTTTGCAACAACTATCTGCGA
TAACTCAGCAAATTTTGCATATTCGTGTTGCAGTATTGCGATAATGGGAGTCTTACTTCCAACATAACGGCAGAA
AGAAATGTGAGAAAATTTTGCATCCTTTGCCTCCGTTCAAGTATATAAAGTCGGCATGCTTGATAATCTTTCTTT
CCATCCTACATTGTTCTAATTATTCTTATTCTCCTTTATTCTTTCCTAACATACCAAGAAATTAATCTTctgtca
ttcgcttaaacactatatcaata SEQ ID NO: 73 is the nucleic acid sequence of promotor pCCW12.Sm
CGTTGTGCTGTAGTGAAGGAAGACTAAAAAGGATAATCACAGTTGTAAAGAGGTATAATGCGGACCCTTTTGCCA
CAAAACACACATCTTTCGTTTCCAAAATAAGAAAGAAGAAAGCAAAAAGATTAGCAGCCACGTTGCTGCGATCTA
ATTATAGACGGTGGCGTCATCATTCTCACCCAAGATTGTGTCTTGAACCTGCCACGGGTCCTGCGTTATCGCCGG
ATGTAAAACTAGACATGCAAAAAAAGGACCTTCCAGGTAGCGTGCTCCACACCACCCATGACCACCACAGTTAGT
CCAAAAGAGGCAGCACCACTTCCCGATGGGGGAATTAGATTGCTGCCACCCTCACCTCACTAATGCTGCGGTGTG
CGGATATGCCCTGCTATATATAGCTCCGCGTTTTTGAACCAGCACAGCGCGAGCACCAAAAAGGAAAATCGCATA
GGCCCAGAACTGATTTCAGCACGGGCTATTGGCGTTGGGTTTCCGTTCTGGGAAACCTTCGCCGCGCGTCCCCCTCA
CAAACCTCCGCACAAGTTCGAGCAAGCGGGAAAAAACGAAAAACGCCATTAATACTAAATAAAGCAAATCCTCGA
AGCGTGGGTGGCAAGCCCCTGGATTTTTCCGCACAAGTACTCTTCTCAGGAGTAAAAAAACCCGTTTGTTTTGGA
ATTCCCCATTTCGCGGCCATCTACGCCGGTATCTTCGCAATATCTATCAGCGATAACTCAGCAATTTTAATATTC
GTGTTGCAGTGCTGCGATAGCGGGAGTCTTGTTTGTAACATAACGGCAGAAAGGAATGAGAGAAAATTTTCCATT
CTTTGGCCTCCGTTCAAGTATATAAAGCCGGCATGCTTGGTAATCTTTCTCTCTCTTCTGTATTGTTTCTATAAT
ACTTTTATCTTCTAATTATTTTCTGAAAAAACCAAGAAATTAATCTTCTGTCATTCGCTTAAACACTATATCAAT
A SEQ ID NO: 74 is the nucleic acid sequence of promotor pCCW12.Sk
TGTAAAATCCTACACGCAAAAAACCTCTTGGGTTGCGCGTTTTCCACCACCCACGACCCGCACAATCAATCCAAA
AGGGGCAACGCCAGTTCCCAATGCGGGAATTAGCTCCTCACCCCCCTCACCCGCTAACGCTGCGGTGTGCGGACA
CGCAGCAGTATTTATAGATCCTCGTGTTGGAACCAGCCCGCGTGAGCACCAAATTGGAAAGTCGCAATGGGCCCA
GAACCGCTTTCAGTACTGGGCCATTGGCGTCTAGTTTCCGTTTTGAGCGTCCTTCGCCGCGTCTCTCTGTGAAAT
CCCCGCACAAGTCTGAGCAGGCAAAAAAAAAAAAACGCCACCAAAAATAAATAAAGCCAATCCTCGAAGGATGAGT
AGGAAAGGAAGCCCCTGGTTTTTTCCCGCACGAATATTTTTCAGGAGTGAAAAAATCCGTTTGTTTTGGAATTCC
CCATTTCGCGCTCACCTACGCCGGTATCTTTGGAACAACTATCAGCGATAACTCAGCAAAATTTGCATATCCGTG

SEQUENCES

CTGCAATAGTGCGATAGTGGGATTGGGAGTCTTGTTGCATCATAACGGCAGAAAGGAATGAATAAAAATTTTCCG
TTCTTTGTCTCCGTTCAAGTATATAAAGTCGGCATGCTTGATTATCTTTTCTTCTCTTCTACTACATTTCTATTT
CACTTTCTACTCTATTCTTCCCTGAAAAACCCAAGAAATAATCTTCTGTCATTCGCTTAAACAATATATCAAAA

SEQ ID NO: 75 is the nucleic acid sequence of promotor pCCW12.Sba
ACCATGCCACGGTGCTGGCCCCACTTCCACCCACGACCCGCACGGTTGGCCCGAAAGGGGCAACACCAGTTCCCA
ATACGGAAATTAGTCCGCCACCACCCTCACCTCGCTAGAGCTGCGGTGTGCGGGCGTGCATCGCTATTTATAGAC
ATGCCTGCTGGCGTCACCGCGCGCGAGCACCAAACAGGAAATCGCACTGGGCCCAGAACCACGCTATGCGCTGG
GCCGATGGCGTCCGGTTTCCCTTTGGGAGCCCCCTGCCACGTTCGCCTAACAAATCCCCGCACCGGCTTGAGAAA
AAAGCGAAAAGCGAAAAAAAAAAATCAACGCCACCAAAATTAAAAAAAAAGAGCCATCCTCGAAGGGTGAATAGT
AGCCCCTGACTTTTCCCGCACAGACAGACACCTTTCAGGAGTGAACAAAAAAGCAGTTTGTTTTGGAATTCCCCC
ATTTCGCGGTGGCCTGCGCAGGTATCTCTGCGTCAACTATCAGCGATAACTCAGCAAATTTTGCATATTCGTGTT
GCGATACTACGATAATGGGAGTCTGTCGCCTAATAACGGCAACAAGGAATGAGAGAGAAAAATTTTCTTCATTCT
CCAGCTCCCGTTCAAGTATATAAGGTCGGCATGGTCGATTGTCTTTCCTTCTCTTCAGTTACGTCTCTCTATTTA
CATTATTCTTATTTTTATTTAATAAAAACCCCAAGAAATTAATCTTCTGTCATTCGCTTAAACACTATATCAAAA SEQ ID NO: 76 is the nucleic acid sequence of promotor pCCW12.Sar
AAAAAACAACCTTCTGCCAACCTGCGTGCTTCTCACCACCCATGACCCACACAATTGACCCGAATGGGGCAACTC
CAGTTCCCAATACGGGAATTAACTCGCCACCATATTTACCGCGTTGAAGCTGTGGTGTGCGGACACTCCGTACTA
TTTATAGACCCACGCGGTGGAACCAGCACGCGCGCGCACTAAACAGGAAAATCGCATTGAGTCCAGAACCGCCAC
CAGCACTTGGCCATTGGCGTCTAATTTCCGTTTTCGGCGCCCCTCACCGCGTCCTTCTAACAAAGCGCGCACAAG
CTTGAGCAAGTGAAAGAAATTAAAAATAAAAAACCGCCACCAAAACAAATAAAGCAATCTTCGAAGTGTGGGT
TGGTGGGAAGCCCCTGGCTTTTCCCGCACCAGTCGTTTTCAGGAGTAAAAAAATACCCGTTTGTTTTGGAATTCC
CCATTTCGCGGCGACCTGCGCCGGTATCTTTGCAACAACTATTTGCGGTAACTCAGCAAAATTTGCATATTCGTG
TTGGGATATTGCGATAGTGGGAGTCTTGTTGCATAATAACGGTAAAAAGAAGTGAAGGAAAAAAATTTGCATCCT
TTAGTCTCAGTTCAAGTATATAAAGTCGGGATATTCAATTATCTTTCTTTCTCTTGCTCAAAGGTTTCTATATTT
TTTTTATAGTATTTCTTTTGTTATAAAATACCAAGAAATTAATCTTCTGTCATTCGCTTAAATACTACATCAATA SEQ ID NO: 77 is the nucleic acid sequence of promotor pNUP57
TCATCTGCGCAATGACTATCAAGACCTTCTGCAAGAATTTCAAATCTCACTGAAAATCTTGACCGAAAAGTGTCT
TGAAAACCCATCAAGCCTGCAAAACCTATCTTTGACATTAGTCTCCATTATAAAAACGGCATAGTTGGGAGAAAA
CTTTCCATACTTCAATTGTGGACTGATATAAGTATTTTAGTTTTGCCCGCATGATCTCCCACATGGCACAGCA
GTTCTCTCATAGGAAAATAGTACAATAGCTACGTGATATAATCTAAATAATTGTTGCCAATGTGTAATTATATCA
TTTTGAACGTACGCGAAATGGATTATTTTCAAAAATTTTGTTTCTTGAAATGAGTAAAAGCAAAAGTCCAACTCT
CCAAGTCGATGTAAACAACTTTTTGCCAAAGGGACTGAAAGACTAAATCGAGGATTATCCCGTTCAAACTATTCC
AGAAACGCTCGTTAGTAACAAAAGACATACCTTGTTGACCAATTGATCAC SEQ ID NO: 78 is the nucleic acid sequence of promotor pCCW10.ago
GGTACCACGGCAACCTCGTTCGCTGTTCATCCCCTTCGTCACACAGGACGTTGGATGCCGTAAGCAGCGTTGCTT
TTGATCCTCAgGATCGGCCGGGTAACCCGCGGCtGCTTCTATTTTAGTATTCATATCTCAAGCACATCCATTCCG
GCCGTTTGGGGGCGCCGCCGCACTCGTGTCCATTCCTACCGTGGCACTTAGGGCTATCCTGTCGGAGCGCCCCGC
CGACCGCCTTATCGGCACCAAAAGTAGAAGCCCCGGCCCCGCGTGGCTCAGACTCACCATCGGTGCTATTTACTT
TTCGATCAGATCGCGGCGCGCGGTGGCCGGCATTTCCGGAAGCGGCCACGGAGCAGAGGTGGCGCATTCGAATCG
CATACGTCTTCGCCACGCCGGAAAAAAAATTTTCGGCTATATAAGGAGAGGCGGCCGTCTTGCTGCAGGCAGTTT
CACTTTCTCTAAAACCAAAGAACATCGATTTCTTTAGTCACTCGCTTCCTTACACCGAACTCGAGGCGGCCGC SEQ ID NO: 79 is the nucleic acid sequence of promotor pCWP2
CTAGCCTCCCCTTTTTATTTTGTGCGGTCACCGCAAGGGACAAAGCTTTTCTTAGAAAACCGTCTGAGAAGCATA
ACGTACGCCATCCCCTAGACATATTAATAATGCTACAGATACTATGCTGCTCGTCTTTTTTTGACGACCCTTTTA
TTGCAATGTGCAACTAATGGCAAACAACCACATAGTATCACAGTATTACATTGCCTCCACCGATGCGGATGTTAG
GGCGCCAAGTCTGTCATGAAGCATGTTCCTGTCATAATCTTGTATGCAAAATACCGCGTTCTGCGCCACTGATAT
GCTAGGCAGCAGCAACCTATGCAGAAGATTGCTTTTCCCACGCCTGTTTTACGTCTCCAGGGCACTTGAAACAAT
GCAGCGATCGCCGCCACAACACGCCAAAGAGAAGCGAAAGTGGGCTGGGCCGGTTCAGTTTCGGCAGAGGTAAA
CAACACGAACTGAACTGCCTTAGCTCCGAAGGGCAATTCCACAGGCACTCCGCGGGGCCCGGCCAAGGCCCAAAA
GGCGTGGAATATGCGCGTTTTGGGGCCATAACACCCAGTACCACGGCCGGAACGGGCCATATAATAAGTTTTTCA
CTCTCAAGAATGGTAAACGTAAATAGGAACATCCCACTACCCTAGAAATTGCGGAAATTTCGCGCTTATCATTAG
AAAATCTGGAACCGTCCTTTTTCCTCTTTCTTGCATTTCCCTTTCCGTATTATTGCCATTCTTTAACTGCATTTG
GGGAACCGTAGACCAAAAGCCAAACAGAGAAATGTAACGTTCTAAAAAAAAAAAACAACGAAAAAATTGAAAAATAA
GATACAATAATCGTATATAAATCAGGCTTCTTGTTCATCATTTTCAATTCTCTTCTTGCCATCCCTTTTCCTATC
TTTGTTCTTTTCTTCTCATAATCAAGAATAAATAACTTCATCA SEQ ID NO: 80 is the nucleic acid sequence of promotor pRPLA1
TCAAGTTGGATACTGATCTGATCTCTCCGCCCTACTACCAGGGACCCTCATGATTACCGCTCGAATGCGACGTTT
CCTGCCTCATAAAACTGGCTTGAAAATATTTATTCGCTGAACAGTAGCCTAGCTTATAAAAATTTCATTTAATTA
ATGTAATATGAAAACTCACATGCCTTCTGTTTCTAAAATTGTCACAGCAAGAAATAACATTACCATACGTGATCT
TATTAAACTCTAGTATCTTGTCTAATACTTCATTTAAAAGAAGCCTTAACCCTGTAGCCTCATCTATGTCTGCTA
CATATCGTGAGGTACGAATATCGTAAGATGATACCACGCAACTTTGTAATGATTTTTTTTTTTTTTCATTTTTTAAA
GAATGCCTTTACATGGTATTTGAAAAAAATATCTTTATAAAGTTTGCGATCTCTTCTGTTCTGAATAATTTTTAG
TAAAAGAAATCAAAAGAATAAAGAAATAGTCCGCTTTGTCCAATACAACAGCTTAAACCGATTATCTCTAAAATA
ACAAGAAGAA SEQ ID NO: 81 is the nucleic acid sequence of promotor pCUP1
CGGCAAACTTCAACGATTTCTATGATGCATTTTATAATTAGTAAGCCGATCCCATTACCGACATTTGGGCGCTAT
ACGTGCATATGTTCATGTATGTATCTGTATTTAAAACACTTTTGTATTATTTTTCCTCATATATGTGTATAGGTT
TATACGGATGATTTAATTATTACTTCACCACCCTTTATTTCAGGCTGATATCTTAGCCTTGTTACTAGTTAGAAA
AAGACATTTTTGCTGTCAGTCACTGTCAAGAGATTCTTTTGCTGGCATTTCTTCTAGAAGCAAAAGAGCGATGC
GTCTTTTCCGCTGAACCGTTCCAGCAAAAAAGACTACCAACGCAATATGGATTGTCAGAATCATATAAAAGAGAA

---

SEQUENCES

```
GCAAATAACTCCTTGTCTTGTATCAATTGCATTATAATATCTTCTTGTTAGTGCAATATCATATAGAAGTCATCG
AAATAGATATTAAGAAAAACAAACTGTACAATCAATCAATCATCACATAAA
```

SEQ ID NO: 82 is the nucleic acid sequence of promotor pMET6
```
CCACAGGAAATATTTCACGTGACTTACAAACAGAGTCGTACGTCAGGACCGGAGTCAGGTGAAAAAATGTGGGCC
GGTAAAGGGAAAAAACCAGAAACGGGACTACTATCGAACTCGTTTAGTCGCGAACGTGCAAAAGGCCAATATTTT
TCGCTAGAGTCATCGCAGTCATGGCAGCTCTTTCGCTCTATCTCCCGGTCGCAAAACTGTGGTAGTCATAGCTCG
TTCTGCTCAATTGAGAACTGTGAATGTGAATATGGAACAAATGCGATAGATGCACTAATTTAAGGGAAGCTAGCT
AGTTTTCCCAACTGCGAAAGAAAAAAGGAAAGAAAAAAAAATTCTATATAAGTGATAGATATTTCCATCTTTAC
TAGCATTAGTTTCTCTTTTACGTATTCAATATTTTTGTTAAACTCTTCCTTTATCATAAAAAAGCAAGCATCTAA
GAGCATTGACAACACTCTAAGAAACAAAATACCAATATAATTTCAAAGTACATATCAAAA
```

SEQ ID NO: 83 is the nucleic acid sequence of promotor pMET25
```
TTACATTATCAATCCTTGCGTTTCAGCTTCCACTAATTTAGATGACTATTTCTCATCATTTGCGTCATCTTCTAA
CACCGTATATGATAATATACTAGTAACGTAAATACTAGTTAGTAGATGATAGTTGATTTTTATTCCAACACTAAG
AAATAATTTCGCCATTTCTTGAATGTATTTAAAGATATTTAATGCTATAATAGACATTTAAATCCAATTCTTCCA
ACATACAATGGGAGTTTGGCCGAGTGGTTTAAGGCGTCAGATTTAGGTGGATTTAACCTCTAAAATCTCTGATAT
CTTCGGATGCAAGGGTTCGAATCCCTTAGCTCTCATTATTTTTTGCTTTTTCTCTTGAGGTCACATGATCGCAAA
ATGGCAAATGGCACGTGAAGCTGTCGATATTGGGGAACTGTGGTGGTTGGCAAATGACTAATTAAGTTAGTCAAG
GCGCCATCCTCATGAAAACTGTGTAACATAATAACCGAAGTGTCGAAAAGGTGGCACCTTGTCCAATTGAACACG
CTCGATGAAAAAAATAAGATATATATAAGGTTAAGTAAAGCGTCTGTTAGAAAGGAAGTTTTTCCTTTTTCTTGC
TCTCTTGTCTTTTCATCTACTATTTCCTTCGTGTAATACAGGGTCGTCAGATACATAGATACAATTCTATTACCC
CCATCCATACA
```

SEQ ID NO: 84 is the nucleic acid sequence of promotor pSAM1
```
GAAACGGACGTAAGACGGAAATAGAATTTGAAGATAAAGTTATATATCACTACACACGAATACTTTCTTTTTTTT
TTTTCACAGGAAAACTGTGGTGGCGCCCTTGCCTACTAGTGCATTTCTTTTTTCGGGTTCTTGTCTCGAGAAAT
TTTAGCCTCATCGTAGTTTTTCACTCTGGTATCGATGAAAAAGGGAAGAGTAAAAAGTTTCCGTTTAGTACTTA
ATGGGATTGGTTTGGGACGTATATATCGACTGGTGTTGTCTGTTATTCATCGTTGTTTTTCGGTTAGCTTCGAAA
AAAAAATAGAGTAAAAACCAGGAATTTACCCTAAAAACAAGAAAAAATAAGATAAACGAAAAT
```

SEQ ID NO: 85 is the nucleic acid sequence of terminator tTPI1
```
GATTAATATAATTATATAAAAATATTATCTTCTTTTCTTTATATCTAGTGTTATGTAAAATAAATTGATGACTAC
GGAAAGCTTTTTTATATTGTTTCTTTTTCATTCTGAGCCACTTAAATTTCGTGAATGTTCTTGTAAGGGACGGTA
GATTTACAAGTGATACAACAAAAAGCAAGGCGCTTTTTCTAATAAAAAGAAGAAAAGCATTTAACAATTGAACAC
CTCTATATCAACGAAGAATATTACTTTGTCTCTAAATCCTTGTAAAATGTGTACGATCTCTATATGGGTTACTCA
```

SEQ ID NO: 86 is the nucleic acid sequence of terminator tMET25
```
GTGTGCGTAATGAGTTGTAAAATTATGTATAAACCTACTTTCTCTCACAAGTACTATACTTTTATAAAACGAACT
TTATTGAAATGAATATCCTTTTTTTCCCTTGTTACATGTCGTGACTCGTACTTTGAACCTAAATTGTTCTAACAT
CAAAGAACAGTGTTAATTCGCAGTCGAGAAGAAAAATATGGTGAACAAGACTCATCTACTTCATGAGACTACTTT
ACGCCTCCTATAAAGCTGTCACACTGGATAAATTTATTGTAGGACCAAGTTACAAAAGAGGATGATGGAGGTTT
```

SEQ ID NO: 87 is the nucleic acid sequence of terminator tDIT1
```
TAAAGTAAGAGCGCTACATTGGTCTACCTTTTTGTTCTTTTACTTAAACATTAGTTAGTTCGTTTTCTTTTTCTC
ATTTTTTTATGTTTCCCCCCCAAAGTTCTGATTTTATAATATTTTATTTCACACAATTCCATTTAACAGAGGGGG
AATAGATTCTTTAGCTTAGAAAATTAGTGATCAATATATATTTGCCTTTCTTTTCATCTTTTCAGTGATATTAAT
GGTTTCGAGACACTGCAATGGCCCTAGTTGTCTAAGAGGATAGATGTTACTGTCAAAGATGATATTTTGAATTTC
```

SEQ ID NO: 88 is the nucleic acid sequence of terminator tRPL3
```
GAAGTTTTGTTAGAAAATAAATCATTTTTTAATTGAGCATTCTTATTCCTATTTTATTTAAATAGTTTTATGTAT
TGTTAGCTACATACAACAGTTTAAATCAAATTTTCTTTTTCCCAAGTCCAAAATGGAGGTTTATTTTGATGACCC
GCATGCGATTATGTTTTGAAAGTATAAGACTACATACATGTACATATATTTAAACATGTAAACCCGTCCATTATA
TTGCTTACTTTCTTCTTTTTTGCCGTTTTGACTTGGACCTCTGGTTTGCTATTTCCTTACAATCTTTGCTACAAT
```

SEQ ID NO: 89 is the nucleic acid sequence of terminator tRPL3.sm
```
GAAGTTTTTAAAGCATTTTTTAGACACTTCTCATTTTTCTAAGTTTTTTAAAATAGTTTTATGTATTTACTACG
TATCACAATTTGAAATAATTCATCTTCCCAAAAAACTAAGATTTTTATCCTTGTCACGATCCGTAACCAGTTTAT
AATATTTTAGAGCTTATACACGTACGTATACACACGTGTCGGTACATGAGAATTACGTTCAAAATTATTCACTTT
TTTTTTCTCTGCCGTTTTACTTTTGAACTCTGTCTCGCTATTTCCTTACAATCTTCGCTACAATACCACTTGCCC
TTGG
```

SEQ ID NO: 90 is the nucleic acid sequence of terminator tRPL3.sba
```
GAAGTTTTCTGACAAAAACATAACGTTTTTTCCAATCATTTCTTATTTTTCCGGTTTATTTAAATAGTTTTTATG
TACTATTATACGTATGACTATTTAACTTAAATTCTTCCTCCCAAGAAATCTCCCAAGTTTTTCATTATCATGGCA
TACACCACTATCAGTTACAAAATGGTAGCTCAACCATATATATATCTCTATATACACATATAAATGCAAACAGGT
CCAAGTCACCGCTCACTGCAGTTTCTTTTGCCGTTTTGACTTCGATCTCTGCTTGGCTATTTTCTCACAATCCT
```

SEQ ID NO: 91 is the nucleic acid sequence of terminator tRPL41B
```
GCGGATTGAGAGCAAATCGTTAAGTTCAGGTCAAGTAAAAATTGATTTCGAAAACTAATTTCTCTTATACAATCC
TTTGATTGGACCGTCATCCTTTCGAATATAAGATTTTGTTAAGAATATTTAGACAGAGATCTACTTTATATTTA
ATATCTAGATATTACATAATTTCCTCTCTAATAAAATATCATTAATAAAATAAAAATGAAGCGATTTGATTTTGT
GTTGTCAACTTAGTTTGCCGCTATGCCTCTTGGGTAATGCTATTATTGAATCGAAGGGCTTTATTATATTACCCT
```

SEQ ID NO: 92 is the nucleic acid sequence of terminator tRPL15A
```
GCTGGTTGATGGAAAATATAATTTTATTGGGCAAACTTTTGTTTATCTGATGTGTTTTATACTATTATCTTTTTA
ATTAATGATTCTATATACAAACCTGTATATTTTTTCTTTAACCAATTTTTTTTTTTTATAGACCTAGAGCTGTACT
```

| SEQUENCES |
| --- |

```
TTTATTCTGCTATCAAGCAAACCCCTACCCCCTCTTCTCAATCCTCCCCTCAGGCAGAACTTATCTACCTGTATC
AAGGAGCGGACGAGGGAGTCCTAATTGTTCTACGTATACCAATGCTAGCAGCTTACATAGGTGGTGGCACTACCA
```

SEQ ID NO: 93 is the nucleic acid sequence of terminator tRPL15A.sba
```
GCTGGCTGATGAAAAATATAGTTCTGTTGGGCAAGCATTTGTTTACCTAGCATCTCTTTTATACTATTATTATCT
TTATATTTGATGATTTTATATACAAGTTGTATACCTTTTCTTTAACCAATTTTTTTTTTTCTAATGGTGCACCTA
GAAGTACATTTTTTCTCACCAATAGATAGTCAAGATACTCCCAGCCTCTATGGCGTTACCACGGAGCCGACAAGG
GAAAGCTGCTTATCTTACATATGCAGATGCCAAGGCCCGTTACAGGCCGCCTTATTGATGTTTAGAAATAGCTTC
```

SEQ ID NO: 94 is the nucleic acid sequence of terminator tIDP1
```
TCGAATTTACGTAGCCCAATCTACCACTTTTTTTTTTTCATTTTTTAAAGTGTTATACTTAGTTATGCTCTAGGAT
AATGAACTACTTTTTTTTTTTTTTTTTTTTACTGTTATCATAAATATATATACCTTATTGTTGTTTGCAACCGTCGG
TTAATTCCTTATCAAGGTTCCCCAAGTTCGGATCATTACCATCAATTTCCAACATTTTCATGAGTTCTTCTTCTT
CATTACCGTGTTTTAGGGGGCTGTTCGCACTTCTAATAGGGCTATCACCAAGCTGTTCTAATTCGTCCAAAAGTT
```

SEQ ID NO: 95 is the nucleic acid sequence of terminator tTEF1.sba
```
GGAGATTGATAGGACTTTTCTAGTTGCATATCTTTTATTTTTAAATCTTATCTATTAGTTAATTTTTTGTAATTT
ATCCTTATATATATAGTTTGGTTATTCTAAAACATCATTTCAGTATCTAAAACCTCTCTTATTCATTACCTTTTT
ATTTAATGGTTTTTGCTACAGGCAAAAATTTAATGGTTTTTGCTACAGGCAAAAATCCCGCCGTGGACTTATTCC
ACGTTAACTCGGTTACAGGGTCATGAACCATTTTGTCAATTATCGAAATAACTTCTTCAAAAGTCCCTCTTACTT
```

SEQ ID NO: 96 is a nucleic acid sequence of Glutamine synthetase (GLN1) originating from
*Saccharomyces cerevisiae*
```
ATGGCTGAAGCAAGCATCGAAAAGACTCAAATTTTACAAAAATATCTAGAACTGGACCAAAGAGGTAGAATAATT
GCCGAATACGTTTGGATCGATGGTACTGGTAACTTACGTTCCAAAGGTAGAACTTTGAAGAAGAGAATCACATCC
ATTGACCAATTGCCAGAATGGAACTTCGACGGTTCTTCTACCAACCAAGCGCCAGGCCACGACTCTGACATCTAT
TTGAAACCCGTTGCTTACTACCCAGATCCCTTCAGGAGAGGTGACAACATTGTTGTCTTGGCCGCATGTTACAAC
AATGACGGTACTCCAAACAAGTTCAACCACAGACACGAAGCTGCCAAGCTATTTGCTGCTCATAAGGATGAAGAA
ATCTGGTTTGGTCTAGAACAAGAATACACTCTATTTGACATGTATGACGATGTTTACGGATGGCCAAAGGGTGGG
TACCCAGCTCCACAAGGTCCTTACTACTGTGGTGTTGGTGCCGGTAAGGTTTATGCCAGAGACATGATCGAAGCT
CACTACAGAGCTTGTTTGTATGCCGGATTAGAAATTTCTGGTATTAACGCTGAAGTCATGCCATCTCAATGGGAA
TTCCAAGTCGGTCCATGTACCGGTATTGACATGGGTGACCAATTATGGATGCCAGATACTTTTTGCACAGAGTG
GCAGAAGAGTTTGGTATCAAGATCTCATTCCATCCAAAGCCATTGAAGGGTGACTGGAACGGTGCCGGTTGTCAC
ACTAACGTTTCCACCAAGGAAATGAGACAACCAGGTGGTATGAAATACATCGAACAAGCCATCGAGAAGTTATCC
AAGAGACACGCTGAACACATTAAGTTGTACGGTAGCGATAACGACATGAGATTAACTGGTAGACATGAAACCGCT
TCCATGACTGCCTTTTCTTCTGGTGTCGCCAACAGAGGTAGCTCAATTAGAATCCCAAGATCCGTCGCCAAGGAA
GGTTACGGTTACTTTGAAGACCGTAGACCAGCTTCCAACATCGACCCATACTTGGTTACAGGTATCATGTGTGAA
ACTGTTTGCGGTGCTATTGACAATGCTGACATGACGAAGGAATTTGAAAGAGAATCTTCATAA
```

SEQ ID NO: 97 is an amino acid sequence of Glutamine synthetase (GLN1) originating from
*Saccharomyces cerevisiae*
```
MAEASIEKTQILQKYLELDQRGRIIAEYVWIDGTGNLRSKGRTLKKRITSIDQLPEWNEDGSSTNQAPGHDSDIY
LKPVAYYPDPFRRGDNIVVLAACYNNDGTPNKFNHRHEAAKLFAAHKDEEIWFGLEQEYTLFDMYDDVYGWPKGG
YPAPQGPYYCGVGAGKVYARDMIEAHYRACLYAGLEISGINAEVMPSQWEFQVGPCTGIDMGDQLWMARYFLHRV
AEEFGIKISFHPKPLKGDWNGAGCHTNVSTKEMRQPGGMKYIEQAIEKLSKRHAEHIKLYGSDNDMRLTGRHETA
SMTAFSSGVANRGSSIRIPRSVAKEGYGYFEDRRPASNIDPYLVTGIMCETVCGAIDNADMTKEFERESS
```

SEQ ID NO: 98 is a nucleic acid sequence of Glutamate synthase (GLT1) originating from
*Saccharomyces cerevisiae*
```
ATGCCAGTGTTGAAATCAGACAATTTCGATCCATTGGAAGAAGCTTACGAAGGTGGGACAATTCAAAACTATAAC
GATGAACACCATCTTCATAAATCTTGGGCAAATGTGATTCCGGACAAACGAGGACTTTACGACCCTGATTATGAA
CATGACGCTTGTGGTGTCGGTTTCGTAGCAAATAAGCATGGTGAACAGTCTCACAAGATTGTTACTGACGCTAGA
TATCTTTTAGTGAATATGACACATCGTGGTGCCGTCTCATCTGATGGGAACGGTGACGGTGCCGGTATTCTGCTA
GGTATTCCTCACGAATTTATGAAAAGAGAATTCAAGTTAGATCTTGATCTAGACATACCTGAGATGGGCAAATAC
GCCGTAGGTAACGTCTTCTTCAAGAAGAACGAAAAAAATAACAAGAAAAATTTAATTAAGTGTCAGAAGATTTTC
GAGGATTTAGCTGCATCCTTCAACTTATCCGTATTAGGTTGGAGAAACGTCCCCGTAGATTCTACTATTTTAGGA
GACGTTGCATTATCTCGTGAACCTACTATTCTACAGCCATTATTGGTTCCATTGTATGATGAAAAACAACCGGAG
TTTAATGAAACTAAATTTAGAACTCAATTGTATCTTTTAAGGAAGGAGGCCTCTCTTCAAATAGGACTGGAAAAC
TGGTTCTATGTTTGTTCCCTAAACAATACCACCATTGTTTACAAGGGTCAATTGACGCCAGCTCAAGTGTATAAC
TACTATCCCGACTTGACTAATGCGCATTTCAAATCCCACATGGCGTTGGTCCATTCAAGATTTTCCACTAATACT
TTCCCCTCTTGGGATAGAGCTCAACCTTTACGTTGGCTAGCTCATAATGGTGAAATTAACCACCTTAAGAGGTAAC
AAGAATTGGATGCGCTCCAGAGAAGGTGTGATGAATTCAGCAACTTTCAAAGATGAGTTAGACAAACTATACCCA
ATTATCGAAGAAGGTGGTTCTGATTCAGCTGCATTGGATAACGTTTTAGAACTATTGACTATTAATGGCACATTA
TCTCTACCTGAAGCTGTTATGATGATGGTTCCTGAAGCGTATCATAAGGATATGGATTCTGACCTAAAAGCATGG
TACGACTGGGCTGCATGTCTGATGGAACCTTGGGATGGTCCAGCTTTGTTAACTTTCACTGATGGACGTTACTGT
GGTGCTATATTGGATAGAAATGGTTTAAGACCTTGTCGTTATTACATCACTAGTGACAACAGAGTTATCTGTGCT
TCAGAGGTAGGTGTCATTCCTATCGAAAATTCATTGGTTGTTCAAAAAGGTAAACTGAAGCCAGGTGATTTATTC
CTAGTGGATACTCAATTGGGTGAAATGGTCGATACTAAAAAGTTAAAATCTCAAATCTCAAAAAGACAAGATTTT
AAGTCTTGGTTATCCAAAGTCATCAAGTTAGACGACTTGTTATCAAAAACCGCTAATTTGGTTCCTAAAGAATTT
ATATCACAGGATTCATTGTCTTTGAAAGTTCAAAGTGACCCACGTCTATTGGCCAATGGTTATACCTTCGAACAA
GTCACATTTCTGTTAACTCCAATGGCTTTAACAGGTAAAGAAGCTTTAGGTTCGATGGGTAACGATGCGCCCACTG
GCTTGTTTAAATGAAAATCCTGTCTTACTTTATGATTATTTCAGACAATTGTTTGCTCAAGTGACCAATCCTCCA
ATTGACCCAATTCGTGAAGCAAATGTTATGTCGTTAGAATGTTATGTCGGACCTCAAGGCAACCTTTTGGAAATG
CATTCATCTCAATGTGATCGTTTATTATTGAAATCTCCTATTTTGCATTGGAATGAGTTCCAAGCTTTGAAAAAC
ATTGAAGCTGCTTACCCATCATGGTCTGTAGCAGAAATTGATATCACATTCGACAAGAGTGAGGGTCTATTGGGC
TATACCGACACAATTGATAAAATCACTAAGTTAGCGAGCGAAGCAATTGATGATGGTAAAAAGATCTTAATAATT
ACTGACAGGAAAATGGGTGCCAACCGTGTGTTTCCATCTCCTCTTTGATTGCAATTTCATGTATTCATCATCACCTA
```

-continued

SEQUENCES

```
ATCAGAAACAAGCAGCGTTCCCAAGTTGCTTTGATTTTGGAAACAGGTGAAGCCAGAGAAATTCACCATTTCTGT
GTCCTACTAGGTTATGGTTGTGATGGTGTTTATCCATACTTAGCCATGGAAACTTTGGTCAGAATGAATAGAGAA
GGTCTACTTCGTAATGTCAACAATGACAATGATACACTTGAGGAAGGGCAAATACTAGAAAATTACAAGCACGCT
ATTGATGCAGGTATCTTGAAGGTTATGTCTAAAATGGGTATCTCCACTCTAGCATCCTACAAAGGTGCTCAAATT
TTTGAAGCCCTAGGTTTAGATAACTCTATTGTTGATTTGTGTTTCACAGGTACTTCTTCCAGAATTAGAGGTGTA
ACTTTCGAGTATTTGGCTCAAGATGCCTTTTCTTTACATGAGCGTGGTTATCCATCCAGACAAACCATTAGTAAA
TCTGTTAACTTACCAGAAAGTGGTGAATACCACTTTAGGGATGGTGGTTCAAACACGTCAACGAACCAACCGCA
ATTGCTTCGTTACAAGATACTGTCAGAAACAAAAATGATGTCTCTTGGCAATTATATGTAAAGAAGGAAATGGAA
GCAATTAGAGACTGTACACTAAGAGGACTGTTAGAATTAGATTTTGAAAATTCTGTCAGTATCCCTCTAGAACAA
GTTGAACCATGGACTGAAATTGCCAGAAGATTTGCGTCAGGTGCAATGTCTTATGGTTCTATTTCTATGGAAGCT
CACTCTACATTGGCTATTGCCATGAATCGTTTAGGGGCCAAATCCAATTGTGGTGAAGGTGGTGAAGACGCAGAA
CGTTCTGCTGTTCAAGAAAACGGTGATACTATGAGATCTGCTATCAAACAAGTTGCTTCCGCTAGATTCGGTGTA
ACTTCATACTACTTGTCAGATGCTGATGAAATCCAAATTAAGATTGCTCAGGGTGCTAAGCCGGGTGAAGGTGGT
GAACTACCAGCCCACAAAGTGTCTAAGGATATCGCAAAAACCAGGCACTCCACCCCTAATGTTGGGTTAATCTCT
CCTCCTCCTCATCACGATATTTATTCCATTGAAGATTTGAAACAACTGATTTATGATTTGAAATGTGCTAATCCA
AGAGCGGGAATTTCTGTAAAGTTGGTTTCCGAAGTTGGTGTTGGTATTGTTGCCTCTGGTGTAGCTAAGGCTAAA
GCCGATCATATCTTAGTTTCTGGTCATGATGGTGGTACAGGTGCTGCAAGATGGACGAGTGTCAAATATGCGGGT
TTGCCATGGGAATTAGGTCTAGCTGAAACTCACCAGACTTTAGTCTTGAATGATTTAAGACGTAATGTTGTTGTC
CAAACCGATGGTCAATTGAGAACTGGGTTTGATATTGCTGTTGCAGTTTTATTAGGGGCAGAATCTTTTACCTTG
GCAACAGTTCCATTAATTGCTATGGGTTGTGTTATGTTAAGAAGATGTCACTTGAACTCTTGTGCTGTTGGTATT
GCCACACAAGATCCATATTTGAGAAGTAAGTTTAAGGGTCAGCCCGAACATGTTATCAACTTCTTCTATTACTTG
ATCCAAGATTTAAGACAAATCATGGCCAAGTTAGGATTCCGTACCATTGACGAAATGGTGGGTCATTCTGAAAAA
TTAAAGAAAAGGGACGACGTAAATGCCAAAGCCATAAATATCGATTTATCTCCTATTTTGACCCCAGCACATGTT
ATTCGTCCAGGTGTTCCAACCAAGTTCACTAAGAAACAAGACCACAAACTCCACACCCGTCTAGATAATAAGTTA
ATCGATGAGGCTGAAGTTACTTTGGATCGTGGCTTACCAGTGAATATTGACGCCTCTATAATCAATACTGATCGT
GCACTCGGTTCTACTTTATCTTACAGAGTCTCGAAGAAATTTGGTGAAGATGGTTTGCCAAAGGACACCGTTGTC
GTTAACATAGAAGGTTCAGCGGGTCAATCTTTTGGTGCTTTCCTAGCTTCTGGTATCACTTTTATCTTGAATGGT
GATGCTAATGATTATGTTGGTAAAGGTTTATCCGGTGGTATTATTGTCATTAAACCACCAAAGGATTCTAAATTC
AAGAGTGATGAAAATGTAATTGTTGGTAACACTTGTTTCTATGGTGCTACTTCTGGTACTGCATTCATTTCAGGT
AGTGCCGGTGAGCGTTTCGGTGTCAGAAACTCTGGTGCCACCATCGTTGTTGAGAGAATTAAGGGTAACAATGCC
TTTGAGTATATGACTGGTGGTCGTGCCATTGTCTTATCACAAATGGAATCCCTAAACGCCTTCTCTGGTGCTACT
GGTGGTATTGCATACTGTTTAACTTCCGATTACGACGATTTTGTTGGAAAGATTAACAAAGATACTGTTGAGTTA
GAATCATTATGTGACCCGGTCGAGATTGCGTTTGTTAAGAATTTGATCCAGGAGCATTGGAACTACACACAATCT
GATCTAGCAGCCAGGATTCTCGGTAATTTCAACCATTATTGAAAGATTTCGTTAAAGTCATTCCAACTGATTAT
AAGAAAGTTTTGTTGAAGGAGAAAGCAGAAGCTGCCAAGGCAAAGGCTAAGGCAACTTCAGAATACTTAAAGAAG
TTTAGATCGAACCAAGAAGTTGATGACGAAGTCAATACTCTATTGATTGCTAATCAAAAAGCTAAAGAGCAAGAA
AAAAAGAAGAGTATTACTATTTCAAATAAGGCCACTTTGAAGGAGCCTAAGGTTGTTGATTTAGAAGATGCAGTT
CCAGATTCCAAACAGCTAGAGAAGAATAGCGAAAGGATTGAAAAAACACGTGGTTTTATGATCCACAAACGTCGT
CATGAGACACACAGAGATCCAAGAACCAGAGTTAATGACTGGAAAGAATTTACTAACCCTATTACCAAGAAGGAT
GCCAAATATCAAACTGCGAGATGTATGGATTGTGGTACACCATTCTGTTTATCTGATACCGGTTGTCCCCTATCT
AACATTATCCCCAAGTTTAATGAATTGTTATTCAAGAACCAATGGAAGTTGGCACTGGAACAAATTGCTAGAGACA
AACAATTTCCCAGAATTCACTGGAAGAGTATGTCCAGCACCCTGTGAGGGAGCTTGTACACTAGGTATTATTGAA
GACCCAGTCGGCATAAAATCGGTTGAAAGAATTATCATTGACAATGCTTTCAAGGAAGGATGGATTAAGCCTTGT
CCACCAAGTACACGCACTGGCTTTACAGTGGGTGTCATTGGTTCTGGTCCAGCAGGTTTAGCGTGTGCTGATATG
TTGAACCGTGCCGGACATACGGTCACTGTTTATGAAAGATCCGACCGTTGTGGTGGGTTATTGATGTATGGTATT
CCAAACATGAAGTTGGATAAGGCTATAGTGCAACGTCGTATTGATCTATTGAGTGCCGAAGGTATTGACTTTGTT
ACCAACACCGAATTGGTAAAACCATAAGCATGGATGAGCTAAAGAACAAGCACAATGCAGTAGTGTATGCTATC
GGTTCTACCATTCCACGTGACTTACCTATTAAGGGTCGTGAATTGAAGAATATTGATTTTGCCATGCAGTTGTTG
GAATCTAACACAAAAGCTTTATTGAACAAAGATCTGGAAATCATTCGTACAAGAACGTCCAAGGTAAGAAAGTAATT
GTTGTCGGTGGTGGTGACACAGGTAACGATTGTTTAGGTACATCGTAAGACACGGTGCAGCATCAGTTTTGAAT
TTCGAATTGTTGCCTGAGCCACCAGTGGAACGTGCCAAAGACAATCCATGGCCTCAATGGCCGCGTGTCATGAGA
GTGGACTACGGTCATGCTGAAGTGAAAGAGCATTATGGTAGAGACCCTCGTGAATACTGCATCTTGTCCAAGGAA
TTTATCGGTAACGATGAGGGTGAAGTCACTGCCATCAGAACTGTGCGCTGAAATGGAAGAAGTCACAAAGTGGC
GTATGGCAAATGGTAGAAATTCCCAACAGTGAAGAGATCTTTGAAGCCGATATCATTTTGTTGTCTATGGGTTTC
GTGGGTCCTGAATTGATCAATGGCAACGATAACGAAGTTAAGAAGACAAGACGTGGTACGATTGCCACACTCGAC
GACTCCTCATACTCTATTGATGGAGGGAAAGACTTTTGCATGTGGTGACTGTAGAAGAGGGCAATCTTTGATTGTC
TGGGCCATCCAAGAAGGTAGAAAATGTGCTGCCTCTGTCGATAAGTTCCTAATGGACGGCACTACGTATCTACCA
AGTAATGGTGGTATCGTTCAACGTGATTACAAACTATTGAAAGAATTAGCTAGTCAAGTCTAA
```

SEQ ID NO: 99 is an amino acid sequence of Glutamate synthase (GLT1) originating from
*Saccharomyces cerevisiae*

```
MPVLKSDNFDPLEEAYEGGTIQNYNDEHHLHKSWANVIPDKRGLYDPDYEHDACGVGFVANKHGEQSHKIVTDAR
YLLVNMTHRGAVSSDGNGDGAGILLGIPHEFMKREFKLDLDLDIPEMGKYAVGNVFFKKNEKNNKKNLIKCQKIF
EDLAASFNLSVLGWRNVPVDSTILGDVALSREPTILQPLLVPLYDEKQPEFNETKERTQLYLLRKEASLQIGLEN
WFYVCSLNNTTIVYKGQLTPAQVYNYYPDLTNAHFKSHMALVHSRFSTNTFPSWDRAQPLRWLAHNGEINTLRGN
KNWMRSREGVMNSATFKDELDKLYPIIEEGGSDSAALDNVLELLTINGILSLPEAVMMMVPEAYHKDMDSDLKAW
YDWAACLMEPWDGPALLTFTDGRYCGAILDRNGLRPCRYYITSDDRVICASEVGVIPIENSLVVQKGKLKPGDLF
LVDTQLGEMVDTKKLKSQISKRQDFKSWLSKVIKLDDLLSKTANLVPKEFISQDSLSLKVQSDPRLLANGYTFEQ
VTFLLTPMALTGKEALGSMGNDAPLACLNENPVLLYDYFRQLFAQVINPPIDPIREANVMSLECYVGPQGNLLEM
HSSQCDRLLLKSPILHWNEFQALKNIEAAYPSWSVAEIDITFDKSEGLLGYTDTIDKITKLASEAIDDGKKILII
TDRKMGANRVSISSLIAISCIHHHLIRNKQRSQVALILETGEAREIHHFCVLLGYGCDGVYPYLAMETLVRMNRE
GLLRNVNNDNDTLEEGQILENYKHAIDAGILKVMSKMGISTLASYKGAQIFEALGLDNSIVDLCFTGTSSRIRGV
TFEYLAQDAFSLHERGYPSRQTISKSVNLPESGEYHFRDGGYKHVNEPTAIASLQDTVRNKNDVSWQLYVKKEME
AIRDCTLRGLLELDFENSVSIPLEQVEPWTEIARRFASGAMSYGSISMEAHSTLAIAMNRLGAKSNCGEGGEDAE
RSAVQENGDTMRSAIKQVASARFGVTSYYLSDADEIQIKIAQGAKPGEGGELPAHKVSKDIAKTRHSTPNVGLIS
PPPHHDIYSIEDLKQLIYDLKCANPRAGISVKLVSEVGVGIVASGVAKAKADHILVSGHDGGTGAARWTSVKYAG
LPWELGLAETHQTLVLNDLRRNVVVQTDGQLRTGFDIAVAVLLGAESFTLATVPLIAMGCVMLRRCHLNSCAVGI
```

-continued

---

SEQUENCES

---

ATQDPYLRSKFKGQPEHVINFFYYLIQDLRQIMAKLGFRTIDEMVGHSEKLKKRDDVNAKAINIDLSPILTPAHV
IRPGVPTKFTKKQDHKLHTRLDNKLIDEAEVTLDRGLPVNIDASIINTDRALGSTLSYRVSKKFGEDGLPKDTVV
VNIEGSAGQSFGAFLASGITFILNGDANDYVGKGLSGGIIVIKPPKDSKFKSDENVIVGNTCFYGATSGTAFISG
SAGERFGVRNSGATIVVERIKGNNAFEYMTGGRAIVLSQMESLNAFSGATGGIAYCLTSDYDDFVGKINKDTVEL
ESLCDPVEIAFVKNLIQEHWNYTQSDLAARILGNFNHYLKDFVKVIPTDYKKVLLKEKAEAAKAKAKATSEYLKK
FRSNQEVDDEVNILLIANQKAKEQEKKKSITISNKATLKEPKVVDLEDAVPDSKQLEKNSERIEKTRGFMIHKRR
HETHRDPRTRVNDWKEFTNPITKKDAKYQTARCMDCGTPFCLSDIGCPLSNIIPKFNELLFKNQWKLALDKLLET
NNFPEFTGRVCPAPCEGACTLGIIEDPVGIKSVERIIIDNAFKEGWIKPCPPSTRTGFTVGVIGSGPAGLACADM
LNRAGHTVTVYERSDRCGGLLMYGIPNMKLDKAIVQRRIDLLSAEGIDFVINTEIGKTISMDELKNKHNAVVYAI
GSTIPRDLPIKGRELKNIDFAMQLLESNTKALLNKDLEIIREKIQGKKVIVVGGGDTGNDCLGTSVRHGAASVLN
FELLPEPPVERAKDNPWPQWPRVMRVDYGHAEVKEHYGRDPREYCILSKEFIGNDEGEVTAIRTVRVEWKKSQSG
VWQMVEIPNSEEIFEADIILLSMGFVGPELINGNDNEVKKTRRGTIATLDDSSYSIDGGKTFACGDCRRGQSLIV
WAIQEGRKCAASVDKFLMDGTTYLPSNGGIVQRDYKLLKELASQV

SEQ ID NO: 100 is the nucleic acid sequence of terminator tTDH3
GTGAATTTACTTTAAATCTTGCATTTAAATAAATTTTCTTTTTATAGCTTTATGACTTAGTTTCAATTTATATAC
TATTTTAATGACATTTTCGATTCATTGATTGAAAGCTTTGTGTTTTTTCTTGATGCGCTATTGCATTGTTCTTGT
CTTTTTCGCCACATGTAATATCTGTAGTAGATACCTGATACATTGTGGATGCTGAGTGAAATTTTAGTTAATAAT
GGAGGCGCTCTTAATAATTTTGGGGATATTGGCTTTTTTTTTTAAAGTTTACAAATGAATTTTTTCCGCCAGGAT SEQ ID NO: 101 is a reencoded nucleic acid sequence of hyaluronan synthase (HASA)
originating from *Chlorella* virus CviK1
ATGCTTTTCAGTTGTTTGTCCTTCGTGATCTGCCATCTTAGTTTTATTTTGCGTTATTACAAGAGGCTTCTAAAA
GTGACGATGGGAAAGAACATTATAATAATGGTGAGTTGGTACACAATAATAACTTCCAACATCATCGCCGTCGGT
GGGGCGTCTCTGATTTTGGCCCCAGCCATCACTGGATACATCTTGCACTGGAACATCGCCTTGTCAACCATCTGG
GGAGTTTCCGCTTATGGGATATTCGTGTTCGGATTCTTCCTGGCTCAGGTTTTATTTAGTGAGCTAAATCGTAAA
AGACTAAGAAAGTGGATTTCTCTAAGACCAAAGGGTTGGAACGACGTGGCTGTCATCATAGCTGGTTAC
AGGGAAGACCCGTACATGTTTCAGAAATGCCTTGAGTCAGTAAGGGACTCTGACTATGGTAATGTCGCTCGTCTT
ATCTGTGTAATTGACGGAGATGAGGACGACGACATGAGGATGGCAGCCGTTTATAAGGCGATATATAATGACAAT
ATCAAGAAGCCAGAGTTTGTGTTATGTGAGAGCGATGATAAGGAAGGCGAGAGAATTGACTCAGATTTTAGCAGG
GACATCTGCGTCTTACAACCACACCGTGGCAAAAGGGAGTGCTTGTATACCGGCTTTCAGCTGGCCAAAATGGAC
CCGTCGGTAAACGCCGTTGTTCTTATTGACTCTGACACGGTCTTTGGAAAAGGACGCAATCTTGGAAGTCGTGTAT
CCATTGGCCTGTGACCCGGAAATTCAAGCTGTCGCAGGAGAGTGCAAAATATGGAACACAGATACACTTTTGTCG
TTGTTGGTGGCTTGGAGATATTATTCAGCCTTTTGCGTGGAGAGATCCGCCCAATCATTCTTTAGGACAGTCCAG
TGTGTAGGTGGACCCTTGGGCGCCTACAAGATAGATATCATCAAAGAGATCAAAGATCCCTGGATCTCCCAACGT
TTCTTAGGTCAGAAGTGCACCTACGGTGACGACCGTAGGTTAACAAATGAAATCTTAATGAGGGGTAAGAAGGTC
GTCTTCACTCCTTTCGCAGTTGGCTGGAGTGACTCACCAACCAACGTGTTCAGGTACATCGTACAACAGACTAGG
TGGAGTAAATCATGGTGCCGTGAGATATGGTACACTTTGTTTGCTGCGTGGAAGCACGGACTAAGCGGAATTTGG
TTGGCATTTGAGTGCCTTTATCAGATTACGTACTTCTTCCTAGTCATATATTTATTTTCGAGACTAGCCGTTGAA
GCTGACCCAAGAGCACAGACCGCAACAGTAATCGTGTCTACCACGGTAGCCCTGATTAAGTGTGGTTACTTCTCT
TTTCGTGCGAAAGATATTCGTGCTTTCTACTTCGTCCTGTACACATTTGTCTACTTCTTCTGTATGATCCCAGCA
AGGGTGACAGCCATGATGACACTTTGGGATATCGGCTGGGGCACGCGTGGCGGAAACGAGAAACCAAGTGTCGGC
ACTAGGGTCGCTCGTCTGTGGGCTAAACAGTATTTGATAGCATACATGTGGTGGGCAGCAGTTGTTGGCGCTGGGGTA
TACTCCATTGTTCATAATTGGATGTTTGACTGGAACTCACTATCCTATAGGTTCGCACTTGTAGGTATATGCTCT
TACATCGTATTCATCACAATCGTTCTAGTCATCTATTTCACAGGAAAGATTACCACATGGAATTTCACCAAATTA
CAGAAGGAGTTAATCAAGGATAGGGTCTTATACGATGCTTCCACTAACGCCCAGACTGTATAA SEQ ID NO: 102 is a reencoded nucleic acid sequence of hyaluronan synthase (HASA)
originating from *Chlorella* virus IL-5-2s1
ATGGCTGCTTCATTCTATGTTATCTTCTTGTTCGTAATATGCCACCTGTCCTTCGTCTTATATCGTCAAGTTCTA
TACATAATTTTGGGTAGATACTGGAGTGTTAACAAGCTGACAATGATCTCTTGGTATACCATTATATCATCTAAT
CTAATCGCAATCGGTGGGGCTTCCCTTATTTTGGCACCGGCCATAACCGGCTACATTTTGCATTGGAACATAGCT
CTAAGCACAATTTGGGGTGTGTCAGCCTATGGCATTTTCGTGGTTCTTTCTTCTTGCTCAGGTTTTGTTCAGT
GAGCTTAACAGGAAGAGGTTGAGAAAATGGATCTCTTTGAGACCAGATAACTGGAACGCGGTGAGAGTTGCCGTG
ATAATCGCTGGTTACCGTGAAGACCCATACATGTTTCAAAAGTGTTTGGAATCGGTGAGAGACTCCGATTATGGT
AACATTGCGAGGCTTATATGCGTTATAGATGGGGACGAAGATGACGACATGAAGATGGCAGATGTATACAAGGCT
ATTTACAATGACAATATAAAGAAGCCGGAAATTATCCTATGTGAGTCCGACGACAAAGAGGGAGAAAGGATAGAC
AGTGATTTTAGCCGTGATATTTGCGTGCTTCAGCCTCACGAGGGTAAGCGTGAATGTTTATATACTGGCTTTCAG
TTAGCTAAAATGGACCCCTCTGTACACGCGGTTGTGCTTATTGACTCGGATACAGTTTTGGAGAAGGATGCCATC
CTGGAAGTGGTCTACCCACTTGCTTGCGACCATGAGATTCAAGCAGTCGCAGGTGAATGCAAGATATGGAATACG
GACACCTTATTATCCATATTAGTCGCCTGGCGTTACTACTCAGCTTTCTGCGTTGAGCGTAGCGCTCAGTCCTTC
TTCCGTACTGTGCAATGCGTCGGCGGTCCGTTAGGGGCATACAAAATAGACATAATTAAAGAGATAAAGGAGCCG
TGGATTTCACAAAGATTTCTGGGTCAGAAGTGTACGTACGGATGATCACGAAGTTACCTAACGAAGTGTTGATG
CGTGGAAAGAAAGTAGTCTTCACACCTTTTGCGGTAGGATGGAGCGACTCGCCTACTAATGTCTTCCGTTATATT
GTGCAGCAGACGAGGTGGAGTAAGAGCTGGTGCAGGGAGATTTGGTATACACTGTTCGCGGCGTGGAAGCATGGG
TTATCAGGCATTTGGTTGGCATTTGAGTGCTTGTATCAGATCACATACTTCTTTCTAGTGATATATCTGTTCAGT
AGACTAGCAGTCGAGGCTGACCCGAGAGCGCAAACTGCAACGGTTATAGTCAGCACAATGGTTTCACTAATCAAG
TGTGGATATTTCTCATTCCGTGCTAAGGACATTAGAGCGTTTTATTTCGTACTATATACTTTTGTGTACTTCTTT
TGCATGATCCCAGCAAGAGTCACTGCTATGATGACCTTGTGGGATATTGGGTGGGGTACTAGGGGTGGAAACGTG
AAACCATCGATCGGAACTAGGATCTCTTTGTGGGCTAAGCAGTACTTAATCGCGTACATGTGGTGGGCAGCTGTG
ATCGCCGCAGGAGTCTATAGTATAATACATAATTGGATGTTTGATTGGAACTCCTTGTCCTATCGTTTCGCGTTA
ATAGGCATCTGCTCGTATATCGTATTCATTGCCATTGTTATAGTGATATACTTCACAGGTAAGATCACCACTTGG
AATTTTACCAAGCTACAGAAAGAGTTAATTGAAGATAGAGTCTTGCATGATGCCGATGTGGACATACAGAACGTA
TAA

SEQUENCES

SEQ ID NO: 103 is a reencoded nucleic acid sequence of hyaluronan synthase (HASA)
originating from *Chlorella* virus CZ-2
ATGACATCTTGGAGAACGATTGTGTCAGCTAACCTTTTCGCAGTTGGTGGGGCTCTTCTAATGTTAGCCCCAGCT
ATCGTGGGCTATGTATTTCAGTGGAATATAGGCGTGTCCGCAGTCTGGGGCATCTCCGTATACGGCGTCTTTGTG
TTGGGATTTTATATCGCTCAAATCGTCTTCTCTGAGTTCAACAGGATGAGATTATCCGATTGGATAAGTCTTAGA
CCAGACAACTGGAACGCCACAAGGGTTGCGGTCATTATAGCTGGATACAGAGAAGATCCTTTTATGTTCAAGAAG
TGCTTAGAGAGTGTGAGGGATTCGGAATACGGCAACGTAGCAAGGCTTATATGCGTAATTGACGGAGACGAAGAA
GAGGACCTAAAGATGGCTGAGATTTACAAGCAGGTTTACAATGACAACGTGAAGAAACCAGGTGTAGTGTTATGC
GAATCGGAGAACAAGAATGGATCGACTATAGATTCGGACGTATCTAAGAATATATGCATACTGCAACCCCACCGT
GGGAAACGTGAGAGCCTATATACCGGTTTCCAATTGGCAAGCATGGACCCTTCCGTACATGCGGTTGTTCTTATA
GATTCCGACACTGTATTAGAGAAGAATGCTATTCTTGAGGTCGTATACCCTCTATCTTGTGACCCCAACATTAAG
GCCGTCGCCGGGGAGTGCAAGATATGGAATACAGACACCATCTTGTCCATGCTTGTCTCTTGGAGATACTTCTCT
GCCTTCAATGTCGAGCGTGGAGCCCAGTCATTATGGAAGACTGTGCAATGCGTAGGCGGGCCACTTGGCGCATAC
ACTATCGACATCATAAATGAAATTAAAGACCCGTGGATTACCCAGACATTCCTGGGCAACAAGTGCACTTATGGC
GACGATAGACGTCTTACCAATGAGGTTTTAATGAGGGGCAAGAAGATTGTATACACTCCGTTTGCCGTCGGTTGG
AGCGACAGTCCGACGAATGTCATGAGGTACATTGTGCAGCAAACTAGATGGAGTAAGTCATGGTGCAGAGAGATA
TGGTACACGTTAGGCAGTGCCTGGAAACATGGATTCTCCGGCATATACCTTGCGTTTGAGTGTATGTACCAGATA
ATGTACTTCTTCTTAGTCATGTACCTGTTTTCGTATATCGCAATAAAGGCAGACATCCGTGCTCAGACTGCAACT
GTGTTGGTTTCTACTCTAGTCACCATAATAAAGAGCAGTTACCTAGCGCTGAGGGCCAAGAACCTGAAGGCTTTC
TATTTCGTTCTGTATACCTATGTCTATTTCTTTTGCATGATACCTGCTAGGATTACCGCTATGTTTACAATGTTT
GATATAGCTTGGGGTGACACGTGGTGGTAATGCGAAAATGACAATCGGGCGTAGAGTTTGGCTGTGGGCGAAGCAG
TTCTTAATAACTTATATGTGGTGGGCAGGAGTACTAGCGGCGGGAGTTTACAGTATAGTTGACAATTGGTACTTC
GATTGGGCTGATATACAGTACAGGTTTGCATTGGTAGGTATTTGCTCGTATTTGGTCTTTGTCAGTATTGTACTG
GTAATCTACTTGATCGGTAAGATAACAACGTGGAACTACACACCGCTACAGAAGGAACTTATTGAGGAGAGATAC
TTGCATAACGCCTCTGAGAATGCCCCGGAAGTTTAA SEQ ID NO: 104 is a reencoded nucleic acid sequence of hyaluronan synthase (HASA)
originating from *Chlorella* virus CVG-1
ATGACTTCTTGGCGTACAATTGTTTCTGCTAACTTGTTCGCAGTTGGTGGCGCCTTGTTGATGTTAGCTCCCGCG
ATAGCCGGTTATGTATTTAAATGGAACATAGGCGTTTCTGCCGTTTGGGGTATTTCAGTGTACGGGGTCTTCGTG
CTTGGTTTCTATATTGCACAGGTAGTCTTCAGCGAGTTTAATAGGATGCAGCTGTCAGATTGGATCTCATTGAGA
CCCGACAACTGGAACGCCACCAGAGTAGCGGTAATTATTGCTGGTTACAGGGAAGACCCCTTTATGTTCAAGAAG
TGCCTAGAATCTGTGAGAGACTCAGAATACGGGAACATAGCGAGGCTAATCTGTGTTATCGACGGCGATGAAGAG
GAAGACCTTAAGATGGCTGAGATATACAAGCAAGTATACAACGACAACGTCAAGACCCCCGGTGTTGTGCTATGC
GAGAATGAAAATAAGAATGGTAGCACCATTGACCCAGATTTTAGTAAGAACATCTGCATTCTGCAACCACACAGG
GGCAAACGTGAATCTTTGTACACCGGATTCCAGATGGCTGGCATGGACCCATCAGTGCACGCAGTTGTACTTATA
GACAGTGATACTGTTCTTGAAAAGAACGCTATCCTAGAGGTTGTGTACCCTCTATCTTGTGATCCAAATATCAAA
GCTGTCGCGGGAGAGTGTAAAATCTGGAACACAGATACCATTTTGTCTATGCTAGTTTCATGGCGTTATTTCTCG
GCTTTCAACGTGGAGAGAGGCGCACAGTCCCTTTGGAAAACAGTCCAGTGTGTCGGCGGGCCTTTGGGAGCATAC
ACTATAGACATCATAAACGAGATAAAAGACCCCTGGATTACTCAGACATTCTTAGGGAAACAAATGTACGTATGGT
GACGACAGAAGGTTAACCAATGAAGTGCTTATGAGGGGAAAGAAGATTGTCTATACTCCCTTTGCTGTCGGTTGG
TCCGATTCGCCCCACAAACGTTATGAGGTACATCGTCCAGCAGACAAGGTGGTCTAAGAGCTGGTGCCGTGAGATT
TGGTACACCTTGGGATCAGCATGGAAACATGGTTTCTCCGGAATCTACTTAGCGTTCGAGTGCATGTACCAGATT
ATGTATTTCTTTATTGTGATGTATTTGTTCAGTTACATTGCCATTAAAGCCAACATCAGGGCACAAGCAGCCACG
GTATTGGTCAGTACGCTTGTCGCAGTAATCAAATCTAGTTATTTGGCATTAAGAGCGAAGAACCTAAAAGCTTTG
TATTTCGTCCTGTATACCTACGTCTACTTCTTCTGCATGATTCCAGCTAGAATAACAGCGATGTTCACGATGTTC
GATATTGCATGGGGTACTAGAGGCGGGTAACGCAAAGATGACGATCGGTGCTCTAGAGTCTGGTTGTGGGCTAAACAA
TTCTTAATTACATACATGTGGTGGGTGGGAGTTTTTGGCCGCTGGGGTCTACAGTATAGTCGATAACTGGTACTTC
GACTGGGCGGACATCCAGTACAGATTCGCGCTAGTGGGGATTTGCAGTTACTTAGGTTTCGTTTCCATAATGCTG
GTATTCTATCTGATTGGTAAAATAACTACGTGGAATTACACTCCTCTACAAAAGGAGCTGATTAAAGAGAGGTTA
CACGCCGCTAATGCAACAGAGGTCTAA SEQ ID NO: 105 is an amino acid sequence of hyaluronan synthase (HASA) originating from
*Chlorella* virus CviK1
MLFSCLSFVICHLSFILRYYKRLLKVTMGKNIIIMVSWYTIITSNIIAVGGASLILAPAITGYILHWNIALSTIW
GVSAYGIFVFGFFLAQVLFSELNRKRLRKWISLRPKGWNDVRLAVIIAGYREDPYMFQKCLESVRDSDYGNVARL
ICVIDGDEDDDMKMAAVYKAIYNDNIKKPEFVLCESDDKEGERIDSDFSRDICVLQPHRGKRECLYTGFQLAKMD
PSVNAVVLIDSDTVLEKDAILEVVYPLACDPEIQAVAGECKIWNTDTLLSLLVAWRYYSAFCVERSAQSFFRTVQ
CVGGPLGAYKIDIIKEIKDPWISQRFLGQKCTYGDDRRLTNEILMRGKKVVPTPFAVGWSDSPTNVFRYIVQQTR
WSKSWCREIWYTLFAAWKHGLSGIWLAFECLYQITYFFLVIYLFSRLAVEADPRAQTATVIVSTTVALIKCGYFS
FRAKDIRAFYFVLYTFVYFFCMIPARVTAMMTLWDIGWGTRGGNEKPSVGTRVALWAKQYLIAYMWWAAVVGAGV
YSIVHNWMFDWNSLSYRFALVGICSYIVFITIVLVIYFTGKITTWNFTKLQKELIKDRVLYDASTNAQTV SEQ ID NO: 106 is an amino acid sequence of hyaluronan synthase (HASA) originating from
*Chlorella* virus IL-5-2s1
MAASFYVIFLFVICHLSFVLYRQVLYIILGRYWSVNKLTMISWYTIISSNLIAIGGASLILAPAITGYILHWNIA
LSTIWGVSAYGIFVFGFFLAQVLFSELNRKRLRKWISLRPDNWNAVRVAVIIAGYREDPYMFQKCLESVRDSDYG
NIARLICVIDGDEDDDMKMADVYKAIYNDNIKKPEIILCESDDKEGERIDSFSRDICVLQPHRGKRECLYTGFQ
LAKMDPSVHAVVLIDSDTVLEKDAILEVVYPLACDHEIQAVAGECKIWNTDILLSILVAWRYYSAFCVERSAQSF
FRTVQCVGGPLGAYKIDIIKEIKEPWISQRFLGQKCTYGDDRRLTNEVLMRGKKVVPTPFAVGWSDSPTNVFRYI
VQQTRWSKSWCREIWYTLFAAWKHGLSGIWLAFECLYQITYFFLVIYLFSRLAVEADPRAQTATVIVSTMVSLIK
CGYFSFRAKDIRAFYFVLYTFVYFFCMIPARVTAMMTLWDIGWGTRGGNVKPSIGTRISLWAKQYLIAYMWWAAV
IAAGVYSIIHNWMFDWNSLSYRFALIGICSYIVFIAIVIVIYFTGKITTWNFTKLQKELIEDRVLHDADVDIQNV -continued

---

SEQUENCES

---

SEQ ID NO: 107 is an amino acid sequence of hyaluronan synthase (HASA) originating from
*Chlorella* virus CZ-2
MTSWRTIVSANLFAVGGALLMLAPAIVGYVFQWNIGVSAVWGISVYGVFVLGFYIAQIVFSEFNRMRLSDWISLR
PDNWNATRVAVIIAGYREDPFMFKKCLESVRDSEYGNVARLICVIDGDEEEDLKMAEIYKQVYNDNVKKPGVVLC
ESENKNGSTIDSDVSKNICILQPHRGKRESLYTGFQLASMDPSVHAVVLIDSDTVLEKNAILEVVYPLSCDPNIK
AVAGECKIWNTDTILSMLVSWRYFSAFNVERGAQSLWKTVQCVGGPLGAYTIDIINEIKDPWITQTFLGNKCTYG
DDRRLTNEVLMRGKKIVYTPFAVGWSDSPINVMRYIVQQTRWSKSWCREIWYTLGSAWKHGFSGIYLAFECMYQI
MYFFLVMYLFSYIAIKADIRAQTATVLVSTLVTIIKSSYLALRAKNLKAFYFVLYTYVYFFCMIPARITAMFTMF
DIAWGTRGGNAKMTIGARVWLWAKQFLITYMWWAGVLAAGVYSIVDNWYFDWADIQYRFALVGICSYLVFVSIVL
VIYLIGKITTWNYTPLQKELIEERYLHNASENAPEV SEQ ID NO: 108 is an amino acid sequence of hyaluronan synthase (HASA) originating from
*Chlorella* virus CVG-1
MTSWRTIVSANLFAVGGALLMLAPAIAGYVFKWNIGVSAVWGISVYGVFVLGFYIAQVVFSEFNRMQLSDWISLR
PDNWNATRVAVIIAGYREDPFMFKKCLESVRDSEYGNIARLICVIDGDEEEDLKMAEIYKQVYNDNVKTPGVVLC
ENENKNGSTIDPDFSKNICILQPHRGKRESLYTGFQMAGMDPSVHAVVLIDSDTVLEKNAILEVVYPLSCDPNIK
AVAGECKIWNTDTILSMLVSWRYFSAFNVERGAQSLWKTVQCVGGPLGAYTIDIINEIKDPWITQTFLGNKCTYG
DDRRLTNEVLMRGKKIVYTPFAVGWSDSPINVMRYIVQQTRWSKSWCREIWYTLGSAWKHGFSGIYLAFECMYQI
MYFFIVMYLFSYIAIKANIRAQAATVLVSILVAVIKSSYLALRAKNLKALYFVLYTYVYFFCMIPARITAMFTMF
DIAWGTRGGNAKMTIGARVWLWAKQFLITYMWWVGVLAAGVYSIVDNWYFDWADIQYRFALVGICSYLGFVSIML
VFYLIGKITTWNYTPLQKELIKERLHAANATEV

---

SEQUENCE LISTING

---

<160> NUMBER OF SEQ ID NOS: 108

<210> SEQ ID NO 1
<211> LENGTH: 1707
<212> TYPE: DNA
<213> ORGANISM: Chorella virus

<400> SEQUENCE: 1
atgggtaaga acatcattat tatggtttct tggtacacta ttattacatc caatctcatc        60
gcagtgggtg gcgcctcact catactagcc ccagctatta cgggctatgt ccttcactgg       120
aacattgccc tttcaacaat ttggggagtg tcggcctacg gaattttcgt gtttggtttc       180
tttcttgccc aggtattatt tagtgaactc aaccggaaaa ggctccggaa gtggatttcc       240
ctccgaccca aagggtggaa tgatgttagg ttggctgtaa ttattgccgg ctaccgtgag       300
gacccgtata tgttccaaaa gtgtcttgaa agtgtgcgtg actcagacta tgggaatgta       360
gctagactaa tatgcgttat tgacggcgat gaagacgacg acatgaggat ggctgcagtg       420
tacaaggcta tctataacga caacatcaag aaacctgagt ttgtcctctg tgagagtgac       480
gataaggagg gtgagagaat agatagcgat ttcagccgtg atatctgcgt gctgcaaccg       540
catcgcggaa agcgtgaatg tttgtacaca gggttccaat ggcaaagat ggacccctca       600 gttaatgccg tcgtcctaat cgacagtgac actgtgttag aaaaggacgc gattctcgaa       660
gtagtatacc cgctggcatg cgatccagaa atacaggctg tagcaggcga atgcaaaata       720
tggaatactg acacactgtt gagtttgctg gtagcctggc gatattacag cgcattttgc       780
gtagagcgta cgcgcccaatc attcttcagg acagtacaat gcgtcggagg acctctcggc       840
gcctacaaga ttgatataat taaggaaatc aaggacccat ggatcagcca acgtttcctt       900
ggccaaaagt gcacatacgg cgacgataga cgactcacta tgaaatact aatgaggggt       960 aagaaagtag ttttcacccc attcgctgtt ggctggtccg acagcccgac gaacgtcttc      1020
cgttacattg tacagcaaac acggtggtcc aagtcgtggt gtagggagat atggtataca      1080
ctgtttgcag catggaagca tggactttcg ggcatttggc tcgcattcga gtgcttatac      1140
cagattactt atttcttcct ggtgatttac ctattctccc gtttggctgt tgaggctgac      1200

```
ccacgggcgc aaacggccac cgtcattgtt tcgaccacag ttgcgcttat taagtgcggt    1260
tactttagct tcagagctaa agacattagg gccttctatt tcgtcctcta cacgttcgtt    1320
tacttcttct gcatgattcc ggcacgaata actgcgatga tgaccctgtg ggacataggt    1380
tggggaacca ggggaggaaa tgagaagcct tccgtaggca ccagagttgc tttgtgggcc    1440
aagcaatatt tgattgctta catgtggtgg gccgctgtcg tcggtgctgg cgtgtactcc    1500
atcgttcata attggatgtt tgactggaat tcactttcct acaggttcgc actggtaggc    1560
atctgttcgt atatagtttt cattgtaata gtgctggtag tctactttac aggaaagatc    1620
acgacctgga acttcacgaa gctacagaaa gaattgatcg aggaccgcgt actgtacgac    1680
gcaacgacca atgcccagtc ggtataa                                       1707
```

```
<210> SEQ ID NO 2
<211> LENGTH: 1647
<212> TYPE: DNA
<213> ORGANISM: Chorella virus

<400> SEQUENCE: 2
gctgtcggtg gagcctcact aatcttagct cccgcgatta cgggttatgt gcttcattgg      60
aatattgctt tatccactat ttggggtgtt agcgcttacg gcatctttgt gttcggtttc     120
ttcttggctc aggtgttatt ctctgagcta aacagaaaga gactcagaaa gtggatttcg     180
ctgcggccga agggatggaa cgatgttcgg ttagcggtga tcattgccgg ttatcgtgaa     240
gatccttata tgtttcagaa gtgtttggaa tctgttcgag actcagacta cggtaacgtt     300
gctaggctga tctgcgtaat cgatggagac gaagatgacg atatgagaat ggccgcggtt     360
tataaagcca tctataacga taacattaag aagccagagt ttgtttttatg cgaatcggat     420 gacaaggagg gtgagaggat tgattctgac ttctcgcgtg acatctgtgt cctgcagccc     480
cacaggggaa agcgagagtg cctctataca ggattccaat tagctaaaat ggacccaagc     540
gttaatgctg tcgtccttat cgatagcgac acggtgttgg aaaaggacgc aatattggaa     600
gtagtctatc cactcgcttg tgatccagag atccaggccg tggctggcga gtgcaagatt     660
tggaatacag atacgcttct gtcattactg gtggcgtggc gttattattc agcattctgt     720
gtggagagga gcgcacaatc gttctttcgg actgtacaat gcgtaggcgg tccactagga     780
gcatataaaa ttgacataat caaagagata aaagatcctt ggatttcgca gagattcctc     840
ggtcaaaagt gtacctatgg ggacgacagg cggttgacta acgagattct aatgagaggt     900
aagaaggtgg tgttcactcc ttttgcggta ggttggagcg attcgcccac aaatgtattc     960
agatacattg ttcaacaaac aaggtggtcg aaatcgtggt gccgagaaat atggtacacg    1020
ttgttcgccg catggaaaca cggcttgtcg ggtatatggc tcgctttcga gtgcctttat    1080
cagatcactt acttcttcct ggttatttac ttgttttcaa gactggcagt ggaagctgat    1140
ccaagggctc agactgctac tgtcatcgtt tcaacaacag tggcgctaat aaagtgtggt    1200
tacttcagct ttcgcgcgaa ggacataaga gcgtttttact ttgttcttta tacctttgta    1260
tatttcttct gtatgatccc ggcccggata acagctatga tgacattatg ggacattggt    1320
tggggcacca ggggtgggaa tgagaagccg tccgtaggaa cgagagtagc gctgtgggcc    1380
aagcagtatc ttatcgcata catgtggtgg gcagctgtcg tcgggcagg tgtatacagc     1440 atagtacata actggatgtt tgactggaac tcactctcat atcgattcgc attggtcggg    1500
atctgctctt acatcgtgtt tattgttata gtcttagtag tatatttcac tggaaagata    1560
```

-continued

```
acaacatgga atttcactaa gcttcaaaag gaattgattg aagacagggt gctctacgat   1620
gcgacaacta atgcacaaag cgtataa                                       1647

<210> SEQ ID NO 3
<211> LENGTH: 2919
<212> TYPE: DNA
<213> ORGANISM: Pasteurella multocida

<400> SEQUENCE: 3
atgaacaccc tttcccaggc aattaaggct tataatagta atgattatca actagccctc     60
aagctgttcg aaaagtcggc agaaatctac ggcagaaaga tagttgagtt ccaaattacg    120
aagtgcaagg agaaactttc tgcgcaccca tccgttaaca gtgcgcatct ctcggttaac    180
aaagaagaga aggtgaatgt ttgcgacagt ccattagaca tagccactca attattgtta    240
tcgaatgtga aaaaactcgt ccttagtgat agcgagaaaa atacactaaa gaataaatgg    300
aagttgttga ctgaaaagaa gtctgagaac gcagaggtcc gggccgtagc tttagttccc    360
aaggactttc cgaaagattt agtgcttgcg ccgttaccag accatgtgaa cgattttacg    420
tggtataaga gcggaagaa acgcctagga atcaaaccag aacaccaaca cgttggcctc    480
tccattattg tgacaacgtt caaccgtcct gccatcctca gcatcaccct ggcttgcctc    540
gtcaatcaaa agaccccatta tccttttgag gtgatcgtga ccgacgatgg ttctcaagag    600
gatttatcgc ctataatccg tcaatatgag aacaagctag acatccgtta tgttcggcaa    660
aaggacaacg gttttcaggc atcggccgca cgtaatatgg cctacgtct agccaaatat    720 gacttcattg ggctccttga ttgtgatatg gctcccaacc ctttgtgggt acactcatac    780
gttgcggaac tattagagga cgatgatttg accataatag gccccaggaa gtacattgac    840
acgcaacaca tagatcccaa ggatttcctt aataacgcct ctctgttaga gtcgttgcca    900
gaggttaaga ccaataattc cgtcgcggct aagggcgagg ggaccgtatc tttagactgg    960
cgtttggaac aatttgagaa gaccgagaac ttgaggctat ccgatagccc tttccgattc   1020
ttcgcagctg ggaatgtggc tttcgccaag aagtggctta acaagtcagg attcttcgac   1080
gaggaattca atcactgggg aggtgaagat gtagagttcg gttatcgtct gtttcggtac   1140
ggttcgttct tcaaaactat agacggcatc atggcctatc atcaggaacc gccaggtaaa   1200
gaaaacgaaa ctgacagaga agcgggcaag aacattaccc tcgatataat gagggagaag   1260
gtgccttaca tctaccgtaa actcctgcct atagaagaca gtcatatcaa ccgagtacca   1320
ttggtatcaa tttacatccc ggcctacaac tgtgctaact atattcaaag atgtgttgat   1380
tcagctttga atcaaacggt agttgatctc gaagtgtgca tttgcaacga cggtagtact   1440
gacaacacgc tggaagttat taacaagctg tatggtaata atccgcgtgt gcgtataatg   1500
tctaaaccca atggcggcat tgcgagtgca tccaacgcag cggtcagctt cgcaaagggt   1560
tattacatag gacagttgga cagcgacgat tacttagaac ccgacgcagt ggagttatgt   1620
ctcaaggaat ttcttaagga taagacccct gcgtgcgttt acaccactaa tcgtaacgtc   1680
aacccagatg gctctttaat agccaatggc tataactggc cagagttcag tcgtgagaag   1740
ttgactacgg ccatgattgc tcatcacttc cggatgttta ccattcgtgc ttggcatctg   1800
acggatgggt tcaatgagaa gattgagaac gctgttgact acgacatgtt tctcaagctc   1860
agtgaagttg gtaaatttaa gcatctgaac aaaatatgtt ataatcgggt gttacacggc   1920
gataacacct caatcaagaa gcttggcata caaaagaaga atcatttcgt agttgtcaat   1980
cagtctctaa accgccaagg tataacttat tataactacg atgaatttga tgatctcgat   2040
```

-continued

```
gagagtcgga aatacatttt caacaagact gcagagtatc aagaagagat agatattctt    2100
aaagatatta agatcattca gaacaaagac gccaaaatag ctgtctccat tttctatccg    2160
aacactctaa acgggttggt gaagaagcta aataatatta tagagtataa taagaatatc    2220
ttcgttattg tacttcatgt cgataagaat cacttaaccc cagacatcaa gaaggagata    2280
ttagccttct accataagca tcaggtgaac atcttattga caatgacat ctcctactat     2340 acatcaaatc gtctgattaa gacagaagcc catttgagta acattaacaa gctaagtcaa    2400
ttaaatctta actgcgaata cattatattc gacaatcacg attccttatt tgtgaagaac    2460
gattcctatg catacatgaa gaagtatgat gttggaatga acttctctgc attgactcat    2520
gattggattg aaaagataaa cgctcacccg ccatttaaga agctgatcaa aacttacttc    2580
aatgacaatg atcttaagtc gatgaatgta aagggtgcct cccagggaat gtttatgaca    2640
tacgcattag cccacgagtt attgacgatc atcaaggagg tgataacctc ttgtcaatcc    2700
attgactccg tccccgaata caacacagaa gatatttggt ttcagtttgc acttttaatt    2760
ctggaaaaga agaccggcca cgtattcaac aagacaagca ctctcacgta tatgccatgg    2820
gaacgtaaac tgcagtggac gaatgaacaa atagagtccg caaagagggg cgaaaacatt    2880
ccggtaaaca agttcatcat taacagcatt acccttttaa                          2919
```

<210> SEQ ID NO 4
<211> LENGTH: 2112
<212> TYPE: DNA
<213> ORGANISM: Pasteurella multocida

<400> SEQUENCE: 4

```
atgaacaccc tttcccaggc aattaaggct tataatagta atgattatca actagccctc     60
aagctgttcg aaaagtcggc agaaatctac ggcagaaaga tagttgagtt ccaaattacg    120
aagtgcaagg agaaactttc tgcgcaccca tccgttaaca gtgcgcatct ctcggttaac    180
aaagaagaga aggtgaatgt ttgcgacagt ccattagaca tagccactca attattgtta    240
tcgaatgtga aaaaactcgt ccttagtgat agcgagaaaa atacactaaa gaataaatgg    300
aagttgttga ctgaaaagaa gtctgagaac gcagaggtcc gggccgtagc tttagttccc    360 aaggacttc cgaaagattt agtgcttgcg ccgttaccag accatgtgaa cgattttacg     420
tggtataaga agcggaagaa acgcctagga atcaaaccag aacaccaaca cgttggcctc    480
tccattattg tgacaacgtt caaccgtcct gccatcctca gcatcaccct ggcttgcctc    540
gtcaatcaaa gacccatta tccttttgag gtgatcgtga ccgacgatgg ttctcaagag     600
gatttatcgc ctataatccg tcaatatgag aacaagctag acatccgtta tgttcggcaa    660
aaggacaacg ttttcaggc atcggccgca cgtaatatgg gcctacgtct agccaaatat      720
gacttcattg ggctccttga ttgtgatatg gctcccaacc ctttgtgggt acactcatac    780
gttgcggaac tattagagga cgatgatttg accataatag gccccaggaa gtacattgac    840
acgcaacaca tagatcccaa ggatttcctt aataacgcct ctctgttaga gtcgttgcca    900
gaggttaaga ccaataattc cgtcgcggct aagggcgagg ggaccgtatc tttagactgg    960
cgtttggaac aatttgagaa gaccgagaac ttgaggctat ccgatagccc tttccgattc    1020
ttcgcagctg ggaatgtggc tttcgccaag aagtggctta acaagtcagg attcttcgac    1080
gaggaattca atcactgggg aggtgaagat gtagagttcg gttatcgtct gtttcggtac    1140
ggttcgttct tcaaaactat agacggcatc atggcctatc atcaggaacc gccaggtaaa    1200
```

-continued

```
gaaaacgaaa ctgacagaga agcgggcaag aacattaccc tcgatataat gagggagaag   1260
gtgccttaca tctaccgtaa actcctgcct atagaagaca gtcatatcaa ccgagtacca   1320
ttggtatcaa tttacatccc ggcctacaac tgtgctaact atattcaaag atgtgttgat   1380
tcagctttga atcaaacggt agttgatctc gaagtgtgca tttgcaacga cggtagtact   1440
gacaacacgc tggaagttat taacaagctg tatggtaata atccgcgtgt gcgtataatg   1500
tctaaaccca atggcggcat tgcgagtgca tccaacgcag cggtcagctt cgcaaagggt   1560
tattacatag gacagttgga cagcgacgat tacttagaac ccgacgcagt ggagttatgt   1620
ctcaaggaat ttcttaagga taagacccct gcgtgcgttt acaccactaa tcgtaacgtc   1680
aacccagatg gctctttaat agccaatggc tataactggc cagagttcag tcgtgagaag   1740
ttgactacgg ccatgattgc tcatcacttc cggatgttta ccattcgtgc ttggcatctg   1800
acggatgggt tcaatgagaa gattgagaac gctgttgact acgacatgtt tctcaagctc   1860
agtgaagttg gtaaatttaa gcatctgaac aaaatatgtt ataatcgggt gttacacggc   1920
gataacacct caatcaagaa gcttggcata caaaagaaga atcatttcgt agttgtcaat   1980
cagtctctaa accgccaagg tataacttat tataactacg atgaatttga tgatctcgat   2040
gagagtcgga aatacatttt caacaagact gcagagtatc aagaagagat agatattctt   2100
aaagatattt aa                                                       2112

<210> SEQ ID NO 5
<211> LENGTH: 2322
<212> TYPE: DNA
<213> ORGANISM: Pasteurella multocida

<400> SEQUENCE: 5
atgaacaccc tttcccaggc aattaaggct tataatagta atgattatca actagccctc     60
aagctgttcg aaaagtcggc agaaatctac ggcagaaaga tagttgagtt ccaaattacg    120
aagtgcaagg agaaactttc tgcgcaccca tccgttaaca gtgcgcatct ctcggttaac    180
aaagaagaga aggtgaatgt ttgcgacagt ccattagaca tagccactca attattgtta    240
tcgaatgtga aaaaactcgt ccttagtgat agcgagaaaa atacactaaa gaataaatgg    300
aagttgttga ctgaaaagaa gtctgagaac gcagaggtcc gggccgtagc tttagttccc    360
aaggactttc cgaaagattt agtgcttgcg ccgttaccag accatgtgaa cgattttacg    420
tggtataaga agcggaagaa acgcctagga atcaaaccag aacaccaaca cgttggcctc    480
tccattattg tgcaacgtt caaccgtcct gccatcctca gcatcaccct ggcttgcctc    540
gtcaatcaaa agacccatta tcctttgag gtgatcgtga ccgacgatgg ttctcaagag    600
gatttatcgc ctataatccg tcaatatgag aacaagctag acatccgtta tgttcggcaa    660
aaggacaacg ttttcaggc atcggccgca cgtaatatgg cctacgtct agccaaatat    720 gacttcattg ggctccttga ttgtgatatg gctcccaacc ctttgtgggt acactcatac    780
gttgcggaac tattagagga cgatgatttg accataatag gccccaggaa gtacattgac    840
acgcaacaca tagatcccaa ggatttcctt aataacgcct ctctgttaga gtcgttgcca    900
gaggttaaga ccaataattc cgtcgcggct aagggcgagg ggaccgtatc tttagactgg    960
cgtttggaac aatttgagaa gaccgagaac ttgaggctat ccgatagccc tttccgattc   1020
ttcgcagctg ggaatgtggc tttcgccaag aagtggctta acaagtcagg attcttcgac   1080
gaggaattca tcactgggg aggtgaagat gtagagttcg gttatcgtct gtttcggtac   1140
ggttcgttct tcaaaactat agacggcatc atggcctatc atcaggaacc gccaggtaaa   1200
```

-continued

```
gaaaacgaaa ctgacagaga agcgggcaag aacattaccc tcgatataat gagggagaag      1260
gtgccttaca tctaccgtaa actcctgcct atagaagaca gtcatatcaa ccgagtacca      1320
ttggtatcaa tttacatccc ggcctacaac tgtgctaact atattcaaag atgtgttgat      1380
tcagctttga atcaaacggt agttgatctc gaagtgtgca tttgcaacga cggtagtact      1440
gacaacacgc tggaagttat taacaagctg tatggtaata tccgcgtgt gcgtataatg      1500 tctaaaccca atggcggcat tgcgagtgca tccaacgcag cggtcagctt cgcaaagggt      1560
tattacatag gacagttgga cagcgacgat tacttagaac ccgacgcagt ggagttatgt      1620
ctcaaggaat ttcttaagga taagacccct gcgtgcgttt acaccactaa tcgtaacgtc      1680
aacccagatg gctctttaat agccaatggc tataactggc cagagttcag tcgtgagaag      1740
ttgactacgg ccatgattgc tcatcacttc cggatgttta ccattcgtgc ttggcatctg      1800
acggatgggt tcaatgagaa gattgagaac gctgttgact acgacatgtt tctcaagctc      1860
agtgaagttg gtaaatttaa gcatctgaac aaaatatgtt ataatcgggt gttacacggc      1920
gataacacct caatcaagaa gcttggcata caaaagaaga atcatttcgt agttgtcaat      1980
cagtctctaa accgccaagg tataacttat tataactacg atgaatttga tgatctcgat      2040
gagagtcgga aatacatttt caacaagact gcagagtatc aagaagagat agatattctt      2100
aaagatattg gatccgccat ttctcaaatc actgacggtc aaatccaagc tactaccact      2160
gctaccaccg aagctaccac cactgctgcc ccatcttcca ccgttgaaac tgtttctcca      2220
tccagcaccg aaactatctc tcaacaaact gaaaatggtg ctgctaaggc cgctgtcggt      2280
atgggtgccg gtgctctagc tgctgctgct atgttgttat aa                        2322
```

<210> SEQ ID NO 6
<211> LENGTH: 1656
<212> TYPE: DNA
<213> ORGANISM: Xenopus laevis
<400> SEQUENCE: 6

```
atgcactgtg aacgatttat ttgtatatta cgaataattg gtacgacttt gttcggagta        60
agtctgctac tagggatatc cgccgcttat atcgtgggat accaattcat tcagacggat       120
aattactact tttccttcgg tctctacggt gctattttag ctttacattt aatcattcag       180
tctctcttcg cattcctgga gcatcgtaag atgaagcggt cacttgaaac ccctataaaa       240
ttaaacaaga gcgtagcatt gtgtatcgct gcataccagg aagacgaaga ttatcttaga       300
aaatgtttgc tttctgtgaa acggctcaca taccccggta tgaaggtaat catggtgata       360
gatggtaact ctgatgacga tctatacatg atgaacatat tcagagagat catgggaaat       420
gatagctgcg ccacctatgt atggaagaat aattttcaca tgaagggacc aaacgagacc       480
gacgagactc accgcgagtc catgcagcat gtaacacaga tggtgctttc taacagaaat       540
gtctgtatca tgcaaaagtg gaacgggaaa cgcgaggtga tgtatactgc attcaaagcg       600
ctgggtcggt cggttgatta cgtccaagtg tgcgactcag atacagtcct tgatccagca       660
agctcggtgg agatggtcaa ggtgttggag gaagacatta tggtcggagg tgtaggcgga       720
gacgtgcaga tactcaataa gtacgactcc tggatcagtt tcttgagttc ggttcgttat       780
tggatggctt tcaatataga acgagcatgc caatcatact ttggctgtgt gcagtgtata       840
tcggggcctc tggcatgta cagaaactca ctcttacatg agttcattga agactggtac       900
aatcaagaat tcctcggttc ccaatgctct ttcggtgatg atcggcattt gactaatcga       960
```

-continued

```
gtactatcat tgggctatgc tactaaatac actgcgcgca gtaagtgtct gacagaaacc      1020
cccacagaat atcttagatg gttgaaccaa caaaccaggt ggagtaagtc ctatttccgc      1080
gagtggttgt acaactcttt gtggttccac aaacaccatt tatggatgac ttatgaagcc      1140
gtaattacgg gtttcttccc cttcttctta atagcgacgg tgattcagct cttctatcgt      1200
ggtcgaattt ggaatatctt actctttcta ctcacagttc aattagttgg tctaataaag      1260
tcgtcgtttg caagtgcgtt gcgtggaaac atcgttatgg tctttatgag tttctacagt      1320
gttttataca tgagtagctt gctgccagca aagatgtttg caatcgccac gataaacaag      1380
gctggatggg gtactagtgg tagaaagacc atagttgtta attttattgg tttaatccct      1440
attacggtat ggttcacaat tttactaggg ggagtatgct acactatatg gcgggaaacc      1500
aagaagccgt ttagcgagtc tgagaagatc gttcttgcgg tcggtgctat attgtatgct      1560
tgttattggg tcatgttgct tacaatgtat gtcagtcttg tcatgaagtg cgggcgccgt      1620
aggaaggaac cacagcacga ccttgtttta gcataa                               1656
```

```
<210> SEQ ID NO 7
<211> LENGTH: 1254
<212> TYPE: DNA
<213> ORGANISM: Streptococcus zooepidemicus

<400> SEQUENCE: 7
atgaggacgt taaagaatct tatcactgtt gtagcgttca gtatattctg ggttttgctg       60
atctatgtaa atgtctatct tttcggtgcg aaggggtctc tatcaatata tggattcttg      120
ctaattgcgt atttgcttgt gaagatgagt ctttcattct tctataaacc attcaaaggt      180
cgagctggtc agtataaagt cgcagcgatt atcccttcat acaacgagga tgcagaatcg      240
ctgttggaaa ccttaaaatc tgttcaacaa caaacctatc cccttgctga aatttatgta      300
gttgatgatg gttccgcaga tgaaaccggt atcaagcgga tcgaggatta tgtcagggat      360
acaggcgact taagttcaaa tgtgattgtg catcgatcag aaaagaatca aggcaagaga      420
cacgcccaag catgggcatt tgaaagatct gatgcagatg tatttctaac agtcgatagt      480
gatacttaca tttatccgga cgcccttgaa gagttattga aaaccttcaa tgatccgaca      540
gtatttgccg caactggcca cttgaacgtt cgtaacaggc agactaatct attgaccaga      600
ctcactgata taagatacga caatgctttt ggcgtcgaac gtgctgctca aagtgtaact      660
ggtaatatac tggtgtgttc cgggccactg tccgtctatc gcagagaagt agtagtcccg      720
aacattgaca ggtatattaa tcagactttt ctgggtatcc ccgtgtcaat tggggacgac      780
cggtgtttaa cgaactacgc tactgatttg ggcaagactg tatatcagtc gacggctaaa      840
tgtattacag acgtcccaga taagatgtcg acttacctta aacagcagaa tagatggaat      900
aagtcattct ttagagaatc tatcatcagc gtgaagaaga tcatgaataa tccattcgtg      960
gcgctttgga ccattttgga ggtttccatg tttatgatgc ttgtctactc tgtcgttgat      1020
ttctttgtag gtaacgttcg agaatttgat tggctcagag ttcttgcttt cttagttatc      1080
atcttcatcg ttgcgctatg caggaatatt cattacatgc taaaacatcc gcttagcttc      1140
ttactcagcc ctttctacgg cgttttgcat ctcttcgttt tgcagccatt gaagctctac      1200 tccttatttta ccattcgaaa cgctgattgg ggtacgcgca agaaactatt ataa           1254
```

```
<210> SEQ ID NO 8
<211> LENGTH: 568
<212> TYPE: PRT
<213> ORGANISM: Chlorella virus
```

-continued

<400> SEQUENCE: 8

Met Gly Lys Asn Ile Ile Ile Met Val Ser Trp Tyr Thr Ile Ile Thr
1               5                   10                  15

Ser Asn Leu Ile Ala Val Gly Gly Ala Ser Leu Ile Leu Ala Pro Ala
                20                  25                  30

Ile Thr Gly Tyr Val Leu His Trp Asn Ile Ala Leu Ser Thr Ile Trp
            35                  40                  45

Gly Val Ser Ala Tyr Gly Ile Phe Val Phe Gly Phe Phe Leu Ala Gln
        50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ile Ala
                85                  90                  95

Gly Tyr Arg Glu Asp Pro Tyr Met Phe Gln Lys Cys Leu Glu Ser Val
            100                 105                 110

Arg Asp Ser Asp Tyr Gly Asn Val Ala Arg Leu Ile Cys Val Ile Asp
            115                 120                 125

Gly Asp Glu Asp Asp Asp Met Arg Met Ala Ala Val Tyr Lys Ala Ile
        130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Val Leu Ile Asp
            195                 200                 205

Ser Asp Thr Val Leu Glu Lys Asp Ala Ile Leu Glu Val Val Tyr Pro
        210                 215                 220

Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Phe Arg Thr Val
            260                 265                 270

Gln Cys Val Gly Gly Pro Leu Gly Ala Tyr Lys Ile Asp Ile Ile Lys
            275                 280                 285

Glu Ile Lys Asp Pro Trp Ile Ser Gln Arg Phe Leu Gly Gln Lys Cys
        290                 295                 300

Thr Tyr Gly Asp Asp Arg Arg Leu Thr Asn Glu Ile Leu Met Arg Gly
305                 310                 315                 320

Lys Lys Val Val Phe Thr Pro Phe Ala Val Gly Trp Ser Asp Ser Pro
                325                 330                 335

Thr Asn Val Phe Arg Tyr Ile Val Gln Gln Thr Arg Trp Ser Lys Ser
            340                 345                 350

Trp Cys Arg Glu Ile Trp Tyr Thr Leu Phe Ala Ala Trp Lys His Gly
            355                 360                 365

Leu Ser Gly Ile Trp Leu Ala Phe Glu Cys Leu Tyr Gln Ile Thr Tyr
        370                 375                 380

Phe Phe Leu Val Ile Tyr Leu Phe Ser Arg Leu Ala Val Glu Ala Asp
385                 390                 395                 400

Pro Arg Ala Gln Thr Ala Thr Val Ile Val Ser Thr Thr Val Ala Leu

-continued

```
                    405                 410                 415

Ile Lys Cys Gly Tyr Phe Ser Phe Arg Ala Lys Asp Ile Arg Ala Phe
            420                 425                 430

Tyr Phe Val Leu Tyr Thr Phe Val Tyr Phe Phe Cys Met Ile Pro Ala
            435                 440                 445

Arg Ile Thr Ala Met Met Thr Leu Trp Asp Ile Gly Trp Gly Thr Arg
    450                 455                 460

Gly Gly Asn Glu Lys Pro Ser Val Gly Thr Arg Val Ala Leu Trp Ala
465                 470                 475                 480

Lys Gln Tyr Leu Ile Ala Tyr Met Trp Trp Ala Ala Val Val Gly Ala
            485                 490                 495

Gly Val Tyr Ser Ile Val His Asn Trp Met Phe Asp Trp Asn Ser Leu
            500                 505                 510

Ser Tyr Arg Phe Ala Leu Val Gly Ile Cys Ser Tyr Ile Val Phe Ile
            515                 520                 525

Val Ile Val Leu Val Val Tyr Phe Thr Gly Lys Ile Thr Thr Trp Asn
    530                 535                 540

Phe Thr Lys Leu Gln Lys Glu Leu Ile Glu Asp Arg Val Leu Tyr Asp
545                 550                 555                 560

Ala Thr Thr Asn Ala Gln Ser Val
            565

<210> SEQ ID NO 9
<211> LENGTH: 972
<212> TYPE: PRT
<213> ORGANISM: Pasteurella multocida

<400> SEQUENCE: 9

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Lys Glu Lys Leu Ser Ala
            35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
            85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
            115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
            165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
            195                 200                 205
```

-continued

```
Tyr Glu Asn Lys Leu Asp Ile Arg Tyr Val Arg Gln Lys Asp Asn Gly
    210             215             220

Phe Gln Ala Ser Ala Ala Arg Asn Met Gly Leu Arg Leu Ala Lys Tyr
225             230             235             240

Asp Phe Ile Gly Leu Leu Asp Cys Asp Met Ala Pro Asn Pro Leu Trp
            245             250             255

Val His Ser Tyr Val Ala Glu Leu Leu Glu Asp Asp Asp Leu Thr Ile
            260             265             270

Ile Gly Pro Arg Lys Tyr Ile Asp Thr Gln His Ile Asp Pro Lys Asp
            275             280             285

Phe Leu Asn Asn Ala Ser Leu Leu Glu Ser Leu Pro Glu Val Lys Thr
    290             295             300

Asn Asn Ser Val Ala Ala Lys Gly Gly Thr Val Ser Leu Asp Trp
305             310             315             320

Arg Leu Glu Gln Phe Glu Lys Thr Glu Asn Leu Arg Leu Ser Asp Ser
            325             330             335

Pro Phe Arg Phe Phe Ala Ala Gly Asn Val Ala Phe Ala Lys Lys Trp
            340             345             350

Leu Asn Lys Ser Gly Phe Phe Asp Glu Glu Phe Asn His Trp Gly Gly
            355             360             365

Glu Asp Val Glu Phe Gly Tyr Arg Leu Phe Arg Tyr Gly Ser Phe Phe
    370             375             380

Lys Thr Ile Asp Gly Ile Met Ala Tyr His Gln Glu Pro Pro Gly Lys
385             390             395             400

Glu Asn Glu Thr Asp Arg Glu Ala Gly Lys Asn Ile Thr Leu Asp Ile
            405             410             415

Met Arg Glu Lys Val Pro Tyr Ile Tyr Arg Lys Leu Leu Pro Ile Glu
            420             425             430

Asp Ser His Ile Asn Arg Val Pro Leu Val Ser Ile Tyr Ile Pro Ala
            435             440             445

Tyr Asn Cys Ala Asn Tyr Ile Gln Arg Cys Val Asp Ser Ala Leu Asn
    450             455             460

Gln Thr Val Val Asp Leu Glu Val Cys Ile Cys Asn Asp Gly Ser Thr
465             470             475             480

Asp Asn Thr Leu Glu Val Ile Asn Lys Leu Tyr Gly Asn Asn Pro Arg
            485             490             495

Val Arg Ile Met Ser Lys Pro Asn Gly Gly Ile Ala Ser Ala Ser Asn
            500             505             510

Ala Ala Val Ser Phe Ala Lys Gly Tyr Tyr Ile Gly Gln Leu Asp Ser
            515             520             525

Asp Asp Tyr Leu Glu Pro Asp Ala Val Glu Leu Cys Leu Lys Glu Phe
    530             535             540

Leu Lys Asp Lys Thr Leu Ala Cys Val Tyr Thr Thr Asn Arg Asn Val
545             550             555             560

Asn Pro Asp Gly Ser Leu Ile Ala Asn Gly Tyr Asn Trp Pro Glu Phe
            565             570             575

Ser Arg Glu Lys Leu Thr Thr Ala Met Ile Ala His His Phe Arg Met
            580             585             590

Phe Thr Ile Arg Ala Trp His Leu Thr Asp Gly Phe Asn Glu Lys Ile
            595             600             605

Glu Asn Ala Val Asp Tyr Asp Met Phe Leu Lys Leu Ser Glu Val Gly
    610             615             620

Lys Phe Lys His Leu Asn Lys Ile Cys Tyr Asn Arg Val Leu His Gly
```

```
625                630                635                640

Asp Asn Thr Ser Ile Lys Lys Leu Gly Ile Gln Lys Lys Asn His Phe
            645                650                655

Val Val Val Asn Gln Ser Leu Asn Arg Gln Gly Ile Thr Tyr Tyr Asn
            660                665                670

Tyr Asp Glu Phe Asp Asp Leu Asp Glu Ser Arg Lys Tyr Ile Phe Asn
            675                680                685

Lys Thr Ala Glu Tyr Gln Glu Glu Ile Asp Ile Leu Lys Asp Ile Lys
            690                695                700

Ile Ile Gln Asn Lys Asp Ala Lys Ile Ala Val Ser Ile Phe Tyr Pro
705                710                715                720

Asn Thr Leu Asn Gly Leu Val Lys Lys Leu Asn Asn Ile Ile Glu Tyr
                725                730                735

Asn Lys Asn Ile Phe Val Ile Val Leu His Val Asp Lys Asn His Leu
            740                745                750

Thr Pro Asp Ile Lys Lys Glu Ile Leu Ala Phe Tyr His Lys His Gln
            755                760                765

Val Asn Ile Leu Leu Asn Asn Asp Ile Ser Tyr Tyr Thr Ser Asn Arg
            770                775                780

Leu Ile Lys Thr Glu Ala His Leu Ser Asn Ile Asn Lys Leu Ser Gln
785                790                795                800

Leu Asn Leu Asn Cys Glu Tyr Ile Ile Phe Asp Asn His Asp Ser Leu
                805                810                815

Phe Val Lys Asn Asp Ser Tyr Ala Tyr Met Lys Lys Tyr Asp Val Gly
            820                825                830

Met Asn Phe Ser Ala Leu Thr His Asp Trp Ile Glu Lys Ile Asn Ala
            835                840                845

His Pro Pro Phe Lys Lys Leu Ile Lys Thr Tyr Phe Asn Asp Asn Asp
            850                855                860

Leu Lys Ser Met Asn Val Lys Gly Ala Ser Gln Gly Met Phe Met Thr
865                870                875                880

Tyr Ala Leu Ala His Glu Leu Leu Thr Ile Ile Lys Glu Val Ile Thr
                885                890                895

Ser Cys Gln Ser Ile Asp Ser Val Pro Glu Tyr Asn Thr Glu Asp Ile
                900                905                910

Trp Phe Gln Phe Ala Leu Leu Ile Leu Glu Lys Lys Thr Gly His Val
                915                920                925

Phe Asn Lys Thr Ser Thr Leu Thr Tyr Met Pro Trp Glu Arg Lys Leu
            930                935                940

Gln Trp Thr Asn Glu Gln Ile Glu Ser Ala Lys Arg Gly Glu Asn Ile
945                950                955                960

Pro Val Asn Lys Phe Ile Ile Asn Ser Ile Thr Leu
                965                970
```

<210> SEQ ID NO 10
<211> LENGTH: 551
<212> TYPE: PRT
<213> ORGANISM: Xenopus laevis
<400> SEQUENCE: 10

```
Met His Cys Glu Arg Phe Ile Cys Ile Leu Arg Ile Ile Gly Thr Thr
1               5                10                15

Leu Phe Gly Val Ser Leu Leu Leu Gly Ile Ser Ala Ala Tyr Ile Val
            20                25                30
```

```
Gly Tyr Gln Phe Ile Gln Thr Asp Asn Tyr Tyr Phe Ser Phe Gly Leu
        35                  40                  45

Tyr Gly Ala Ile Leu Ala Leu His Leu Ile Ile Gln Ser Leu Phe Ala
    50                  55                  60

Phe Leu Glu His Arg Lys Met Lys Arg Ser Leu Glu Thr Pro Ile Lys
65                  70                  75                  80

Leu Asn Lys Ser Val Ala Leu Cys Ile Ala Ala Tyr Gln Glu Asp Glu
                85                  90                  95

Asp Tyr Leu Arg Lys Cys Leu Leu Ser Val Lys Arg Leu Thr Tyr Pro
            100                 105                 110

Gly Met Lys Val Ile Met Val Ile Asp Gly Asn Ser Asp Asp Asp Leu
            115                 120                 125

Tyr Met Met Asn Ile Phe Arg Glu Ile Met Gly Asn Asp Ser Cys Ala
    130                 135                 140

Thr Tyr Val Trp Lys Asn Asn Phe His Met Lys Gly Pro Asn Glu Thr
145                 150                 155                 160

Asp Glu Thr His Arg Glu Ser Met Gln His Val Thr Gln Met Val Leu
                165                 170                 175

Ser Asn Arg Asn Val Cys Ile Met Gln Lys Trp Asn Gly Lys Arg Glu
            180                 185                 190

Val Met Tyr Thr Ala Phe Lys Ala Leu Gly Arg Ser Val Asp Tyr Val
    195                 200                 205

Gln Val Cys Asp Ser Asp Thr Val Leu Asp Pro Ala Ser Ser Val Glu
    210                 215                 220

Met Val Lys Val Leu Glu Glu Asp Ile Met Val Gly Gly Val Gly Gly
225                 230                 235                 240

Asp Val Gln Ile Leu Asn Lys Tyr Asp Ser Trp Ile Ser Phe Leu Ser
            245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
            275                 280                 285

Asn Ser Leu Leu His Glu Phe Ile Glu Asp Trp Tyr Asn Gln Glu Phe
    290                 295                 300

Leu Gly Ser Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Thr Glu Tyr Leu Arg Trp Leu Asn Gln Gln Thr
            340                 345                 350

Arg Trp Ser Lys Ser Tyr Phe Arg Glu Trp Leu Tyr Asn Ser Leu Trp
            355                 360                 365

Phe His Lys His His Leu Trp Met Thr Tyr Glu Ala Val Ile Thr Gly
    370                 375                 380

Phe Phe Pro Phe Phe Leu Ile Ala Thr Val Ile Gln Leu Phe Tyr Arg
385                 390                 395                 400

Gly Arg Ile Trp Asn Ile Leu Leu Phe Leu Leu Thr Val Gln Leu Val
                405                 410                 415

Gly Leu Ile Lys Ser Ser Phe Ala Ser Ala Leu Arg Gly Asn Ile Val
            420                 425                 430

Met Val Phe Met Ser Phe Tyr Ser Val Leu Tyr Met Ser Ser Leu Leu
    435                 440                 445

Pro Ala Lys Met Phe Ala Ile Ala Thr Ile Asn Lys Ala Gly Trp Gly
```

-continued

```
        450             455             460

Thr Ser Gly Arg Lys Thr Ile Val Val Asn Phe Ile Gly Leu Ile Pro
465             470             475             480

Ile Thr Val Trp Phe Thr Ile Leu Leu Gly Gly Val Cys Tyr Thr Ile
            485             490             495

Trp Arg Glu Thr Lys Lys Pro Phe Ser Glu Ser Glu Lys Ile Val Leu
            500             505             510

Ala Val Gly Ala Ile Leu Tyr Ala Cys Tyr Trp Val Met Leu Leu Thr
            515             520             525

Met Tyr Val Ser Leu Val Met Lys Cys Gly Arg Arg Arg Lys Glu Pro
            530             535             540

Gln His Asp Leu Val Leu Ala
545             550

<210> SEQ ID NO 11
<211> LENGTH: 417
<212> TYPE: PRT
<213> ORGANISM: Streptococcus zooepidemicus

<400> SEQUENCE: 11

Met Arg Thr Leu Lys Asn Leu Ile Thr Val Val Ala Phe Ser Ile Phe
1               5               10              15

Trp Val Leu Leu Ile Tyr Val Asn Val Tyr Leu Phe Gly Ala Lys Gly
            20              25              30

Ser Leu Ser Ile Tyr Gly Phe Leu Leu Ile Ala Tyr Leu Leu Val Lys
            35              40              45

Met Ser Leu Ser Phe Phe Tyr Lys Pro Phe Lys Gly Arg Ala Gly Gln
            50              55              60

Tyr Lys Val Ala Ala Ile Ile Pro Ser Tyr Asn Glu Asp Ala Glu Ser
65              70              75              80

Leu Leu Glu Thr Leu Lys Ser Val Gln Gln Gln Thr Tyr Pro Leu Ala
            85              90              95

Glu Ile Tyr Val Val Asp Asp Gly Ser Ala Asp Glu Thr Gly Ile Lys
            100             105             110

Arg Ile Glu Asp Tyr Val Arg Asp Thr Gly Asp Leu Ser Ser Asn Val
            115             120             125

Ile Val His Arg Ser Glu Lys Asn Gln Gly Lys Arg His Ala Gln Ala
            130             135             140

Trp Ala Phe Glu Arg Ser Asp Ala Asp Val Phe Leu Thr Val Asp Ser
145             150             155             160

Asp Thr Tyr Ile Tyr Pro Asp Ala Leu Glu Glu Leu Leu Lys Thr Phe
            165             170             175

Asn Asp Pro Thr Val Phe Ala Ala Thr Gly His Leu Asn Val Arg Asn
            180             185             190

Arg Gln Thr Asn Leu Leu Thr Arg Leu Thr Asp Ile Arg Tyr Asp Asn
            195             200             205

Ala Phe Gly Val Glu Arg Ala Ala Gln Ser Val Thr Gly Asn Ile Leu
            210             215             220

Val Cys Ser Gly Pro Leu Ser Val Tyr Arg Arg Glu Val Val Val Pro
225             230             235             240

Asn Ile Asp Arg Tyr Ile Asn Gln Thr Phe Leu Gly Ile Pro Val Ser
            245             250             255

Ile Gly Asp Asp Arg Cys Leu Thr Asn Tyr Ala Thr Asp Leu Gly Lys
            260             265             270
```

```
Thr Val Tyr Gln Ser Thr Ala Lys Cys Ile Thr Asp Val Pro Asp Lys
        275             280             285

Met Ser Thr Tyr Leu Lys Gln Gln Asn Arg Trp Asn Lys Ser Phe Phe
    290             295             300

Arg Glu Ser Ile Ile Ser Val Lys Lys Ile Met Asn Asn Pro Phe Val
305             310             315             320

Ala Leu Trp Thr Ile Leu Glu Val Ser Met Phe Met Met Leu Val Tyr
            325             330             335

Ser Val Val Asp Phe Phe Val Gly Asn Val Arg Glu Phe Asp Trp Leu
            340             345             350

Arg Val Leu Ala Phe Leu Val Ile Ile Phe Ile Val Ala Leu Cys Arg
            355             360             365

Asn Ile His Tyr Met Leu Lys His Pro Leu Ser Phe Leu Leu Ser Pro
    370             375             380

Phe Tyr Gly Val Leu His Leu Phe Val Leu Gln Pro Leu Lys Leu Tyr
385             390             395             400

Ser Leu Phe Thr Ile Arg Asn Ala Asp Trp Gly Thr Arg Lys Lys Leu
            405             410             415

Leu
```

```
<210> SEQ ID NO 12
<211> LENGTH: 1446
<212> TYPE: DNA
<213> ORGANISM: Arabidopsis thaliana

<400> SEQUENCE: 12
atggtcaaaa tatgctgtat cggggctgga tatgtcggtg ggcctacaat ggccgttatg        60
gccctaaagt gtccagagat tgaagtcgtg gtagttgata tatcggagcc acgaattaac       120
gcatggaact cagaccgtct accaatttat gagccagggt tagaggatgt cgtcaaacag       180
tgtagaggga agaatttgtt cttctctaca gatgtagaga agcatgtatt tgagtcagat       240
atagtgtttg tttcggtaaa cactcctacg aaaacgcagg gtctgggtgc aggtaaagca       300
gcagatttga catattggga gtccgctgct cgcatgatag ctgatgtgag caaatcgtcg       360
aaaatcgtcg ttgaaaagag tacagtacca gttcgtacag ccgaggctat agaaaagatt       420
ttaacgcaca attcgaaggg tatcgaattc cagatcttat caaatccaga attcttggcc       480
gaagggacgg cgattaaaga cttatataac cctgatagag ttctaatcgg tggcagggac       540
accgctgcgg gacaaaaggc cattaaggcg ttgcgtgacg tgtatgccca ctgggttcct       600
gttgagcaaa taatctgtac taatttatgg agtgccgagc tatcaaagtt ggctgcgaac       660
gcatttctag ctcaaaggat aagttcagta aacgcaatgt cagcgctttg tgaggcaact       720
ggtgctgacg taacccaagt cgctcacgcc gttggaaccg acactagaat tggaccgaag       780
tttcttaacg catccgtagg cttcggcgga tcttgctttc agaaagacat cctgaatctt       840
atttacatct gcgaatgcaa tggtcttcca gaagcagcca attattggaa acaggtagtc       900
aaggtaaatg actaccaaaa gattaggttt gctaatcgag tcgtatcttc tatgttcaac       960
accgtctccg gtaagaaaat tgctattttg ggatttgcgt tcaagaagga caccggcgac      1020
acgcgtgaaa ctcctgccat agatgtgtgt aatcgcctcg tggctgataa agcaaagctg      1080
tcgatctatg atccgcaagt attagaagag cagatccgcc gtgatctgtc catggcccga      1140
ttcgattggg accatccagt cccactccag cagatcaaag ctgaaggtat ctccgaacag      1200
gttaacgttg tgtccgacgc ctacgaggct acgaaggatg ctcatggttt atgtgtttta      1260
```

```
accgaatggg acgaattcaa gtcacttgat tttaagaaga tctttgataa tatgcagaaa   1320
cccgctttcg ttttcgacgg aagaaacgtg gtcgacgctg tgaaattgag agaaattgga   1380
ttcatagtat attccatagg taaacctctg gatagttggc tcaaggatat gccggctgtt   1440
gcataa                                                             1446

<210> SEQ ID NO 13
<211> LENGTH: 1166
<212> TYPE: DNA
<213> ORGANISM: Chlorella virus

<400> SEQUENCE: 13
atgagtagaa ttgctgtcgt tggatgcggt tacgtgggta cggcctgcgc cgtacttttg     60
gcgcagaaga acgaagttat cgtttttggat atctcggagg accgggtaca actgattaag   120
aataagaagt cacctataga agataaggaa atcgaagaat tcctggagac gaaagatttg    180
aatctaacag cgacgacgga taaggtgctc gcctatgaga atgctgaatt cgttataata    240
gctacaccga ccgattacga tgtcgtcact agatatttca acactaagtc tgttgaaaat    300
gtgataggcg atgtcattaa gaacactcag acacaccct ctatagtgat caagagtact     360
attccaatcg gtttcgtgga taaagttaga gaacagttcg attatcaaaa tattatcttc    420
tcgccggaat tcttgagaga aggacgagca ttatatgata tctttaccc ctcccgtatc     480 atcgtcggtg atgactcccc aattgcctta aaattcgcga atctcttggt cgagggtagc    540
aaaactccac tagctcccgt attaactatg ggtacgcgag aggccgaagc tgtaaaacta    600
ttttcaaata catatttggc tatgagagta gcatacttca atgagctaga cacatttgca    660
atgtcccatg gtatgaacgc aaaagagatt atcgacggag tcacactaga accaaggata    720
gggcagggtt attcgaatcc ttcatttggg tatggagcct attgtttccc aaaagataca    780
aagcaattgt tggctaattt tgaagggggtt ccacaagata ttattggcgc aatcgtagag    840
tctaacgaaa ctagaaagga ggttattgtt tctgaggtcg agaacagatt ccgaccaca     900 gttggcgtat ataagttggc tgctaaagct ggttcggata atttcaggtc tagtgcgata    960
gtcgatatca tggaaaggtt ggctaataag ggctaccaca tcaaaatatt tgaacctacc   1020
gttgaacaat ttgagaattt tgaggtagat aataatctca caacttttgc aaccgagtct   1080
gatgtaataa ttgcgaacag agttccagtc gaacatcgca ttctgtttgg gaagaagtta   1140
ataacacggg atgtctatgg ggataa                                       1166

<210> SEQ ID NO 14
<211> LENGTH: 1170
<212> TYPE: DNA
<213> ORGANISM: Chlorella virus

<400> SEQUENCE: 14
atgtcacgaa tcgcagtagt tggctgtggg tacgtgggaa ccgcatgcgc tgtactgctg     60
gcgcaaaaga atgaggtaat cgttcttgat attagtgagg atagggtcca actaatcaag   120
aacaagaaat ccccgatcga agataaggag attgaagaat tcttggaaac aaaagaccta   180
aacttaactg caacaactga caaagtttta gcctacgaaa acgctgagtt tgtgattata    240
gcgacaccca cagattatga cgtagttacc agatactta acacgaagtc cgtagagaac     300
gtcattggag atgttataaa gaatactcag actcatccta cgatagtaat aaagtcaacc    360
attcccatag gtttcgtaga taaggttagg gagcaattcg attaccagaa cattatattt    420
tcgccagaat ttctgagaga gggtcgcgcc ctgtatgata atctatatcc atcacggatt    480
```

-continued

_____

```
atagtgggcg atgactctcc gattgcactt aagtttgcta atcttttagt tgagggctcc        540
aaaactccgc tcgccccagt acttacgatg ggtacacgtg aggctgaagc tgtcaagctg        600
ttttcaaaca cataccttgc tatgcgagtc gcatacttta acgaactaga tacctttgct        660
atgtcgcacg gtatgaatgc taaagaaatc atagatggcg taacgttgga gcctcggata        720
ggtcaaggat attccaatcc atcttttggc tacggtgcgt attgtttccc aaaggacacg        780
aagcaattat tagctaactt tgagggtgtt ccgcaagata taattggggc gatagtagaa        840
agcaatgaaa cacggaagga ggtaatcgtg agtgaagtgg aaaaccgatt ccccactacg        900
gtcggcgttt acaaattagc cgccaaggct ggttccgaca atttccgatc cagcgcaata        960
gtagatatta tggaaagatt agctaataag ggataccaca ttaaaatctt tgaacctact       1020
gtcgaacagt tcgagaactt cgaggttgat aataacttga cgactttcgc aacggagagc       1080
gatgtaatta ttgcaaaccg cgtacctgtg gaacatcgaa ttttgttcgg aaagaagctg       1140
attacacgcg atgtatatgg cgataactaa                                        1170
```

<210> SEQ ID NO 15
<211> LENGTH: 1199
<212> TYPE: DNA
<213> ORGANISM: Streptococcus zooepidemicus

<400> SEQUENCE: 15

```
atgaagatat cggtagcggg ttcggggtac gtggggttat ccttgtcaat cttgcttgcc         60
caacataacg atgtgactgt tgtagatata atcgacgaaa aggtacggct aattaaccag        120
ggcatatctc cgattaagga tgcggacatt gaggaatatc tgaagaatgc accgttgaat        180
cttacggcta cactagacgg agcttcggct tatagtaatg ctgatctgat tataatcgca        240
acgccaacta attacgattc agaacgcaat tatttcgaca ccagacacgt tgaagaagta        300
attgagcaag tattggattt aaatgcctcc gctactataa tcatcaagag taccataccc        360
ttgggtttta ttaaacacgt aagagagaaa taccaaacag acagaatcat cttttctcca        420
gagttcttaa gagagtcaaa ggcattgtac gataacttat acccctctcg tataatagtc        480
agttatgaga aggatgactc tccaagagtt atacaagcag ctaaggcgtt cgcgggttta        540
ttaaaagagg gggcaaagag caaggatacc ccagttctgt ttatgggctc tcaagaagct        600
gaagctgtca agctgtttgc taatactttt ctcgccatga gggtcagtta cttcaacgag        660
cttgacactt atagcgaatc aaaaggacta gacgcccaaa gagttataga aggcgtctgc        720
catgatcaaa ggataggtaa tcattacaat aatccatcct tcggatatgg cggttattgt        780
ttacccaaag actcaaagca acttttggct aattatagag gcatacctca gtctctaatg        840
tctgccatcg ttgaatcgaa caagatccgt aagtcgtatt tagctgaaca aatattagat        900
agggcttctt cacaaaagca ggctggtgta cctttaacca taggatttta ccgtttgatt        960
atgaagtcca actccgataa ctttagagaa tcagccatta aagatattat tgacatcatt       1020
aatgactacg gtgtcaatat tgtcatttat gaacctatgt tgggagaaga cattggttat       1080
agagtcgtta agatttgga acagtttaag aacgaaagta caattattgt tagtaacagg       1140
tttgaagatg atttaggtga tgttattgat aaagtttata cacgtgacgt ctttggtag       1199
```

<210> SEQ ID NO 16
<211> LENGTH: 481
<212> TYPE: PRT
<213> ORGANISM: Arabidopsis thaliana

```
<400> SEQUENCE: 16

Met Val Lys Ile Cys Cys Ile Gly Ala Gly Tyr Val Gly Gly Pro Thr
1               5                   10                  15

Met Ala Val Met Ala Leu Lys Cys Pro Glu Ile Glu Val Val Val Val
                20                  25                  30

Asp Ile Ser Glu Pro Arg Ile Asn Ala Trp Asn Ser Asp Arg Leu Pro
            35                  40                  45

Ile Tyr Glu Pro Gly Leu Glu Asp Val Val Lys Gln Cys Arg Gly Lys
        50                  55                  60

Asn Leu Phe Phe Ser Thr Asp Val Glu Lys His Val Phe Glu Ser Asp
65                  70                  75                  80

Ile Val Phe Val Ser Val Asn Thr Pro Thr Lys Thr Gln Gly Leu Gly
                85                  90                  95

Ala Gly Lys Ala Ala Asp Leu Thr Tyr Trp Glu Ser Ala Ala Arg Met
                100                 105                 110

Ile Ala Asp Val Ser Lys Ser Ser Lys Ile Val Val Glu Lys Ser Thr
                115                 120                 125

Val Pro Val Arg Thr Ala Glu Ala Ile Glu Lys Ile Leu Thr His Asn
        130                 135                 140

Ser Lys Gly Ile Glu Phe Gln Ile Leu Ser Asn Pro Glu Phe Leu Ala
145                 150                 155                 160

Glu Gly Thr Ala Ile Lys Asp Leu Tyr Asn Pro Asp Arg Val Leu Ile
                165                 170                 175

Gly Gly Arg Asp Thr Ala Ala Gly Gln Lys Ala Ile Lys Ala Leu Arg
                180                 185                 190

Asp Val Tyr Ala His Trp Val Pro Val Glu Gln Ile Ile Cys Thr Asn
            195                 200                 205

Leu Trp Ser Ala Glu Leu Ser Lys Leu Ala Ala Asn Ala Phe Leu Ala
        210                 215                 220

Gln Arg Ile Ser Ser Val Asn Ala Met Ser Ala Leu Cys Glu Ala Thr
225                 230                 235                 240

Gly Ala Asp Val Thr Gln Val Ala His Ala Val Gly Thr Asp Thr Arg
                245                 250                 255

Ile Gly Pro Lys Phe Leu Asn Ala Ser Val Gly Phe Gly Gly Ser Cys
                260                 265                 270

Phe Gln Lys Asp Ile Leu Asn Leu Ile Tyr Ile Cys Glu Cys Asn Gly
                275                 280                 285

Leu Pro Glu Ala Ala Asn Tyr Trp Lys Gln Val Val Lys Val Asn Asp
        290                 295                 300

Tyr Gln Lys Ile Arg Phe Ala Asn Arg Val Val Ser Ser Met Phe Asn
305                 310                 315                 320

Thr Val Ser Gly Lys Lys Ile Ala Ile Leu Gly Phe Ala Phe Lys Lys
                325                 330                 335

Asp Thr Gly Asp Thr Arg Glu Thr Pro Ala Ile Asp Val Cys Asn Arg
                340                 345                 350

Leu Val Ala Asp Lys Ala Lys Leu Ser Ile Tyr Asp Pro Gln Val Leu
                355                 360                 365

Glu Glu Gln Ile Arg Arg Asp Leu Ser Met Ala Arg Phe Asp Trp Asp
        370                 375                 380

His Pro Val Pro Leu Gln Gln Ile Lys Ala Glu Gly Ile Ser Glu Gln
385                 390                 395                 400

Val Asn Val Val Ser Asp Ala Tyr Glu Ala Thr Lys Asp Ala His Gly
                405                 410                 415
```

```
Leu Cys Val Leu Thr Glu Trp Asp Glu Phe Lys Ser Leu Asp Phe Lys
            420                 425                 430

Lys Ile Phe Asp Asn Met Gln Lys Pro Ala Phe Val Phe Asp Gly Arg
            435                 440                 445

Asn Val Val Asp Ala Val Lys Leu Arg Glu Ile Gly Phe Ile Val Tyr
    450                 455                 460

Ser Ile Gly Lys Pro Leu Asp Ser Trp Leu Lys Asp Met Pro Ala Val
465                 470                 475                 480

Ala

<210> SEQ ID NO 17
<211> LENGTH: 389
<212> TYPE: PRT
<213> ORGANISM: Chlorella virus

<400> SEQUENCE: 17

Met Ser Arg Ile Ala Val Val Gly Cys Gly Tyr Val Gly Thr Ala Cys
1               5                   10                  15

Ala Val Leu Leu Ala Gln Lys Asn Glu Val Ile Val Leu Asp Ile Ser
            20                  25                  30

Glu Asp Arg Val Gln Leu Ile Lys Asn Lys Lys Ser Pro Ile Glu Asp
            35                  40                  45

Lys Glu Ile Glu Glu Phe Leu Glu Thr Lys Asp Leu Asn Leu Thr Ala
    50                  55                  60

Thr Thr Asp Lys Val Leu Ala Tyr Glu Asn Ala Glu Phe Val Ile Ile
65                  70                  75                  80

Ala Thr Pro Thr Asp Tyr Asp Val Val Thr Arg Tyr Phe Asn Thr Lys
                85                  90                  95

Ser Val Glu Asn Val Ile Gly Asp Val Ile Lys Asn Thr Gln Thr His
            100                 105                 110

Pro Thr Ile Val Ile Lys Ser Thr Ile Pro Ile Gly Phe Val Asp Lys
            115                 120                 125

Val Arg Glu Gln Phe Asp Tyr Gln Asn Ile Ile Phe Ser Pro Glu Phe
    130                 135                 140

Leu Arg Glu Gly Arg Ala Leu Tyr Asp Asn Leu Tyr Pro Ser Arg Ile
145                 150                 155                 160

Ile Val Gly Asp Asp Ser Pro Ile Ala Leu Lys Phe Ala Asn Leu Leu
            165                 170                 175

Val Glu Gly Ser Lys Thr Pro Leu Ala Pro Val Leu Thr Met Gly Thr
            180                 185                 190

Arg Glu Ala Glu Ala Val Lys Leu Phe Ser Asn Thr Tyr Leu Ala Met
            195                 200                 205

Arg Val Ala Tyr Phe Asn Glu Leu Asp Thr Phe Ala Met Ser His Gly
    210                 215                 220

Met Asn Ala Lys Glu Ile Ile Asp Gly Val Thr Leu Glu Pro Arg Ile
225                 230                 235                 240

Gly Gln Gly Tyr Ser Asn Pro Ser Phe Gly Tyr Gly Ala Tyr Cys Phe
                245                 250                 255

Pro Lys Asp Thr Lys Gln Leu Leu Ala Asn Phe Glu Gly Val Pro Gln
            260                 265                 270

Asp Ile Ile Gly Ala Ile Val Glu Ser Asn Glu Thr Arg Lys Glu Val
            275                 280                 285

Ile Val Ser Glu Val Glu Asn Arg Phe Pro Thr Thr Val Gly Val Tyr
    290                 295                 300
```

-continued

```
Lys Leu Ala Ala Lys Ala Gly Ser Asp Asn Phe Arg Ser Ser Ala Ile
305                 310                 315                 320

Val Asp Ile Met Glu Arg Leu Ala Asn Lys Gly Tyr His Ile Lys Ile
                325                 330                 335

Phe Glu Pro Thr Val Glu Gln Phe Glu Asn Phe Glu Val Asp Asn Asn
            340                 345                 350

Leu Thr Thr Phe Ala Thr Glu Ser Asp Val Ile Ile Ala Asn Arg Val
            355                 360                 365

Pro Val Glu His Arg Ile Leu Phe Gly Lys Lys Leu Ile Thr Arg Asp
        370                 375                 380

Val Tyr Gly Asp Asn
385

<210> SEQ ID NO 18
<211> LENGTH: 401
<212> TYPE: PRT
<213> ORGANISM: Streptococcus zooepidemicus

<400> SEQUENCE: 18

Met Lys Ile Ser Val Ala Gly Ser Gly Tyr Val Gly Leu Ser Leu Ser
1               5                   10                  15

Ile Leu Leu Ala Gln His Asn Asp Val Thr Val Val Asp Ile Ile Asp
                20                  25                  30

Glu Lys Val Arg Leu Ile Asn Gln Gly Ile Ser Pro Ile Lys Asp Ala
            35                  40                  45

Asp Ile Glu Glu Tyr Leu Lys Asn Ala Pro Leu Asn Leu Thr Ala Thr
        50                  55                  60

Leu Asp Gly Ala Ser Ala Tyr Ser Asn Ala Asp Leu Ile Ile Ile Ala
65                  70                  75                  80

Thr Pro Thr Asn Tyr Asp Ser Glu Arg Asn Tyr Phe Asp Thr Arg His
                85                  90                  95

Val Glu Glu Val Ile Glu Gln Val Leu Asp Leu Asn Ala Ser Ala Thr
            100                 105                 110

Ile Ile Ile Lys Ser Thr Ile Pro Leu Gly Phe Ile Lys His Val Arg
            115                 120                 125

Glu Lys Tyr Gln Thr Asp Arg Ile Ile Phe Ser Pro Glu Phe Leu Arg
        130                 135                 140

Glu Ser Lys Ala Leu Tyr Asp Asn Leu Tyr Pro Ser Arg Ile Ile Val
145                 150                 155                 160

Ser Tyr Glu Lys Asp Asp Ser Pro Arg Val Ile Gln Ala Ala Lys Ala
                165                 170                 175

Phe Ala Gly Leu Leu Lys Glu Gly Ala Lys Ser Lys Asp Thr Pro Val
            180                 185                 190

Leu Phe Met Gly Ser Gln Glu Ala Glu Ala Val Lys Leu Phe Ala Asn
            195                 200                 205

Thr Phe Leu Ala Met Arg Val Ser Tyr Phe Asn Glu Leu Asp Thr Tyr
        210                 215                 220

Ser Glu Ser Lys Gly Leu Asp Ala Gln Arg Val Ile Glu Gly Val Cys
225                 230                 235                 240

His Asp Gln Arg Ile Gly Asn His Tyr Asn Asn Pro Ser Phe Gly Tyr
                245                 250                 255

Gly Gly Tyr Cys Leu Pro Lys Asp Ser Lys Gln Leu Leu Ala Asn Tyr
            260                 265                 270

Arg Gly Ile Pro Gln Ser Leu Met Ser Ala Ile Val Glu Ser Asn Lys
```

```
            275              280              285
Ile Arg Lys Ser Tyr Leu Ala Glu Gln Ile Leu Asp Arg Ala Ser Ser
    290              295              300

Gln Lys Gln Ala Gly Val Pro Leu Thr Ile Gly Phe Tyr Arg Leu Ile
305              310              315              320

Met Lys Ser Asn Ser Asp Asn Phe Arg Glu Ser Ala Ile Lys Asp Ile
                 325              330              335

Ile Asp Ile Ile Asn Asp Tyr Gly Val Asn Ile Val Ile Tyr Glu Pro
             340              345              350

Met Leu Gly Glu Asp Ile Gly Tyr Arg Val Val Lys Asp Leu Glu Gln
         355              360              365

Phe Lys Asn Glu Ser Thr Ile Ile Val Ser Asn Arg Phe Glu Asp Asp
    370              375              380

Leu Gly Asp Val Ile Asp Lys Val Tyr Thr Arg Asp Val Phe Gly Arg
385              390              395              400

Asp
```

```
<210> SEQ ID NO 19
<211> LENGTH: 1326
<212> TYPE: DNA
<213> ORGANISM: Bothrops atrox

<400> SEQUENCE: 19
atgcaattta gcacagtcgc atcagtagcc ttcgttgcct tggccaactt cgtggcagca      60
ccgatgtatc cgaacgaacc gttcttagtc ttttggaacg cgcctacaac tcagtgtaga     120
cttcgatata aggttgacct tgatctgaag acattccata tcgtgacaaa tgctaatgac     180
tcgctgtcag gatcggctgt cacgattttc tatcccacgc acttaggggt ttacccacat     240
attgatgaca gggggcactt cttcaatggc atcatacccc aaaatgaatc cctggtaaag     300
catttaaaca aatctaaatc agatattaat cgaatgattc ccttaagaac attccacggg     360
ctgggagtca tagactggga aaactggcgg ccacagtggg ataggaattg gggaagtaag     420
aacgtttata ggaatagatc aatccaattc gcgcgtgatc tccacccaga gcttagtgag     480
gacaagatta aacgcttggc aaaacaggaa ttcgagaaag ctgcaaagag ttttatgagg     540
gatacactat tattagccga ggagatgcga ccagacggct actggggata ctatctgtac     600
cccgattgtc acaattacaa ttataagact aagccagatc agtacacagg agagtgccct     660
gacatcgaga tgtcacgtaa caatcaactc ttgtggcttt ggcgggatag cactgccctt     720
ttccccaata tctacttaga gactatacta agaagctctg acaatgccct gaagtttgtg     780
caccataggc tcaaggaggc aatgaggata gcctcaatgg ctcgaaatga ctacgcgttg     840
cctttctttg tttatgctcg accattctat gcctatacct tcgaaccatt gactcaggaa     900
gaccttgtga ctacggtcgg agagaccgcg gacatgggcg ccgctgggat cgtattttgg     960
gggagtatgc agtacgcaag cacggttgaa tcttgcggca aagtcaagga ctacatgaat    1020
ggcccactgg ggcgttacat tgtgaatgtt acaactgccg ccaaaatttg ctcacgattc    1080
ttgtgcaaac gtcatggtag gtgtgtaaga aagcactcag actccaatgc attccttcac    1140
ctatttcccg attcgtttcg cataatggtg cacgggaatg caaccgagaa gaaagttata    1200
gtaaagggga agctggaatt aaagaatctt atattcttac gtaataactt tatgtgccag    1260
tgttatcaag ctggaaagg tctatattgc gagaagcatt cgataaagga aattcggaaa    1320
atctaa                                                               1326
```

-continued

```
<210> SEQ ID NO 20
<211> LENGTH: 1537
<212> TYPE: DNA
<213> ORGANISM: Bothrops atrox

<400> SEQUENCE: 20
atgcaattta gcacagtcgc atcagtagcc ttcgttgcct tggccaactt cgtggcagca       60
ccgatgtatc cgaacgaacc gttcttagtc ttttggaacg cgcctacaac tcagtgtaga      120
cttcgatata aggttgacct tgatctgaag acattccata tcgtgacaaa tgctaatgac      180
tcgctgtcag gatcggctgt cacgattttc tatcccacgc acttaggggt ttacccacat      240
attgatgaca gggggcactt cttcaatggc atcatacccc aaaatgaatc cctggtaaag      300
catttaaaca aatctaaatc agatattaat cgaatgattc ccttaagaac attccacggg      360
ctgggagtca tagactggga aaactggcgg ccacagtggg ataggaattg gggaagtaag      420
aacgtttata ggaatagatc aatccaattc gcgcgtgatc tccacccaga gcttagtgag      480
gacaagatta aacgcttggc aaaacaggaa ttcgagaaag ctgcaaagag ttttatgagg      540
gatacactat tattagccga ggagatgcga ccagacggct actggggata ctatctgtac      600
cccgattgtc acaattacaa ttataagact aagccagatc agtacacagg agagtgccct      660
gacatcgaga tgtcacgtaa caatcaactc ttgtggcttt ggcgggatag cactgccctt      720
ttccccaata tctacttaga gactatacta agaagctctg acaatgccct gaagtttgtg      780
caccataggc tcaaggaggc aatgaggata gcctcaatgg ctcgaaatga ctacgcgttg      840
cctttctttg tttatgctcg accattctat gcctatacct tcgaaccatt gactcaggaa      900
gaccttgtga ctacggtcgg agagaccgcg gacatgggcg ccgctgggat cgtattttgg      960
gggagtatgc agtacgcaag cacggttgaa tcttgcggca aagtcaagga ctacatgaat     1020
ggcccactgg ggcgttacat tgtgaatgtt acaactgccg ccaaaatttg ctcacgattc     1080
ttgtgcaaac gtcatggtag gtgtgtaaga aagcactcag actccaatgc attccttcac     1140
ctatttcccg attcgtttcg cataatggtg cacgggaatg caaccgagaa gaaagttata     1200
gtaaagggga agctggaatt aaagaatctt atattcttac gtaataactt tatgtgccag     1260
tgttatcaag gctggaaagg tctatattgc gagaagcatt cgataaagga aattcggaaa     1320
atcggatccg ccatttctca aatcactgac ggtcaaatcc aagctactac cactgctacc     1380
accgaagcta ccaccactgc tgccccatct tccaccgttg aaactgtttc tccatccagc     1440
accgaaacta tctctcaaca aactgaaaat ggtgctgcta aggccgctgt cggtatgggt     1500
gccggtgctc tagctgctgc tgctatgttg ttataaa                             1537

<210> SEQ ID NO 21
<211> LENGTH: 1197
<212> TYPE: DNA
<213> ORGANISM: Cupiennius salei

<400> SEQUENCE: 21
atgcaattca gcactgttgc atcagttgca tttgtcgccc tggcgaattt tgtagccgcg       60
ttcaagattt actggaacgt cccaactttt cagtgcacgc ataactacaa aatcgattat      120
gtcaaattgt tgtccactta cgggatacag gtcaatgatg gcggtaagtt tcaaggaaac      180
caagtgacta tcttttatga aacccagttg ggtttgtatc cacgaatcct aaaatctggt      240
aaaatggaaa acggcggaat ccctcaacgc ggtaactttg agaacacct agaaaaggca      300 agcacggacc tccagaaagt gatcccttgg aaagagtttta gcggattagg tgtgatagat      360
```

-continued

```
tgggaggctt ggagacccac atgggaattt aactgggaac cgttgaggat atatcaaacc        420
gaatcaatta agagagctaa agaactacac cctaccgcaa acgattccgc agtaaaagaa        480
attgcagagc ggcaatggga agattcagcc aagttataca tgttagaaac actgcggctg        540
gcaaagaaac ttcgacctca agcgccttgg tgttactact tatttcctga ttgctataat        600
tacgtcggaa agaaaccaaa agatttccaa tgtagtgcct cgatacgtaa aggtaacgat        660
aagctaagct ggttgtggaa agattctacg gcattgtgtc catcgatata cgtatatgaa        720
tcacaattag acaggtattc ttttgaacaa aggacatggc gcgacaatga gaaacttcgg        780
gaagcgttgc gtgtagccac gagaacctct aaaatatacc catacgttaa ctatttcgat        840
aaggagctta taccggagca agaagtatgg agaatgcttg cgcaggcagc tgctgtcggt        900
ggcagtggtg cggtaatttg gggctcatct gctgcagttg catctgaaga gttatgtaaa        960
tctttaaaac agtatattat tgaaacgctt gggccggcgg cagagaaggt ggcttggcgt       1020
agtgacttat gcagcaaaga aatttgtaat aatcagggtc gctgcacatt cccggacgat       1080
gattatgcaa acgcatggaa attatttaca gatgatactg ttaagtttta tgctggtaat       1140
attacatgta ggtgctccga gaattattct ggtcgtttct gcgaaaagaa gaattaa         1197
```

<210> SEQ ID NO 22
<211> LENGTH: 1407
<212> TYPE: DNA
<213> ORGANISM: Cupiennius salei

<400> SEQUENCE: 22

```
atgcaattca gcactgttgc atcagttgca tttgtcgccc tggcgaattt tgtagccgcg         60
ttcaagattt actggaacgt cccaactttt cagtgcacgc ataactacaa aatcgattat        120
gtcaaattgt tgtccactta cgggatacag gtcaatgatg gcggtaagtt tcaaggaaac        180
caagtgacta tcttttatga aacccagttg ggtttgtatc cacgaatcct aaaatctggt        240
aaaatggaaa acggcggaat ccctcaacgc ggtaactttg agaaacacct agaaaaggca        300
agcacggacc tccagaaagt gatcccttgg aaagagttta gcggattagg tgtgatagat        360
tgggaggctt ggagacccac atgggaattt aactgggaac cgttgaggat atatcaaacc        420
gaatcaatta agagagctaa agaactacac cctaccgcaa acgattccgc agtaaaagaa        480
attgcagagc ggcaatggga agattcagcc aagttataca tgttagaaac actgcggctg        540
gcaaagaaac ttcgacctca agcgccttgg tgttactact tatttcctga ttgctataat        600
tacgtcggaa agaaaccaaa agatttccaa tgtagtgcct cgatacgtaa aggtaacgat        660
aagctaagct ggttgtggaa agattctacg gcattgtgtc catcgatata cgtatatgaa        720
tcacaattag acaggtattc ttttgaacaa aggacatggc gcgacaatga gaaacttcgg        780
gaagcgttgc gtgtagccac gagaacctct aaaatatacc catacgttaa ctatttcgat        840
aaggagctta taccggagca agaagtatgg agaatgcttg cgcaggcagc tgctgtcggt        900
ggcagtggtg cggtaatttg gggctcatct gctgcagttg catctgaaga gttatgtaaa        960
tctttaaaac agtatattat tgaaacgctt gggccggcgg cagagaaggt ggcttggcgt       1020
agtgacttat gcagcaaaga aatttgtaat aatcagggtc gctgcacatt cccggacgat       1080
gattatgcaa acgcatggaa attatttaca gatgatactg ttaagtttta tgctggtaat       1140
attacatgta ggtgctccga gaattattct ggtcgtttct gcgaaaagaa gaatggatcc       1200
gccatttctc aaatcactga cggtcaaatc caagctacta ccactgctac caccgaagct       1260
```

-continued

```
accaccactg ctgccccatc ttccaccgtt gaaactgttt ctccatccag caccgaaact     1320
atctctcaac aaactgaaaa tggtgctgct aaggccgctg tcggtatggg tgccggtgct     1380
ctagctgctg ctgctatgtt gttataa                                          1407

<210> SEQ ID NO 23
<211> LENGTH: 1530
<212> TYPE: DNA
<213> ORGANISM: Hirudo nipponia

<400> SEQUENCE: 23
atgcaattct ctactgtcgc ttccgttgct ttcgtcgctt tggctaactt tgttgccgct       60
atgaaggaga tagcagttac catcgatgat aagaatgtta tagcgtctgt cagtgaaagc      120
ttccatggtg tggctttcga cgcaagccta ttctcaccta aagggctatg gtcgtttgtt      180
gacattactt cacccaagtt attcaagctt ctggagggac tctcccctgg ttatttccgt      240
gtcggcggca catttgcgaa ctggttattc ttcgacctcg atgaaaacaa caagtggaag      300
gattactggg cttttaagga caagactcca gagaccgcca cgattacccg acggtggctc      360
ttcaggaagc aaaacaacct caagaaggaa acctttgatg atttggtaaa gcttacaaag      420
gggtccaaga tgcggctgct atttgatcta aacgcagagg tccgtacagg atatgagata      480
ggcaagaaga tgacatcaac ttgggactca agcgaggcag aaaagttgtt caaatattgc      540
gttagcaagg gatatggaga taatatcgat tgggagttag gcaacgaacc tgatcacacg      600
tcagcacaca atttgacaga gaagcaagta ggtgaagatt ttaaggccct acacaaggtg      660
ttggaaaagt atccaacact taataaaggt agcttggttg tccagacgt tgggtggatg      720 ggagtgtcgt acgtcaaggg tctggctgac ggggctggag atcatgtgac cgcttttact      780
ctacatcagt attatttcga tggaaatacg agtgatgtta gtacctactt ggatgcgacg      840
tactttaaga agttgcaaca gttattcgat aaggtaaaag acgtactcaa gaattctcca      900
cataaggaca aacccttgtg gctaggggaa acctcttccg gctacaacag tgggactaaa      960
gatgtatccg atagatacgt gtcggggttc ttgacgctgg acaagttggg gctttcggcg     1020
gcaaataacg tcaaggtggt catcagacaa acgatttata atggttacta tggtttgctt     1080
gacaagaata ctttggagcc caatccggac tactggctga tgcacgtcca caattcctta     1140
gttggtaata ccgttttcaa ggtcgatgtc agcgatccca caaacaaagc ccgtgtttac     1200
gctcagtgta cgaagaccaa tagtaaacat acccagtcac gttattataa ggggtcccta     1260
accattttcg cgttgaatgt aggtgatgaa gatgttacac tcaagattga tcaatacagt     1320
ggtaagaaaa tatactcata tattctgacg cctgaaggcg gccagttaac ctctcaaaag     1380
gtactgctta acggtaaaga attgaagtta gtgtcagatc aacttccaga acttaacgcg     1440
gacgaaagta aaacatcctt cacattgtct cccaaaactt ttggattctt tgtgggtctcg    1500 gatgccaacg ttgaagcttg caagaaataa                                       1530

<210> SEQ ID NO 24
<211> LENGTH: 1740
<212> TYPE: DNA
<213> ORGANISM: Hirudo nipponia

<400> SEQUENCE: 24
atgcaattct ctactgtcgc ttccgttgct ttcgtcgctt tggctaactt tgttgccgct       60
atgaaggaga tagcagttac catcgatgat aagaatgtta tagcgtctgt cagtgaaagc      120
ttccatggtg tggctttcga cgcaagccta ttctcaccta aagggctatg gtcgtttgtt      180
```

-continued

```
gacattactt cacccaagtt attcaagctt ctggagggac tctcccctgg ttatttccgt      240
gtcggcggca catttgcgaa ctggttattc ttcgacctcg atgaaaacaa caagtggaag      300
gattactggg cttttaagga caagactcca gagaccgcca cgattacccg acggtggctc      360
ttcaggaagc aaaacaacct caagaaggaa acctttgatg atttggtaaa gcttacaaag      420
gggtccaaga tgcggctgct atttgatcta aacgcagagg tccgtacagg atatgagata      480
ggcaagaaga tgacatcaac ttgggactca agcgaggcag aaaagttgtt caaatattgc      540
gttagcaagg gatatggaga taatatcgat tgggagttag caacgaacc tgatcacacg       600 tcagcacaca atttgacaga gaagcaagta ggtgaagatt ttaaggccct acacaaggtg      660
ttggaaaagt atccaacact taataaaggt agcttggttg gtccagacgt tgggtggatg      720
ggagtgtcgt acgtcaaggg tctggctgac ggggctggag atcatgtgac cgctttttact    780 ctacatcagt attatttcga tggaaatacg agtgatgtta gtacctactt ggatgcgacg      840
tactttaaga agttgcaaca gttattcgat aaggtaaaag acgtactcaa gaattctcca      900
cataaggaca aacccttgtg gctaggggaa acctcttccg gctacaacag tgggactaaa      960
gatgtatccg atagatacgt gtcggggttc ttgacgctgg acaagttggg gctttcggcg     1020
gcaaataacg tcaaggtggt catcagacaa acgatttata atggttacta tggtttgctt     1080
gacaagaata ctttggagcc caatccggac tactggctga tgcacgtcca caattcctta     1140
gttggtaata ccgtttttcaa ggtcgatgtc agcgatccca caaacaaagc ccgtgtttac    1200
gctcagtgta cgaagaccaa tagtaaacat acccagtcac gttattataa ggggtcccta     1260
accattttcg cgttgaatgt aggtgatgaa gatgttacac tcaagattga tcaatacagt     1320
ggtaagaaaa tatactcata tattctgacg cctgaaggcg gccagttaac ctctcaaaag     1380
gtactgctta acggtaaaga attgaagtta gtgtcagatc aacttccaga acttaacgcg     1440
gacgaaagta aaacatcctt cacattgtct cccaaaactt ttggattctt tgtggtctcg     1500
gatgccaacg ttgaagcttg caagaaagga tccgccattt ctcaaatcac tgacggtcaa     1560
atccaagcta ctaccactgc taccaccgaa gctaccacca ctgctgcccc atcttccacc     1620
gttgaaactg tttctccatc cagcaccgaa actatctctc aacaaactga aaatggtgct     1680
gctaaggccg ctgtcggtat gggtgccggt gctctagctg ctgctgctat gttgttataa     1740
```

<210> SEQ ID NO 25
<211> LENGTH: 1206
<212> TYPE: DNA
<213> ORGANISM: Loxosceles intermedia

<400> SEQUENCE: 25

```
atgcagtttt caaccgttgc gagcgtcgct tttgtggctc ttgctaattt cgttgccgcc       60
ttcgatgtct tctggaatgt tccgtcgcag caatgcaaga aatatggtat gaaattcgtt      120
ccgctcttag agcaatactc tatcctagtc aacaaagaag acaatttcaa gggcgacaaa      180
ataacgatct tttatgagtc acagctcggg ctttacccac atattggtgc aaacgacgag      240
tcgtttaatg gcgggatacc acaattaggt gacctgaaag cacacttaga aaagtcagcg      300
gttgatatac gacgtgatat tttggataag tcggcgactg gtctaagaat tatagactgg      360
gaagcatgga gaccaatatg ggaattcaac tggtctagcc tacgaaagta ccaagataaa      420
atgaagaaag tcgtccgcca gtttaacccg actgctcatg aatccacagt ggccaaacta      480
gcacataatg agtgggaaaa tagtagtaag tcttggatgc tttctacatt gcagttgggt      540
```

-continued

```
aagcaacttc gtccaaactc tgtatggtgc tattatttat ttcccgactg ttataactat      600
gatggcaact cagtccaaga atttcagtgt tctgaagcta tccgtaaggg gaacgatagg      660
ttgaaatggt tgtgggaaga atcgacagct gtatgcccat ctatctacat aaaagaaggc      720
caactgacca attatacctt gcaaaagaga atctggttta ccaatgggag attacaggaa      780
gccttgagag tagctcaacc taaagcgcgt atttatccat acataaatta ctccatcaaa      840
cccggaatga tggtgcctga agttgagttt tggcggttaa tcgctcagat agcctcgctg      900
ggtatggatg gagcagtgat ttggggatca agtgcgagtg taggcagtaa gaatcattgt      960
gcgcaattaa tgaagtacat tgcagacgta ttgggtcctg caactttgcg cataaaagaa     1020
aatgtagcac ggtgcagtaa acaggcgtgc tctggtaggg gtagatgtac ctggcctaaa     1080
gatacctctg ttattgcttg gaagttcctc gttgaaaagg aagactatga cttttatctg     1140
ggtgatatag agtgtaaatg tgttgaaggc tacgaaggta ggtactgtga acaaaagact     1200
aagtaa                                                                 1206
```

```
<210> SEQ ID NO 26
<211> LENGTH: 1416
<212> TYPE: DNA
<213> ORGANISM: Loxosceles intermedia

<400> SEQUENCE: 26
```

```
atgcagtttt caaccgttgc gagcgtcgct tttgtggctc ttgctaattt cgttgccgcc       60
ttcgatgtct tctggaatgt tccgtcgcag caatgcaaga aatatggtat gaaattcgtt      120
ccgctcttag agcaatactc tatcctagtc aacaaagaag acaatttcaa gggcgacaaa      180
ataacgatct tttatgagtc acagctcggg ctttacccac atattggtgc aaacgacgag      240
tcgtttaatg gcgggatacc acaattaggt gacctgaaag cacacttaga aaagtcagcg      300
gttgatatac gacgtgatat tttggataag tcggcgactg gtctaagaat tatagactgg      360
gaagcatgga gaccaatatg ggaattcaac tggtctagcc tacgaaagta ccaagataaa      420
atgaagaaag tcgtccgcca gtttaacccg actgctcatg aatccacagt ggccaaacta      480
gcacataatg agtgggaaaa tagtagtaag tcttggatgc tttctacatt gcagttgggt      540
aagcaacttc gtccaaactc tgtatggtgc tattatttat ttcccgactg ttataactat      600
gatggcaact cagtccaaga atttcagtgt tctgaagcta tccgtaaggg gaacgatagg      660
ttgaaatggt tgtgggaaga atcgacagct gtatgcccat ctatctacat aaaagaaggc      720
caactgacca attatacctt gcaaaagaga atctggttta ccaatgggag attacaggaa      780
gccttgagag tagctcaacc taaagcgcgt atttatccat acataaatta ctccatcaaa      840
cccggaatga tggtgcctga agttgagttt tggcggttaa tcgctcagat agcctcgctg      900
ggtatggatg gagcagtgat ttggggatca agtgcgagtg taggcagtaa gaatcattgt      960
gcgcaattaa tgaagtacat tgcagacgta ttgggtcctg caactttgcg cataaaagaa     1020
aatgtagcac ggtgcagtaa acaggcgtgc tctggtaggg gtagatgtac ctggcctaaa     1080
gatacctctg ttattgcttg gaagttcctc gttgaaaagg aagactatga cttttatctg     1140
ggtgatatag agtgtaaatg tgttgaaggc tacgaaggta ggtactgtga acaaaagact     1200
aagggatccg ccatttctca aatcactgac ggtcaaatcc aagctactac cactgctacc     1260
accgaagcta ccaccactgc tgccccatct tccaccgttg aaactgtttc tccatccagc     1320
accgaaacta tctctcaaca aactgaaaat ggtgctgcta aggccgctgt cggtatgggt     1380
gccggtgctc tagctgctgc tgctatgttg ttataa                                1416
```

-continued

```
<210> SEQ ID NO 27
<211> LENGTH: 1218
<212> TYPE: DNA
<213> ORGANISM: Tityus serrulatus

<400> SEQUENCE: 27
atgcaattct ctactgtcgc ttccgttgct ttcgtcgctt tggctaactt tgttgccgct       60
gctgatttta aagtttactg ggaagtgcct tccttccttt gttctaaacg tttttaaaatt      120 aatgtaacgg aagtttttaac aagtcacgag attcttgtca atcagggtga gagtttcaac     180
ggtgacaaga tagtaatctt ttacgaaaac caattgggga agtacccgca tattgactca      240
aacaatgtgg agatcaatgg aggaatactt caagtagccg atttggcgaa gcatttgaaa      300
gtagccaagg ataatatcac taaattcgtc ccgaatccta atttcaacgg tgtcggagtg      360
atcgactggg aagcttggcg gccatcatgg gaatttaact ggggtaagtt aaaagtatat      420
aaagaaaaga gcattgactt ggtcaagtcg aaacatccgg agtggccctc cgacagggtt      480
gaaaaggttg ctaaagagga gtgggaggag agtgccaaag aatggatggt gaagaccctg      540
aagttagcac aggaaatgcg accgaacgca gtttggtgct attatctatt ccctgactgc      600
tacaattatt tcggtaagga tcaaccctct caattcagct gctcgtctcg aattcagaag      660
gaaaattctc gtctttcttg ctctggaat caatcaacag ccatttgcct aagcatttat       720
atccaggaat cccatgttac caaatataat atgtcccagc ggacatggtg gatcgatgcg      780
agattaagag aagcaattcg agtcagcgaa cacagaccaa acatacccat ctacccttac      840
attaattata ttctacctgg aactaatcaa actgtaccag caatggactt taaaaggaca      900
ctgggtcaaa tagctagcct cggcctagat ggtgctttgt tatggggatc tagctatcat      960 gtttaacag aatctcaatg caaaatcact tctgattatg tgaaatcagt gattgctcct       1020
accgtggcta ctgtcgttct caatacaaac agatgctcac agataatttg taagggtcgc     1080
ggcaactgtg tttggcctga agaaccattt agttcttgga aatacttagt tgaccccaaa     1140
atgccagtgt tcaagccaac caacatccac tgtaaatgta aaggttacct aggtagatac     1200
tgtgagatcc caaagtaa                                                    1218

<210> SEQ ID NO 28
<211> LENGTH: 1428
<212> TYPE: DNA
<213> ORGANISM: Tityus serrulatus

<400> SEQUENCE: 28
atgcaattct ctactgtcgc ttccgttgct ttcgtcgctt tggctaactt tgttgccgct       60
gctgatttta aagtttactg ggaagtgcct tccttccttt gttctaaacg tttttaaaatt      120 aatgtaacgg aagtttttaac aagtcacgag attcttgtca atcagggtga gagtttcaac     180
ggtgacaaga tagtaatctt ttacgaaaac caattgggga agtacccgca tattgactca      240
aacaatgtgg agatcaatgg aggaatactt caagtagccg atttggcgaa gcatttgaaa      300
gtagccaagg ataatatcac taaattcgtc ccgaatccta atttcaacgg tgtcggagtg      360
atcgactggg aagcttggcg gccatcatgg gaatttaact ggggtaagtt aaaagtatat      420
aaagaaaaga gcattgactt ggtcaagtcg aaacatccgg agtggccctc cgacagggtt      480
gaaaaggttg ctaaagagga gtgggaggag agtgccaaag aatggatggt gaagaccctg      540
aagttagcac aggaaatgcg accgaacgca gtttggtgct attatctatt ccctgactgc      600
```

-continued

| | | | | |
|---|---|---|---|---|
| tacaattatt | tcggtaagga | tcaaccctct | caattcagct | gctcgtctcg | aattcagaag | 660 |
| gaaaattctc | gtctttcttg | gctctggaat | caatcaacag | ccatttgcct | aagcatttat | 720 |
| atccaggaat | cccatgttac | caaatataat | atgtcccagc | ggacatggtg | gatcgatgcg | 780 |
| agattaagag | aagcaattcg | agtcagcgaa | cacagaccaa | acatacccat | ctacccttac | 840 |
| attaattata | ttctacctgg | aactaatcaa | actgtaccag | caatggactt | taaaaggaca | 900 |
| ctgggtcaaa | tagctagcct | cggcctagat | ggtgctttgt | tatggggatc | tagctatcat | 960 |
| gttttaacag | aatctcaatg | caaaatcact | tctgattatg | tgaaatcagt | gattgctcct | 1020 |
| accgtggcta | ctgtcgttct | caatacaaac | agatgctcac | agataatttg | taagggtcgc | 1080 |
| ggcaactgtg | tttggcctga | agaaccattt | agttcttgga | aatacttagt | tgaccccaaa | 1140 |
| atgccagtgt | tcaagccaac | caacatccac | tgtaaatgta | aaggttacct | aggtagatac | 1200 |
| tgtgagatcc | caaagggatc | cgccatttct | caaatcactg | acggtcaaat | ccaagctact | 1260 |
| accactgcta | ccaccgaagc | taccaccact | gctgccccat | cttccaccgt | tgaaactgtt | 1320 |
| tctccatcca | gcaccgaaac | tatctctcaa | caaactgaaa | atggtgctgc | taaggccgct | 1380 |
| gtcggtatgg | gtgccggtgc | tctagctgct | gctgctatgt | tgttataa | | 1428 |

```
<210> SEQ ID NO 29
<211> LENGTH: 1083
<212> TYPE: DNA
<213> ORGANISM: Vespa magnifica

<400> SEQUENCE: 29
```

| | | | | |
|---|---|---|---|---|
| atgcaatttt | ctacagtggc | aagtgttgca | ttcgttgcac | tagccaactt | tgtggcggca | 60 |
| gatagctgtg | ggtcaaactg | cgaaaagagt | gagagaccga | aaagggtctt | caacatttac | 120 |
| tggaacgtac | ctacattcat | gtgtcaccag | tacggactat | actttgacga | ggtcacgaat | 180 |
| tttaatataa | agcacaacag | caaagacaat | tttcaagggg | acaagatcgc | gatcttttat | 240 |
| gaccccgggg | agtttcccgc | tctgctgcca | ctaaactatg | gtaagtacaa | gatcaggaat | 300 |
| ggtggtgttc | cacaagaggg | taacatcacc | atccatctgc | agagattcat | agagtaccta | 360 |
| gataagacct | atccgaaccg | taacttttca | ggcatcggtg | tgatcgattt | cgagaggtgg | 420 |
| agaccaattt | tcagacagaa | ttggggtaat | atgaagattt | acaagaactt | ctccatcgat | 480 |
| cttgtgcgta | aagagcatcc | tttctggaat | aagaaaatga | tcgagttgga | agcttctaaa | 540 |
| agattcgaga | aatacgcccg | tctgttcatg | gaagaaacat | aaagttggc | taagaaaact | 600 |
| agaaaacagg | ccgattgggg | ctactacggt | taccccctatt | gcttcaacat | gtctcctact | 660 |
| aatttcgttc | ctgactgcga | tgtcacagct | agggatgaga | caacgagat | gtcttggttg | 720 |
| tttaacaacc | agaatgtcct | attaccaagt | gtatacatta | ggagagagct | aactcctgac | 780 |
| cagaggattg | ggcttgtaca | ggggagagtg | aaggaagctg | tgagaatttc | aaataaactg | 840 |
| aagcactcac | ctaaagtctt | cagctattgg | tggtatgttt | accaagacga | gaccaacacc | 900 |
| ttcttaacgg | agaccgacgt | caagaagacg | tttcaggaga | ttgtgatcaa | cggtggagat | 960 |
| gggattataa | tctggggttc | gtcctctgat | gtaaacagct | tgtccaagtg | tacgaggtta | 1020 |
| agggagtacc | tattgacagt | cttgggacca | attgctgtta | acgtgactga | agcagtaaac | 1080 |
| taa | | | | | | 1083 |

```
<210> SEQ ID NO 30
<211> LENGTH: 1293
<212> TYPE: DNA
<213> ORGANISM: Vespa magnifica
```

-continued

```
<400> SEQUENCE: 30
atgcaatttt ctacagtggc aagtgttgca ttcgttgcac tagccaactt tgtggcggca        60
gatagctgtg ggtcaaactg cgaaaagagt gagagaccga aaagggtctt caacatttac       120
tggaacgtac ctacattcat gtgtcaccag tacggactat actttgacga ggtcacgaat       180
tttaatataa agcacaacag caaagacaat tttcaagggg acaagatcgc gatcttttat       240
gaccccgggg agtttcccgc tctgctgcca ctaaactatg gtaagtacaa gatcaggaat       300
ggtggtgttc cacaagaggg taacatcacc atccatctgc agagattcat agagtaccta       360
gataagacct atccgaaccg taactttca ggcatcggtg tgatcgattt cgagaggtgg        420
agaccaattt tcagacagaa ttggggtaat atgaagattt acaagaactt ctccatcgat       480
cttgtgcgta aagagcatcc tttctggaat aagaaaatga tcgagttgga agcttctaaa       540
agattcgaga aatacgcccg tctgttcatg gaagaaacat aaagttggc taagaaaact        600 agaaaacagg ccgattgggg ctactacggt taccctatt gcttcaacat gtctcctact        660
aatttcgttc ctgactgcga tgtcacagct agggatgaga caacgagat gtcttggttg        720 tttaacaacc agaatgtcct attaccaagt gtatacatta ggagagagct aactcctgac       780
cagaggattg ggcttgtaca ggggagagtg aaggaagctg tgagaatttc aaataaactg       840
aagcactcac ctaaagtctt cagctattgg tggtatgttt accaagacga gaccaacacc       900
ttcttaacgg agaccgacgt caagaagacg tttcaggaga ttgtgatcaa cggtggagat       960
gggattataa tctgggggttc gtcctctgat gtaaacagct gtccaagtg tacgaggtta      1020 agggagtacc tattgacagt cttgggacca attgctgtta acgtgactga agcagtaaac      1080
ggatccgcca tttctcaaat cactgacggt caaatccaag ctactaccac tgctaccacc      1140
gaagctacca ccactgctgc cccatcttcc accgttgaaa ctgtttctcc atccagcacc      1200
gaaactatct ctcaacaaac tgaaaatggt gctgctaagg ccgctgtcgg tatgggtgcc      1260
ggtgctctag ctgctgctgc tatgttgtta taa                                  1293

<210> SEQ ID NO 31
<211> LENGTH: 441
<212> TYPE: PRT
<213> ORGANISM: Bothrops atrox

<400> SEQUENCE: 31

Met Gln Phe Ser Thr Val Ala Ser Val Ala Phe Val Ala Leu Ala Asn
1               5                   10                  15

Phe Val Ala Ala Pro Met Tyr Pro Asn Glu Pro Phe Leu Val Phe Trp
            20                  25                  30

Asn Ala Pro Thr Thr Gln Cys Arg Leu Arg Tyr Lys Val Asp Leu Asp
        35                  40                  45

Leu Lys Thr Phe His Ile Val Thr Asn Ala Asn Asp Ser Leu Ser Gly
    50                  55                  60

Ser Ala Val Thr Ile Phe Tyr Pro Thr His Leu Gly Val Tyr Pro His
65                  70                  75                  80

Ile Asp Asp Arg Gly His Phe Phe Asn Gly Ile Ile Pro Gln Asn Glu
                85                  90                  95

Ser Leu Val Lys His Leu Asn Lys Ser Lys Ser Asp Ile Asn Arg Met
            100                 105                 110

Ile Pro Leu Arg Thr Phe His Gly Leu Gly Val Ile Asp Trp Glu Asn
        115                 120                 125
```

```
Trp Arg Pro Gln Trp Asp Arg Asn Trp Gly Ser Lys Asn Val Tyr Arg
    130             135             140

Asn Arg Ser Ile Gln Phe Ala Arg Asp Leu His Pro Glu Leu Ser Glu
145             150             155             160

Asp Lys Ile Lys Arg Leu Ala Lys Gln Glu Phe Glu Lys Ala Ala Lys
                165             170             175

Ser Phe Met Arg Asp Thr Leu Leu Ala Glu Glu Met Arg Pro Asp
                180             185             190

Gly Tyr Trp Gly Tyr Tyr Leu Tyr Pro Asp Cys His Asn Tyr Asn Tyr
            195             200             205

Lys Thr Lys Pro Asp Gln Tyr Thr Gly Glu Cys Pro Asp Ile Glu Met
    210             215             220

Ser Arg Asn Asn Gln Leu Leu Trp Leu Trp Arg Asp Ser Thr Ala Leu
225             230             235             240

Phe Pro Asn Ile Tyr Leu Glu Thr Ile Leu Arg Ser Ser Asp Asn Ala
            245             250             255

Leu Lys Phe Val His His Arg Leu Lys Glu Ala Met Arg Ile Ala Ser
            260             265             270

Met Ala Arg Asn Asp Tyr Ala Leu Pro Phe Phe Val Tyr Ala Arg Pro
    275             280             285

Phe Tyr Ala Tyr Thr Phe Glu Pro Leu Thr Gln Glu Asp Leu Val Thr
    290             295             300

Thr Val Gly Glu Thr Ala Asp Met Gly Ala Ala Gly Ile Val Phe Trp
305             310             315             320

Gly Ser Met Gln Tyr Ala Ser Thr Val Glu Ser Cys Gly Lys Val Lys
                325             330             335

Asp Tyr Met Asn Gly Pro Leu Gly Arg Tyr Ile Val Asn Val Thr Thr
            340             345             350

Ala Ala Lys Ile Cys Ser Arg Phe Leu Cys Lys Arg His Gly Arg Cys
            355             360             365

Val Arg Lys His Ser Asp Ser Asn Ala Phe Leu His Leu Phe Pro Asp
    370             375             380

Ser Phe Arg Ile Met Val His Gly Asn Ala Thr Glu Lys Lys Val Ile
385             390             395             400

Val Lys Gly Lys Leu Glu Leu Lys Asn Leu Ile Phe Leu Arg Asn Asn
            405             410             415

Phe Met Cys Gln Cys Tyr Gln Gly Trp Lys Gly Leu Tyr Cys Glu Lys
            420             425             430

His Ser Ile Lys Glu Ile Arg Lys Ile
        435             440
```

```
<210> SEQ ID NO 32
<211> LENGTH: 511
<212> TYPE: PRT
<213> ORGANISM: Bothrops atrox

<400> SEQUENCE: 32

Met Gln Phe Ser Thr Val Ala Ser Val Ala Phe Val Ala Leu Ala Asn
1               5               10              15

Phe Val Ala Ala Pro Met Tyr Pro Asn Glu Pro Phe Leu Val Phe Trp
                20              25              30

Asn Ala Pro Thr Thr Gln Cys Arg Leu Arg Tyr Lys Val Asp Leu Asp
            35              40              45

Leu Lys Thr Phe His Ile Val Thr Asn Ala Asn Asp Ser Leu Ser Gly
    50              55              60
```

-continued

```
Ser Ala Val Thr Ile Phe Tyr Pro Thr His Leu Gly Val Tyr Pro His
65              70              75              80

Ile Asp Asp Arg Gly His Phe Phe Asn Gly Ile Ile Pro Gln Asn Glu
                85              90              95

Ser Leu Val Lys His Leu Asn Lys Ser Lys Ser Asp Ile Asn Arg Met
            100             105             110

Ile Pro Leu Arg Thr Phe His Gly Leu Gly Val Ile Asp Trp Glu Asn
            115             120             125

Trp Arg Pro Gln Trp Asp Arg Asn Trp Gly Ser Lys Asn Val Tyr Arg
    130             135             140

Asn Arg Ser Ile Gln Phe Ala Arg Asp Leu His Pro Glu Leu Ser Glu
145             150             155             160

Asp Lys Ile Lys Arg Leu Ala Lys Gln Glu Phe Glu Lys Ala Ala Lys
            165             170             175

Ser Phe Met Arg Asp Thr Leu Leu Leu Ala Glu Glu Met Arg Pro Asp
            180             185             190

Gly Tyr Trp Gly Tyr Tyr Leu Tyr Pro Asp Cys His Asn Tyr Asn Tyr
    195             200             205

Lys Thr Lys Pro Asp Gln Tyr Thr Gly Glu Cys Pro Asp Ile Glu Met
    210             215             220

Ser Arg Asn Asn Gln Leu Leu Trp Leu Trp Arg Asp Ser Thr Ala Leu
225             230             235             240

Phe Pro Asn Ile Tyr Leu Glu Thr Ile Leu Arg Ser Ser Asp Asn Ala
            245             250             255

Leu Lys Phe Val His His Arg Leu Lys Glu Ala Met Arg Ile Ala Ser
            260             265             270

Met Ala Arg Asn Asp Tyr Ala Leu Pro Phe Phe Val Tyr Ala Arg Pro
    275             280             285

Phe Tyr Ala Tyr Thr Phe Glu Pro Leu Thr Gln Glu Asp Leu Val Thr
    290             295             300

Thr Val Gly Glu Thr Ala Asp Met Gly Ala Ala Gly Ile Val Phe Trp
305             310             315             320

Gly Ser Met Gln Tyr Ala Ser Thr Val Glu Ser Cys Gly Lys Val Lys
            325             330             335

Asp Tyr Met Asn Gly Pro Leu Gly Arg Tyr Ile Val Asn Val Thr Thr
            340             345             350

Ala Ala Lys Ile Cys Ser Arg Phe Leu Cys Lys Arg His Gly Arg Cys
            355             360             365

Val Arg Lys His Ser Asp Ser Asn Ala Phe Leu His Leu Phe Pro Asp
    370             375             380

Ser Phe Arg Ile Met Val His Gly Asn Ala Thr Glu Lys Lys Val Ile
385             390             395             400

Val Lys Gly Lys Leu Glu Leu Lys Asn Leu Ile Phe Leu Arg Asn Asn
            405             410             415

Phe Met Cys Gln Cys Tyr Gln Gly Trp Lys Gly Leu Tyr Cys Glu Lys
            420             425             430

His Ser Ile Lys Glu Ile Arg Lys Ile Gly Ser Ala Ile Ser Gln Ile
            435             440             445

Thr Asp Gly Gln Ile Gln Ala Thr Thr Thr Ala Thr Thr Glu Ala Thr
    450             455             460

Thr Thr Ala Ala Pro Ser Ser Thr Val Glu Thr Val Ser Pro Ser Ser
465             470             475             480
```

Thr Glu Thr Ile Ser Gln Gln Thr Glu Asn Gly Ala Ala Lys Ala Ala
                485                     490                 495

Val Gly Met Gly Ala Gly Ala Leu Ala Ala Ala Ala Met Leu Leu
        500                 505                 510

<210> SEQ ID NO 33
<211> LENGTH: 398
<212> TYPE: PRT
<213> ORGANISM: Cupiennius salei

<400> SEQUENCE: 33

Met Gln Phe Ser Thr Val Ala Ser Val Ala Phe Val Ala Leu Ala Asn
1               5                   10                  15

Phe Val Ala Ala Phe Lys Ile Tyr Trp Asn Val Pro Thr Phe Gln Cys
            20                  25                  30

Thr His Asn Tyr Lys Ile Asp Tyr Val Lys Leu Leu Ser Thr Tyr Gly
        35                  40                  45

Ile Gln Val Asn Asp Gly Gly Lys Phe Gln Gly Asn Gln Val Thr Ile
    50                  55                  60

Phe Tyr Glu Thr Gln Leu Gly Leu Tyr Pro Arg Ile Leu Lys Ser Gly
65                  70                  75                  80

Lys Met Glu Asn Gly Gly Ile Pro Gln Arg Gly Asn Phe Glu Lys His
                85                  90                  95

Leu Glu Lys Ala Ser Thr Asp Leu Gln Lys Val Ile Pro Trp Lys Glu
            100                 105                 110

Phe Ser Gly Leu Gly Val Ile Asp Trp Glu Ala Trp Arg Pro Thr Trp
            115                 120                 125

Glu Phe Asn Trp Glu Pro Leu Arg Ile Tyr Gln Thr Glu Ser Ile Lys
    130                 135                 140

Arg Ala Lys Glu Leu His Pro Thr Ala Asn Asp Ser Ala Val Lys Glu
145                 150                 155                 160

Ile Ala Glu Arg Gln Trp Glu Asp Ser Ala Lys Leu Tyr Met Leu Glu
                165                 170                 175

Thr Leu Arg Leu Ala Lys Lys Leu Arg Pro Gln Ala Pro Trp Cys Tyr
            180                 185                 190

Tyr Leu Phe Pro Asp Cys Tyr Asn Tyr Val Gly Lys Lys Pro Lys Asp
            195                 200                 205

Phe Gln Cys Ser Ala Ser Ile Arg Lys Gly Asn Asp Lys Leu Ser Trp
    210                 215                 220

Leu Trp Lys Asp Ser Thr Ala Leu Cys Pro Ser Ile Tyr Val Tyr Glu
225                 230                 235                 240

Ser Gln Leu Asp Arg Tyr Ser Phe Glu Gln Arg Thr Trp Arg Asp Asn
                245                 250                 255

Glu Lys Leu Arg Glu Ala Leu Arg Val Ala Thr Arg Thr Ser Lys Ile
            260                 265                 270

Tyr Pro Tyr Val Asn Tyr Phe Asp Lys Glu Leu Ile Pro Glu Gln Glu
            275                 280                 285

Val Trp Arg Met Leu Ala Gln Ala Ala Ala Val Gly Gly Ser Gly Ala
    290                 295                 300

Val Ile Trp Gly Ser Ser Ala Ala Val Ala Ser Glu Glu Leu Cys Lys
305                 310                 315                 320

Ser Leu Lys Gln Tyr Ile Ile Glu Thr Leu Gly Pro Ala Ala Glu Lys
                325                 330                 335

Val Ala Trp Arg Ser Asp Leu Cys Ser Lys Glu Ile Cys Asn Asn Gln
            340                 345                 350

Gly Arg Cys Thr Phe Pro Asp Asp Asp Tyr Ala Asn Ala Trp Lys Leu
        355                 360                 365

Phe Thr Asp Asp Thr Val Lys Phe Tyr Ala Gly Asn Ile Thr Cys Arg
    370                 375                 380

Cys Ser Glu Asn Tyr Ser Gly Arg Phe Cys Glu Lys Lys Asn
385                 390                 395

<210> SEQ ID NO 34
<211> LENGTH: 468
<212> TYPE: PRT
<213> ORGANISM: Cupiennius salei

<400> SEQUENCE: 34

Met Gln Phe Ser Thr Val Ala Ser Val Ala Phe Val Ala Leu Ala Asn
1               5                   10                  15

Phe Val Ala Ala Phe Lys Ile Tyr Trp Asn Val Pro Thr Phe Gln Cys
            20                  25                  30

Thr His Asn Tyr Lys Ile Asp Tyr Val Lys Leu Leu Ser Thr Tyr Gly
        35                  40                  45

Ile Gln Val Asn Asp Gly Gly Lys Phe Gln Gly Asn Gln Val Thr Ile
    50                  55                  60

Phe Tyr Glu Thr Gln Leu Gly Leu Tyr Pro Arg Ile Leu Lys Ser Gly
65                  70                  75                  80

Lys Met Glu Asn Gly Gly Ile Pro Gln Arg Gly Asn Phe Glu Lys His
            85                  90                  95

Leu Glu Lys Ala Ser Thr Asp Leu Gln Lys Val Ile Pro Trp Lys Glu
            100                 105                 110

Phe Ser Gly Leu Gly Val Ile Asp Trp Glu Ala Trp Arg Pro Thr Trp
        115                 120                 125

Glu Phe Asn Trp Glu Pro Leu Arg Ile Tyr Gln Thr Glu Ser Ile Lys
    130                 135                 140

Arg Ala Lys Glu Leu His Pro Thr Ala Asn Asp Ser Ala Val Lys Glu
145                 150                 155                 160

Ile Ala Glu Arg Gln Trp Glu Asp Ser Ala Lys Leu Tyr Met Leu Glu
            165                 170                 175

Thr Leu Arg Leu Ala Lys Lys Leu Arg Pro Gln Ala Pro Trp Cys Tyr
            180                 185                 190

Tyr Leu Phe Pro Asp Cys Tyr Asn Tyr Val Gly Lys Lys Pro Lys Asp
        195                 200                 205

Phe Gln Cys Ser Ala Ser Ile Arg Lys Gly Asn Asp Lys Leu Ser Trp
    210                 215                 220

Leu Trp Lys Asp Ser Thr Ala Leu Cys Pro Ser Ile Tyr Val Tyr Glu
225                 230                 235                 240

Ser Gln Leu Asp Arg Tyr Ser Phe Glu Gln Arg Thr Trp Arg Asp Asn
            245                 250                 255

Glu Lys Leu Arg Glu Ala Leu Arg Val Ala Thr Arg Thr Ser Lys Ile
            260                 265                 270

Tyr Pro Tyr Val Asn Tyr Phe Asp Lys Glu Leu Ile Pro Glu Gln Glu
        275                 280                 285

Val Trp Arg Met Leu Ala Gln Ala Ala Ala Val Gly Gly Ser Gly Ala
    290                 295                 300

Val Ile Trp Gly Ser Ser Ala Ala Val Ala Ser Glu Glu Leu Cys Lys
305                 310                 315                 320

Ser Leu Lys Gln Tyr Ile Ile Glu Thr Leu Gly Pro Ala Ala Glu Lys

-continued

```
                325                 330                 335

Val Ala Trp Arg Ser Asp Leu Cys Ser Lys Glu Ile Cys Asn Asn Gln
            340                 345                 350

Gly Arg Cys Thr Phe Pro Asp Asp Tyr Ala Asn Ala Trp Lys Leu
            355                 360                 365

Phe Thr Asp Asp Thr Val Lys Phe Tyr Ala Gly Asn Ile Thr Cys Arg
    370                 375                 380

Cys Ser Glu Asn Tyr Ser Gly Arg Phe Cys Glu Lys Lys Asn Gly Ser
385                 390                 395                 400

Ala Ile Ser Gln Ile Thr Asp Gly Gln Ile Gln Ala Thr Thr Thr Ala
                405                 410                 415

Thr Thr Glu Ala Thr Thr Thr Ala Ala Pro Ser Ser Thr Val Glu Thr
            420                 425                 430

Val Ser Pro Ser Ser Thr Glu Thr Ile Ser Gln Gln Thr Glu Asn Gly
            435                 440                 445

Ala Ala Lys Ala Ala Val Gly Met Gly Ala Gly Ala Leu Ala Ala Ala
    450                 455                 460

Ala Met Leu Leu
465

<210> SEQ ID NO 35
<211> LENGTH: 579
<212> TYPE: PRT
<213> ORGANISM: Hirudo nipponia

<400> SEQUENCE: 35

Met Gln Phe Ser Thr Val Ala Ser Val Ala Phe Val Ala Leu Ala Asn
1               5                   10                  15

Phe Val Ala Ala Met Lys Glu Ile Ala Val Thr Ile Asp Asp Lys Asn
            20                  25                  30

Val Ile Ala Ser Val Ser Glu Ser Phe His Gly Val Ala Phe Asp Ala
            35                  40                  45

Ser Leu Phe Ser Pro Lys Gly Leu Trp Ser Phe Val Asp Ile Thr Ser
    50                  55                  60

Pro Lys Leu Phe Lys Leu Leu Glu Gly Leu Ser Pro Gly Tyr Phe Arg
65                  70                  75                  80

Val Gly Gly Thr Phe Ala Asn Trp Leu Phe Phe Asp Leu Asp Glu Asn
            85                  90                  95

Asn Lys Trp Lys Asp Tyr Trp Ala Phe Lys Asp Lys Thr Pro Glu Thr
            100                 105                 110

Ala Thr Ile Thr Arg Arg Trp Leu Phe Arg Lys Gln Asn Asn Leu Lys
            115                 120                 125

Lys Glu Thr Phe Asp Asp Leu Val Lys Leu Thr Lys Gly Ser Lys Met
    130                 135                 140

Arg Leu Leu Phe Asp Leu Asn Ala Glu Val Arg Thr Gly Tyr Glu Ile
145                 150                 155                 160

Gly Lys Lys Met Thr Ser Thr Trp Asp Ser Ser Glu Ala Glu Lys Leu
            165                 170                 175

Phe Lys Tyr Cys Val Ser Lys Gly Tyr Gly Asp Asn Ile Asp Trp Glu
            180                 185                 190

Leu Gly Asn Glu Pro Asp His Thr Ser Ala His Asn Leu Thr Glu Lys
            195                 200                 205

Gln Val Gly Glu Asp Phe Lys Ala Leu His Lys Val Leu Glu Lys Tyr
    210                 215                 220
```

-continued

```
Pro Thr Leu Asn Lys Gly Ser Leu Val Gly Pro Asp Val Gly Trp Met
225             230             235             240

Gly Val Ser Tyr Val Lys Gly Leu Ala Asp Gly Ala Gly Asp His Val
            245             250             255

Thr Ala Phe Thr Leu His Gln Tyr Tyr Phe Asp Gly Asn Thr Ser Asp
            260             265             270

Val Ser Thr Tyr Leu Asp Ala Thr Tyr Phe Lys Lys Leu Gln Gln Leu
            275             280             285

Phe Asp Lys Val Lys Asp Val Leu Lys Asn Ser Pro His Lys Asp Lys
            290             295             300

Pro Leu Trp Leu Gly Glu Thr Ser Ser Gly Tyr Asn Ser Gly Thr Lys
305             310             315             320

Asp Val Ser Asp Arg Tyr Val Ser Gly Phe Leu Thr Leu Asp Lys Leu
            325             330             335

Gly Leu Ser Ala Ala Asn Asn Val Lys Val Val Ile Arg Gln Thr Ile
            340             345             350

Tyr Asn Gly Tyr Tyr Gly Leu Leu Asp Lys Asn Thr Leu Glu Pro Asn
            355             360             365

Pro Asp Tyr Trp Leu Met His Val His Asn Ser Leu Val Gly Asn Thr
            370             375             380

Val Phe Lys Val Asp Val Ser Asp Pro Thr Asn Lys Ala Arg Val Tyr
385             390             395             400

Ala Gln Cys Thr Lys Thr Asn Ser Lys His Thr Gln Ser Arg Tyr Tyr
            405             410             415

Lys Gly Ser Leu Thr Ile Phe Ala Leu Asn Val Gly Asp Glu Asp Val
            420             425             430

Thr Leu Lys Ile Asp Gln Tyr Ser Gly Lys Lys Ile Tyr Ser Tyr Ile
            435             440             445

Leu Thr Pro Glu Gly Gly Gln Leu Thr Ser Gln Lys Val Leu Leu Asn
            450             455             460

Gly Lys Glu Leu Lys Leu Val Ser Asp Gln Leu Pro Glu Leu Asn Ala
465             470             475             480

Asp Glu Ser Lys Thr Ser Phe Thr Leu Ser Pro Lys Thr Phe Gly Phe
            485             490             495

Phe Val Val Ser Asp Ala Asn Val Glu Ala Cys Lys Lys Gly Ser Ala
            500             505             510

Ile Ser Gln Ile Thr Asp Gly Gln Ile Gln Ala Thr Thr Thr Ala Thr
            515             520             525

Thr Glu Ala Thr Thr Thr Ala Ala Pro Ser Ser Thr Val Glu Thr Val
            530             535             540

Ser Pro Ser Ser Thr Glu Thr Ile Ser Gln Gln Thr Glu Asn Gly Ala
545             550             555             560

Ala Lys Ala Ala Val Gly Met Gly Ala Gly Ala Leu Ala Ala Ala Ala
            565             570             575

Met Leu Leu

<210> SEQ ID NO 36
<211> LENGTH: 509
<212> TYPE: PRT
<213> ORGANISM: Hirudo nipponia

<400> SEQUENCE: 36

Met Gln Phe Ser Thr Val Ala Ser Val Ala Phe Val Ala Leu Ala Asn
1               5               10              15
```

-continued

```
Phe Val Ala Ala Met Lys Glu Ile Ala Val Thr Ile Asp Asp Lys Asn
        20              25              30

Val Ile Ala Ser Val Ser Glu Ser Phe His Gly Val Ala Phe Asp Ala
        35              40              45

Ser Leu Phe Ser Pro Lys Gly Leu Trp Ser Phe Val Asp Ile Thr Ser
    50              55              60

Pro Lys Leu Phe Lys Leu Leu Glu Gly Leu Ser Pro Gly Tyr Phe Arg
65              70              75              80

Val Gly Gly Thr Phe Ala Asn Trp Leu Phe Phe Asp Leu Asp Glu Asn
            85              90              95

Asn Lys Trp Lys Asp Tyr Trp Ala Phe Lys Asp Lys Thr Pro Glu Thr
        100             105             110

Ala Thr Ile Thr Arg Arg Trp Leu Phe Arg Lys Gln Asn Asn Leu Lys
        115             120             125

Lys Glu Thr Phe Asp Asp Leu Val Lys Leu Thr Lys Gly Ser Lys Met
        130             135             140

Arg Leu Leu Phe Asp Leu Asn Ala Glu Val Arg Thr Gly Tyr Glu Ile
145             150             155             160

Gly Lys Lys Met Thr Ser Thr Trp Asp Ser Ser Glu Ala Glu Lys Leu
            165             170             175

Phe Lys Tyr Cys Val Ser Lys Gly Tyr Gly Asp Asn Ile Asp Trp Glu
            180             185             190

Leu Gly Asn Glu Pro Asp His Thr Ser Ala His Asn Leu Thr Glu Lys
            195             200             205

Gln Val Gly Glu Asp Phe Lys Ala Leu His Lys Val Leu Glu Lys Tyr
        210             215             220

Pro Thr Leu Asn Lys Gly Ser Leu Val Gly Pro Asp Val Gly Trp Met
225             230             235             240

Gly Val Ser Tyr Val Lys Gly Leu Ala Asp Gly Ala Gly Asp His Val
            245             250             255

Thr Ala Phe Thr Leu His Gln Tyr Tyr Phe Asp Gly Asn Thr Ser Asp
            260             265             270

Val Ser Thr Tyr Leu Asp Ala Thr Tyr Phe Lys Lys Leu Gln Gln Leu
        275             280             285

Phe Asp Lys Val Lys Asp Val Leu Lys Asn Ser Pro His Lys Asp Lys
        290             295             300

Pro Leu Trp Leu Gly Glu Thr Ser Ser Gly Tyr Asn Ser Gly Thr Lys
305             310             315             320

Asp Val Ser Asp Arg Tyr Val Ser Gly Phe Leu Thr Leu Asp Lys Leu
            325             330             335

Gly Leu Ser Ala Ala Asn Asn Val Lys Val Val Ile Arg Gln Thr Ile
            340             345             350

Tyr Asn Gly Tyr Tyr Gly Leu Leu Asp Lys Asn Thr Leu Glu Pro Asn
        355             360             365

Pro Asp Tyr Trp Leu Met His Val His Asn Ser Leu Val Gly Asn Thr
    370             375             380

Val Phe Lys Val Asp Val Ser Asp Pro Thr Asn Lys Ala Arg Val Tyr
385             390             395             400

Ala Gln Cys Thr Lys Thr Asn Ser Lys His Thr Gln Ser Arg Tyr Tyr
            405             410             415

Lys Gly Ser Leu Thr Ile Phe Ala Leu Asn Val Gly Asp Glu Asp Val
            420             425             430

Thr Leu Lys Ile Asp Gln Tyr Ser Gly Lys Lys Ile Tyr Ser Tyr Ile
```

-continued

```
            435                   440                   445
Leu Thr Pro Glu Gly Gly Gln Leu Thr Ser Gln Lys Val Leu Leu Asn
    450                   455                   460

Gly Lys Glu Leu Lys Leu Val Ser Asp Gln Leu Pro Glu Leu Asn Ala
465                   470                   475                   480

Asp Glu Ser Lys Thr Ser Phe Thr Leu Ser Pro Lys Thr Phe Gly Phe
                485                   490                   495

Phe Val Val Ser Asp Ala Asn Val Glu Ala Cys Lys Lys
                500                   505

<210> SEQ ID NO 37
<211> LENGTH: 401
<212> TYPE: PRT
<213> ORGANISM: Loxosceles intermedia

<400> SEQUENCE: 37

Met Gln Phe Ser Thr Val Ala Ser Val Ala Phe Val Ala Leu Ala Asn
1               5                   10                  15

Phe Val Ala Ala Phe Asp Val Phe Trp Asn Val Pro Ser Gln Gln Cys
                20                  25                  30

Lys Lys Tyr Gly Met Lys Phe Val Pro Leu Leu Glu Gln Tyr Ser Ile
        35                  40                  45

Leu Val Asn Lys Glu Asp Asn Phe Lys Gly Asp Lys Ile Thr Ile Phe
    50                  55                  60

Tyr Glu Ser Gln Leu Gly Leu Tyr Pro His Ile Gly Ala Asn Asp Glu
65                  70                  75                  80

Ser Phe Asn Gly Gly Ile Pro Gln Leu Gly Asp Leu Lys Ala His Leu
                85                  90                  95

Glu Lys Ser Ala Val Asp Ile Arg Arg Asp Ile Leu Asp Lys Ser Ala
            100                 105                 110

Thr Gly Leu Arg Ile Ile Asp Trp Glu Ala Trp Arg Pro Ile Trp Glu
        115                 120                 125

Phe Asn Trp Ser Ser Leu Arg Lys Tyr Gln Asp Lys Met Lys Lys Val
    130                 135                 140

Val Arg Gln Phe Asn Pro Thr Ala His Glu Ser Thr Val Ala Lys Leu
145                 150                 155                 160

Ala His Asn Glu Trp Glu Asn Ser Ser Lys Ser Trp Met Leu Ser Thr
                165                 170                 175

Leu Gln Leu Gly Lys Gln Leu Arg Pro Asn Ser Val Trp Cys Tyr Tyr
            180                 185                 190

Leu Phe Pro Asp Cys Tyr Asn Tyr Asp Gly Asn Ser Val Gln Glu Phe
        195                 200                 205

Gln Cys Ser Glu Ala Ile Arg Lys Gly Asn Asp Arg Leu Lys Trp Leu
    210                 215                 220

Trp Glu Glu Ser Thr Ala Val Cys Pro Ser Ile Tyr Ile Lys Glu Gly
225                 230                 235                 240

Gln Leu Thr Asn Tyr Thr Leu Gln Lys Arg Ile Trp Phe Thr Asn Gly
                245                 250                 255

Arg Leu Gln Glu Ala Leu Arg Val Ala Gln Pro Lys Ala Arg Ile Tyr
            260                 265                 270

Pro Tyr Ile Asn Tyr Ser Ile Lys Pro Gly Met Met Val Pro Glu Val
        275                 280                 285

Glu Phe Trp Arg Leu Ile Ala Gln Ile Ala Ser Leu Gly Met Asp Gly
    290                 295                 300
```

-continued

```
Ala Val Ile Trp Gly Ser Ser Ala Ser Val Gly Ser Lys Asn His Cys
305             310             315             320

Ala Gln Leu Met Lys Tyr Ile Ala Asp Val Leu Gly Pro Ala Thr Leu
                325             330             335

Arg Ile Lys Glu Asn Val Ala Arg Cys Ser Lys Gln Ala Cys Ser Gly
            340             345             350

Arg Gly Arg Cys Thr Trp Pro Lys Asp Thr Ser Val Ile Ala Trp Lys
            355             360             365

Phe Leu Val Glu Lys Glu Asp Tyr Asp Phe Tyr Leu Gly Asp Ile Glu
    370             375             380

Cys Lys Cys Val Glu Gly Tyr Glu Gly Arg Tyr Cys Glu Gln Lys Thr
385             390             395             400

Lys

<210> SEQ ID NO 38
<211> LENGTH: 471
<212> TYPE: PRT
<213> ORGANISM: Loxosceles intermedia

<400> SEQUENCE: 38

Met Gln Phe Ser Thr Val Ala Ser Val Ala Phe Val Ala Leu Ala Asn
1               5               10              15

Phe Val Ala Ala Phe Asp Val Phe Trp Asn Val Pro Ser Gln Gln Cys
                20              25              30

Lys Lys Tyr Gly Met Lys Phe Val Pro Leu Leu Glu Gln Tyr Ser Ile
            35              40              45

Leu Val Asn Lys Glu Asp Asn Phe Lys Gly Asp Lys Ile Thr Ile Phe
    50              55              60

Tyr Glu Ser Gln Leu Gly Leu Tyr Pro His Ile Gly Ala Asn Asp Glu
65              70              75              80

Ser Phe Asn Gly Gly Ile Pro Gln Leu Gly Asp Leu Lys Ala His Leu
                85              90              95

Glu Lys Ser Ala Val Asp Ile Arg Arg Asp Ile Leu Asp Lys Ser Ala
            100             105             110

Thr Gly Leu Arg Ile Ile Asp Trp Glu Ala Trp Arg Pro Ile Trp Glu
            115             120             125

Phe Asn Trp Ser Ser Leu Arg Lys Tyr Gln Asp Lys Met Lys Lys Val
    130             135             140

Val Arg Gln Phe Asn Pro Thr Ala His Glu Ser Thr Val Ala Lys Leu
145             150             155             160

Ala His Asn Glu Trp Glu Asn Ser Ser Lys Ser Trp Met Leu Ser Thr
                165             170             175

Leu Gln Leu Gly Lys Gln Leu Arg Pro Asn Ser Val Trp Cys Tyr Tyr
            180             185             190

Leu Phe Pro Asp Cys Tyr Asn Tyr Asp Gly Asn Ser Val Gln Glu Phe
            195             200             205

Gln Cys Ser Glu Ala Ile Arg Lys Gly Asn Asp Arg Leu Lys Trp Leu
    210             215             220

Trp Glu Glu Ser Thr Ala Val Cys Pro Ser Ile Tyr Ile Lys Glu Gly
225             230             235             240

Gln Leu Thr Asn Tyr Thr Leu Gln Lys Arg Ile Trp Phe Thr Asn Gly
                245             250             255

Arg Leu Gln Glu Ala Leu Arg Val Ala Gln Pro Lys Ala Arg Ile Tyr
            260             265             270
```

-continued

```
Pro Tyr Ile Asn Tyr Ser Ile Lys Pro Gly Met Met Val Pro Glu Val
        275                 280                 285

Glu Phe Trp Arg Leu Ile Ala Gln Ile Ala Ser Leu Gly Met Asp Gly
        290                 295                 300

Ala Val Ile Trp Gly Ser Ser Ala Ser Val Gly Ser Lys Asn His Cys
305                 310                 315                 320

Ala Gln Leu Met Lys Tyr Ile Ala Asp Val Leu Gly Pro Ala Thr Leu
                325                 330                 335

Arg Ile Lys Glu Asn Val Ala Arg Cys Ser Lys Gln Ala Cys Ser Gly
                340                 345                 350

Arg Gly Arg Cys Thr Trp Pro Lys Asp Thr Ser Val Ile Ala Trp Lys
                355                 360                 365

Phe Leu Val Glu Lys Glu Asp Tyr Asp Phe Tyr Leu Gly Asp Ile Glu
        370                 375                 380

Cys Lys Cys Val Glu Gly Tyr Glu Gly Arg Tyr Cys Glu Gln Lys Thr
385                 390                 395                 400

Lys Gly Ser Ala Ile Ser Gln Ile Thr Asp Gly Gln Ile Gln Ala Thr
                405                 410                 415

Thr Thr Ala Thr Thr Glu Ala Thr Thr Thr Ala Ala Pro Ser Ser Thr
                420                 425                 430

Val Glu Thr Val Ser Pro Ser Ser Thr Glu Thr Ile Ser Gln Gln Thr
        435                 440                 445

Glu Asn Gly Ala Ala Lys Ala Ala Val Gly Met Gly Ala Gly Ala Leu
        450                 455                 460

Ala Ala Ala Ala Met Leu Leu
465                 470
```

```
<210> SEQ ID NO 39
<211> LENGTH: 405
<212> TYPE: PRT
<213> ORGANISM: Tityus serrulatus

<400> SEQUENCE: 39
```

```
Met Gln Phe Ser Thr Val Ala Ser Val Ala Phe Val Ala Leu Ala Asn
1               5                   10                  15

Phe Val Ala Ala Ala Asp Phe Lys Val Tyr Trp Glu Val Pro Ser Phe
                20                  25                  30

Leu Cys Ser Lys Arg Phe Lys Ile Asn Val Thr Glu Val Leu Thr Ser
            35                  40                  45

His Glu Ile Leu Val Asn Gln Gly Glu Ser Phe Asn Gly Asp Lys Ile
        50                  55                  60

Val Ile Phe Tyr Glu Asn Gln Leu Gly Lys Tyr Pro His Ile Asp Ser
65                  70                  75                  80

Asn Asn Val Glu Ile Asn Gly Gly Ile Leu Gln Val Ala Asp Leu Ala
                85                  90                  95

Lys His Leu Lys Val Ala Lys Asp Asn Ile Thr Lys Phe Val Pro Asn
            100                 105                 110

Pro Asn Phe Asn Gly Val Gly Val Ile Asp Trp Glu Ala Trp Arg Pro
        115                 120                 125

Ser Trp Glu Phe Asn Trp Gly Lys Leu Lys Val Tyr Lys Glu Lys Ser
        130                 135                 140

Ile Asp Leu Val Lys Ser Lys His Pro Glu Trp Pro Ser Asp Arg Val
145                 150                 155                 160

Glu Lys Val Ala Lys Glu Glu Trp Glu Glu Ser Ala Lys Glu Trp Met
                165                 170                 175
```

-continued

```
Val Lys Thr Leu Lys Leu Ala Gln Glu Met Arg Pro Asn Ala Val Trp
        180                 185                 190

Cys Tyr Tyr Leu Phe Pro Asp Cys Tyr Asn Tyr Phe Gly Lys Asp Gln
        195                 200                 205

Pro Ser Gln Phe Ser Cys Ser Ser Arg Ile Gln Lys Glu Asn Ser Arg
    210                 215                 220

Leu Ser Trp Leu Trp Asn Gln Ser Thr Ala Ile Cys Leu Ser Ile Tyr
225                 230                 235                 240

Ile Gln Glu Ser His Val Thr Lys Tyr Asn Met Ser Gln Arg Thr Trp
                245                 250                 255

Trp Ile Asp Ala Arg Leu Arg Glu Ala Ile Arg Val Ser Glu His Arg
        260                 265                 270

Pro Asn Ile Pro Ile Tyr Pro Tyr Ile Asn Tyr Ile Leu Pro Gly Thr
        275                 280                 285

Asn Gln Thr Val Pro Ala Met Asp Phe Lys Arg Thr Leu Gly Gln Ile
    290                 295                 300

Ala Ser Leu Gly Leu Asp Gly Ala Leu Leu Trp Gly Ser Ser Tyr His
305                 310                 315                 320

Val Leu Thr Glu Ser Gln Cys Lys Ile Thr Ser Asp Tyr Val Lys Ser
                325                 330                 335

Val Ile Ala Pro Thr Val Ala Thr Val Val Leu Asn Thr Asn Arg Cys
        340                 345                 350

Ser Gln Ile Ile Cys Lys Gly Arg Gly Asn Cys Val Trp Pro Glu Glu
        355                 360                 365

Pro Phe Ser Ser Trp Lys Tyr Leu Val Asp Pro Lys Met Pro Val Phe
    370                 375                 380

Lys Pro Thr Asn Ile His Cys Lys Cys Lys Gly Tyr Leu Gly Arg Tyr
385                 390                 395                 400

Cys Glu Ile Pro Lys
                405
```

```
<210> SEQ ID NO 40
<211> LENGTH: 475
<212> TYPE: PRT
<213> ORGANISM: Tityus serrulatus

<400> SEQUENCE: 40

Met Gln Phe Ser Thr Val Ala Ser Val Ala Phe Val Ala Leu Ala Asn
1               5                   10                  15

Phe Val Ala Ala Ala Asp Phe Lys Val Tyr Trp Glu Val Pro Ser Phe
        20                  25                  30

Leu Cys Ser Lys Arg Phe Lys Ile Asn Val Thr Glu Val Leu Thr Ser
        35                  40                  45

His Glu Ile Leu Val Asn Gln Gly Glu Ser Phe Asn Gly Asp Lys Ile
    50                  55                  60

Val Ile Phe Tyr Glu Asn Gln Leu Gly Lys Tyr Pro His Ile Asp Ser
65                  70                  75                  80

Asn Asn Val Glu Ile Asn Gly Gly Ile Leu Gln Val Ala Asp Leu Ala
                85                  90                  95

Lys His Leu Lys Val Ala Lys Asp Asn Ile Thr Lys Phe Val Pro Asn
        100                 105                 110

Pro Asn Phe Asn Gly Val Gly Val Ile Asp Trp Glu Ala Trp Arg Pro
        115                 120                 125

Ser Trp Glu Phe Asn Trp Gly Lys Leu Lys Val Tyr Lys Glu Lys Ser
```

```
           130                  135                  140

Ile Asp Leu Val Lys Ser Lys His Pro Glu Trp Pro Ser Asp Arg Val
145                 150                  155                  160

Glu Lys Val Ala Lys Glu Glu Trp Glu Glu Ser Ala Lys Glu Trp Met
                165                  170                  175

Val Lys Thr Leu Lys Leu Ala Gln Glu Met Arg Pro Asn Ala Val Trp
                180                  185                  190

Cys Tyr Tyr Leu Phe Pro Asp Cys Tyr Asn Tyr Phe Gly Lys Asp Gln
                195                  200                  205

Pro Ser Gln Phe Ser Cys Ser Ser Arg Ile Gln Lys Glu Asn Ser Arg
                210                  215                  220

Leu Ser Trp Leu Trp Asn Gln Ser Thr Ala Ile Cys Leu Ser Ile Tyr
225                 230                  235                  240

Ile Gln Glu Ser His Val Thr Lys Tyr Asn Met Ser Gln Arg Thr Trp
                245                  250                  255

Trp Ile Asp Ala Arg Leu Arg Glu Ala Ile Arg Val Ser Glu His Arg
                260                  265                  270

Pro Asn Ile Pro Ile Tyr Pro Tyr Ile Asn Tyr Ile Leu Pro Gly Thr
                275                  280                  285

Asn Gln Thr Val Pro Ala Met Asp Phe Lys Arg Thr Leu Gly Gln Ile
                290                  295                  300

Ala Ser Leu Gly Leu Asp Gly Ala Leu Leu Trp Gly Ser Ser Tyr His
305                 310                  315                  320

Val Leu Thr Glu Ser Gln Cys Lys Ile Thr Ser Asp Tyr Val Lys Ser
                325                  330                  335

Val Ile Ala Pro Thr Val Ala Thr Val Val Leu Asn Thr Asn Arg Cys
                340                  345                  350

Ser Gln Ile Ile Cys Lys Gly Arg Gly Asn Cys Val Trp Pro Glu Glu
                355                  360                  365

Pro Phe Ser Ser Trp Lys Tyr Leu Val Asp Pro Lys Met Pro Val Phe
                370                  375                  380

Lys Pro Thr Asn Ile His Cys Lys Cys Lys Gly Tyr Leu Gly Arg Tyr
385                 390                  395                  400

Cys Glu Ile Pro Lys Gly Ser Ala Ile Ser Gln Ile Thr Asp Gly Gln
                405                  410                  415

Ile Gln Ala Thr Thr Thr Ala Thr Thr Glu Ala Thr Thr Thr Ala Ala
                420                  425                  430

Pro Ser Ser Thr Val Glu Thr Val Ser Pro Ser Ser Thr Glu Thr Ile
                435                  440                  445

Ser Gln Gln Thr Glu Asn Gly Ala Ala Lys Ala Ala Val Gly Met Gly
                450                  455                  460

Ala Gly Ala Leu Ala Ala Ala Ala Met Leu Leu
465                 470                  475

<210> SEQ ID NO 41
<211> LENGTH: 360
<212> TYPE: PRT
<213> ORGANISM: Vespa magnifica

<400> SEQUENCE: 41

Met Gln Phe Ser Thr Val Ala Ser Val Ala Phe Val Ala Leu Ala Asn
1               5                   10                  15

Phe Val Ala Ala Asp Ser Cys Gly Ser Asn Cys Glu Lys Ser Glu Arg
                20                  25                  30
```

-continued

```
Pro Lys Arg Val Phe Asn Ile Tyr Trp Asn Val Pro Thr Phe Met Cys
        35                  40                  45

His Gln Tyr Gly Leu Tyr Phe Asp Glu Val Thr Asn Phe Asn Ile Lys
    50                  55                  60

His Asn Ser Lys Asp Asn Phe Gln Gly Asp Lys Ile Ala Ile Phe Tyr
65                  70                  75                  80

Asp Pro Gly Glu Phe Pro Ala Leu Leu Pro Leu Asn Tyr Gly Lys Tyr
                85                  90                  95

Lys Ile Arg Asn Gly Gly Val Pro Gln Glu Gly Asn Ile Thr Ile His
                100                 105                 110

Leu Gln Arg Phe Ile Glu Tyr Leu Asp Lys Thr Tyr Pro Asn Arg Asn
            115                 120                 125

Phe Ser Gly Ile Gly Val Ile Asp Phe Glu Arg Trp Arg Pro Ile Phe
    130                 135                 140

Arg Gln Asn Trp Gly Asn Met Lys Ile Tyr Lys Asn Phe Ser Ile Asp
145                 150                 155                 160

Leu Val Arg Lys Glu His Pro Phe Trp Asn Lys Lys Met Ile Glu Leu
                165                 170                 175

Glu Ala Ser Lys Arg Phe Glu Lys Tyr Ala Arg Leu Phe Met Glu Glu
                180                 185                 190

Thr Leu Lys Leu Ala Lys Lys Thr Arg Lys Gln Ala Asp Trp Gly Tyr
            195                 200                 205

Tyr Gly Tyr Pro Tyr Cys Phe Asn Met Ser Pro Thr Asn Phe Val Pro
    210                 215                 220

Asp Cys Asp Val Thr Ala Arg Asp Glu Asn Asn Glu Met Ser Trp Leu
225                 230                 235                 240

Phe Asn Asn Gln Asn Val Leu Leu Pro Ser Val Tyr Ile Arg Arg Glu
                245                 250                 255

Leu Thr Pro Asp Gln Arg Ile Gly Leu Val Gln Gly Arg Val Lys Glu
                260                 265                 270

Ala Val Arg Ile Ser Asn Lys Leu Lys His Ser Pro Lys Val Phe Ser
            275                 280                 285

Tyr Trp Trp Tyr Val Tyr Gln Asp Glu Thr Asn Thr Phe Leu Thr Glu
    290                 295                 300

Thr Asp Val Lys Lys Thr Phe Gln Glu Ile Val Ile Asn Gly Gly Asp
305                 310                 315                 320

Gly Ile Ile Ile Trp Gly Ser Ser Ser Asp Val Asn Ser Leu Ser Lys
                325                 330                 335

Cys Thr Arg Leu Arg Glu Tyr Leu Leu Thr Val Leu Gly Pro Ile Ala
            340                 345                 350

Val Asn Val Thr Glu Ala Val Asn
            355                 360

<210> SEQ ID NO 42
<211> LENGTH: 428
<212> TYPE: PRT
<213> ORGANISM: Vespa magnifica

<400> SEQUENCE: 42

Met Gln Phe Ser Thr Val Ala Ser Val Ala Phe Val Ala Leu Ala Asn
1                   5                   10                  15

Phe Val Ala Ala Asp Ser Cys Gly Ser Asn Cys Glu Lys Ser Glu Arg
                20                  25                  30

Pro Lys Arg Val Phe Asn Ile Tyr Trp Asn Val Pro Thr Phe Met Cys
        35                  40                  45
```

```
His Gln Tyr Gly Leu Tyr Phe Asp Glu Val Thr Asn Phe Asn Ile Lys
    50              55                  60

His Asn Ser Lys Asp Asn Phe Gln Gly Asp Lys Ile Ala Ile Phe Tyr
65              70                  75                  80

Asp Pro Gly Glu Phe Pro Ala Leu Leu Pro Leu Asn Tyr Gly Lys Tyr
                85                  90                  95

Lys Ile Arg Asn Gly Gly Val Pro Gln Glu Gly Asn Ile Thr Ile His
                100                 105                 110

Leu Gln Arg Phe Ile Glu Tyr Leu Asp Lys Thr Tyr Pro Asn Arg Asn
            115                 120                 125

Phe Ser Gly Ile Gly Val Ile Asp Phe Glu Arg Trp Arg Pro Ile Phe
    130                 135                 140

Arg Gln Asn Trp Gly Asn Met Lys Ile Tyr Lys Asn Phe Ser Ile Asp
145                 150                 155                 160

Leu Val Arg Lys Glu His Pro Phe Trp Asn Lys Lys Met Ile Glu Leu
                165                 170                 175

Glu Ala Ser Lys Arg Phe Glu Lys Tyr Ala Arg Leu Phe Met Glu Glu
            180                 185                 190

Thr Leu Lys Leu Ala Lys Lys Thr Arg Lys Gln Ala Asp Trp Gly Tyr
            195                 200                 205

Tyr Gly Tyr Pro Tyr Cys Phe Asn Met Ser Pro Thr Asn Phe Val Pro
    210                 215                 220

Asp Cys Asp Val Thr Ala Arg Asp Glu Asn Asn Glu Met Ser Trp Leu
225                 230                 235                 240

Phe Asn Asn Gln Asn Val Leu Leu Pro Ser Val Tyr Ile Arg Arg Glu
                245                 250                 255

Leu Thr Pro Asp Gln Arg Ile Gly Leu Val Gln Gly Arg Val Lys Glu
                260                 265                 270

Ala Val Arg Ile Ser Asn Lys Leu Lys His Ser Pro Lys Val Phe Ser
            275                 280                 285

Tyr Trp Trp Tyr Val Tyr Gln Asp Glu Thr Asn Thr Phe Leu Thr Glu
    290                 295                 300

Thr Asp Val Lys Lys Thr Phe Gln Glu Ile Val Ile Asn Gly Gly Asp
305                 310                 315                 320

Gly Ile Ile Ile Trp Gly Ser Ser Ser Asp Val Asn Ser Leu Ser Lys
                325                 330                 335

Cys Thr Arg Leu Arg Glu Tyr Leu Leu Thr Val Leu Gly Pro Ile Ala
            340                 345                 350

Val Asn Val Thr Glu Ala Val Asn Ala Ile Ser Gln Ile Thr Asp Gly
            355                 360                 365

Gln Ile Gln Ala Thr Thr Thr Ala Thr Thr Glu Ala Thr Thr Thr Ala
    370                 375                 380

Ala Pro Ser Ser Thr Val Glu Thr Val Ser Pro Ser Ser Thr Glu Thr
385                 390                 395                 400

Ile Ser Gln Gln Thr Glu Asn Gly Ala Ala Lys Ala Ala Val Gly Met
                405                 410                 415

Gly Ala Gly Ala Leu Ala Ala Ala Ala Met Leu Leu
            420                 425
```

<210> SEQ ID NO 43
<211> LENGTH: 60
<212> TYPE: DNA
<213> ORGANISM: Artificial Sequence
<220> FEATURE:

<223> OTHER INFORMATION: secretion sequence

<400> SEQUENCE: 43
atgcaattta gcacagtcgc atcagtagcc ttcgttgcct tggccaactt cgtggcagca        60

<210> SEQ ID NO 44
<211> LENGTH: 20
<212> TYPE: PRT
<213> ORGANISM: Artificial Sequence
<220> FEATURE:
<223> OTHER INFORMATION: Synthetic secretion sequence added in N-ter

<400> SEQUENCE: 44

Met Gln Phe Ser Thr Val Ala Ser Val Ala Phe Val Ala Leu Ala Asn
1               5                   10                  15

Phe Val Ala Ala
            20

<210> SEQ ID NO 45
<211> LENGTH: 213
<212> TYPE: DNA
<213> ORGANISM: Artificial Sequence
<220> FEATURE:
<223> OTHER INFORMATION: anchoring sequence

<400> SEQUENCE: 45
ggatccgcca tttctcaaat cactgacggt caaatccaag ctactaccac tgctaccacc        60
gaagctacca ccactgctgc cccatcttcc accgttgaaa ctgtttctcc atccagcacc       120
gaaactatct ctcaacaaac tgaaaatggt gctgctaagg ccgctgtcgg tatgggtgcc       180
ggtgctctag ctgctgctgc tatgttgtta taa                                   213

<210> SEQ ID NO 46
<211> LENGTH: 68
<212> TYPE: PRT
<213> ORGANISM: Artificial Sequence
<220> FEATURE:
<223> OTHER INFORMATION: Synthetic anchoring sequence added in C-ter

<400> SEQUENCE: 46

Ala Ile Ser Gln Ile Thr Asp Gly Gln Ile Gln Ala Thr Thr Thr Ala
1               5                   10                  15

Thr Thr Glu Ala Thr Thr Thr Ala Ala Pro Ser Ser Thr Val Glu Thr
            20                  25                  30

Val Ser Pro Ser Ser Thr Glu Thr Ile Ser Gln Gln Thr Glu Asn Gly
        35                  40                  45

Ala Ala Lys Ala Ala Val Gly Met Gly Ala Gly Ala Leu Ala Ala Ala
    50                  55                  60

Ala Met Leu Leu
65

<210> SEQ ID NO 47
<211> LENGTH: 2154
<212> TYPE: DNA
<213> ORGANISM: Saccharomyces cerevisiae

<400> SEQUENCE: 47
atgtgtggta tctttggtta ctgcaattat ctagtggaaa gatccagagg agaaattatc        60
gacaccttag tggatggttt acaaagatta gaatatagag ctatgattc caccggtatt        120 gctatcgatg gtgacgaagc tgattctact ttcatctata agcaaatcgg taaagtgagt       180

-continued

```
gctttgaaag aggagattac taagcaaaat ccgaacagag acgttacttt tgtctctcat        240
tgtggtattg cgcatactag atgggctact cacggtcgac cagaacaagt taactgtcac        300
cctcaaagat ctgacccaga agaccaattt gtggtcgttc ataatggtat catcacaaat        360
tttagagaac tgaagactct tttaattaac aaaggttata aattcgaaag tgataccgat        420
accgagtgta ttgctaaact atatttgcat ttatacaata caaatttaca aaatgggcat        480
gacttagatt tccacgaatt aaccaagcta gttcttttag aactagaagg ttcatacggg        540
ttattatgta aatcttgtca ctatcctaat gaggttatcg ccactagaaa agggtcccct        600
ttactgattg gtgtcaaatc tgaaaaaaaa ctaaaagtcg acttcgtgga tgtggaattt        660
cccgaagaaa acgctggtca accggaaatt ccattgaaat ctaacaacaa atcatttggc        720
ttgggcccaa agaaagctcg tgaatttgaa gctggttccc aaaatgccaa tttactacca        780
attgccgcca atgaatttaa cttgagacat tctcaatcca gggctttcct atcagaagat        840
ggatctccaa caccggtgga attttttgtt tcttcggatg cggcatctgt tgttaaacat        900
accaagaagg tgctattttt agaagatgac gatttggctc atatttacga tggtgagtta        960
catattcata gatctagaag agaagtaggc gcatcaatga caaggtccat tcaaacttta       1020
gagatggagt tagctcagat catgaagggc ccttacgacc attttatgca aaaggaaatc       1080
tatgagcaac cagaatctac tttcaatact atgagaggta gaatcgacta tgaaaataat       1140
aaagtgatat tgggtggttt aaaggcatgg ttaccagttg tcagaagagc acggagactg       1200
atcatgatcg catgcggtac ttcttatcat tcatgtttgg ctactcgtgc tatcttcgaa       1260
gaattatcag atatcccagt tagtgtggaa ttagcgtctg actttctgga cagaaaatgc       1320
cctgtcttca gagacgatgt atgcgtgttt gtttcacaaa gtggtgaaac tgcggatacc       1380
atgctggctc taaattattg tttagaaaga ggagccttaa ctgtcggaat tgttaacagt       1440
gttggttctt ctatctctcg tgtcacccac tgtggtgttc atattaacgc tggtcctgaa       1500
attggtgttg cctctacaaa agcttatact tcccagtata ttgccttagt gatgtttgct       1560
ctatcgctgt cagatgaccg tgtatcgaaa atagacagaa gaattgaaat cattcaaggc       1620
ttgaagttaa tcccgggcca aattaagcag gtattaaagc tggaaccaag aataaaaaag       1680
ctctgtgcga ctgaattaaa ggatcaaaaa tctctattgt tattgggtag aggttaccaa       1740
tttgctgctg ctctggaagg tgctttgaag atcaaagaaa tttcttatat gcattctgaa       1800
ggtgtttttg caggtgagtt gaagcacggt gtcttggcct tggtggacga aaacttgcca       1860
atcattgctt ttggtaccag agactctcta ttccctaaag tagtttcctc tattgagcaa       1920
gttactgtaa gaaagggcca tccaattatt atttgtaacg aaaatgatga agtgtgggcg       1980
caaaaatcta aatcaatcga cctgcaaacc ttagaagttc cacaaactgt tgattgttta       2040
caaggtctaa ttaatattat tccattacaa ctaatgtcat attggttggc tgttaataaa       2100
gggattgatg ttgattttcc aagaaacttg gctaaatctg ttaccgtcga ataa            2154
```

```
<210> SEQ ID NO 48
<211> LENGTH: 1788
<212> TYPE: DNA
<213> ORGANISM: Chlorella virus

<400> SEQUENCE: 48
```

```
atgtgcggga tcttcggtgc tgtgtcgaac aataatagca tagaagtttc catcaagggt         60
atacagaagc tagagtaccg cgggtacgat tcgtgtggaa tagcctatac agacggaggc        120
gccattgaac ggatcaggtc aatagatggg atcgacgact taaggaagaa aacaataaca        180
```

-continued

```
gagtcttccc cggtagctat cgctcattca aggtggagta ccactgggat tccaagtgtt      240
gtgaacgccc acccgcacat ctctcggggc acgtctggat gcgagtcgcg cattgcagtc      300
gtacacaatg gcattattga aaattaccag cagatccgca agtacttgat aaatcttggg      360
tatactttcg attcacagac cgacacggaa gtcattgctc atctaataga ctcgcagtat      420
aacgggaaca tcctgcacac cgtccaaatg gcagttaagc acctcaaagg aagctacgcc      480
atagcagtca tgtgccataa ggagtccggg aagatcgtgg tggcaaaaca gaagagtccg      540
ttggtattgg gtataggaag cgacggagct tattatatcg catcggacgt attggctctt      600
cccactaaca aagtggtcta cataagtgac ggattctctg ctgagttaag tcctggatcg      660
atgactatct atgatctgga tggcaataag gtagaatacg aggtggaaga cgttgaaatg      720
gagcagacgt cgatgtcttt agataacttt gatcactaca tgatcaaaga gatcaatgaa      780
cagccgatat caattctcaa tactattaag aacaaaggat tctatgcaga gatatttggt      840
gatctagcac atgaaatatt tcagaagatc gacaatatat tgattctagc ctgcggaact      900
tcgtatcatg caggtctcgt cgggaagcaa tggatagaga ccatctcacg catcccggtg      960
gatgttcata ttgcaagcga gtatgagccg acaattccac gagccaatac acttgtgata     1020
acgattagtc aaagcggcga gactgcggat acaatcgcag cccttcaacg agcgcaaaac     1080
gcaggaatga tatacacttt gtgtatctgc aacagcccca agtcaactct agtgcgcgag     1140
tcgataatga aatacataac caaatgcggt tcagaagttt ctgttgccag tactaaagca     1200
tttacgtcgc aacttgtggt gttgtatatg cttgcgaacg ttcttgcgaa caaaactgat     1260
gatctgctag gggatcttcc tcaagctatc gagagagtaa tctgtcttac taatgacgaa     1320
atgaagcgtt gggcggatga aatttgtact gccaaaagtg ccatcttctt agggagagga     1380
ctgaacgcac ctgtagcatt tgagggcgcg ctaaagttga aggaaatctc atatatccat     1440
gccgagggtt tcctcggtgg agagttgaag catgggccgc tggctttgtt ggacgataag     1500
atccctgtaa tcgtgactgt tgctgaccac gcttatttgg atcacattaa ggctaacatc     1560
gacgaggtat tggcacgaaa cgttaccgta tacgcgatcg tcgatcagta tgttaatatt     1620
gaaccacagg agcgactgca tgtagtaaaa gtgccgtttg tgagtaaaga gttttctccc     1680
atcatccaca caattccgat gcaattgtta tcgtattatg tcgcgatcaa gctgggcaag     1740
aacgttgaca agccacgtaa cctggcgaaa agtgttacaa cattctaa               1788
```

<210> SEQ ID NO 49
<211> LENGTH: 1788
<212> TYPE: DNA
<213> ORGANISM: Chlorella virus

<400> SEQUENCE: 49

```
atgtgtggca tctttggagc agtgtcaaac aacaactcta tcgaggtgtc aatcaagggt       60
attcagaagc tagaatatcg tggggtatgat tcgtgccggta ttgcgtatac agatggggggt     120 gcgattgagc gtatacgttc tattgacggc attgacgatc tgcgtaagaa aacaatcaca      180
gaatcatcac cagtggccat tgctcactcg cggtggagca ccactggaat tccatcagtg      240
gtgaacgcac atcctcatat ttctcgcgga accagtgggt gtgagtctcg tatcgcggta      300
gtccacaacg gtatcattga aaactatcag cagatccgaa aatatctcat caatcttggt      360
tatacgtttg atagtcaaac ggacacagag gtcattgcgc atttgattga ttctcagtac      420
aatgggaata tcttgcacac cgtccaaatg gctgtcaagc acctgaaggg ctcttatgcc      480
```

```
attgcagtta tgtgtcataa agagtctggt aaaatagtcg tggcgaaaca gaagtcaccc          540
ctcgtacttg gaatcggctc agatggtgct tactacatcg cttcggacgt gctggcgctg          600
ccgacaaata aagttgttta tatttcagac ggtttctccg cagaactatc tccagggagt          660
atgaccattt acgatcttga tggaaataaa gtagaatatg aagtagagga cgttgaaatg          720
gaacaaacta gtatgtctct cgataacttt gatcattaca tgattaagga aattaatgag          780
caaccaatca gtattctaaa cactataaaa aataaagggt tctatgcaga aatattcggt          840
gatttggctc atgaaatctt ccaaaaaata gacaacatcc tgatactggc ttgtggtaca          900
agttatcacg ccggtcttgt aggaaaacag tggatagaga ccatctctag aatccccgtg          960
gatgttcaca tcgcgagtga atacgaacct actattccga gagcgaacac attggtaatc         1020
actatttcac agtcgggtga aactgcggac acgatagcgg ctttgcaacg ggcccaaaac         1080
gccgggatga tttatacatt gtgtatttgc aattcaccaa agagcactct tgttcgtgag         1140
agcattatga agtacatcac gaaatgtggt tctgaggtgt cagtggcatc aacgaaggcg         1200
tttacttctc agctcgtagt actgtacatg ctggcaaacg tattggcaaa taaaaccgat         1260
gatttgctgg gagacctccc acaggcaata gaacgggtaa tttgtttgac aaatgacgaa         1320
atgaaacgat gggccgacga aatttgcact gcgaaatccg cgatcttcct gggaagagga         1380
ctaaacgcac cagttgcctt tgagggagcg ttgaagctca agaaatctc ttacattcat         1440 gcagagggct cctgggagg tgagttgaaa cacggcccccc tcgcactcct tgatgacaag         1500
attcctgtta tcgtaaccgt agcagatcat gcttatttgg accatatcaa agcaaatatc         1560
gacgaagtgc ttgcgaggaa cgttacggta tacgccatag tagaccagta tgtgaacatc         1620 gagcccagg aacgccttca cgtcgtcaag gttccgtttg tatccaaaga attttctccg         1680
ataattcaca ctatcccgat gcaactgctt tcgtattacg tggcaattaa gcttggaaag         1740
aacgttgaca aaccaaggaa tcttgcaaaa tccgtgacta ccttttaa                      1788
```

```
<210> SEQ ID NO 50
<211> LENGTH: 717
<212> TYPE: PRT
<213> ORGANISM: Saccharomyces cerevisiae

<400> SEQUENCE: 50

Met Cys Gly Ile Phe Gly Tyr Cys Asn Tyr Leu Val Glu Arg Ser Arg
1               5                   10                  15

Gly Glu Ile Ile Asp Thr Leu Val Asp Gly Leu Gln Arg Leu Glu Tyr
            20                  25                  30

Arg Gly Tyr Asp Ser Thr Gly Ile Ala Ile Asp Gly Asp Glu Ala Asp
        35                  40                  45

Ser Thr Phe Ile Tyr Lys Gln Ile Gly Lys Val Ser Ala Leu Lys Glu
    50                  55                  60

Glu Ile Thr Lys Gln Asn Pro Asn Arg Asp Val Thr Phe Val Ser His
65                  70                  75                  80

Cys Gly Ile Ala His Thr Arg Trp Ala Thr His Gly Arg Pro Glu Gln
                85                  90                  95

Val Asn Cys His Pro Gln Arg Ser Asp Pro Glu Asp Gln Phe Val Val
            100                 105                 110

Val His Asn Gly Ile Ile Thr Asn Phe Arg Glu Leu Lys Thr Leu Leu
        115                 120                 125

Ile Asn Lys Gly Tyr Lys Phe Glu Ser Asp Thr Asp Thr Glu Cys Ile
    130                 135                 140
```

-continued

```
Ala Lys Leu Tyr Leu His Leu Tyr Asn Thr Asn Leu Gln Asn Gly His
145                 150                 155                 160

Asp Leu Asp Phe His Glu Leu Thr Lys Leu Val Leu Leu Glu Leu Glu
                165                 170                 175

Gly Ser Tyr Gly Leu Leu Cys Lys Ser Cys His Tyr Pro Asn Glu Val
                180                 185                 190

Ile Ala Thr Arg Lys Gly Ser Pro Leu Leu Ile Gly Val Lys Ser Glu
                195                 200                 205

Lys Lys Leu Lys Val Asp Phe Val Asp Val Glu Phe Pro Glu Glu Asn
        210                 215                 220

Ala Gly Gln Pro Glu Ile Pro Leu Lys Ser Asn Asn Lys Ser Phe Gly
225                 230                 235                 240

Leu Gly Pro Lys Lys Ala Arg Glu Phe Glu Ala Gly Ser Gln Asn Ala
                245                 250                 255

Asn Leu Leu Pro Ile Ala Ala Asn Glu Phe Asn Leu Arg His Ser Gln
                260                 265                 270

Ser Arg Ala Phe Leu Ser Glu Asp Gly Ser Pro Thr Pro Val Glu Phe
        275                 280                 285

Phe Val Ser Ser Asp Ala Ala Ser Val Val Lys His Thr Lys Lys Val
    290                 295                 300

Leu Phe Leu Glu Asp Asp Asp Leu Ala His Ile Tyr Asp Gly Glu Leu
305                 310                 315                 320

His Ile His Arg Ser Arg Arg Glu Val Gly Ala Ser Met Thr Arg Ser
                325                 330                 335

Ile Gln Thr Leu Glu Met Glu Leu Ala Gln Ile Met Lys Gly Pro Tyr
                340                 345                 350

Asp His Phe Met Gln Lys Glu Ile Tyr Glu Gln Pro Glu Ser Thr Phe
                355                 360                 365

Asn Thr Met Arg Gly Arg Ile Asp Tyr Glu Asn Asn Lys Val Ile Leu
        370                 375                 380

Gly Gly Leu Lys Ala Trp Leu Pro Val Val Arg Arg Ala Arg Arg Leu
385                 390                 395                 400

Ile Met Ile Ala Cys Gly Thr Ser Tyr His Ser Cys Leu Ala Thr Arg
                405                 410                 415

Ala Ile Phe Glu Glu Leu Ser Asp Ile Pro Val Ser Val Glu Leu Ala
                420                 425                 430

Ser Asp Phe Leu Asp Arg Lys Cys Pro Val Phe Arg Asp Asp Val Cys
        435                 440                 445

Val Phe Val Ser Gln Ser Gly Glu Thr Ala Asp Thr Met Leu Ala Leu
    450                 455                 460

Asn Tyr Cys Leu Glu Arg Gly Ala Leu Thr Val Gly Ile Val Asn Ser
465                 470                 475                 480

Val Gly Ser Ser Ile Ser Arg Val Thr His Cys Gly Val His Ile Asn
                485                 490                 495

Ala Gly Pro Glu Ile Gly Val Ala Ser Thr Lys Ala Tyr Thr Ser Gln
                500                 505                 510

Tyr Ile Ala Leu Val Met Phe Ala Leu Ser Leu Ser Asp Asp Arg Val
                515                 520                 525

Ser Lys Ile Asp Arg Arg Ile Glu Ile Ile Gln Gly Leu Lys Leu Ile
        530                 535                 540

Pro Gly Gln Ile Lys Gln Val Leu Lys Leu Glu Pro Arg Ile Lys Lys
545                 550                 555                 560

Leu Cys Ala Thr Glu Leu Lys Asp Gln Lys Ser Leu Leu Leu Leu Gly
```

-continued

```
                    565                 570                 575
Arg Gly Tyr Gln Phe Ala Ala Ala Leu Glu Gly Ala Leu Lys Ile Lys
                580                 585                 590
Glu Ile Ser Tyr Met His Ser Glu Gly Val Leu Ala Gly Glu Leu Lys
                595                 600                 605
His Gly Val Leu Ala Leu Val Asp Glu Asn Leu Pro Ile Ile Ala Phe
        610                 615                 620
Gly Thr Arg Asp Ser Leu Phe Pro Lys Val Val Ser Ser Ile Glu Gln
625                 630                 635                 640
Val Thr Ala Arg Lys Gly His Pro Ile Ile Ile Cys Asn Glu Asn Asp
                645                 650                 655
Glu Val Trp Ala Gln Lys Ser Lys Ser Ile Asp Leu Gln Thr Leu Glu
                660                 665                 670
Val Pro Gln Thr Val Asp Cys Leu Gln Gly Leu Ile Asn Ile Ile Pro
                675                 680                 685
Leu Gln Leu Met Ser Tyr Trp Leu Ala Val Asn Lys Gly Ile Asp Val
        690                 695                 700
Asp Phe Pro Arg Asn Leu Ala Lys Ser Val Thr Val Glu
705                 710                 715
```

<210> SEQ ID NO 51
<211> LENGTH: 595
<212> TYPE: PRT
<213> ORGANISM: Chlorella virus

<400> SEQUENCE: 51

```
Met Cys Gly Ile Phe Gly Ala Val Ser Asn Asn Asn Ser Ile Glu Val
1               5                   10                  15
Ser Ile Lys Gly Ile Gln Lys Leu Glu Tyr Arg Gly Tyr Asp Ser Cys
                20                  25                  30
Gly Ile Ala Tyr Thr Asp Gly Gly Ala Ile Glu Arg Ile Arg Ser Ile
        35                  40                  45
Asp Gly Ile Asp Asp Leu Arg Lys Lys Thr Ile Thr Glu Ser Ser Pro
    50                  55                  60
Val Ala Ile Ala His Ser Arg Trp Ser Thr Thr Gly Ile Pro Ser Val
65                  70                  75                  80
Val Asn Ala His Pro His Ile Ser Arg Gly Thr Ser Gly Cys Glu Ser
                85                  90                  95
Arg Ile Ala Val Val His Asn Gly Ile Ile Glu Asn Tyr Gln Gln Ile
                100                 105                 110
Arg Lys Tyr Leu Ile Asn Leu Gly Tyr Thr Phe Asp Ser Gln Thr Asp
        115                 120                 125
Thr Glu Val Ile Ala His Leu Ile Asp Ser Gln Tyr Asn Gly Asn Ile
        130                 135                 140
Leu His Thr Val Gln Met Ala Val Lys His Leu Lys Gly Ser Tyr Ala
145                 150                 155                 160
Ile Ala Val Met Cys His Lys Glu Ser Gly Lys Ile Val Val Ala Lys
                165                 170                 175
Gln Lys Ser Pro Leu Val Leu Gly Ile Gly Ser Asp Gly Ala Tyr Tyr
        180                 185                 190
Ile Ala Ser Asp Val Leu Ala Leu Pro Thr Asn Lys Val Val Tyr Ile
        195                 200                 205
Ser Asp Gly Phe Ser Ala Glu Leu Ser Pro Gly Ser Met Thr Ile Tyr
        210                 215                 220
```

-continued

```
Asp Leu Asp Gly Asn Lys Val Glu Tyr Glu Val Glu Asp Val Glu Met
225                 230                 235                 240

Glu Gln Thr Ser Met Ser Leu Asp Asn Phe Asp His Tyr Met Ile Lys
                245                 250                 255

Glu Ile Asn Glu Gln Pro Ile Ser Ile Leu Asn Thr Ile Lys Asn Lys
                260                 265                 270

Gly Phe Tyr Ala Glu Ile Phe Gly Asp Leu Ala His Glu Ile Phe Gln
                275                 280                 285

Lys Ile Asp Asn Ile Leu Ile Leu Ala Cys Gly Thr Ser Tyr His Ala
            290                 295                 300

Gly Leu Val Gly Lys Gln Trp Ile Glu Thr Ile Ser Arg Ile Pro Val
305                 310                 315                 320

Asp Val His Ile Ala Ser Glu Tyr Glu Pro Thr Ile Pro Arg Ala Asn
                325                 330                 335

Thr Leu Val Ile Thr Ile Ser Gln Ser Gly Glu Thr Ala Asp Thr Ile
                340                 345                 350

Ala Ala Leu Gln Arg Ala Gln Asn Ala Gly Met Ile Tyr Thr Leu Cys
            355                 360                 365

Ile Cys Asn Ser Pro Lys Ser Thr Leu Val Arg Glu Ser Ile Met Lys
            370                 375                 380

Tyr Ile Thr Lys Cys Gly Ser Glu Val Ser Val Ala Ser Thr Lys Ala
385                 390                 395                 400

Phe Thr Ser Gln Leu Val Val Leu Tyr Met Leu Ala Asn Val Leu Ala
                405                 410                 415

Asn Lys Thr Asp Asp Leu Leu Gly Asp Leu Pro Gln Ala Ile Glu Arg
                420                 425                 430

Val Ile Cys Leu Thr Asn Asp Glu Met Lys Arg Trp Ala Asp Glu Ile
            435                 440                 445

Cys Thr Ala Lys Ser Ala Ile Phe Leu Gly Arg Gly Leu Asn Ala Pro
            450                 455                 460

Val Ala Phe Glu Gly Ala Leu Lys Leu Lys Glu Ile Ser Tyr Ile His
465                 470                 475                 480

Ala Glu Gly Phe Leu Gly Gly Glu Leu Lys His Gly Pro Leu Ala Leu
                485                 490                 495

Leu Asp Asp Lys Ile Pro Val Ile Val Thr Val Ala Asp His Ala Tyr
                500                 505                 510

Leu Asp His Ile Lys Ala Asn Ile Asp Glu Val Leu Ala Arg Asn Val
            515                 520                 525

Thr Val Tyr Ala Ile Val Asp Gln Tyr Val Asn Ile Glu Pro Gln Glu
            530                 535                 540

Arg Leu His Val Val Lys Val Pro Phe Val Ser Lys Glu Phe Ser Pro
545                 550                 555                 560

Ile Ile His Thr Ile Pro Met Gln Leu Leu Ser Tyr Tyr Val Ala Ile
                565                 570                 575

Lys Leu Gly Lys Asn Val Asp Lys Pro Arg Asn Leu Ala Lys Ser Val
                580                 585                 590

Thr Thr Phe
        595
```

```
<210> SEQ ID NO 52
<211> LENGTH: 1434
<212> TYPE: DNA
<213> ORGANISM: Saccharomyces cerevisiae

<400> SEQUENCE: 52
```

-continued

```
atgactgaca caaaacagct attcattgaa gccggacaaa gtcaactttt ccacaattgg     60
gaaagcttgt ctcgcaaaga ccaagaagaa ttgctttcaa acctggagca aatatcttcc    120
aagaggtccc ctgcaaaact actggaagac tgtcaaaatg ctattaaatt ctcactagct    180
aactcttcta aggatactgg cgtcgaaatt tcaccattgc cccctacttc gtacgagtcg    240
cttattggca acagtaagaa agaaaatgaa tactggcgtt taggccttga agctattggc    300
aagggtgaag tcgcagtgat tttaatggct ggcggacaag tacgcggtt aggatcctct     360 caaccaaagg ctgttacga cattggattg ccttctaaga aatctctttt tcaaattcaa     420
gctgaaaagt tgatcaggtt gcaagatatg gtaaaggaca aaaaggtaga aattccttgg    480
tatattatga catcaggccc cactagagcg gctactgagg catactttca agaacacaat    540
tattttggct tgaataaaga acaaattacg ttcttcaacc agggaaccct gcctgccttt    600
gatttaaccg ggaagcattt cctaatgaaa gacccagtaa acctatctca atcaccagat    660
ggaaatggtg gactctaccg tgccatcaag gaaaacaagt gaacgaaga ctttgatagg     720 agaggaatca agcatgttta catgtactgt gtcgataatg tcctatctaa aatcgcagac    780
cctgtattta ttggttttgc catcaagcat ggcttcgaac tggccaccaa agccgttaga    840
aagagagatg cgcatgaatc agttgggtta attgctacta aaaacgagaa accatgtgtc    900
atagaatatt ctgaaatttc caatgaattg gctgaagcaa aggataaaga tggcttatta    960
aaactacgcg caggcaacat tgtaaatcat tattacctag tggatttact aaaacgtgat   1020
ttggatcagt ggtgtgagaa tatgccatat cacattgcga agaagaaat tccagcttat    1080 gatagtgtta ccggcaagta cactaagcct accgaaccaa acggtataaa attagagcaa   1140
ttcatatttg atgtctttga cactgtacca ctgaacaagt ttgggtgctt agaagtagat   1200
agatgcaaag aatttttcacc tttaaaaaac ggtcctggtt ctaagaacga taatcctgag   1260
accagcagac tagcatattt gaaactagga acctcgtggt tggaagatgc aggcgctatt   1320
gtaaaagatg gggtactagt cgaagtttcc agcaaattga gttatgcagg tgaaaatcta   1380
tcccagttca aggtaaagt ctttgacaga agtggtatag tattagaaaa ataa          1434
```

```
<210> SEQ ID NO 53
<211> LENGTH: 477
<212> TYPE: PRT
<213> ORGANISM: Saccharomyces cerevisiae

<400> SEQUENCE: 53

Met Thr Asp Thr Lys Gln Leu Phe Ile Glu Ala Gly Gln Ser Gln Leu
1               5                   10                  15

Phe His Asn Trp Glu Ser Leu Ser Arg Lys Asp Gln Glu Glu Leu Leu
            20                  25                  30

Ser Asn Leu Glu Gln Ile Ser Ser Lys Arg Ser Pro Ala Lys Leu Leu
        35                  40                  45

Glu Asp Cys Gln Asn Ala Ile Lys Phe Ser Leu Ala Asn Ser Ser Lys
        50                  55                  60

Asp Thr Gly Val Glu Ile Ser Pro Leu Pro Pro Thr Ser Tyr Glu Ser
65                  70                  75                  80

Leu Ile Gly Asn Ser Lys Lys Glu Asn Glu Tyr Trp Arg Leu Gly Leu
                    85                  90                  95

Glu Ala Ile Gly Lys Gly Glu Val Ala Val Ile Leu Met Ala Gly Gly
                100                 105                 110

Gln Gly Thr Arg Leu Gly Ser Ser Gln Pro Lys Gly Cys Tyr Asp Ile
```

-continued

```
            115                 120                 125

Gly Leu Pro Ser Lys Lys Ser Leu Phe Gln Ile Gln Ala Glu Lys Leu
    130                 135                 140

Ile Arg Leu Gln Asp Met Val Lys Asp Lys Lys Val Glu Ile Pro Trp
145                 150                 155                 160

Tyr Ile Met Thr Ser Gly Pro Thr Arg Ala Ala Thr Glu Ala Tyr Phe
                165                 170                 175

Gln Glu His Asn Tyr Phe Gly Leu Asn Lys Glu Gln Ile Thr Phe Phe
                180                 185                 190

Asn Gln Gly Thr Leu Pro Ala Phe Asp Leu Thr Gly Lys His Phe Leu
                195                 200                 205

Met Lys Asp Pro Val Asn Leu Ser Gln Ser Pro Asp Gly Asn Gly Gly
    210                 215                 220

Leu Tyr Arg Ala Ile Lys Glu Asn Lys Leu Asn Glu Asp Phe Asp Arg
225                 230                 235                 240

Arg Gly Ile Lys His Val Tyr Met Tyr Cys Val Asp Asn Val Leu Ser
                245                 250                 255

Lys Ile Ala Asp Pro Val Phe Ile Gly Phe Ala Ile Lys His Gly Phe
                260                 265                 270

Glu Leu Ala Thr Lys Ala Val Arg Lys Arg Asp Ala His Glu Ser Val
                275                 280                 285

Gly Leu Ile Ala Thr Lys Asn Glu Lys Pro Cys Val Ile Glu Tyr Ser
    290                 295                 300

Glu Ile Ser Asn Glu Leu Ala Glu Ala Lys Asp Lys Asp Gly Leu Leu
305                 310                 315                 320

Lys Leu Arg Ala Gly Asn Ile Val Asn His Tyr Tyr Leu Val Asp Leu
                325                 330                 335

Leu Lys Arg Asp Leu Asp Gln Trp Cys Glu Asn Met Pro Tyr His Ile
                340                 345                 350

Ala Lys Lys Lys Ile Pro Ala Tyr Asp Ser Val Thr Gly Lys Tyr Thr
                355                 360                 365

Lys Pro Thr Glu Pro Asn Gly Ile Lys Leu Glu Gln Phe Ile Phe Asp
    370                 375                 380

Val Phe Asp Thr Val Pro Leu Asn Lys Phe Gly Cys Leu Glu Val Asp
385                 390                 395                 400

Arg Cys Lys Glu Phe Ser Pro Leu Lys Asn Gly Pro Gly Ser Lys Asn
                405                 410                 415

Asp Asn Pro Glu Thr Ser Arg Leu Ala Tyr Leu Lys Leu Gly Thr Ser
                420                 425                 430

Trp Leu Glu Asp Ala Gly Ala Ile Val Lys Asp Gly Val Leu Val Glu
                435                 440                 445

Val Ser Ser Lys Leu Ser Tyr Ala Gly Glu Asn Leu Ser Gln Phe Lys
    450                 455                 460

Gly Lys Val Phe Asp Arg Ser Gly Ile Val Leu Glu Lys
465                 470                 475
```

<210> SEQ ID NO 54
<211> LENGTH: 1713
<212> TYPE: DNA
<213> ORGANISM: Saccharomyces cerevisiae

<400> SEQUENCE: 54
atgtcacttc taatagattc tgtaccaaca gttgcttata aggaccaaaa accgggtact      60
tcaggtttac gtaagaagac caaggttttc atggatgagc tcattatac tgagaacttc     120

-continued

```
attcaagcaa caatgcaatc tatccctaat ggctcagagg gaaccacttt agttgttgga      180
ggagatggtc gtttctacaa cgatgttatc atgaacaaga ttgccgcagt aggtgctgca      240
aacggtgtca gaaagttagt cattggtcaa ggcggtttac tttcaacacc agctgcttct      300
catataatta gaacatacga ggaaaagtgt accggtggtg gtatcatatt aactgcctca      360
cacaacccag gcggtccaga gaatgattta ggtatcaagt ataatttacc taatggtggg      420
ccagctccag agagtgtcac taacgctatc tgggaagcgt ctaaaaaatt aactcactat      480
aaaattataa agaacttccc caagttgaat ttgaacaagc ttggtaaaaa ccaaaaatat      540
ggcccattgt tagtggacat aattgatcct gccaaagcat acgttcaatt tctgaaggaa      600
atttttgatt ttgacttaat taaaagcttc ttagcgaaac agcgcaaaga caaagggtgg      660
aagttgttgt ttgactcctt aaatggtatt acaggaccat atggtaaggc tatatttgtt      720
gatgaatttg gtttaccggc agaggaagtt cttcaaaatt ggcacccttt acctgatttc      780
ggcggtttac atcccgatcc gaatctaacc tatgcacgaa ctcttgttga cagggttgac      840
cgcgaaaaaa ttgcctttgg agcagcctcc gatggtgatg gtgataggaa tatgatttac      900
ggttatggcc ctgctttcgt ttcgccaggt gattctgttg ccattattgc cgaatatgca      960
cccgaaattc catacttcgc caaacaaggt atttatggct tggcacgttc atttcctaca     1020
tcctcagcca ttgatcgtgt tgcagcaaaa aagggattaa gatgttacga agttccaacc     1080
ggctggaaat tcttctgtgc cttatttgat gctaaaaagc tatcaatctg tggtgaagaa     1140
tccttcggta caggttccaa tcatatcaga gaaaaggacg gtctatgggc cattattgct     1200
tggttaaata tcttggctat ctaccatagg cgtaaccctg aaaaggaagc ttcgatcaaa     1260
actattcagg acgaattttg gaacgagtat ggccgtactt tcttcacaag atacgattac     1320
gaacatatcg aatgcgagca ggccgaaaaa gttgtagctc ttttgagtga atttgtatca     1380
aggccaaacg tttgtggctc ccacttccca gctgatgagt ctttaaccgt tatcgattgt     1440
ggtgattttt cgtatagaga tctagatggc tccatctctg aaaatcaagg ccttttcgta     1500
aagttttcga atgggactaa atttgttttg aggttatccg gcacaggcag ttctggtgca     1560
acaataagat tatacgtaga aaagtatact gataaaaagg agaactatgg ccaaacagct     1620
gacgtcttct tgaaacccgt catcaactcc attgtaaaat tcttaagatt taaagaaatt     1680
ttaggaacag acgaaccaac agtccgcaca tag                                 1713
```

```
<210> SEQ ID NO 55
<211> LENGTH: 554
<212> TYPE: PRT
<213> ORGANISM: Saccharomyces cerevisiae

<400> SEQUENCE: 55
```

```
Lys Pro Gly Thr Ser Gly Leu Arg Lys Lys Thr Lys Val Phe Met Asp
1               5                   10                  15

Glu Pro His Tyr Thr Glu Asn Phe Ile Gln Ala Thr Met Gln Ser Ile
            20                  25                  30

Pro Asn Gly Ser Glu Gly Thr Thr Leu Val Val Gly Gly Asp Gly Arg
        35                  40                  45

Phe Tyr Asn Asp Val Ile Met Asn Lys Ile Ala Ala Val Gly Ala Ala
    50                  55                  60

Asn Gly Val Arg Lys Leu Val Ile Gly Gln Gly Gly Leu Leu Ser Thr
65                  70                  75                  80

Pro Ala Ala Ser His Ile Ile Arg Thr Tyr Glu Glu Lys Cys Thr Gly
```

-continued

```
                  85              90              95
Gly Gly Ile Ile Leu Thr Ala Ser His Asn Pro Gly Gly Pro Glu Asn
            100             105             110

Asp Leu Gly Ile Lys Tyr Asn Leu Pro Asn Gly Gly Pro Ala Pro Glu
        115             120             125

Ser Val Thr Asn Ala Ile Trp Glu Ala Ser Lys Lys Leu Thr His Tyr
        130             135             140

Lys Ile Ile Lys Asn Phe Pro Lys Leu Asn Leu Asn Lys Leu Gly Lys
145             150             155             160

Asn Gln Lys Tyr Gly Pro Leu Leu Val Asp Ile Ile Asp Pro Ala Lys
            165             170             175

Ala Tyr Val Gln Phe Leu Lys Glu Ile Phe Asp Phe Asp Leu Ile Lys
            180             185             190

Ser Phe Leu Ala Lys Gln Arg Lys Asp Lys Gly Trp Lys Leu Leu Phe
            195             200             205

Asp Ser Leu Asn Gly Ile Thr Gly Pro Tyr Gly Lys Ala Ile Phe Val
        210             215             220

Asp Glu Phe Gly Leu Pro Ala Glu Glu Val Leu Gln Asn Trp His Pro
225             230             235             240

Leu Pro Asp Phe Gly Gly Leu His Pro Asp Pro Asn Leu Thr Tyr Ala
            245             250             255

Arg Thr Leu Val Asp Arg Val Asp Arg Glu Lys Ile Ala Phe Gly Ala
            260             265             270

Ala Ser Asp Gly Asp Gly Asp Arg Asn Met Ile Tyr Gly Tyr Gly Pro
            275             280             285

Ala Phe Val Ser Pro Gly Asp Ser Val Ala Ile Ile Ala Glu Tyr Ala
        290             295             300

Pro Glu Ile Pro Tyr Phe Ala Lys Gln Gly Ile Tyr Gly Leu Ala Arg
305             310             315             320

Ser Phe Pro Thr Ser Ser Ala Ile Asp Arg Val Ala Ala Lys Lys Gly
            325             330             335

Leu Arg Cys Tyr Glu Val Pro Thr Gly Trp Lys Phe Phe Cys Ala Leu
            340             345             350

Phe Asp Ala Lys Lys Leu Ser Ile Cys Gly Glu Glu Ser Phe Gly Thr
        355             360             365

Gly Ser Asn His Ile Arg Glu Lys Asp Gly Leu Trp Ala Ile Ile Ala
        370             375             380

Trp Leu Asn Ile Leu Ala Ile Tyr His Arg Arg Asn Pro Glu Lys Glu
385             390             395             400

Ala Ser Ile Lys Thr Ile Gln Asp Glu Phe Trp Asn Glu Tyr Gly Arg
            405             410             415

Thr Phe Phe Thr Arg Tyr Asp Tyr Glu His Ile Glu Cys Glu Gln Ala
            420             425             430

Glu Lys Val Val Ala Leu Leu Ser Glu Phe Val Ser Arg Pro Asn Val
            435             440             445

Cys Gly Ser His Phe Pro Ala Asp Glu Ser Leu Thr Val Ile Asp Cys
        450             455             460

Gly Asp Phe Ser Tyr Arg Asp Leu Asp Gly Ser Ile Ser Glu Asn Gln
465             470             475             480

Gly Leu Phe Val Lys Phe Ser Asn Gly Thr Lys Phe Val Leu Arg Leu
            485             490             495

Ser Gly Thr Gly Ser Ser Gly Ala Thr Ile Arg Leu Tyr Val Glu Lys
            500             505             510
```

```
Tyr Thr Asp Lys Lys Glu Asn Tyr Gly Gln Thr Ala Asp Val Phe Leu
        515                 520                 525

Lys Pro Val Ile Asn Ser Ile Val Lys Phe Leu Arg Phe Lys Glu Ile
        530                 535                 540

Leu Gly Thr Asp Glu Pro Thr Val Arg Thr
545                 550

<210> SEQ ID NO 56
<211> LENGTH: 1500
<212> TYPE: DNA
<213> ORGANISM: Saccharomyces cerevisiae

<400> SEQUENCE: 56
atgtccacta agaagcacac caaaacacat tccacttatg cattcgagag caacacaaac      60
agcgttgctg cctcacaaat gagaaacgcc ttaaacaagt tggcggactc tagtaaactt     120
gacgatgctg ctcgcgctaa gtttgagaac gaactggatt cgttttttcac gcttttcagg    180 agatatttgg tagagaagtc ttctagaacc accttggaat gggacaagat caagtctccc     240
aacccggatg aagtggttaa gtatgaaatt atttctcagc agcccgagaa tgtctcaaac     300
ctttccaaat tggctgtttt gaagttgaac ggtgggctgg gtacctccat gggctgcgtt     360
ggccctaaat ctgttattga agtgagagag ggaaacacct ttttggattt gtctgttcgt     420
caaattgaat acttgaacag acagtacgat agcgacgtgc cattgttatt gatgaattct     480
ttcaacactg acaaggatac ggaacacttg attaagaagt attccgctaa cagaatcaga     540
atcagatctt tcaatcaatc caggttccca agagtctaca aggattcttt attgcctgtc     600
cccaccgaat acgattctcc actggatgct tggtatccac caggtcacgg tgatttgttt     660
gaatctttac acgtatctgg tgaactggat gccttaattg cccaaggaag agaaatatta     720
tttgtttcta acggtgacaa cttgggtgct accgtcgact taaaaatttt aaaccacatg     780
atcgagactg gtgccgaata tataatggaa ttgactgata gaccagagc cgatgttaaa     840 ggtggtactt tgatttctta cgatggtcaa gtccgtttat tggaagtcgc ccaagttcca     900
aaagaacaca ttgacgaatt caaaaatatc agaaagttta ccaacttcaa cacgaataac     960
ttatggatca atctgaaagc agtaaagagg ttgatcgaat cgagcaattt ggagatggaa    1020
atcattccaa accaaaaaac tataacaaga gacggtcatg aaattaatgt cttacaatta    1080
gaaaccgctt gtggtgctgc tatcaggcat tttgatggtg ctcacggtgt tgtcgttcca    1140
agatcaagat tcttgcctgt caagacctgt tccgatttgt tgctggttaa atcagatcta    1200
ttccgtctgg aacacggttc tttgaagtta gacccatccc gttttggtcc aaacccatta    1260
atcaagttgg gctcgcattt caaaaaggtt tctggtttta acgcaagaat ccctcacatc    1320
ccaaaaatcg tcgagctaga tcatttgacc atcactggta acgtcttttt aggtaaagat    1380
gtcactttga ggggtactgt catcatcgtt tgctccgacg tcataaaat cgatattcca    1440 aacggctcca tattggaaaa tgttgtcgtt actggtaatt tgcaaatctt ggaacattga    1500

<210> SEQ ID NO 57
<211> LENGTH: 499
<212> TYPE: PRT
<213> ORGANISM: Saccharomyces cerevisiae

<400> SEQUENCE: 57

Met Ser Thr Lys Lys His Thr Lys Thr His Ser Thr Tyr Ala Phe Glu
1               5                   10                  15
```

-continued

```
Ser Asn Thr Asn Ser Val Ala Ala Ser Gln Met Arg Asn Ala Leu Asn
        20              25              30

Lys Leu Ala Asp Ser Ser Lys Leu Asp Asp Ala Ala Arg Ala Lys Phe
        35              40              45

Glu Asn Glu Leu Asp Ser Phe Phe Thr Leu Phe Arg Arg Tyr Leu Val
    50              55              60

Glu Lys Ser Ser Arg Thr Thr Leu Glu Trp Asp Lys Ile Lys Ser Pro
65              70              75              80

Asn Pro Asp Glu Val Val Lys Tyr Glu Ile Ile Ser Gln Gln Pro Glu
                85              90              95

Asn Val Ser Asn Leu Ser Lys Leu Ala Val Leu Lys Leu Asn Gly Gly
            100             105             110

Leu Gly Thr Ser Met Gly Cys Val Gly Pro Lys Ser Val Ile Glu Val
        115             120             125

Arg Glu Gly Asn Thr Phe Leu Asp Leu Ser Val Arg Gln Ile Glu Tyr
    130             135             140

Leu Asn Arg Gln Tyr Asp Ser Asp Val Pro Leu Leu Leu Met Asn Ser
145             150             155             160

Phe Asn Thr Asp Lys Asp Thr Glu His Leu Ile Lys Lys Tyr Ser Ala
            165             170             175

Asn Arg Ile Arg Ile Arg Ser Phe Asn Gln Ser Arg Phe Pro Arg Val
            180             185             190

Tyr Lys Asp Ser Leu Leu Pro Val Pro Thr Glu Tyr Asp Ser Pro Leu
        195             200             205

Asp Ala Trp Tyr Pro Pro Gly His Gly Asp Leu Phe Glu Ser Leu His
    210             215             220

Val Ser Gly Glu Leu Asp Ala Leu Ile Ala Gln Gly Arg Glu Ile Leu
225             230             235             240

Phe Val Ser Asn Gly Asp Asn Leu Gly Ala Thr Val Asp Leu Lys Ile
            245             250             255

Leu Asn His Met Ile Glu Thr Gly Ala Glu Tyr Ile Met Glu Leu Thr
            260             265             270

Asp Lys Thr Arg Ala Asp Val Lys Gly Gly Thr Leu Ile Ser Tyr Asp
        275             280             285

Gly Gln Val Arg Leu Leu Glu Val Ala Gln Val Pro Lys Glu His Ile
    290             295             300

Asp Glu Phe Lys Asn Ile Arg Lys Phe Thr Asn Phe Asn Thr Asn Asn
305             310             315             320

Leu Trp Ile Asn Leu Lys Ala Val Lys Arg Leu Ile Glu Ser Ser Asn
            325             330             335

Leu Glu Met Glu Ile Ile Pro Asn Gln Lys Thr Ile Thr Arg Asp Gly
            340             345             350

His Glu Ile Asn Val Leu Gln Leu Glu Thr Ala Cys Gly Ala Ala Ile
        355             360             365

Arg His Phe Asp Gly Ala His Gly Val Val Val Pro Arg Ser Arg Phe
    370             375             380

Leu Pro Val Lys Thr Cys Ser Asp Leu Leu Leu Val Lys Ser Asp Leu
385             390             395             400

Phe Arg Leu Glu His Gly Ser Leu Lys Leu Asp Pro Ser Arg Phe Gly
            405             410             415

Pro Asn Pro Leu Ile Lys Leu Gly Ser His Phe Lys Lys Val Ser Gly
            420             425             430

Phe Asn Ala Arg Ile Pro His Ile Pro Lys Ile Val Glu Leu Asp His
```

-continued

```
              435              440              445
Leu Thr Ile Thr Gly Asn Val Phe Leu Gly Lys Asp Val Thr Leu Arg
      450              455              460
Gly Thr Val Ile Ile Val Cys Ser Asp Gly His Lys Ile Asp Ile Pro
465              470              475              480
Asn Gly Ser Ile Leu Glu Asn Val Val Val Thr Gly Asn Leu Gln Ile
              485              490              495
Leu Glu His

<210> SEQ ID NO 58
<211> LENGTH: 480
<212> TYPE: DNA
<213> ORGANISM: Saccharomyces cerevisiae

<400> SEQUENCE: 58
atgagcttac ccgatggatt ttatataagg cgaatggaag aggggatttt ggaacaggtc      60
actgagacgc taaaggtttt gaccaccgtg ggcactatta cccccgaatc cttcagcaaa     120
ctcataaaat actggaatga agccacagta tggaatgata cgaagataa aaaaataatg      180 caatataacc ccatggtgat tgtggacaag cgcaccgaga cggttgccgc tacggggaat     240
atcatcatcg aaagaaagat cattcatgaa ctggggctat gtggccacat cgaggacatt     300
gcagtaaact ccaagtatca gggccaaggt ttgggcaagc tcttgattga tcaattggta     360
actatcggct ttgactacgg ttgttataag attattttag attgcgatga gaaaaatgtc     420
aaattctatg aaaaatgtgg gtttagcaac gcaggcgtgg aaatgcaaat tagaaaatag     480

<210> SEQ ID NO 59
<211> LENGTH: 159
<212> TYPE: PRT
<213> ORGANISM: Saccharomyces cerevisiae

<400> SEQUENCE: 59

Met Ser Leu Pro Asp Gly Phe Tyr Ile Arg Arg Met Glu Glu Gly Asp
1               5                  10                  15
Leu Glu Gln Val Thr Glu Thr Leu Lys Val Leu Thr Thr Val Gly Thr
              20                  25                  30
Ile Thr Pro Glu Ser Phe Ser Lys Leu Ile Lys Tyr Trp Asn Glu Ala
          35                  40                  45
Thr Val Trp Asn Asp Asn Glu Asp Lys Lys Ile Met Gln Tyr Asn Pro
      50                  55                  60
Met Val Ile Val Asp Lys Arg Thr Glu Thr Val Ala Ala Thr Gly Asn
65                  70                  75                  80
Ile Ile Ile Glu Arg Lys Ile Ile His Glu Leu Gly Leu Cys Gly His
              85                  90                  95
Ile Glu Asp Ile Ala Val Asn Ser Lys Tyr Gln Gly Gln Gly Leu Gly
          100                 105                 110
Lys Leu Leu Ile Asp Gln Leu Val Thr Ile Gly Phe Asp Tyr Gly Cys
          115                 120                 125
Tyr Lys Ile Ile Leu Asp Cys Asp Glu Lys Asn Val Lys Phe Tyr Glu
      130                 135                 140
Lys Cys Gly Phe Ser Asn Ala Gly Val Glu Met Gln Ile Arg Lys
145                 150                 155

<210> SEQ ID NO 60
<211> LENGTH: 1674
<212> TYPE: DNA
```

<213> ORGANISM: Saccharomyces cerevisiae

<400> SEQUENCE: 60

```
atgaaggttg attacgagca attgtgcaaa ctctacgatg acacgtgccg cacaaagaat       60
gtgcagttca gttacggtac ggccggattc agaacgctgg ccaagaattt ggatacggtg      120
atgttcagta ctggtatact ggcggttctc aggtcgctga agcttcaggg tcagtatgtg      180
ggggtgatga tcacggcgtc gcacaaccca taccaggaca acgggtcaa gatcgtggaa       240 ccagacggat cgatgctttt ggccacatgg gagccatatg ccatgcagtt ggccaatgcg      300
gcctcttttg ccactaattt tgaagaattt cgtgttgagt tggccaagct gattgaacac      360
gaaaagattg atttgaatac aaccgtcgtg cctcacatcg tggttgggag agactctagg      420
gaaagtagtc catacttgct gcgctgcttt acttcctcca tggccagcgt cttccacgcg      480
caagttttgg acctaggctg tgtcactacg cctcaattgc attacattac tgatttgtcc      540
aacaggcgga aactggaagg agacacagcg ccagttgcca cagaacagga ctactattcg      600
ttctttatag gagccttcaa cgagctcttc gccacgtatc agctggagaa gaggctgtct      660
gtcccaaaat tgttcataga cacagccaat ggtatcggtg tccacagtt gaaaaaacta       720 ctggcctccg aagattggga cgtgccagcg gagcaagttg aggtaatcaa cgacaggtcc      780
gatgttccag aactgttgaa ttttgaatgc ggtgcggatt atgtgaagac taaccagaga     840
ttacccaagg gtctttctcc atcctcgttt gattcgctat attgctcctt tgatggtgac      900
gcagacaggg ttgtgttcta ctatgtcgac tcaggatcaa aatttcattt gttggatggt      960
gacaaaattt ccactttgtt tgcaaagttc ttgtctaaac aactagaatt ggcacaccta     1020
gaacattctt tgaagattgg tgttgtgcaa actgcctatg caaacggcag ttccaccgct     1080
tacataaaaa atacgttgca ctgtcccgtg tcttgcacta agacaggtgt taaacacttg     1140
catcatgaag ctgccactca gtacgatatt ggcatttatt tcgaagcaaa tggacatggt     1200
acgattatat tcagcgaaaa atttcatcga actatcaaat ctgaattatc caagtccaag     1260
ttaaatggtg atacgttagc tttgagaact ttgaagtgtt tctctgaatt gattaatcag     1320
accgtgggag atgctatttc agacatgctt gctgtccttg ctactttggc gattttgaaa     1380
atgtcgccaa tggattggga tgaagagtat actgatttgc ccaacaagct ggttaagtgc     1440
atcgttcctg ataggtcaat tttccaaacc acggaccagg aaagaaaatt gctcaatcca     1500
gtggggttgc aagacaagat agatcttgtg gtagccaagt atcccatggg aagaagcttt     1560
gtcagagcca gtggtacgga ggatgcggtg agggtttatg cggaatgtaa ggactcctct     1620
aagttaggtc aattttgtga cgaagtggtg gagcacgtta aggcatctgc ttga           1674
```

<210> SEQ ID NO 61
<211> LENGTH: 557
<212> TYPE: PRT
<213> ORGANISM: Saccharomyces cerevisiae

<400> SEQUENCE: 61

```
Met Lys Val Asp Tyr Glu Gln Leu Cys Lys Leu Tyr Asp Asp Thr Cys
1               5                   10                  15

Arg Thr Lys Asn Val Gln Phe Ser Tyr Gly Thr Ala Gly Phe Arg Thr
            20                  25                  30

Leu Ala Lys Asn Leu Asp Thr Val Met Phe Ser Thr Gly Ile Leu Ala
        35                  40                  45

Val Leu Arg Ser Leu Lys Leu Gln Gly Gln Tyr Val Gly Val Met Ile
    50                  55                  60
```

-continued

```
Thr Ala Ser His Asn Pro Tyr Gln Asp Asn Gly Val Lys Ile Val Glu
65                  70                  75                  80

Pro Asp Gly Ser Met Leu Leu Ala Thr Trp Glu Pro Tyr Ala Met Gln
                85                  90                  95

Leu Ala Asn Ala Ala Ser Phe Ala Thr Asn Phe Glu Glu Phe Arg Val
                100                 105                 110

Glu Leu Ala Lys Leu Ile Glu His Glu Lys Ile Asp Leu Asn Thr Thr
                115                 120                 125

Val Val Pro His Ile Val Val Gly Arg Asp Ser Arg Glu Ser Ser Pro
                130                 135                 140

Tyr Leu Leu Arg Cys Leu Thr Ser Ser Met Ala Ser Val Phe His Ala
145                 150                 155                 160

Gln Val Leu Asp Leu Gly Cys Val Thr Thr Pro Gln Leu His Tyr Ile
                165                 170                 175

Thr Asp Leu Ser Asn Arg Arg Lys Leu Glu Gly Asp Thr Ala Pro Val
                180                 185                 190

Ala Thr Glu Gln Asp Tyr Tyr Ser Phe Phe Ile Gly Ala Phe Asn Glu
                195                 200                 205

Leu Phe Ala Thr Tyr Gln Leu Glu Lys Arg Leu Ser Val Pro Lys Leu
                210                 215                 220

Phe Ile Asp Thr Ala Asn Gly Ile Gly Gly Pro Gln Leu Lys Lys Leu
225                 230                 235                 240

Leu Ala Ser Glu Asp Trp Asp Val Pro Ala Glu Gln Val Glu Val Ile
                245                 250                 255

Asn Asp Arg Ser Asp Val Pro Glu Leu Leu Asn Phe Glu Cys Gly Ala
                260                 265                 270

Asp Tyr Val Lys Thr Asn Gln Arg Leu Pro Lys Gly Leu Ser Pro Ser
                275                 280                 285

Ser Phe Asp Ser Leu Tyr Cys Ser Phe Asp Gly Asp Ala Asp Arg Val
                290                 295                 300

Val Phe Tyr Tyr Val Asp Ser Gly Ser Lys Phe His Leu Leu Asp Gly
305                 310                 315                 320

Asp Lys Ile Ser Thr Leu Phe Ala Lys Phe Leu Ser Lys Gln Leu Glu
                325                 330                 335

Leu Ala His Leu Glu His Ser Leu Lys Ile Gly Val Val Gln Thr Ala
                340                 345                 350

Tyr Ala Asn Gly Ser Ser Thr Ala Tyr Ile Lys Asn Thr Leu His Cys
                355                 360                 365

Pro Val Ser Cys Thr Lys Thr Gly Val Lys His Leu His His Glu Ala
                370                 375                 380

Ala Thr Gln Tyr Asp Ile Gly Ile Tyr Phe Glu Ala Asn Gly His Gly
385                 390                 395                 400

Thr Ile Ile Phe Ser Glu Lys Phe His Arg Thr Ile Lys Ser Glu Leu
                405                 410                 415

Ser Lys Ser Lys Leu Asn Gly Asp Thr Leu Ala Leu Arg Thr Leu Lys
                420                 425                 430

Cys Phe Ser Glu Leu Ile Asn Gln Thr Val Gly Asp Ala Ile Ser Asp
                435                 440                 445

Met Leu Ala Val Leu Ala Thr Leu Ala Ile Leu Lys Met Ser Pro Met
                450                 455                 460

Asp Trp Asp Glu Glu Tyr Thr Asp Leu Pro Asn Lys Leu Val Lys Cys
465                 470                 475                 480
```

```
Ile Val Pro Asp Arg Ser Ile Phe Gln Thr Thr Asp Gln Glu Arg Lys
                485                 490                 495

Leu Leu Asn Pro Val Gly Leu Gln Asp Lys Ile Asp Leu Val Val Ala
            500                 505                 510

Lys Tyr Pro Met Gly Arg Ser Phe Val Arg Ala Ser Gly Thr Glu Asp
        515                 520                 525

Ala Val Arg Val Tyr Ala Glu Cys Lys Asp Ser Ser Lys Leu Gly Gln
    530                 535                 540

Phe Cys Asp Glu Val Val Glu His Val Lys Ala Ser Ala
545                 550                 555

<210> SEQ ID NO 62
<211> LENGTH: 574
<212> TYPE: DNA
<213> ORGANISM: Artificial Sequence
<220> FEATURE:
<223> OTHER INFORMATION: Synthetic Nucleic acid sequence of promotor
      pTDH3

<400> SEQUENCE: 62
ctgctgtaac ccgtacatgc ccaaaatagg gggcgggtta cacagaatat ataacatcgt      60
aggtgtctgg gtgaacagtt tattcctggc atccactaaa tataatggag cccgcttttt     120
aagctggcat ccagaaaaaa aaagaatccc agcaccaaaa tattgttttc ttcaccaacc     180
atcagttcat aggtccattc tcttagcgca actacagaga acaggggcac aaacaggcaa     240
aaaacgggca caacctcaat ggagtgatgc aacctgcctg gagtaaatga tgacacaagg     300 caattgacccc acgcatgtat ctatctcatt ttcttacacc ttctattacc ttctgctctc     360
tctgatttgg aaaaagctga aaaaaaaggt tgaaaccagt tccctgaaat tattccccta     420
cttgactaat aagtatataa agacggtagg tattgattgt aattctgtaa atctatttct     480
taaacttctt aaattctact tttatagtta gtctttttt tagttttaaa acaccaagaa     540
cttagtttcg aataaacaca cataaacaaa caaa                                574

<210> SEQ ID NO 63
<211> LENGTH: 585
<212> TYPE: DNA
<213> ORGANISM: Saccharomyces kudriavzevii

<400> SEQUENCE: 63
caattcatcg gccctttttag cggctacccg cgccatctaa atgatagggc gggtgacact      60
atggtaaatc ccataattag gtgtctgggt gagtggttct gatgccggca tccactaaat     120
atattggagc ccatttttta cgcgggcttc cagaaaaaaa gagaatccca gcaccaaaag     180
gtggttctct tcaccaacca tcagatcata ggtccacaac cacacataac aggggcacaa     240
aaaggcaaaa aacggacata acctcaatgg agtgatgcaa attgactgga gcaaaagctg     300
acacaaggca ttgattgacc tacgcatgta tctgtattct tttcttacac cttctattac     360
cttctaactc tttgggttgg aaaaaactga aaaaaaaggt tgggacctgg ttcccccaag     420 ttgtcccccct acttggttat aaatatata aagacagcaa gtgttgatta taatcttgta     480
aatctatagt tcttaatcta tacttctatt tatattttaa attagtcttt ttatttccaa     540
gtccccaaga acttagtttc gaataaacac acacaaataa acaca                    585

<210> SEQ ID NO 64
<211> LENGTH: 700
<212> TYPE: DNA
<213> ORGANISM: Saccharomyces bayanus
```

-continued

<400> SEQUENCE: 64

```
gcagcgcttc ttccgctcta gtttttatag ttattattac taccacctta aaaatacgta    60
aatactcaaa atagtagtga tattcccaac cttattcatc caaggcacat catcatcatc   120
agccattcat ctttcacctg ccattagtaa cccgtcttct cattgagcgg gttacggcag   180
ccacaggcca cattccgaat gtctgggtga gcggtccctt ttccagcatc cactaaatat   240
ctccgatccc gctttttaat ctggcttcct gaaaaaaaga gaatcccagc accaaaaaat   300
ggctctcttc accaaccatc agatcatagg tcccattctc ttaccgcaac cgtacagaac   360
aggggaaaac gggtacaacc tcaatggagt gatgcaaact gactggagca aaaagctgac   420
acaaggcaat cgacctacgt gtctgtctat tttctcacac cttctattac cttctaactc   480
tctgggttgg aaaaaactga aaaaaaggtt gagaccagtt tccacaaatc atccccctgt   540
ttgattaata aatatataaa gacgacaact atcgatcata aactcataaa actataactc   600
ctttacactt cttattttat agttattcta ttttaattct tattgatttt aaaaccccaa   660
gaacttagtt tcgaaaacac acacacacaa acaattaaaa                          700
```

<210> SEQ ID NO 65
<211> LENGTH: 600
<212> TYPE: DNA
<213> ORGANISM: Saccharomyces arboricola

<400> SEQUENCE: 65

```
gagctaaata tcagcccttc gggtcctgcc tgctacccgg tcctgttcga ataaaaacgc    60
gggtaacacg acccagtaac acctgtcgtt gggtgtctgg gtcagaagtt ctgataccgg   120
cttccactaa atagattggg ttccgctctt tacgctggct tcctgaaaaa agagattccg   180
ggcaccaaaa aattggtctc tttgccaacc atcagatcat aggtccattc tcttaccata   240
accacacagg atagggcac cacaggcgaa aatgggcaca aaatctcaat ggagtgatgc   300
aaattagctg gaacaaaagc tgacacaagg caattaacct gcgcatgtat ccatctcctt   360
ttcttacacc ttctcttacg ttctaactgt ttgggttgga aaaattaaaa aaaaaaggtt   420
gagaccagtt tccccaaatc gtcccctac ttgattcata aatatataaa gacgacaact   480
attgattata atcttgtaaa tctataactc tttactttct cctatttata atttaactta   540
atctttttag atttaaaacc ccaagaactt agtttcgaac aaacacacac aaataaacaa   600
```

<210> SEQ ID NO 66
<211> LENGTH: 550
<212> TYPE: DNA
<213> ORGANISM: Artificial Sequence
<220> FEATURE:
<223> OTHER INFORMATION: Synthetic Nucleic acid sequence of promotor
      pENO2

<400> SEQUENCE: 66

```
cgctcagcat ctgcttcttc ccaaagatga acgcggcgtt atgtcactaa cgacgtgcac    60
caacttgcgg aaagtggaat cccgttccaa aactggcatc cactaattga tacatctaca   120
caccgcacgc ctttttctg aagcccactt tcgtggactt tgccatatgc aaaattcatg   180
aagtgtgata ccaagtcagc atacacctca ctagggtagt ttctttggtt gtattgatca   240
tttggttcat cgtggttcat taattttttt tctccattgc tttctggctt tgatcttact   300
atcatttgga tttttgtcga aggttgtaga attgtatgtg acaagtggca ccaagcatat   360
ataaaaaaaa aaagcattat cttcctacca gagttgattg ttaaaaacgt atttatagca   420
```

-continued

```
aacgcaattg taattaattc ttattttgta tcttttcttc ccttgtctca atctttattt       480
tttattttat ttttcttttc ttagtttctt tcataacacc aagcaactaa tactataaca       540
tacaataata                                                               550

<210> SEQ ID NO 67
<211> LENGTH: 598
<212> TYPE: DNA
<213> ORGANISM: Artificial Sequence
<220> FEATURE:
<223> OTHER INFORMATION: Synthetic Nucleic acid sequence of promotor
      pTEF3

<400> SEQUENCE: 67
ggctgataat agcgtataaa caatgcatac tttgtacgtt caaaatacaa tgcagtagat        60
atatttatgc atattacata taatacatat cacataggaa gcaacaggcg cgttggactt       120
ttaattttcg aggaccgcga atccttacat cacacccaat cccccacaag tgatcccca        180 cacaccatag cttcaaaatg tttctactcc ttttttactc ttccagattt tctcggactc       240
cgcgcatcgc cgtaccactt caaaacaccc aagcacagca tactaaattt ccctctcttc       300
ttcctctagg gtgtcgttaa ttacccgtac taaaggtttg gaaaagaaaa aagagaccgc       360
ctcgtttctt tttcttcgtc gaaaaaggca ataaaaattt ttatcacgtt tcttttttctt     420 gaaaatttt ttttttgatt tttttctctt tcgatgacct cccattgata tttaagttaa       480
taaacggtct tcaatttctc aagtttcagt ttcatttttc ttgttctatt acaacttttt      540
ttacttcttg ctcattagaa agaaagcata gcaatctaat ctaagtttta attacaaa        598

<210> SEQ ID NO 68
<211> LENGTH: 383
<212> TYPE: DNA
<213> ORGANISM: Artificial Sequence
<220> FEATURE:
<223> OTHER INFORMATION: Synthetic Nucleic acid sequence of promotor
      pTEF1

<400> SEQUENCE: 68
gtttagcttg cctcgtcccc gccgggtcac ccggccagcg acatggaggc ccagaatacc        60
ctccttgaca gtcttgacgt gcgcagctca ggggcatgat gtgactgtcg cccgtacatt       120
tagcccatac atccccatgt ataatcattt gcatccacat attttgatgg ccgcacggcg       180
cgaagcaaaa attacggctc ctcgctgcag acctgcgagc agggaaacgc tcccctcaca       240
gacgcgttga attgtcccca cgccgcgccc ctgtagagaa atataaaagg ttaggatttg       300
ccactgaggt tcttctttca tatacttcct tttaaaatct tgctacgata cagttctcac       360
atcacatccg aacataaaca acc                                              383

<210> SEQ ID NO 69
<211> LENGTH: 383
<212> TYPE: DNA
<213> ORGANISM: Ashbya gossypii

<400> SEQUENCE: 69
gtttagcttg cctcgtcccc gccgggtcac ccggccagcg acatggaggc ccagaatacc        60
ctccttgaca gtcttgacgt gcgcagctca ggggcatgat gtgactgtcg cccgtacatt       120
tagcccatac atccccatgt ataatcattt gcatccacat attttgatgg ccgcacggcg       180
cgaagcaaaa attacggctc ctcgctgcag acctgcgagc agggaaacgc tcccctcaca       240
```

-continued

```
gacgcgttga attgtcccca cgccgcgccc ctgtagagaa atataaaagg ttaggatttg        300
ccactgaggt tcttctttca tatacttcct tttaaaatct tgctacgata cagttctcac        360
atcacatccg aacataaaca acc                                                383

<210> SEQ ID NO 70
<211> LENGTH: 498
<212> TYPE: DNA
<213> ORGANISM: Saccharomyces bayanus

<400> SEQUENCE: 70
cgccaacaaa ccttcgaaca ctttaatttt cgaggaccgc agatcctcac atcacaccca         60
cacccaagac tgcttccccc acacaccctg catctgtaca ctttcttctg ctctgttttt        120
ctctccggcg ttctctcggg tcgcccgcat cgccgcgccg gctggaaccg cccacgcacc        180
gcatattgca aatcgcctgc cccctcttgc tccttttga gggcgcgccg ttacccgcgc        240
ccagggtccg gaaaagaaa caaggctcta ccgcgtttct ttttccttgt cgaaaaaggc        300
aaaaatgaaa atttttatca cgtttctttt tttttgaaaa atttttttt tggtttttt        360 tctttcgatg gcctcccatt gatatttaag ttaataaatg gtttcagtt ttcaagtttc        420 agtttgtgtt cttctttgct aactttcact tacacctcga aagaaagtat agcaatctaa        480
tcttagtttt aattacaa                                                      498

<210> SEQ ID NO 71
<211> LENGTH: 76
<212> TYPE: DNA
<213> ORGANISM: Artificial Sequence
<220> FEATURE:
<223> OTHER INFORMATION: Synthetic Nucleic acid sequence of promotor
     pPDC1

<400> SEQUENCE: 71
ttatttacct atctctaaac ttcaacacct tatatcataa ctaatatttc ttgagataag         60
cacactgcac ccatac                                                         76

<210> SEQ ID NO 72
<211> LENGTH: 998
<212> TYPE: DNA
<213> ORGANISM: Artificial Sequence
<220> FEATURE:
<223> OTHER INFORMATION: Synthetic Nucleic acid sequence of promotor
     pCCW1

<400> SEQUENCE: 72
aaccagggca aagcaaaata aaagaaactt aatacgttat gccgtaatga agggctacca         60
aaaacgataa tctcaactgt aaacaggtac aatgcggacc cttttgccac aaaacataca        120
tcattcattg ccggaaaaag aaagaagtga agacagcagt gcagccagcc atgttgcgcc        180
aatctaatta tagatgctgg tgccctgagg atgtatctgg agccagccat ggcatcatgc        240
gctaccgccg gatgtaaaat ccgacacgca aaagaaaacc ttcgaggttg cgcacttcgc        300
ccacccatga accacacggt tagtccaaaa ggggcagttc agattccaga tgcgggaatt        360
agcttgctgc caccctcacc tcactaacgc tgcggtgtgc ggtacttca tgctatttat        420 agacgcgcgt gtcggaatca gcacgcgcaa gaaccaaatg ggaaaatcgg aatgggtcca        480
gaactgcttt gagtgctggc tattggcgtc tgatttccgt tttgggaatc ctttgccgcg        540 cgccctctc aaaactccgc acaagtccca gaaagcggga agaaataaa acgccaccaa        600 aaaaaaaaat aaaagccaat cctcgaagcg tgggtggtag gccctggatt atcccgtaca        660
```

-continued

```
agtatttctc aggagtaaaa aaaccgtttg ttttggaatt ccccatttcg cggccaccta      720
cgccgctatc tttgcaacaa ctatctgcga taactcagca aattttgcat attcgtgttg      780
cagtattgcg ataatgggag tcttacttcc aacataacgg cagaaagaaa tgtgagaaaa      840
ttttgcatcc tttgcctccg ttcaagtata taaagtcggc atgcttgata atctttcttt      900
ccatcctaca ttgttctaat tattcttatt ctcctttatt ctttcctaac ataccaagaa      960
attaatcttc tgtcattcgc ttaaacacta tatcaata                              998
```

```
<210> SEQ ID NO 73
<211> LENGTH: 976
<212> TYPE: DNA
<213> ORGANISM: Saccharomyces mikatae

<400> SEQUENCE: 73
cgttgtgctg tagtgaagga agactaaaaa ggataatcac agttgtaaag aggtataatg       60
cggacccttt tgccacaaaa cacacatctt tcgtttccaa aataagaaag aagaaagcaa      120
aaagattagc agccacgttg ctgcgatcta attatagacg gtggcgtcat cattctcacc      180
caagattgtg tcttgaacct gccacgggtc ctgcgttatc gccggatgta aaactagaca      240
tgcaaaaaaa ggaccttcca ggtagcgtgc tccacaccac ccatgaccac cacagttagt      300
ccaaaagagg cagcaccact tcccgatggg ggaattagat tgctgccacc ctcacctcac      360
taatgctgcg gtgtgcggat atgccctgct atatatagct ccgcgttttt gaaccagcac      420
agcgcgagca ccaaaaagga aaatcgcata ggcccagaac tgatttcagc acgggctatt      480
ggcgttgggt ttccgttctg ggaaaccttc gccgcgtccc cctcacaaac ctccgcacaa      540
gttcgagcaa gcgggaaaaa acgaaaaacg ccattaatac taaataaagc aaatcctcga      600
agcgtgggtg gcaagcccct ggattttttcc gcacaagtac tcttctcagg agtaaaaaaa      660
cccgtttgtt ttggaattcc ccatttcgcg gccatctacg ccggtatctt cgcaatatct      720
atcagcgata actcagcaat tttaatattc gtgttgcagt gctgcgatag cgggagtctt      780
gtttgtaaca taacggcaga aaggaatgag agaaaatttt ccattctttg gcctccgttc      840
aagtatataa agccggcatg cttggtaatc tttctctctc ttctgtattg tttctataat      900
acttttatct tctaattatt ttctgaaaaa accaagaaat taatcttctg tcattcgctt      960
aaacactata tcaata                                                      976
```

```
<210> SEQ ID NO 74
<211> LENGTH: 750
<212> TYPE: DNA
<213> ORGANISM: Saccharomyces kudriavzevii

<400> SEQUENCE: 74
tgtaaaatcc tacacgcaaa aaacctcttg ggttgcgcgt tttccaccac ccacgacccg       60
cacaatcaat ccaaaagggg caacgccagt tcccaatgcg ggaattagct cctcacccccc     120 ctcacccgct aacgctgcgg tgtgcggaca cgcagcagta tttatagatc ctcgtgttgg      180
aaccagcccg cgtgagcacc aaattggaaa gtcgcaatgg gcccagaacc gctttcagta      240
ctgggccatt ggcgtctagt ttccgttttg agcgtccttc gccgcgtctc tctgtgaaat      300
ccccgcacaa gtctgagcag gcaaaaaaaa aaaacgccac caaaaataaa taaagccaat      360
cctcgaagga tgagtaggaa aggaagcccc tggttttttc ccgcacgaat atttttcagg      420
agtgaaaaaa tccgtttgtt ttggaattcc ccatttcgcg ctcacctacg ccggtatctt      480
```

```
tggaacaact atcagcgata actcagcaaa atttgcatat ccgtgctgca atagtgcgat      540
agtgggattg ggagtcttgt tgcatcataa cggcagaaag gaatgaataa aaattttccg      600
ttctttgtct ccgttcaagt atataaagtc ggcatgcttg attatctttt cttctcttct      660
actacatttc tatttcactt tctactctat tcttccctga aaaacccaag aaaataatct      720
tctgtcattc gcttaaacaa tatatcaaaa                                       750
```

```
<210> SEQ ID NO 75
<211> LENGTH: 750
<212> TYPE: DNA
<213> ORGANISM: Saccharomyces bayanus

<400> SEQUENCE: 75
accatgccac ggtgctggcc ccacttccac ccacgacccg cacggttggc ccgaaagggg       60
caacaccagt tcccaatacg gaaattagtc cgccaccacc ctcacctcgc tagagctgcg      120
gtgtgcgggc gtgcatcgct atttatagac atgcctgctg gcgtcaccgc gcgcgagcac      180
caaacaggaa aatcgcactg ggcccagaac cacgctatgc gctgggccga tggcgtccgg      240
tttccctttg ggagcccct gccacgttcg cctaacaaat ccccgcaccg gcttgagaaa      300
aaagcgaaaa gcgaaaaaaa aaaatcaacg ccaccaaaat taaaaaaaaa gagccatcct      360
cgaagggtga atagtagccc ctgactttc ccgcacagac agacaccttt caggagtgaa      420
caaaaaagca gtttgttttg gaattccccc atttcgcggt ggcctgcgca ggtatctctg      480
cgtcaactat cagcgataac tcagcaaatt ttgcatattc gtgttgcgat actacgataa      540
tgggagtctg tcgcctaata acggcaacaa ggaatgagag agaaaaattt tcttcattct      600
ccagctcccg ttcaagtata taaggtcggc atggtcgatt gtctttcctt ctcttcagtt      660
acgtctctct atttacatta ttcttatttt tatttaataa aaaccccaag aaattaatct      720
tctgtcattc gcttaaacac tatatcaaaa                                       750
```

```
<210> SEQ ID NO 76
<211> LENGTH: 750
<212> TYPE: DNA
<213> ORGANISM: Saccharomyces arboricola

<400> SEQUENCE: 76
aaaaaacaac cttctgccaa cctgcgtgct tctcaccacc catgacccac acaattgacc       60
cgaatggggc aactccagtt cccaatacgg gaattaactc gccaccatat ttaccgcgtt      120
gaagctgtgg tgtgcggaca ctccgtacta tttatagacc cacgcggtgg aaccagcacg      180
cgcgcgcact aaacaggaaa atcgcattga gtccagaacc gccaccagca cttggccatt      240
ggcgtctaat ttccgttttc ggcgcccctc accgcgtcct tctaacaaag cgcgcacaag      300
cttgagcaag tgaaagaaa attaaaaata aaaaaccgcc accaaaacaa ataaagcaat      360
cttcgaagtg tgggttggtg ggaagcccct ggcttttccc gcaccagtcg ttttcaggag      420
taaaaaaata cccgtttgtt ttggaattcc ccatttcgcg gcgacctgcg ccggtatctt      480
tgcaacaact atttgcgata actcagcaaa atttgcatat tcgtgttggg atattgcgat      540
agtgggagtc ttgttgcata ataacggtaa aaagaagtga aggaaaaaaa tttgcatcct      600
ttagtctcag ttcaagtata taaagtcggg atattcaatt atctttctttt ctcttgctca      660 aaggtttcta tatttttttt atagtatttc ttttgttata aaataccaag aaattaatct      720
tctgtcattc gcttaaatac tacatcaata                                       750
```

-continued

```
<210> SEQ ID NO 77
<211> LENGTH: 500
<212> TYPE: DNA
<213> ORGANISM: Artificial Sequence
<220> FEATURE:
<223> OTHER INFORMATION: Synthetic Nucleic acid sequence of promotor
      pNUP57

<400> SEQUENCE: 77
tcatctgcgc aatgactatc aagaccttct gcaagaattt caaatctcac tgaaaatctt      60
gaccgaaaag tgtcttgaaa acccatcaag cctgcaaaac ctatctttga cattagtctc     120
cattataaaa acggcatagt tgggagaaaa ctttccatac ttcaattgtg gactgatata     180
agtattttag ttttgcccgc atgatcatcc cacatggcta cagcagttct ctcataggaa     240
aatagtacaa tagctacgtg atataatcta ataaattgtt gccaatgtgt aattatatca     300
ttttgaacgt acgcgaaatg gattattttc aaaaattttg tttcttgaaa tgagtaaaag     360
caaaagtcca actctccaag tcgatgtaaa caactttttg ccaaagggac tgaaagacta     420
aatcgaggat tatcccgttc aaactattcc agaaacgctc gttagtaaca aaagacatac     480
cttgttgacc aattgatcac                                                 500

<210> SEQ ID NO 78
<211> LENGTH: 523
<212> TYPE: DNA
<213> ORGANISM: Ashbya gossypii

<400> SEQUENCE: 78
ggtaccacgg caacctcgtt cgctgttcat ccccttcgtc acacaggacg ttggatgccg      60
taagcagcgt tgcttttgat cctcaggatc ggccgggtaa cccgcggctg cttctatttt     120
agtattcata tctcaagcac atccattccg gccgtttggg ggcgccgccg cactcgtgtc     180
cattcctacc gtggcactta gggctatcct gtcggagcgc cccgccgacc gccttatcgg     240
caccaaaagt agaagccccg gccccgcgtg gctcagactc accatcggtg ctatttactt     300
ttcgatcaga tcgcggcgcg cggtggccgg catttccgga agcggccacg gagcagaggt     360
ggcgcattcg aatcgcatac gtcttcgcca cgccggaaaa aaaattttcg gctatataag     420
gagaggcggc cgtcttgctg caggcagttt cactttctct aaaaccaaag aacatcgatt     480
tctttagtca ctcgcttcct tacaccgaac tcgaggcggc cgc                       523

<210> SEQ ID NO 79
<211> LENGTH: 943
<212> TYPE: DNA
<213> ORGANISM: Artificial Sequence
<220> FEATURE:
<223> OTHER INFORMATION: Synthetic Nucleic acid sequence of promotor
      pCWP2

<400> SEQUENCE: 79
ctagcctccc cttttttattt tgtgcggtca ccgcaaggga caaagctttt cttagaaaac      60
cgtctgagaa gcataacgta cgccatcccc tagacatatt aataatgcta cagatactat     120
gctgctcgtc ttttttttgac gacccttttta ttgcaatgtg caactaatgg caaacaacca     180
catagtatca cagtattaca ttgcctccac cgatgcggat gttagggcgc caagtctgtc     240
atgaagcatg ttcctgtcat aatcttgtat gcaaaatacc gcgttctgcg ccactgatat     300
gctaggcagc agcaacctat gcagaagatt gcttttccca cgcctgtttt acgtctccag     360
ggcacttgaa acaatgcagc gatcgccgcc acaacacgcc aaagagaagc gaaagtgggc     420
```

```
ctgggcggcc tcagtttcgg cagaggtaaa caacacgaac tgaactgcct tagctccgaa      480
gggcaattcc acaggcactc cgcggggccc ggccaaggcc caaaaggcgt ggaatatgcg      540
cgttttgggg ccataacacc cagtaccacg gccggaacgg gccatataat aagttttca       600 ctctcaagaa tggtaaacgt aaataggaac atcccactac cctagaaatt gcggaaattt      660
cgcgcttatc attagaaaat ctggaaccgt ccttttcct ctttcttgca tttcccttc        720 cgtattattg ccattcttta actgcatttg gggaaccgta gaccaaaagc caaacagaga      780
aatgtaacgt tctaaaaaaa aaacaacgaa aaaattgaaa aataagatac aataatcgta      840
tataaatcag gcttcttgtt catcattttc aattctcttc ttgccatccc ttttcctatc      900
tttgttcttt tcttctcata atcaagaata aataacttca tca                       943
```

<210> SEQ ID NO 80
<211> LENGTH: 535
<212> TYPE: DNA
<213> ORGANISM: Artificial Sequence
<220> FEATURE:
<223> OTHER INFORMATION: Synthetic Nucleic acid sequence of promotor
      pRPLA1

<400> SEQUENCE: 80

```
tcaagttgga tactgatctg atctctccgc cctactacca gggaccctca tgattaccgc       60
tcgaatgcga cgtttcctgc ctcataaaac tggcttgaaa atatttattc gctgaacagt      120
agcctagctt ataaaaattt catttaatta atgtaatatg aaaactcaca tgccttctgt      180
ttctaaaatt gtcacagcaa gaaataacat taccatacgt gatcttatta aactctagta     240
tcttgtctaa tacttcattt aaaagaagcc ttaaccctgt agcctcatct atgtctgcta      300
catatcgtga ggtacgaata tcgtaagatg ataccacgca actttgtaat gattttttt      360 ttttcatttt ttaaagaatg cctttacatg gtatttgaaa aaaatatctt tataaagttt     420
gcgatctctt ctgttctgaa taattttag taaaagaaat caaaagaata aagaaatagt      480
ccgctttgtc caatacaaca gcttaaaccg attatctcta aaataacaag aagaa          535
```

<210> SEQ ID NO 81
<211> LENGTH: 505
<212> TYPE: DNA
<213> ORGANISM: Artificial Sequence
<220> FEATURE:
<223> OTHER INFORMATION: Synthetic Nucleic acid sequence of promotor
      pCUP1

<400> SEQUENCE: 81

```
cggcaaactt caacgatttc tatgatgcat tttataatta gtaagccgat cccattaccg       60
acatttgggc gctatacgtg catatgttca tgtatgtatc tgtatttaaa cacttttgt       120 attattttc ctcatatatg tgtataggtt tatacggatg atttaattat tacttcacca      180 cccttattt caggctgata tcttagcctt gttactagtt agaaaaagac atttttgctg       240
tcagtcactg tcaagagatt cttttgctgg catttcttct agaagcaaaa agagcgatgc      300
gtcttttccg ctgaaccgtt ccagcaaaaa agactaccaa cgcaatatgg attgtcagaa      360
tcatataaaa gagaagcaaa taactccttg tcttgtatca attgcattat aatatcttct      420
tgttagtgca atatcatata gaagtcatcg aaatagatat taagaaaaac aaactgtaca      480
atcaatcaat caatcatcac ataaa                                            505
```

<210> SEQ ID NO 82
<211> LENGTH: 510

```
<212> TYPE: DNA
<213> ORGANISM: Artificial Sequence
<220> FEATURE:
<223> OTHER INFORMATION: Synthetic Nucleic acid sequence of promotor
      pMET6

<400> SEQUENCE: 82
ccacaggaaa tatttcacgt gacttacaaa cagagtcgta cgtcaggacc ggagtcaggt        60
gaaaaaatgt gggccggtaa agggaaaaaa ccagaaacgg gactactatc gaactcgttt       120
agtcgcgaac gtgcaaaagg ccaatatttt tcgctagagt catcgcagtc atggcagctc       180
tttcgctcta tctcccggtc gcaaaactgt ggtagtcata gctcgttctg ctcaattgag       240
aactgtgaat gtgaatatgg aacaaatgcg atagatgcac taatttaagg gaagctagct       300
agttttccca actgcgaaag aaaaaaagga aagaaaaaaa aattctatat aagtgataga       360
tatttccatc tttactagca ttagtttctc ttttacgtat tcaatatttt tgttaaactc       420
ttcctttatc ataaaaaagc aagcatctaa gagcattgac aacactctaa gaaacaaaat      480
accaatataa tttcaaagta catatcaaaa                                         510

<210> SEQ ID NO 83
<211> LENGTH: 686
<212> TYPE: DNA
<213> ORGANISM: Artificial Sequence
<220> FEATURE:
<223> OTHER INFORMATION: Synthetic Nucleic acid sequence of promotor
      pMET25

<400> SEQUENCE: 83
ttacattatc aatccttgcg tttcagcttc cactaattta gatgactatt tctcatcatt        60
tgcgtcatct tctaacaccg tatatgataa tatactagta acgtaaatac tagttagtag       120
atgatagttg attttttattc caacactaag aaataaattc gccatttctt gaatgtattt       180
aaagatattt aatgctataa tagacattta aatccaattc ttccaacata caatgggagt       240
ttggccgagt ggtttaaggc gtcagattta ggtggattta acctctaaaa tctctgatat       300
cttcggatgc aagggttcga atcccttagc tctcattatt ttttgctttt tctcttgagg       360
tcacatgatc gcaaaatggc aaatggcacg tgaagctgtc gatattgggg aactgtggtg       420
gttggcaaat gactaattaa gttagtcaag gcgccatcct catgaaaact gtgtaacata       480
ataaccgaag tgtcgaaaag gtggcacctt gtccaattga acacgctcga tgaaaaaaat       540
aagatatata taaggttaag taaagcgtct gttagaaagg aagtttttcc tttttcttgc       600
tctcttgtct tttcatctac tatttccttc gtgtaataca gggtcgtcag atacatagat       660
acaattctat tacccccatc cataca                                             686

<210> SEQ ID NO 84
<211> LENGTH: 363
<212> TYPE: DNA
<213> ORGANISM: Artificial Sequence
<220> FEATURE:
<223> OTHER INFORMATION: Synthetic Nucleic acid sequence of promotor
      pSAM1

<400> SEQUENCE: 84
gaaacggacg taagacggaa atagaatttg aagataaagt tatatatcac tacacacgaa        60
tactttcttt ttttttttttc acaggaaaac tgtggtggcg cccttgccta ctagtgcatt       120
tcttttttcg ggttcttgtc tcgacgaaat tttagcctca tcgtagtttt tcactctggt       180
atcgatgaaa aagggaagag taaaaagttt tccgtttagt acttaatggg attggtttgg       240
```

```
gacgtatata tcgactggtg ttgtctgtta ttcatcgttg tttttcggtt agcttcgaaa        300
aaaaaataga gtaaaaacca ggaatttacc ctaaaaacaa gaaaaaataa gataaacgaa        360
aat                                                                       363
```

```
<210> SEQ ID NO 85
<211> LENGTH: 300
<212> TYPE: DNA
<213> ORGANISM: Artificial Sequence
<220> FEATURE:
<223> OTHER INFORMATION: Synthetic Nucleic acid sequence of terminator
      tTPI1

<400> SEQUENCE: 85
gattaatata attatataaa aatattatct tcttttcttt atatctagtg ttatgtaaaa         60
taaattgatg actacggaaa gctttttttat attgtttctt tttcattctg agccacttaa       120
atttcgtgaa tgttcttgta agggacggta gatttacaag tgatacaaca aaaagcaagg       180 cgcttttttct aataaaaaga agaaaagcat ttaacaattg aacacctcta tatcaacgaa      240
gaatattact ttgtctctaa atccttgtaa aatgtgtacg atctctatat gggttactca       300
```

```
<210> SEQ ID NO 86
<211> LENGTH: 299
<212> TYPE: DNA
<213> ORGANISM: Artificial Sequence
<220> FEATURE:
<223> OTHER INFORMATION: Synthetic Nucleic acid sequence of terminator
      tMET25

<400> SEQUENCE: 86
gtgtgcgtaa tgagttgtaa aattatgtat aaacctactt tctctcacaa gtactatact         60
tttataaaac gaactttatt gaaatgaata tcctttttttt cccttgttac atgtcgtgac       120
tcgtactttg aacctaaatt gttctaacat caaagaacag tgttaattcg cagtcgagaa       180
gaaaaatatg gtgaacaaga ctcatctact tcatgagact actttacgcc tcctataaag       240
ctgtcacact ggataaattt attgtaggac caagttacaa aagaggatga tggaggttt       299
```

```
<210> SEQ ID NO 87
<211> LENGTH: 300
<212> TYPE: DNA
<213> ORGANISM: Artificial Sequence
<220> FEATURE:
<223> OTHER INFORMATION: Synthetic Nucleic acid sequence of terminator
      tDIT1

<400> SEQUENCE: 87
taaagtaaga gcgctacatt ggtctacctt tttgttcttt tacttaaaca ttagttagtt         60 cgtttttcttt ttctcatttt tttatgtttc cccccccaaag ttctgatttt ataatatttt      120
atttcacaca attccattta acagaggggg aatagattct ttagcttaga aaattagtga       180
tcaatatata tttgcctttc ttttcatctt ttcagtgata ttaatggttt cgagacactg       240
caatggccct agttgtctaa gaggatagat gttactgtca aagatgatat tttgaatttc       300
```

```
<210> SEQ ID NO 88
<211> LENGTH: 300
<212> TYPE: DNA
<213> ORGANISM: Artificial Sequence
<220> FEATURE:
<223> OTHER INFORMATION: Synthetic Nucleic acid sequence of terminator
      tRPL3
```

-continued

```
<400> SEQUENCE: 88
gaagttttgt tagaaaataa atcatttttt aattgagcat tcttattcct attttattta      60
aatagtttta tgtattgtta gctacataca acagtttaaa tcaaattttc tttttcccaa     120
gtccaaaatg gaggtttatt ttgatgaccc gcatgcgatt atgttttgaa agtataagac     180
tacatacatg tacatatatt taaacatgta aacccgtcca ttatattgct tactttcttc     240
ttttttgccg ttttgacttg gacctctggt ttgctatttc cttacaatct ttgctacaat     300

<210> SEQ ID NO 89
<211> LENGTH: 300
<212> TYPE: DNA
<213> ORGANISM: Saccharomyces mikatae

<400> SEQUENCE: 89
gaagtttTta aagcattttt tagacacttc tcattttTct aagtttTttt aaaatagttt      60
tatgtattta ctacgtatca caatttgaaa taattcatct tcccaaaaaa ctaagatttt     120
tatccttgtc acgatccgta accagtttat aatattttag agcttataca cgtacgtata     180
cacacgtgtc ggtacatgag aattacgttc aaaattattc actttTttTt tctctgccgt     240
tttacttttg aactctgtct cgctatttcc ttacaatctt cgctacaata ccacttgccc     300

<210> SEQ ID NO 90
<211> LENGTH: 299
<212> TYPE: DNA
<213> ORGANISM: Saccharomyces bayanus

<400> SEQUENCE: 90
gaagttttct gacaaaaaca taacgttttt tccaatcatt tcttattttt ccggtttatt      60
taaatagttt ttatgtacta ttatacgtat gactatttaa cttaaattct tcctcccaag     120
aaatctccca agtttTttcat tatcatggca tacaccacta tcagttacaa aatggtagct     180
caaccatata tatatctcta tatacacata taaatgcaaa caggtccaag tcaccgctca     240
ctgcagtttc ttttgccgtt ttgacttcga tctctgcttg gctattttct cacaatcct      299

<210> SEQ ID NO 91
<211> LENGTH: 300
<212> TYPE: DNA
<213> ORGANISM: Artificial Sequence
<220> FEATURE:
<223> OTHER INFORMATION: Synthetic Nucleic acid sequence of terminator
     tRPL41B

<400> SEQUENCE: 91
gcggattgag agcaaatcgt taagttcagg tcaagtaaaa attgatttcg aaaactaatt      60
tctcttatac aatcctttga ttggaccgtc atccttcga atataagatt ttgttaagaa     120
tattttagac agagatctac tttatattta atatctagat attacataat ttcctctcta     180
ataaaatatc attaataaaa taaaaatgaa gcgatttgat tttgtgttgt caacttagtt     240
tgccgctatg cctcttgggt aatgctatta ttgaatcgaa gggctttatt atattaccct     300

<210> SEQ ID NO 92
<211> LENGTH: 300
<212> TYPE: DNA
<213> ORGANISM: Artificial Sequence
<220> FEATURE:
<223> OTHER INFORMATION: Synthetic Nucleic acid sequence of terminator
     tRPL15A

<400> SEQUENCE: 92
```

-continued

```
gctggttgat ggaaaatata attttattgg gcaaactttt gtttatctga tgtgtttat        60 actattatct ttttaattaa tgattctata tacaaacctg tatatttttt ctttaaccaa       120
tttttttttt tatagaccta gagctgtact tttattctgc tatcaagcaa accccaccc       180 cctcttctca atcctcccct caggcagaac ttatctacct gtatcaagga gcggacgagg      240
gagtcctaat tgttctacgt ataccaatgc tagcagctta cataggtggt ggcactacca      300

<210> SEQ ID NO 93
<211> LENGTH: 300
<212> TYPE: DNA
<213> ORGANISM: Saccharomyces bayanus

<400> SEQUENCE: 93
gctggctgat gaaaaatata gttctgttgg gcaagcattt gtttacctag catctctttt        60
atactattat tatctttata tttgatgatt ttatatacaa gttgtatacc ttttctttaa       120
ccaatttttt tttttctaat ggtgcaccta gaagtacatt ttttctcacc aatagatagt       180
caagatactc ccagcctcta tggcgttacc acggagccga caagggaaag ctgcttatct      240
tacatatgca gatgccaagg cccgttacag gccgccttat tgatgtttag aaatagcttc      300

<210> SEQ ID NO 94
<211> LENGTH: 300
<212> TYPE: DNA
<213> ORGANISM: Artificial Sequence
<220> FEATURE:
<223> OTHER INFORMATION: Synthetic Nucleic acid sequence of terminator
     tIDP1

<400> SEQUENCE: 94
tcgaatttac gtagcccaat ctaccacttt tttttttcat tttttaaagt gttatactta        60
gttatgctct aggataatga actacttttt tttttttttt tttactgtta tcataaatat       120 atataccta ttgttgtttg caaccgtcgg ttaattcctt atcaaggttc cccaagttcg       180
gatcattacc atcaatttcc aacattttca tgagttcttc ttcttcatta ccgtgtttta      240
gggggctgtt cgcacttcta atagggctat caccaagctg ttctaattcg tccaaaagtt      300

<210> SEQ ID NO 95
<211> LENGTH: 300
<212> TYPE: DNA
<213> ORGANISM: Saccharomyces bayanus

<400> SEQUENCE: 95
ggagattgat aggactttc tagttgcata tcttttattt ttaaatctta tctattagtt        60
aattttttgt aatttatcct tatatatata gtttggttat ctaaaacat catttcagta       120 tctaaaacct ctcttattca ttaccttttt atttaatggt ttttgctaca ggcaaaaatt       180
taatggtttt tgctacaggc aaaaatcccg ccgtggactt attccacgtt aactcggtta      240
cagggtcatg aaccattttg tcaattatcg aaataacttc ttcaaaagtc cctcttactt      300

<210> SEQ ID NO 96
<211> LENGTH: 1113
<212> TYPE: DNA
<213> ORGANISM: Saccharomyces cerevisiae

<400> SEQUENCE: 96
atggctgaag caagcatcga aaagactcaa attttacaaa aatatctaga actggaccaa        60
agaggtagaa taattgccga atacgtttgg atcgatggta ctggtaactt acgttccaaa       120
```

```
ggtagaactt tgaagaagag aatcacatcc attgaccaat tgccagaatg gaacttcgac      180
ggttcttcta ccaaccaagc gccaggccac gactctgaca tctatttgaa acccgttgct      240
tactacccag atcccttcag gagaggtgac aacattgttg tcttggccgc atgttacaac      300
aatgacggta ctccaaacaa gttcaaccac agacacgaag ctgccaagct atttgctgct      360
cataaggatg aagaaatctg gtttggtcta gaacaagaat acactctatt tgacatgtat      420
gacgatgttt acgatggcc aaagggtggg tacccagctc cacaaggtcc ttactactgt      480
ggtgttggtg ccggtaaggt ttatgccaga gacatgatcg aagctcacta cagagcttgt      540
ttgtatgccg gattagaaat ttctggtatt aacgctgaag tcatgccatc tcaatgggaa      600
ttccaagtcg gtccatgtac cggtattgac atgggtgacc aattatggat ggccagatac      660
tttttgcaca gagtggcaga agagtttggt atcaagatct cattccatcc aaagccattg      720
aagggtgact ggaacggtgc cggttgtcac actaacgttt ccaccaagga aatgagacaa      780
ccaggtggta tgaaatacat cgaacaagcc atcgagaagt tatccaagag acacgctgaa      840
cacattaagt tgtacggtag cgataacgac atgagattaa ctggtagaca tgaaaccgct      900
tccatgactg ccttttcttc tggtgtcgcc aacagaggta gctcaattag aatcccaaga      960
tccgtcgcca aggaaggtta cggttacttt gaagaccgta gaccagcttc caacatcgac     1020
ccatacttgg ttacaggtat catgtgtgaa actgtttgcg gtgctattga caatgctgac     1080
atgacgaagg aatttgaaag agaatcttca taa                                   1113
```

<210> SEQ ID NO 97
<211> LENGTH: 370
<212> TYPE: PRT
<213> ORGANISM: Saccharomyces cerevisiae

<400> SEQUENCE: 97

```
Met Ala Glu Ala Ser Ile Glu Lys Thr Gln Ile Leu Gln Lys Tyr Leu
1               5                   10                  15

Glu Leu Asp Gln Arg Gly Arg Ile Ile Ala Glu Tyr Val Trp Ile Asp
            20                  25                  30

Gly Thr Gly Asn Leu Arg Ser Lys Gly Arg Thr Leu Lys Lys Arg Ile
        35                  40                  45

Thr Ser Ile Asp Gln Leu Pro Glu Trp Asn Phe Asp Gly Ser Ser Thr
    50                  55                  60

Asn Gln Ala Pro Gly His Asp Ser Asp Ile Tyr Leu Lys Pro Val Ala
65                  70                  75                  80

Tyr Tyr Pro Asp Pro Phe Arg Arg Gly Asp Asn Ile Val Val Leu Ala
                85                  90                  95

Ala Cys Tyr Asn Asn Asp Gly Thr Pro Asn Lys Phe Asn His Arg His
            100                 105                 110

Glu Ala Ala Lys Leu Phe Ala Ala His Lys Asp Glu Glu Ile Trp Phe
        115                 120                 125

Gly Leu Glu Gln Glu Tyr Thr Leu Phe Asp Met Tyr Asp Asp Val Tyr
    130                 135                 140

Gly Trp Pro Lys Gly Gly Tyr Pro Ala Pro Gln Gly Pro Tyr Tyr Cys
145                 150                 155                 160

Gly Val Gly Ala Gly Lys Val Tyr Ala Arg Asp Met Ile Glu Ala His
                165                 170                 175

Tyr Arg Ala Cys Leu Tyr Ala Gly Leu Glu Ile Ser Gly Ile Asn Ala
            180                 185                 190
```

-continued

```
Glu Val Met Pro Ser Gln Trp Glu Phe Gln Val Gly Pro Cys Thr Gly
        195                 200                 205

Ile Asp Met Gly Asp Gln Leu Trp Met Ala Arg Tyr Phe Leu His Arg
        210                 215                 220

Val Ala Glu Glu Phe Gly Ile Lys Ile Ser Phe His Pro Lys Pro Leu
225                     230                 235                 240

Lys Gly Asp Trp Asn Gly Ala Gly Cys His Thr Asn Val Ser Thr Lys
                245                 250                 255

Glu Met Arg Gln Pro Gly Gly Met Lys Tyr Ile Glu Gln Ala Ile Glu
                260                 265                 270

Lys Leu Ser Lys Arg His Ala Glu His Ile Lys Leu Tyr Gly Ser Asp
            275                 280                 285

Asn Asp Met Arg Leu Thr Gly Arg His Glu Thr Ala Ser Met Thr Ala
        290                 295                 300

Phe Ser Ser Gly Val Ala Asn Arg Gly Ser Ser Ile Arg Ile Pro Arg
305                     310                 315                 320

Ser Val Ala Lys Glu Gly Tyr Gly Tyr Phe Glu Asp Arg Arg Pro Ala
                325                 330                 335

Ser Asn Ile Asp Pro Tyr Leu Val Thr Gly Ile Met Cys Glu Thr Val
                340                 345                 350

Cys Gly Ala Ile Asp Asn Ala Asp Met Thr Lys Glu Phe Glu Arg Glu
            355                 360                 365

Ser Ser
    370
```

<210> SEQ ID NO 98
<211> LENGTH: 6438
<212> TYPE: DNA
<213> ORGANISM: Saccharomyces cerevisiae

<400> SEQUENCE: 98

```
atgccagtgt tgaaatcaga caatttcgat ccattggaag aagcttacga aggtgggaca        60
attcaaaact ataacgatga acaccatctt cataaatctt gggcaaatgt gattccggac       120
aaacgaggac tttacgaccc tgattatgaa catgacgctt gtggtgtcgg tttcgtagca       180
aataagcatg gtgaacagtc tcacaagatt gttactgacg ctagatatct tttagtgaat       240
atgacacatc gtggtgccgt ctcatctgat gggaacggtg acggtgccgg tattctgcta       300
ggtattcctc acgaatttat gaaaagagaa ttcaagttag atcttgatct agacatacct       360
gagatgggca aatacgccgt aggtaacgtc ttcttcaaga agaacgaaaa aaataacaag       420
aaaaatttaa ttaagtgtca gaagattttc gaggatttag ctgcatcctt caacttatcc       480
gtattaggtt ggagaaacgt cccccgtagat tctactattt taggagacgt tgcattatct       540
cgtgaaccta ctattctaca gccattattg gttccattgt atgatgaaaa acaaccggag       600
tttaatgaaa ctaaatttag aactcaattg tatctttttaa ggaaggaggc ctctcttcaa       660
ataggactgg aaaactggtt ctatgtttgt tccctaaaca ataccaccat tgtttacaag       720
ggtcaattga cgccagctca agtgtataac tactatcccg acttgactaa tgcgcatttc       780
aaatcccaca tggcgttggt ccattcaaga ttttccacta atactttccc ctcttgggat       840
agagctcaac ctttacgttg gctagctcat aatggtgaaa ttaacacctt aagaggtaac       900
aagaattgga tgcgctccag agaaggtgtg atgaattcag caactttcaa agatgagtta       960
gacaaactat acccaattat cgaagaaggt ggttctgatt cagctgcatt ggataacgtt      1020
ttagaactat tgactattaa tggcacatta tctctacctg aagctgttat gatgatggtt      1080
```

-continued

```
cctgaagcgt atcataagga tatggattct gacctaaaag catggtacga ctgggctgca    1140
tgtctgatgg aaccttggga tggtccagct ttgttaactt tcactgatgg acgttactgt    1200
ggtgctatat tggatagaaa tggtttaaga ccttgtcgtt attacatcac tagtgatgac    1260
agagttatct gtgcttcaga ggtaggtgtc attcctatcg aaaattcatt ggttgttcaa    1320
aaaggtaaac tgaagccagg tgatttattc ctagtggata ctcaattggg tgaaatggtc    1380
gatactaaaa agttaaaatc tcaaatctca aaaagacaag attttaagtc ttggttatcc    1440
aaagtcatca agttagacga cttgttatca aaaaccgcta atttggttcc taaagaattt    1500
atatcacagg attcattgtc tttgaaagtt caaagtgacc cacgtctatt ggccaatggt    1560
tataccttcg aacaagtcac atttctgtta actccaatgg ctttaacagg taaagaagct    1620
ttaggttcga tgggtaacga tgcgccactg gcttgtttaa atgaaaatcc tgtcttactt    1680
tatgattatt tcagacaatt gtttgctcaa gtgaccaatc ctccaattga cccaattcgt    1740
gaagcaaatg ttatgtcgtt agaatgttat gtcggacctc aaggcaacct tttggaaatg    1800
cattcatctc aatgtgatcg tttattattg aaatctccta ttttgcattg gaatgagttc    1860
caagctttga aaaacattga agctgcttac ccatcatggt ctgtagcaga aattgatatc    1920
acattcgaca agagtgaggg tctattgggc tataccgaca caattgataa aatcactaag    1980
ttagcgagcg aagcaattga tgatggtaaa aagatcttaa taattactga caggaaaatg    2040
ggtgccaacc gtgtttccat ctcctctttg attgcaattt catgtattca tcatcaccta    2100
atcagaaaca agcagcgttc ccaagttgct ttgattttgg aaacaggtga agccagagaa    2160
attcaccatt tctgtgtcct actaggttat ggttgtgatg gtgtttatcc atacttagcc    2220
atggaaactt tggtcagaat gaatagagaa ggtctacttc gtaatgtcaa caatgacaat    2280
gatacacttg aggaagggca aatactagaa aattacaagc acgctattga tgcaggtatc    2340
ttgaaggtta tgtctaaaat gggtatctcc actctagcat cctacaaagg tgctcaaatt    2400
tttgaagccc taggtttaga taactctatt gttgatttgt gtttcacagg tacttcttcc    2460
agaattagag gtgtaacttt cgagtatttg gctcaagatg cctttctctt acatgagcgt    2520
ggttatccat ccagacaaac cattagtaaa tctgttaact taccagaaag tggtgaatac    2580
cactttaggg atggtggtta caaacacgtc aacgaaccaa ccgcaattgc ttcgttacaa    2640
gatactgtca gaaacaaaaa tgatgtctct tggcaattat atgtaaagaa ggaaatggaa    2700
gcaattagag actgtacact aagaggactg ttagaattag attttgaaaa ttctgtcagt    2760
atccctctag aacaagttga accatggact gaaattgcca gaagatttgc gtcaggtgca    2820
atgtcttatg gttctatttc tatggaagct cactctacat tggctattgc catgaatcgt    2880
ttaggggcca aatccaattg tggtgaaggt ggtgaagacg cagaacgttc tgctgttcaa    2940
gaaaacggtg atactatgag atctgctatc aaacaagttg cttccgctag attcggtgta    3000
acttcatact acttgtcaga tgctgatgaa atccaaatta agattgctca gggtgctaag    3060
ccgggtgaag gtggtgaact accagcccac aaagtgtcta aggatatcgc aaaaaccagg    3120
cactccaccc ctaatgttgg gttaatctct cctcctcctc atcacgatat ttattccatt    3180
gaagatttga aacaactgat ttatgatttg aaatgtgcta atccaagagc gggaatttct    3240
gtaaagttgg tttccgaagt tggtgttggt attgttgcct ctggtgtagc taaggctaaa    3300
gccgatcata tcttagtttc tggtcatgat ggtggtacag gtgctgcaag atggacgagt    3360
gtcaaatatg cgggtttgcc atgggaatta ggtctagctg aaactcacca gactttagtc    3420
```

-continued

```
ttgaatgatt taagacgtaa tgttgttgtc caaaccgatg gtcaattgag aactgggttt   3480
gatattgctg ttgcagtttt attaggggca gaatctttta ccttggcaac agttccatta   3540
attgctatgg gttgtgttat gttaagaaga tgtcacttga actcttgtgc tgttggtatt   3600
gccacacaag atccatattt gagaagtaag tttaagggtc agcccgaaca tgttatcaac   3660
ttcttctatt acttgatcca agatttaaga caaatcatgg ccaagttagg attccgtacc   3720
attgacgaaa tggtgggtca ttctgaaaaa ttaaagaaaa gggacgacgt aaatgccaaa   3780
gccataaata tcgatttatc tcctattttg accccagcac atgttattcg tccaggtgtt   3840
ccaaccaagt tcactaagaa acaagaccac aaactccaca cccgtctaga taataagtta   3900
atcgatgagg ctgaagttac tttggatcgt ggcttaccag tgaatattga cgcctctata   3960
atcaatactg atcgtgcact cggttctact ttatcttaca gagtctcgaa gaaatttggt   4020
gaagatggtt tgccaaagga caccgttgtc gttaacatag aaggttcagc gggtcaatct   4080
tttggtgctt tcctagcttc tggtatcact tttatcttga atggtgatgc taatgattat   4140
gttggtaaag gtttatccgg tggtattatt gtcattaaac caccaaagga ttctaaattc   4200
aagagtgatg aaaatgtaat tgttggtaac acttgtttct atggtgctac ttctggtact   4260
gcattcattt caggtagtgc cggtgagcgt ttcggtgtca gaaactctgg tgccaccatc   4320
gttgttgaga gaattaaggg taacaatgcc tttgagtata tgactggtgg tcgtgccatt   4380
gtcttatcac aaatggaatc cctaaacgcc ttctctggtg ctactggtgg tattgcatac   4440
tgtttaactt ccgattacga cgattttgtt ggaaagatta caaagatac tgttgagtta   4500 gaatcattat gtgacccggt cgagattgcg tttgttaaga atttgatcca ggagcattgg   4560
aactacacac aatctgatct agcagccagg attctcggta atttcaacca ttatttgaaa   4620
gatttcgtta aagtcattcc aactgattat aagaaagttt tgttgaagga gaaagcagaa   4680
gctgccaagg caaaggctaa ggcaacttca gaatacttaa agaagtttag atcgaaccaa   4740
gaagttgatg acgaagtcaa tactctattg attgctaatc aaaaagctaa agagcaagaa   4800
aaaaagaaga gtattactat ttcaaataag gccactttga aggagcctaa ggttgttgat   4860
ttagaagatg cagttccaga ttccaaacag ctagagaaga atagcgaaag gattgaaaaa   4920
acacgtggtt ttatgatcca caaacgtcgt catgagacac acagagatcc aagaaccaga   4980
gttaatgact ggaaagaatt tactaaccct attaccaaga aggatgccaa atatcaaact   5040
gcgagatgta tggattgtgg tacaccattc tgtttatctg ataccggttg tccctatct   5100 aacattatcc ccaagtttaa tgaattgtta ttcaagaacc aatggaagtt ggcactggac   5160
aaattgctag agacaaacaa tttcccagaa ttcactggaa gagtatgtcc agcaccctgt   5220
gagggagctt gtacactagg tattattgaa gacccagtcg gcataaaatc ggttgaaaga   5280
attatcattg acaatgcttt caaggaagga tggattaagc cttgtccacc aagtacacgc   5340
actggcttta cagtgggtgt cattggttct ggtccagcag gtttagcgtg tgctgatatg   5400
ttgaaccgtg ccggacatac ggtcactgtt tatgaaagat ccgaccgttg tggtgggtta   5460
ttgatgtatg gtattccaaa catgaagttg gataaggcta tagtgcaacg tcgtattgat   5520
ctattgagtg ccgaaggtat tgactttgtt accaacaccg aaattggtaa aaccataagc   5580
atggatgagc taaagaacaa gcacaatgca gtagtgtatg ctatcggttc taccattcca   5640
cgtgacttac ctattaaggg tcgtgaattg aagaatattg attttgccat gcagttgttg   5700
gaatctaaca caaaagcttt attgaacaaa gatctggaaa tcattcgtga aaagatccaa   5760
ggtaagaaag taattgttgt cggtggtggt gacacaggta acgattgttt aggtacatct   5820
```

-continued

```
gtaagacacg gtgcagcatc agttttgaat ttcgaattgt tgcctgagcc accagtggaa      5880
cgtgccaaag acaatccatg gcctcaatgg ccgcgtgtca tgagagtgga ctacggtcat      5940
gctgaagtga aagagcatta tggtagagac cctcgtgaat actgcatctt gtccaaggaa      6000
tttatcggta cgatgagggg tgaagtcact gccatcagaa ctgtgcgcgt agaatggaag      6060
aagtcacaaa gtggcgtatg gcaaatggta gaaattccca acagtgaaga gatctttgaa      6120
gccgatatca ttttgttgtc tatgggtttc gtgggtcctg aattgatcaa tggcaacgat      6180
aacgaagtta agaagacaag acgtggtacg attgccacac tcgacgactc ctcatactct      6240
attgatggag gaaagacttt tgcatgtggt gactgtagaa gagggcaatc tttgattgtc      6300
tgggccatcc aagaaggtag aaaatgtgct gcctctgtcg ataagttcct aatggacggc      6360
actacgtatc taccaagtaa tggtggtatc gttcaacgtg attacaaact attgaaagaa      6420
ttagctagtc aagtctaa                                                    6438
```

<210> SEQ ID NO 99
<211> LENGTH: 2145
<212> TYPE: PRT
<213> ORGANISM: Saccharomyces cerevisiae

<400> SEQUENCE: 99

```
Met Pro Val Leu Lys Ser Asp Asn Phe Asp Pro Leu Glu Glu Ala Tyr
1               5                   10                  15

Glu Gly Gly Thr Ile Gln Asn Tyr Asn Asp Glu His His Leu His Lys
                20                  25                  30

Ser Trp Ala Asn Val Ile Pro Asp Lys Arg Gly Leu Tyr Asp Pro Asp
            35                  40                  45

Tyr Glu His Asp Ala Cys Gly Val Gly Phe Val Ala Asn Lys His Gly
        50                  55                  60

Glu Gln Ser His Lys Ile Val Thr Asp Ala Arg Tyr Leu Leu Val Asn
65                  70                  75                  80

Met Thr His Arg Gly Ala Val Ser Ser Asp Gly Asn Gly Asp Gly Ala
                85                  90                  95

Gly Ile Leu Leu Gly Ile Pro His Glu Phe Met Lys Arg Glu Phe Lys
                100                 105                 110

Leu Asp Leu Asp Leu Asp Ile Pro Glu Met Gly Lys Tyr Ala Val Gly
            115                 120                 125

Asn Val Phe Phe Lys Lys Asn Glu Lys Asn Asn Lys Lys Asn Leu Ile
        130                 135                 140

Lys Cys Gln Lys Ile Phe Glu Asp Leu Ala Ala Ser Phe Asn Leu Ser
145                 150                 155                 160

Val Leu Gly Trp Arg Asn Val Pro Val Asp Ser Thr Ile Leu Gly Asp
                165                 170                 175

Val Ala Leu Ser Arg Glu Pro Thr Ile Leu Gln Pro Leu Leu Val Pro
                180                 185                 190

Leu Tyr Asp Glu Lys Gln Pro Glu Phe Asn Glu Thr Lys Phe Arg Thr
            195                 200                 205

Gln Leu Tyr Leu Leu Arg Lys Glu Ala Ser Leu Gln Ile Gly Leu Glu
        210                 215                 220

Asn Trp Phe Tyr Val Cys Ser Leu Asn Asn Thr Thr Ile Val Tyr Lys
225                 230                 235                 240

Gly Gln Leu Thr Pro Ala Gln Val Tyr Asn Tyr Tyr Pro Asp Leu Thr
                245                 250                 255
```

```
Asn Ala His Phe Lys Ser His Met Ala Leu Val His Ser Arg Phe Ser
            260             265             270

Thr Asn Thr Phe Pro Ser Trp Asp Arg Ala Gln Pro Leu Arg Trp Leu
        275             280             285

Ala His Asn Gly Glu Ile Asn Thr Leu Arg Gly Asn Lys Asn Trp Met
    290             295             300

Arg Ser Arg Glu Gly Val Met Asn Ser Ala Thr Phe Lys Asp Glu Leu
305             310             315             320

Asp Lys Leu Tyr Pro Ile Ile Glu Glu Gly Gly Ser Asp Ser Ala Ala
            325             330             335

Leu Asp Asn Val Leu Glu Leu Leu Thr Ile Asn Gly Thr Leu Ser Leu
        340             345             350

Pro Glu Ala Val Met Met Met Val Pro Glu Ala Tyr His Lys Asp Met
        355             360             365

Asp Ser Asp Leu Lys Ala Trp Tyr Asp Trp Ala Ala Cys Leu Met Glu
    370             375             380

Pro Trp Asp Gly Pro Ala Leu Leu Thr Phe Thr Asp Gly Arg Tyr Cys
385             390             395             400

Gly Ala Ile Leu Asp Arg Asn Gly Leu Arg Pro Cys Arg Tyr Tyr Ile
            405             410             415

Thr Ser Asp Asp Arg Val Ile Cys Ala Ser Glu Val Gly Val Ile Pro
        420             425             430

Ile Glu Asn Ser Leu Val Val Gln Lys Gly Lys Leu Lys Pro Gly Asp
        435             440             445

Leu Phe Leu Val Asp Thr Gln Leu Gly Glu Met Val Asp Thr Lys Lys
    450             455             460

Leu Lys Ser Gln Ile Ser Lys Arg Gln Asp Phe Lys Ser Trp Leu Ser
465             470             475             480

Lys Val Ile Lys Leu Asp Asp Leu Leu Ser Lys Thr Ala Asn Leu Val
            485             490             495

Pro Lys Glu Phe Ile Ser Gln Asp Ser Leu Ser Leu Lys Val Gln Ser
            500             505             510

Asp Pro Arg Leu Leu Ala Asn Gly Tyr Thr Phe Glu Gln Val Thr Phe
        515             520             525

Leu Leu Thr Pro Met Ala Leu Thr Gly Lys Glu Ala Leu Gly Ser Met
    530             535             540

Gly Asn Asp Ala Pro Leu Ala Cys Leu Asn Glu Asn Pro Val Leu Leu
545             550             555             560

Tyr Asp Tyr Phe Arg Gln Leu Phe Ala Gln Val Thr Asn Pro Pro Ile
            565             570             575

Asp Pro Ile Arg Glu Ala Asn Val Met Ser Leu Glu Cys Tyr Val Gly
        580             585             590

Pro Gln Gly Asn Leu Leu Glu Met His Ser Ser Gln Cys Asp Arg Leu
        595             600             605

Leu Leu Lys Ser Pro Ile Leu His Trp Asn Glu Phe Gln Ala Leu Lys
    610             615             620

Asn Ile Glu Ala Ala Tyr Pro Ser Trp Ser Val Ala Glu Ile Asp Ile
625             630             635             640

Thr Phe Asp Lys Ser Glu Gly Leu Leu Gly Tyr Thr Asp Thr Ile Asp
            645             650             655

Lys Ile Thr Lys Leu Ala Ser Glu Ala Ile Asp Asp Gly Lys Lys Ile
            660             665             670

Leu Ile Ile Thr Asp Arg Lys Met Gly Ala Asn Arg Val Ser Ile Ser
```

-continued

```
              675                 680                 685

Ser Leu Ile Ala Ile Ser Cys Ile His His His Leu Ile Arg Asn Lys
    690                 695                 700

Gln Arg Ser Gln Val Ala Leu Ile Leu Glu Thr Gly Glu Ala Arg Glu
705                 710                 715                 720

Ile His His Phe Cys Val Leu Leu Gly Tyr Gly Cys Asp Gly Val Tyr
                725                 730                 735

Pro Tyr Leu Ala Met Glu Thr Leu Val Arg Met Asn Arg Glu Gly Leu
            740                 745                 750

Leu Arg Asn Val Asn Asn Asp Asn Asp Thr Leu Glu Glu Gly Gln Ile
            755                 760                 765

Leu Glu Asn Tyr Lys His Ala Ile Asp Ala Gly Ile Leu Lys Val Met
    770                 775                 780

Ser Lys Met Gly Ile Ser Thr Leu Ala Ser Tyr Lys Gly Ala Gln Ile
785                 790                 795                 800

Phe Glu Ala Leu Gly Leu Asp Asn Ser Ile Val Asp Leu Cys Phe Thr
                805                 810                 815

Gly Thr Ser Ser Arg Ile Arg Gly Val Thr Phe Glu Tyr Leu Ala Gln
                820                 825                 830

Asp Ala Phe Ser Leu His Glu Arg Gly Tyr Pro Ser Arg Gln Thr Ile
            835                 840                 845

Ser Lys Ser Val Asn Leu Pro Glu Ser Gly Glu Tyr His Phe Arg Asp
    850                 855                 860

Gly Gly Tyr Lys His Val Asn Glu Pro Thr Ala Ile Ala Ser Leu Gln
865                 870                 875                 880

Asp Thr Val Arg Asn Lys Asn Asp Val Ser Trp Gln Leu Tyr Val Lys
                885                 890                 895

Lys Glu Met Glu Ala Ile Arg Asp Cys Thr Leu Arg Gly Leu Leu Glu
            900                 905                 910

Leu Asp Phe Glu Asn Ser Val Ser Ile Pro Leu Glu Gln Val Glu Pro
            915                 920                 925

Trp Thr Glu Ile Ala Arg Arg Phe Ala Ser Gly Ala Met Ser Tyr Gly
    930                 935                 940

Ser Ile Ser Met Glu Ala His Ser Thr Leu Ala Ile Ala Met Asn Arg
945                 950                 955                 960

Leu Gly Ala Lys Ser Asn Cys Gly Glu Gly Gly Glu Asp Ala Glu Arg
                965                 970                 975

Ser Ala Val Gln Glu Asn Gly Asp Thr Met Arg Ser Ala Ile Lys Gln
            980                 985                 990

Val Ala Ser Ala Arg Phe Gly Val  Thr Ser Tyr Tyr Leu  Ser Asp Ala
        995                 1000                1005

Asp Glu  Ile Gln Ile Lys Ile  Ala Gln Gly Ala Lys  Pro Gly Glu
    1010                1015                1020

Gly Gly  Glu Leu Pro Ala His  Lys Val Ser Lys Asp  Ile Ala Lys
    1025                1030                1035

Thr Arg  His Ser Thr Pro Asn  Val Gly Leu Ile Ser  Pro Pro Pro
    1040                1045                1050

His His  Asp Ile Tyr Ser Ile  Glu Asp Leu Lys Gln  Leu Ile Tyr
    1055                1060                1065

Asp Leu  Lys Cys Ala Asn Pro  Arg Ala Gly Ile Ser  Val Lys Leu
    1070                1075                1080

Val Ser  Glu Val Gly Val Gly  Ile Val Ala Ser Gly  Val Ala Lys
    1085                1090                1095
```

-continued

```
Ala Lys Ala Asp His Ile Leu  Val Ser Gly His Asp  Gly Gly Thr
    1100                1105                1110

Gly Ala Ala Arg Trp Thr Ser  Val Lys Tyr Ala Gly  Leu Pro Trp
    1115                1120                1125

Glu Leu Gly Leu Ala Glu Thr  His Gln Thr Leu Val  Leu Asn Asp
    1130                1135                1140

Leu Arg Arg Asn Val Val Val  Gln Thr Asp Gly Gln  Leu Arg Thr
    1145                1150                1155

Gly Phe Asp Ile Ala Val Ala  Val Leu Leu Gly Ala  Glu Ser Phe
    1160                1165                1170

Thr Leu Ala Thr Val Pro Leu  Ile Ala Met Gly Cys  Val Met Leu
    1175                1180                1185

Arg Arg Cys His Leu Asn Ser  Cys Ala Val Gly Ile  Ala Thr Gln
    1190                1195                1200

Asp Pro Tyr Leu Arg Ser Lys  Phe Lys Gly Gln Pro  Glu His Val
    1205                1210                1215

Ile Asn Phe Phe Tyr Tyr Leu  Ile Gln Asp Leu Arg  Gln Ile Met
    1220                1225                1230

Ala Lys Leu Gly Phe Arg Thr  Ile Asp Glu Met Val  Gly His Ser
    1235                1240                1245

Glu Lys Leu Lys Lys Arg Asp  Asp Val Asn Ala Lys  Ala Ile Asn
    1250                1255                1260

Ile Asp Leu Ser Pro Ile Leu  Thr Pro Ala His Val  Ile Arg Pro
    1265                1270                1275

Gly Val Pro Thr Lys Phe Thr  Lys Lys Gln Asp His  Lys Leu His
    1280                1285                1290

Thr Arg Leu Asp Asn Lys Leu  Ile Asp Glu Ala Glu  Val Thr Leu
    1295                1300                1305

Asp Arg Gly Leu Pro Val Asn  Ile Asp Ala Ser Ile  Ile Asn Thr
    1310                1315                1320

Asp Arg Ala Leu Gly Ser Thr  Leu Ser Tyr Arg Val  Ser Lys Lys
    1325                1330                1335

Phe Gly Glu Asp Gly Leu Pro  Lys Asp Thr Val Val  Val Asn Ile
    1340                1345                1350

Glu Gly Ser Ala Gly Gln Ser  Phe Gly Ala Phe Leu  Ala Ser Gly
    1355                1360                1365

Ile Thr Phe Ile Leu Asn Gly  Asp Ala Asn Asp Tyr  Val Gly Lys
    1370                1375                1380

Gly Leu Ser Gly Gly Ile Ile  Val Ile Lys Pro Pro  Lys Asp Ser
    1385                1390                1395

Lys Phe Lys Ser Asp Glu Asn  Val Ile Val Gly Asn  Thr Cys Phe
    1400                1405                1410

Tyr Gly Ala Thr Ser Gly Thr  Ala Phe Ile Ser Gly  Ser Ala Gly
    1415                1420                1425

Glu Arg Phe Gly Val Arg Asn  Ser Gly Ala Thr Ile  Val Val Glu
    1430                1435                1440

Arg Ile Lys Gly Asn Asn Ala  Phe Glu Tyr Met Thr  Gly Gly Arg
    1445                1450                1455

Ala Ile Val Leu Ser Gln Met  Glu Ser Leu Asn Ala  Phe Ser Gly
    1460                1465                1470

Ala Thr Gly Gly Ile Ala Tyr  Cys Leu Thr Ser Asp  Tyr Asp Asp
    1475                1480                1485
```

```
Phe Val Gly Lys Ile Asn Lys Asp Thr Val Glu Leu Glu Ser Leu
    1490              1495              1500

Cys Asp Pro Val Glu Ile Ala Phe Val Lys Asn Leu Ile Gln Glu
1505              1510              1515

His Trp Asn Tyr Thr Gln Ser Asp Leu Ala Ala Arg Ile Leu Gly
1520              1525              1530

Asn Phe Asn His Tyr Leu Lys Asp Phe Val Lys Val Ile Pro Thr
1535              1540              1545

Asp Tyr Lys Lys Val Leu Leu Lys Glu Lys Ala Glu Ala Ala Lys
1550              1555              1560

Ala Lys Ala Lys Ala Thr Ser Glu Tyr Leu Lys Lys Phe Arg Ser
1565              1570              1575

Asn Gln Glu Val Asp Asp Glu Val Asn Thr Leu Leu Ile Ala Asn
    1580              1585              1590

Gln Lys Ala Lys Glu Gln Glu Lys Lys Lys Ser Ile Thr Ile Ser
    1595              1600              1605

Asn Lys Ala Thr Leu Lys Glu Pro Lys Val Val Asp Leu Glu Asp
    1610              1615              1620

Ala Val Pro Asp Ser Lys Gln Leu Glu Lys Asn Ser Glu Arg Ile
    1625              1630              1635

Glu Lys Thr Arg Gly Phe Met Ile His Lys Arg Arg His Glu Thr
    1640              1645              1650

His Arg Asp Pro Arg Thr Arg Val Asn Asp Trp Lys Glu Phe Thr
    1655              1660              1665

Asn Pro Ile Thr Lys Lys Asp Ala Lys Tyr Gln Thr Ala Arg Cys
    1670              1675              1680

Met Asp Cys Gly Thr Pro Phe Cys Leu Ser Asp Thr Gly Cys Pro
1685              1690              1695

Leu Ser Asn Ile Ile Pro Lys Phe Asn Glu Leu Leu Phe Lys Asn
1700              1705              1710

Gln Trp Lys Leu Ala Leu Asp Lys Leu Leu Glu Thr Asn Asn Phe
1715              1720              1725

Pro Glu Phe Thr Gly Arg Val Cys Pro Ala Pro Cys Glu Gly Ala
    1730              1735              1740

Cys Thr Leu Gly Ile Ile Glu Asp Pro Val Gly Ile Lys Ser Val
1745              1750              1755

Glu Arg Ile Ile Ile Asp Asn Ala Phe Lys Glu Gly Trp Ile Lys
    1760              1765              1770

Pro Cys Pro Pro Ser Thr Arg Thr Gly Phe Thr Val Gly Val Ile
1775              1780              1785

Gly Ser Gly Pro Ala Gly Leu Ala Cys Ala Asp Met Leu Asn Arg
    1790              1795              1800

Ala Gly His Thr Val Thr Val Tyr Glu Arg Ser Asp Arg Cys Gly
    1805              1810              1815

Gly Leu Leu Met Tyr Gly Ile Pro Asn Met Lys Leu Asp Lys Ala
    1820              1825              1830

Ile Val Gln Arg Arg Ile Asp Leu Leu Ser Ala Glu Gly Ile Asp
    1835              1840              1845

Phe Val Thr Asn Thr Glu Ile Gly Lys Thr Ile Ser Met Asp Glu
    1850              1855              1860

Leu Lys Asn Lys His Asn Ala Val Val Tyr Ala Ile Gly Ser Thr
    1865              1870              1875

Ile Pro Arg Asp Leu Pro Ile Lys Gly Arg Glu Leu Lys Asn Ile
```

-continued

```
        1880            1885            1890

Asp Phe Ala Met Gln Leu Leu  Glu Ser Asn Thr Lys  Ala Leu Leu
    1895            1900            1905

Asn Lys Asp Leu Glu Ile Ile  Arg Glu Lys Ile Gln  Gly Lys Lys
    1910            1915            1920

Val Ile Val Val Gly Gly Gly  Asp Thr Gly Asn Asp  Cys Leu Gly
    1925            1930            1935

Thr Ser Val Arg His Gly Ala  Ala Ser Val Leu Asn  Phe Glu Leu
    1940            1945            1950

Leu Pro Glu Pro Pro Val Glu  Arg Ala Lys Asp Asn  Pro Trp Pro
    1955            1960            1965

Gln Trp Pro Arg Val Met Arg  Val Asp Tyr Gly His  Ala Glu Val
    1970            1975            1980

Lys Glu His Tyr Gly Arg Asp  Pro Arg Glu Tyr Cys  Ile Leu Ser
    1985            1990            1995

Lys Glu Phe Ile Gly Asn Asp  Glu Gly Glu Val Thr  Ala Ile Arg
    2000            2005            2010

Thr Val Arg Val Glu Trp Lys  Lys Ser Gln Ser Gly  Val Trp Gln
    2015            2020            2025

Met Val Glu Ile Pro Asn Ser  Glu Glu Ile Phe Glu  Ala Asp Ile
    2030            2035            2040

Ile Leu Leu Ser Met Gly Phe  Val Gly Pro Glu Leu  Ile Asn Gly
    2045            2050            2055

Asn Asp Asn Glu Val Lys Lys  Thr Arg Arg Gly Thr  Ile Ala Thr
    2060            2065            2070

Leu Asp Asp Ser Ser Tyr Ser  Ile Asp Gly Gly Lys  Thr Phe Ala
    2075            2080            2085

Cys Gly Asp Cys Arg Arg Gly  Gln Ser Leu Ile Val  Trp Ala Ile
    2090            2095            2100

Gln Glu Gly Arg Lys Cys Ala  Ala Ser Val Asp Lys  Phe Leu Met
    2105            2110            2115

Asp Gly Thr Thr Tyr Leu Pro  Ser Asn Gly Gly Ile  Val Gln Arg
    2120            2125            2130

Asp Tyr Lys Leu Leu Lys Glu  Leu Ala Ser Gln Val
    2135            2140            2145
```

<210> SEQ ID NO 100
<211> LENGTH: 300
<212> TYPE: DNA
<213> ORGANISM: Saccharomyces cerevisiae

<400> SEQUENCE: 100
gtgaatttac tttaaatctt gcatttaaat aaattttctt tttatagctt tatgacttag       60
tttcaattta tatactattt taatgacatt ttcgattcat tgattgaaag ctttgtgttt      120
tttcttgatg cgctattgca ttgttcttgt ctttttcgcc acatgtaata tctgtagtag      180
atacctgata cattgtggat gctgagtgaa attttagtta ataatggagg cgctcttaat      240
aattttgggg atattggctt tttttttttaa agtttacaaa tgaatttttt ccgccaggat      300

<210> SEQ ID NO 101
<211> LENGTH: 1788
<212> TYPE: DNA
<213> ORGANISM: Artificial Sequence
<220> FEATURE:
<223> OTHER INFORMATION: Synthetic reencoded nucleic acid sequence of
      hyaluronan synthase (HASA) originating from Chlorella virus CviKI

```
<400> SEQUENCE: 101 atgctttca gttgtttgtc cttcgtgatc tgccatctta gttttatttt gcgttattac        60
aagaggcttc taaaagtgac gatgggaaag aacattataa taatggtgag ttggtacaca       120
ataataactt ccaacatcat cgccgtcggt ggggcgtctc tgattttggc cccagccatc       180
actggataca tcttgcactg gaacatcgcc ttgtcaacca tctggggagt ttccgcttat       240
gggatattcg tgttcggatt cttcctggct caggttttat ttagtgagct aaatcgtaaa       300
agactaagaa agtggatttc tctaagacca aagggttgga acgacgtacg tctggctgtc       360
atcatagctg gttacaggga agacccgtac atgtttcaga aatgccttga gtcagtaagg       420
gactctgact atggtaatgt cgctcgtctt atctgtgtaa ttgacggaga tgaggacgac       480
gacatgaaga tggcagccgt ttataaggcg atatataatg acaatatcaa gaagccagag       540
tttgtgttat gtgagagcga tgataaggaa ggcgagagaa ttgactcaga ttttagcagg       600
gacatctgcg tcttacaacc acaccgtggc aaaagggagt gcttgtatac cggctttcag       660
ctggccaaaa tggacccgtc ggtaaacgcc gttgttctta ttgactctga cacggtcttg       720
gaaaaggacg caatcttgga agtcgtgtat ccattggcct gtgacccgga aattcaagct       780
gtcgcaggag agtgcaaaat atggaacaca gatacacttt tgtcgttgtt ggtggcttgg       840
agatattatt cagcctttg cgtggagaga tccgcccaat cattctttag gacagtccag       900
tgtgtaggtg gacccttggg cgcctacaag atagatatca tcaaagagat caaagatccc       960
tggatctccc aacgtttctt aggtcagaag tgcacctacg gtgacgaccg taggttaaca      1020
aatgaaatct taatgagggg taagaaggtc gtcttcactc ctttcgcagt tggctggagt      1080
gactcaccaa ccaacgtgtt caggtacatc gtacaacaga ctaggtggag taaatcatgg      1140
tgccgtgaga tatggtacac tttgtttgct gcgtggaagc acggactaag cggaatttgg      1200
ttggcatttg agtgccttta tcagattacg tacttcttcc tagtcatata tttattttcg      1260
agactagccg ttgaagctga cccaagagca cagaccgcaa cagtaatcgt gtctaccacg      1320
gtagccctga ttaagtgtgg ttacttctct tttcgtgcga aagatattcg tgctttctac      1380
ttcgtcctgt acacatttgt ctacttcttc tgtatgatcc cagcaagggt gacagccatg      1440
atgacacttt gggatatcgg ctggggcacg cgtggcggaa acgagaaacc aagtgtcggc      1500
actagggtcg ctctgtgggc taaacagtat ttgatagcat acatgtggtg ggcagcagtt      1560
gttggcgctg gggtatactc cattgttcat aattggatgt ttgactggaa ctcactatcc      1620
tataggttcg cacttgtagg tatatgctct tacatcgtat tcatcacaat cgttctagtc      1680
atctatttca caggaaagat taccacatgg aatttcacca aattacagaa ggagttaatc      1740
aaggataggg tcttatacga tgcttccact aacgcccaga ctgtataa               1788
```

```
<210> SEQ ID NO 102
<211> LENGTH: 1803
<212> TYPE: DNA
<213> ORGANISM: Artificial Sequence
<220> FEATURE:
<223> OTHER INFORMATION: Synthetic reencoded nucleic acid sequence of
      hyaluronan synthase (HASA) originating from Chlorella virus
      IL-5-2s1

<400> SEQUENCE: 102
atggctgctt cattctatgt tatcttcttg ttcgtaatat gccacctgtc cttcgtctta        60
tatcgtcaag ttctatacat aattttgggt agatactgga gtgttaacaa gctgacaatg       120
```

-continued

```
atctcttggt ataccattat atcatctaat ctaatcgcaa tcggtggggc ttcccttatt      180
ttggcaccgg ccataaccgg ctacattttg cattggaaca tagctctaag cacaatttgg      240
ggtgtgtcag cctatggcat tttcgtgttc gggttctttc ttgctcaggt tttgttcagt      300
gagcttaaca ggaagaggtt gagaaaatgg atctctttga gaccagataa ctggaacgcg      360
gtgagagttg ccgtgataat cgctggttac cgtgaagacc catacatgtt tcaaaagtgt      420
ttggaatcgg tgagagactc cgattatggt aacattgcga ggcttatatg cgttatagat      480
ggggacgaag atgacgacat gaagatggca gatgtataca aggctattta caatgacaat      540
ataaagaagc cggaaattat cctatgtgag tccgacgaca aagagggaga aaggatagac      600
agtgatttta gccgtgatat ttgcgtgctt cagcctcaca gaggtaagcg tgaatgttta      660
tatactggct ttcagttagc taaaatggac ccctctgtac acgcggttgt gcttattgac      720
tcggatacag ttttggagaa ggatgccatc ctggaagtgg tctacccact tgcttgcgac      780
catgagattc aagcagtcgc aggtgaatgc aagatatgga atacggacac cttattatcc      840
atattagtcg cctggcgtta ctactcagct ttctgcgttg agcgtagcgc tcagtccttc      900
ttccgtactg tgcaatgcgt cggcggtccg ttaggggcat acaaaataga cataattaaa      960
gagataaagg agccgtggat ttcacaaaga tttctgggtc agaagtgtac gtacggagat     1020
gacagaagat taactaacga agtgttgatg cgtggaaaga aagtagtctt cacacctttt     1080
gcggtaggat ggagcgactc gcctactaat gtcttccgtt atattgtgca gcagacgagg     1140
tggagtaaga gctggtgcag ggagatttgg tatacactgt tcgcggcgtg gaagcatggg     1200
ttatcaggca tttggttggc atttgagtgc ttgtatcaga tcacatactt ctttctagtg     1260
atatatctgt tcagtagact agcagtcgag gctgacccga gagcgcaaac tgcaacggtt     1320
atagtcagca caatggtttc actaatcaag tgtggatatt tctcattccg tgctaaggac     1380
attagagcgt tttatttcgt actatatact tttgtgtact tcttttgcat gatcccagca     1440
agagtcactg ctatgatgac cttgtgggat attgggtggg gtactagggg tggaaacgtg     1500
aaaccatcga tcggaactag gatctctttg tgggctaagc agtacttaat cgcgtacatg     1560
tggtgggcag ctgtgatcgc cgcaggagtc tatagtataa tacataattg gatgtttgat     1620
tggaactcct tgtcctatcg tttcgcgtta ataggcatct gctcgtatat cgtattcatt     1680
gccattgtta tagtgatata cttcacaggt aagatcacca cttggaattt taccaagcta     1740
cagaaagagt taattgaaga tagagtcttg catgatgccg atgtggacat acagaacgta     1800
taa                                                                   1803
```

<210> SEQ ID NO 103
<211> LENGTH: 1686
<212> TYPE: DNA
<213> ORGANISM: Artificial Sequence
<220> FEATURE:
<223> OTHER INFORMATION: Synthetic reencoded nucleic acid sequence of
     hyaluronan synthase (HASA) originating from Chlorella virus CZ-2

<400> SEQUENCE: 103

```
atgacatctt ggagaacgat tgtgtcagct aaccttttcg cagttggtgg ggctcttcta       60
atgttagccc cagctatcgt gggctatgta tttcagtgga atataggcgt gtccgcagtc      120
tggggcatct ccgtatacgg cgtctttgtg ttgggatttt atatcgctca aatcgtcttc      180
tctgagttca acaggatgag attatccgat tggataagtc ttagaccaga caactggaac      240
gccacaaggg ttgcggtcat tatagctgga tacagagaag atccttttat gttcaagaag      300
```

```
tgcttagaga gtgtgaggga ttcggaatac ggcaacgtag caaggcttat atgcgtaatt      360
gacggagacg aagaagagga cctaaagatg gctgagattt acaagcaggt ttacaatgac      420
aacgtgaaga aaccaggtgt agtgttatgc gaatcggaga acaagaatgg atcgactata      480
gattcggacg tatctaagaa tatatgcata ctgcaacccc accgtgggaa acgtgagagc      540
ctatataccg gtttccaatt ggcaagcatg gacccttccg tacatgcggt tgttcttata      600
gattccgaca ctgtattaga gaagaatgct attcttgagg tcgtataccc tctatcttgt      660
gaccccaaca ttaaggccgt cgccggggag tgcaagatat ggaatacaga caccatcttg      720
tccatgcttg tctcttggag atacttctct gccttcaatg tcgagcgtgg agcccagtca      780
ttatggaaga ctgtgcaatg cgtaggcggg ccacttggcg catacactat cgacatcata      840
aatgaaatta aagacccgtg gattacccag acattcctgg gcaacaagtg cacttatggc      900
gacgatagac gtcttaccaa tgaggtttta atgaggggca agaagattgt atacactccg      960
tttgccgtcg gttggagcga cagtccgacg aatgtcatga ggtacattgt gcagcaaact     1020
agatggagta agtcatggtg cagagagata tggtacacgt taggcagtgc ctggaaacat     1080
ggattctccg gcatatacct tgcgtttgag tgtatgtacc agataatgta cttcttctta     1140
gtcatgtacc tgttttcgta tatcgcaata aaggcagaca tccgtgctca gactgcaact     1200
gtgttggttt ctactctagt caccataata aagagcagtt acctagcgct gagggccaag     1260
aacctgaagg ctttctattt cgttctgtat acctatgtct atttcttttg catgatacct     1320
gctaggatta ccgctatgtt tacaatgttt gatatagctt ggggtacacg tggtggtaat     1380
gcgaaaatga caatcggggc tagagtttgg ctgtgggcga agcagttctt aataacttat     1440
atgtggtggg caggagtact agcggcggga gtttacagta tagttgacaa ttggtacttc     1500
gattgggctg atatacagta caggtttgca ttggtaggta tttgctcgta tttggtcttt     1560
gtcagtattg tactggtaat ctacttgatc ggtaagataa caacgtggaa ctacacaccg     1620
ctacagaagg aacttattga ggagagatac ttgcataacg cctctgagaa tgccccggaa     1680
gtttaa                                                                1686
```

<210> SEQ ID NO 104
<211> LENGTH: 1677
<212> TYPE: DNA
<213> ORGANISM: Artificial Sequence
<220> FEATURE:
<223> OTHER INFORMATION: Synthetic reencoded nucleic acid sequence of
      hyaluronan synthase (HASA) originating from Chlorella virus CVG-1

<400> SEQUENCE: 104

```
atgacttctt ggcgtacaat tgtttctgct aacttgttcg cagttggtgg cgccttgttg       60
atgttagctc ccgcgatagc cggttatgta tttaaatgga acataggcgt ttctgccgtt      120
tggggtattt cagtgtacgg ggtcttcgtg cttggtttct atattgcaca ggtagtcttc      180
agcgagttta ataggatgca gctgtcagac tggatctcat tgagacccga caactggaac      240
gccaccagag tagcggtaat tattgctggt tacaggaag accccttat gttcaagaag      300 tgcctagaat ctgtgagaga ctcagaatac gggaacatag cgaggctaat ctgtgttatc      360
gacggcgatg aagaggaaga ccttaagatg gctgagatat acaagcaagt atacaacgac      420
aacgtcaaga cccccggtgt gtgctatgc gagaatgaaa ataagaatgg tagcaccatt      480
gacccagatt ttagtaagaa catctgcatt ctgcaaccac acaggggcaa acgtgaatct      540
ttgtacaccg gattccagat ggctggcatg gacccatcag tgcacgcagt tgtacttata      600
```

```
gacagtgata ctgttcttga aaagaacgct atcctagagg ttgtgtaccc tctatcttgt     660
gatccaaata tcaaagctgt cgcgggagag tgtaaaatct ggaacacaga taccattttg     720
tctatgctag tttcatggcg ttatttctcg gctttcaacg tggagagagg cgcacagtcc     780
ctttggaaaa cagtccagtg tgtcggcggg cctttgggag catacactat agacatcata     840
aacgagataa aagacccctg gattactcag acattcttag gaaacaaatg tacgtatggt     900
gacgacagaa ggttaaccaa tgaagtgctt atgaggggaa agaagattgt ctatactccc     960
tttgctgtcg gttggtccga ttcgcccaca aacgttatga ggtacatcgt ccagcagaca    1020
aggtggtcta agagctggtg ccgtgagatt tggtacacct tgggatcagc atggaaacat    1080
ggtttctccg gaatctactt agcgttcgag tgcatgtacc agattatgta tttctttatt    1140
gtgatgtatt tgttcagtta cattgccatt aaagccaaca tcagggcaca agcagccacg    1200
gtattggtca gtacgcttgt cgcagtaatc aaatctagtt atttggcatt aagagcgaag    1260
aacctaaaag ctttgtattt cgtcctgtat acctacgtct acttcttctg catgattcca    1320
gctagaataa cagcgatgtt cacgatgttc gatattgcat ggggtactag aggcggtaac    1380
gcaaagatga cgatcggtgc tagagtctgg ttgtgggcta acaattctt aattacatac    1440 atgtggtggg tgggagtttt ggccgctggg gtctacagta tagtcgataa ctggtacttc    1500
gactgggcgg acatccagta cagattcgcg ctagtgggga tttgcagtta cttaggtttc    1560
gtttccataa tgctggtatt ctatctgatt ggtaaaataa ctacgtggaa ttacactcct    1620
ctacaaaagg agctgattaa agagaggtta cacgccgcta atgcaacaga ggtctaa       1677
```

```
<210> SEQ ID NO 105
<211> LENGTH: 595
<212> TYPE: PRT
<213> ORGANISM: Artificial Sequence
<220> FEATURE:
<223> OTHER INFORMATION: Synthetic amino acid sequence of hyaluronan
      synthase (HASA) originating from Chlorella virus CviKI

<400> SEQUENCE: 105

Met Leu Phe Ser Cys Leu Ser Phe Val Ile Cys His Leu Ser Phe Ile
1               5                   10                  15

Leu Arg Tyr Tyr Lys Arg Leu Leu Lys Val Thr Met Gly Lys Asn Ile
            20                  25                  30

Ile Ile Met Val Ser Trp Tyr Thr Ile Ile Thr Ser Asn Ile Ile Ala
        35                  40                  45

Val Gly Gly Ala Ser Leu Ile Leu Ala Pro Ala Ile Thr Gly Tyr Ile
    50                  55                  60

Leu His Trp Asn Ile Ala Leu Ser Thr Ile Trp Gly Val Ser Ala Tyr
65                  70                  75                  80

Gly Ile Phe Val Phe Gly Phe Phe Leu Ala Gln Val Leu Phe Ser Glu
                85                  90                  95

Leu Asn Arg Lys Arg Leu Arg Lys Trp Ile Ser Leu Arg Pro Lys Gly
            100                 105                 110

Trp Asn Asp Val Arg Leu Ala Val Ile Ile Ala Gly Tyr Arg Glu Asp
        115                 120                 125

Pro Tyr Met Phe Gln Lys Cys Leu Glu Ser Val Arg Asp Ser Asp Tyr
    130                 135                 140

Gly Asn Val Ala Arg Leu Ile Cys Val Ile Asp Gly Asp Glu Asp Asp
145                 150                 155                 160

Asp Met Lys Met Ala Ala Val Tyr Lys Ala Ile Tyr Asn Asp Asn Ile
                165                 170                 175
```

-continued

```
Lys Lys Pro Glu Phe Val Leu Cys Glu Ser Asp Asp Lys Glu Gly Glu
        180                 185                 190

Arg Ile Asp Ser Asp Phe Ser Arg Asp Ile Cys Val Leu Gln Pro His
        195                 200                 205

Arg Gly Lys Arg Glu Cys Leu Tyr Thr Gly Phe Gln Leu Ala Lys Met
        210                 215                 220

Asp Pro Ser Val Asn Ala Val Val Leu Ile Asp Ser Asp Thr Val Leu
225                 230                 235                 240

Glu Lys Asp Ala Ile Leu Glu Val Val Tyr Pro Leu Ala Cys Asp Pro
                245                 250                 255

Glu Ile Gln Ala Val Ala Gly Glu Cys Lys Ile Trp Asn Thr Asp Thr
                260                 265                 270

Leu Leu Ser Leu Leu Val Ala Trp Arg Tyr Tyr Ser Ala Phe Cys Val
        275                 280                 285

Glu Arg Ser Ala Gln Ser Phe Phe Arg Thr Val Gln Cys Val Gly Gly
        290                 295                 300

Pro Leu Gly Ala Tyr Lys Ile Asp Ile Ile Lys Glu Ile Lys Asp Pro
305                 310                 315                 320

Trp Ile Ser Gln Arg Phe Leu Gly Gln Lys Cys Thr Tyr Gly Asp Asp
                325                 330                 335

Arg Arg Leu Thr Asn Glu Ile Leu Met Arg Gly Lys Lys Val Val Phe
                340                 345                 350

Thr Pro Phe Ala Val Gly Trp Ser Asp Ser Pro Thr Asn Val Phe Arg
        355                 360                 365

Tyr Ile Val Gln Gln Thr Arg Trp Ser Lys Ser Trp Cys Arg Glu Ile
        370                 375                 380

Trp Tyr Thr Leu Phe Ala Ala Trp Lys His Gly Leu Ser Gly Ile Trp
385                 390                 395                 400

Leu Ala Phe Glu Cys Leu Tyr Gln Ile Thr Tyr Phe Phe Leu Val Ile
                405                 410                 415

Tyr Leu Phe Ser Arg Leu Ala Val Glu Ala Asp Pro Arg Ala Gln Thr
                420                 425                 430

Ala Thr Val Ile Val Ser Thr Thr Val Ala Leu Ile Lys Cys Gly Tyr
        435                 440                 445

Phe Ser Phe Arg Ala Lys Asp Ile Arg Ala Phe Tyr Phe Val Leu Tyr
        450                 455                 460

Thr Phe Val Tyr Phe Phe Cys Met Ile Pro Ala Arg Val Thr Ala Met
465                 470                 475                 480

Met Thr Leu Trp Asp Ile Gly Trp Gly Thr Arg Gly Gly Asn Glu Lys
                485                 490                 495

Pro Ser Val Gly Thr Arg Val Ala Leu Trp Ala Lys Gln Tyr Leu Ile
        500                 505                 510

Ala Tyr Met Trp Trp Ala Ala Val Val Gly Ala Gly Val Tyr Ser Ile
        515                 520                 525

Val His Asn Trp Met Phe Asp Trp Asn Ser Leu Ser Tyr Arg Phe Ala
        530                 535                 540

Leu Val Gly Ile Cys Ser Tyr Ile Val Phe Ile Thr Ile Val Leu Val
545                 550                 555                 560

Ile Tyr Phe Thr Gly Lys Ile Thr Thr Trp Asn Phe Thr Lys Leu Gln
                565                 570                 575

Lys Glu Leu Ile Lys Asp Arg Val Leu Tyr Asp Ala Ser Thr Asn Ala
                580                 585                 590
```

```
Gln Thr Val
        595

<210> SEQ ID NO 106
<211> LENGTH: 600
<212> TYPE: PRT
<213> ORGANISM: Artificial Sequence
<220> FEATURE:
<223> OTHER INFORMATION: Synthetic amino acid sequence of hyaluronan
      synthase (HASA) originating from Chlorella virus IL-5-2s1

<400> SEQUENCE: 106

Met Ala Ala Ser Phe Tyr Val Ile Phe Leu Phe Val Ile Cys His Leu
1               5                   10                  15

Ser Phe Val Leu Tyr Arg Gln Val Leu Tyr Ile Ile Leu Gly Arg Tyr
            20                  25                  30

Trp Ser Val Asn Lys Leu Thr Met Ile Ser Trp Tyr Thr Ile Ile Ser
        35                  40                  45

Ser Asn Leu Ile Ala Ile Gly Gly Ala Ser Leu Ile Leu Ala Pro Ala
    50                  55                  60

Ile Thr Gly Tyr Ile Leu His Trp Asn Ile Ala Leu Ser Thr Ile Trp
65                  70                  75                  80

Gly Val Ser Ala Tyr Gly Ile Phe Val Phe Gly Phe Phe Leu Ala Gln
                85                  90                  95

Val Leu Phe Ser Glu Leu Asn Arg Lys Arg Leu Arg Lys Trp Ile Ser
            100                 105                 110

Leu Arg Pro Asp Asn Trp Asn Ala Val Arg Val Ala Val Ile Ile Ala
            115                 120                 125

Gly Tyr Arg Glu Asp Pro Tyr Met Phe Gln Lys Cys Leu Glu Ser Val
    130                 135                 140

Arg Asp Ser Asp Tyr Gly Asn Ile Ala Arg Leu Ile Cys Val Ile Asp
145                 150                 155                 160

Gly Asp Glu Asp Asp Asp Met Lys Met Ala Asp Val Tyr Lys Ala Ile
                165                 170                 175

Tyr Asn Asp Asn Ile Lys Lys Pro Glu Ile Ile Leu Cys Glu Ser Asp
            180                 185                 190

Asp Lys Glu Gly Glu Arg Ile Asp Ser Asp Phe Ser Arg Asp Ile Cys
            195                 200                 205

Val Leu Gln Pro His Arg Gly Lys Arg Glu Cys Leu Tyr Thr Gly Phe
    210                 215                 220

Gln Leu Ala Lys Met Asp Pro Ser Val His Ala Val Val Leu Ile Asp
225                 230                 235                 240

Ser Asp Thr Val Leu Glu Lys Asp Ala Ile Leu Glu Val Val Tyr Pro
                245                 250                 255

Leu Ala Cys Asp His Glu Ile Gln Ala Val Ala Gly Glu Cys Lys Ile
                260                 265                 270

Trp Asn Thr Asp Thr Leu Leu Ser Ile Leu Val Ala Trp Arg Tyr Tyr
            275                 280                 285

Ser Ala Phe Cys Val Glu Arg Ser Ala Gln Ser Phe Phe Arg Thr Val
    290                 295                 300

Gln Cys Val Gly Gly Pro Leu Gly Ala Tyr Lys Ile Asp Ile Ile Lys
305                 310                 315                 320

Glu Ile Lys Glu Pro Trp Ile Ser Gln Arg Phe Leu Gly Gln Lys Cys
                325                 330                 335

Thr Tyr Gly Asp Asp Arg Arg Leu Thr Asn Glu Val Leu Met Arg Gly
            340                 345                 350
```

-continued

```
Lys Lys Val Val Phe Thr Pro Phe Ala Val Gly Trp Ser Asp Ser Pro
        355                 360                 365

Thr Asn Val Phe Arg Tyr Ile Val Gln Gln Thr Arg Trp Ser Lys Ser
    370                 375                 380

Trp Cys Arg Glu Ile Trp Tyr Thr Leu Phe Ala Ala Trp Lys His Gly
385                 390                 395                 400

Leu Ser Gly Ile Trp Leu Ala Phe Glu Cys Leu Tyr Gln Ile Thr Tyr
                405                 410                 415

Phe Phe Leu Val Ile Tyr Leu Phe Ser Arg Leu Ala Val Glu Ala Asp
            420                 425                 430

Pro Arg Ala Gln Thr Ala Thr Val Ile Val Ser Thr Met Val Ser Leu
        435                 440                 445

Ile Lys Cys Gly Tyr Phe Ser Phe Arg Ala Lys Asp Ile Arg Ala Phe
    450                 455                 460

Tyr Phe Val Leu Tyr Thr Phe Val Tyr Phe Phe Cys Met Ile Pro Ala
465                 470                 475                 480

Arg Val Thr Ala Met Met Thr Leu Trp Asp Ile Gly Trp Gly Thr Arg
                485                 490                 495

Gly Gly Asn Val Lys Pro Ser Ile Gly Thr Arg Ile Ser Leu Trp Ala
                500                 505                 510

Lys Gln Tyr Leu Ile Ala Tyr Met Trp Trp Ala Ala Val Ile Ala Ala
            515                 520                 525

Gly Val Tyr Ser Ile Ile His Asn Trp Met Phe Asp Trp Asn Ser Leu
        530                 535                 540

Ser Tyr Arg Phe Ala Leu Ile Gly Ile Cys Ser Tyr Ile Val Phe Ile
545                 550                 555                 560

Ala Ile Val Ile Val Ile Tyr Phe Thr Gly Lys Ile Thr Thr Trp Asn
                565                 570                 575

Phe Thr Lys Leu Gln Lys Glu Leu Ile Glu Asp Arg Val Leu His Asp
            580                 585                 590

Ala Asp Val Asp Ile Gln Asn Val
        595                 600

<210> SEQ ID NO 107
<211> LENGTH: 561
<212> TYPE: PRT
<213> ORGANISM: Artificial Sequence
<220> FEATURE:
<223> OTHER INFORMATION: Synthetic amino acid sequence of hyaluronan
      synthase (HASA) originating from Chlorella virus CZ-2

<400> SEQUENCE: 107

Met Thr Ser Trp Arg Thr Ile Val Ser Ala Asn Leu Phe Ala Val Gly
1               5                   10                  15

Gly Ala Leu Leu Met Leu Ala Pro Ala Ile Val Gly Tyr Val Phe Gln
            20                  25                  30

Trp Asn Ile Gly Val Ser Ala Val Trp Gly Ile Ser Val Tyr Gly Val
        35                  40                  45

Phe Val Leu Gly Phe Tyr Ile Ala Gln Ile Val Phe Ser Glu Phe Asn
    50                  55                  60

Arg Met Arg Leu Ser Asp Trp Ile Ser Leu Arg Pro Asp Asn Trp Asn
65                  70                  75                  80

Ala Thr Arg Val Ala Val Ile Ile Ala Gly Tyr Arg Glu Asp Pro Phe
                85                  90                  95

Met Phe Lys Lys Cys Leu Glu Ser Val Arg Asp Ser Glu Tyr Gly Asn
```

-continued

```
                  100               105                110

Val Ala Arg Leu Ile Cys Val Ile Asp Gly Asp Glu Glu Glu Asp Leu
              115               120               125

Lys Met Ala Glu Ile Tyr Lys Gln Val Tyr Asn Asp Asn Val Lys Lys
    130               135               140

Pro Gly Val Val Leu Cys Glu Ser Glu Asn Lys Asn Gly Ser Thr Ile
145               150               155               160

Asp Ser Asp Val Ser Lys Asn Ile Cys Ile Leu Gln Pro His Arg Gly
              165               170               175

Lys Arg Glu Ser Leu Tyr Thr Gly Phe Gln Leu Ala Ser Met Asp Pro
              180               185               190

Ser Val His Ala Val Val Leu Ile Asp Ser Asp Thr Val Leu Glu Lys
              195               200               205

Asn Ala Ile Leu Glu Val Val Tyr Pro Leu Ser Cys Asp Pro Asn Ile
    210               215               220

Lys Ala Val Ala Gly Glu Cys Lys Ile Trp Asn Thr Asp Thr Ile Leu
225               230               235               240

Ser Met Leu Val Ser Trp Arg Tyr Phe Ser Ala Phe Asn Val Glu Arg
              245               250               255

Gly Ala Gln Ser Leu Trp Lys Thr Val Gln Cys Val Gly Gly Pro Leu
              260               265               270

Gly Ala Tyr Thr Ile Asp Ile Ile Asn Glu Ile Lys Asp Pro Trp Ile
              275               280               285

Thr Gln Thr Phe Leu Gly Asn Lys Cys Thr Tyr Gly Asp Asp Arg Arg
    290               295               300

Leu Thr Asn Glu Val Leu Met Arg Gly Lys Lys Ile Val Tyr Thr Pro
305               310               315               320

Phe Ala Val Gly Trp Ser Asp Ser Pro Thr Asn Val Met Arg Tyr Ile
              325               330               335

Val Gln Gln Thr Arg Trp Ser Lys Ser Trp Cys Arg Glu Ile Trp Tyr
              340               345               350

Thr Leu Gly Ser Ala Trp Lys His Gly Phe Ser Gly Ile Tyr Leu Ala
              355               360               365

Phe Glu Cys Met Tyr Gln Ile Met Tyr Phe Phe Leu Val Met Tyr Leu
    370               375               380

Phe Ser Tyr Ile Ala Ile Lys Ala Asp Ile Arg Ala Gln Thr Ala Thr
385               390               395               400

Val Leu Val Ser Thr Leu Val Thr Ile Ile Lys Ser Ser Tyr Leu Ala
              405               410               415

Leu Arg Ala Lys Asn Leu Lys Ala Phe Tyr Phe Val Leu Tyr Thr Tyr
              420               425               430

Val Tyr Phe Phe Cys Met Ile Pro Ala Arg Ile Thr Ala Met Phe Thr
              435               440               445

Met Phe Asp Ile Ala Trp Gly Thr Arg Gly Gly Asn Ala Lys Met Thr
    450               455               460

Ile Gly Ala Arg Val Trp Leu Trp Ala Lys Gln Phe Leu Ile Thr Tyr
465               470               475               480

Met Trp Trp Ala Gly Val Leu Ala Ala Gly Val Tyr Ser Ile Val Asp
              485               490               495

Asn Trp Tyr Phe Asp Trp Ala Asp Ile Gln Tyr Arg Phe Ala Leu Val
              500               505               510

Gly Ile Cys Ser Tyr Leu Val Phe Val Ser Ile Val Leu Val Ile Tyr
              515               520               525
```

-continued

```
Leu Ile Gly Lys Ile Thr Thr Trp Asn Tyr Thr Pro Leu Gln Lys Glu
    530             535             540

Leu Ile Glu Glu Arg Tyr Leu His Asn Ala Ser Glu Asn Ala Pro Glu
545             550             555             560

Val

<210> SEQ ID NO 108
<211> LENGTH: 558
<212> TYPE: PRT
<213> ORGANISM: Artificial Sequence
<220> FEATURE:
<223> OTHER INFORMATION: Synthetic amino acid sequence of hyaluronan
      synthase (HASA) originating from Chlorella virus CVG-1

<400> SEQUENCE: 108

Met Thr Ser Trp Arg Thr Ile Val Ser Ala Asn Leu Phe Ala Val Gly
1               5               10              15

Gly Ala Leu Leu Met Leu Ala Pro Ala Ile Ala Gly Tyr Val Phe Lys
            20              25              30

Trp Asn Ile Gly Val Ser Ala Val Trp Gly Ile Ser Val Tyr Gly Val
        35              40              45

Phe Val Leu Gly Phe Tyr Ile Ala Gln Val Val Phe Ser Glu Phe Asn
    50              55              60

Arg Met Gln Leu Ser Asp Trp Ile Ser Leu Arg Pro Asp Asn Trp Asn
65              70              75              80

Ala Thr Arg Val Ala Val Ile Ile Ala Gly Tyr Arg Glu Asp Pro Phe
                85              90              95

Met Phe Lys Lys Cys Leu Glu Ser Val Arg Asp Ser Glu Tyr Gly Asn
            100             105             110

Ile Ala Arg Leu Ile Cys Val Ile Asp Gly Asp Glu Glu Glu Asp Leu
            115             120             125

Lys Met Ala Glu Ile Tyr Lys Gln Val Tyr Asn Asp Asn Val Lys Thr
    130             135             140

Pro Gly Val Val Leu Cys Glu Asn Glu Asn Lys Asn Gly Ser Thr Ile
145             150             155             160

Asp Pro Asp Phe Ser Lys Asn Ile Cys Ile Leu Gln Pro His Arg Gly
            165             170             175

Lys Arg Glu Ser Leu Tyr Thr Gly Phe Gln Met Ala Gly Met Asp Pro
            180             185             190

Ser Val His Ala Val Val Leu Ile Asp Ser Asp Thr Val Leu Glu Lys
            195             200             205

Asn Ala Ile Leu Glu Val Val Tyr Pro Leu Ser Cys Asp Pro Asn Ile
    210             215             220

Lys Ala Val Ala Gly Glu Cys Lys Ile Trp Asn Thr Asp Thr Ile Leu
225             230             235             240

Ser Met Leu Val Ser Trp Arg Tyr Phe Ser Ala Phe Asn Val Glu Arg
            245             250             255

Gly Ala Gln Ser Leu Trp Lys Thr Val Gln Cys Val Gly Gly Pro Leu
            260             265             270

Gly Ala Tyr Thr Ile Asp Ile Ile Asn Glu Ile Lys Asp Pro Trp Ile
            275             280             285

Thr Gln Thr Phe Leu Gly Asn Lys Cys Thr Tyr Gly Asp Asp Arg Arg
    290             295             300

Leu Thr Asn Glu Val Leu Met Arg Gly Lys Lys Ile Val Tyr Thr Pro
305             310             315             320
```

-continued

```
Phe Ala Val Gly Trp Ser Asp Ser Pro Thr Asn Val Met Arg Tyr Ile
                325             330             335

Val Gln Gln Thr Arg Trp Ser Lys Ser Trp Cys Arg Glu Ile Trp Tyr
            340             345             350

Thr Leu Gly Ser Ala Trp Lys His Gly Phe Ser Gly Ile Tyr Leu Ala
        355             360             365

Phe Glu Cys Met Tyr Gln Ile Met Tyr Phe Phe Ile Val Met Tyr Leu
    370             375             380

Phe Ser Tyr Ile Ala Ile Lys Ala Asn Ile Arg Ala Gln Ala Ala Thr
385             390             395             400

Val Leu Val Ser Thr Leu Val Ala Val Ile Lys Ser Ser Tyr Leu Ala
            405             410             415

Leu Arg Ala Lys Asn Leu Lys Ala Leu Tyr Phe Val Leu Tyr Thr Tyr
            420             425             430

Val Tyr Phe Phe Cys Met Ile Pro Ala Arg Ile Thr Ala Met Phe Thr
        435             440             445

Met Phe Asp Ile Ala Trp Gly Thr Arg Gly Gly Asn Ala Lys Met Thr
    450             455             460

Ile Gly Ala Arg Val Trp Leu Trp Ala Lys Gln Phe Leu Ile Thr Tyr
465             470             475             480

Met Trp Trp Val Gly Val Leu Ala Ala Gly Val Tyr Ser Ile Val Asp
            485             490             495

Asn Trp Tyr Phe Asp Trp Ala Asp Ile Gln Tyr Arg Phe Ala Leu Val
            500             505             510

Gly Ile Cys Ser Tyr Leu Gly Phe Val Ser Ile Met Leu Val Phe Tyr
        515             520             525

Leu Ile Gly Lys Ile Thr Thr Trp Asn Tyr Thr Pro Leu Gln Lys Glu
    530             535             540

Leu Ile Lys Glu Arg Leu His Ala Ala Asn Ala Thr Glu Val
545             550             555
```

40

The invention claimed is:

1. A recombinant host cell (i) or a *Saccharomyces cerevisiae* recombinant yeast cell (ii) producing hyaluronic acid (HA) wherein the recombinant host cell (i) or the *S. cerevisiae* recombinant yeast cell (ii) comprises:

(a) one or more recombinant nucleic acids encoding a polypeptide having hyaluronan synthase activity;

(b) one or more recombinant nucleic acids encoding a polypeptide having UDP-Glucose dehydrogenase (UDP-GlcDH or HASB) activity;

(c) one or more recombinant nucleic acids encoding a polypeptide having hyaluronidase activity wherein the polypeptide having hyaluronidase activity comprises a secretion signal so that hyaluronic acid-is produced by the recombinant host cell (i) or the *S. cerevisiae* recombinant yeast cell (ii), wherein the hyaluronic acid produced by the recombinant host cell (i) is of a desired molecular weight (HAMW), and wherein the polypeptide having hyaluronidase activity comprised in the recombinant host cell (i) further comprises an anchoring signal; and (d) (i) one or more recombinant nucleic acids encoding a polypeptide having a glutamine synthetase (GLN1) activity; and/or (ii) one or more disrupted endogeneous nucleic acids encoding a glutamate synthase (GLT1).

2. The *S. cerevisiae* recombinant yeast cell (ii) according to claim 1 wherein the hyaluronic acid is of the desired molecular weight (HAMW).

3. The recombinant host cell (i) or the *S. cerevisiae* recombinant yeast cell (ii) according to claim 1, wherein the molecular weight of the HA is less than 50 kDa, or in a range of 20 kDa to 50 kDa.

4. The recombinant host cell (i) or the *S. cerevisiae* recombinant yeast cell (ii) according to claim 1, wherein the molecular weight of the HA is greater than 50 kDa, or in a range of 50 kDa to 250 kDa or is greater than 100 kDa, or is in a range of 100 kDa to 1500 kDa.

5. The recombinant host cell (i) or the *S. cerevisiae* recombinant yeast cell (ii) according to claim 1, wherein the nucleic acid encoding a polypeptide having a glutamine synthetase activity is obtained or derived from *Saccharomyces cerevisiae*.

6. The recombinant host cell (i) or the *S. cerevisiae* recombinant yeast cell (ii) according to claim 1, wherein the nucleic acid encoding a polypeptide having hyaluronidase activity is obtained or derived from at least one of *Cupiennius salei, Loxosceles intermedia, Hirudo nipponia, Bothrops atrox* and *Tityus serrulatus*.

7. The recombinant host cell (i) or the *S. cerevisiae* recombinant yeast cell (ii) according to claim 1, wherein the nucleic acid encoding a polypeptide having hyaluronan synthase activity is obtained or derived from *Streptococcus zooepidemicus, Chlorella* virus PBCV1, *Chlorella* virus CviK1, *Chlorella* virus IL-5-2s1, *Chlorella* virus CZ-2, *Chlorella* virus CVG-1, *Xenopus laevis* or *Pasteurella multocida.*

8. The recombinant host cell (i) or the *S. cerevisiae* recombinant yeast cell (ii) according to claim 1, wherein the nucleic acid encoding a polypeptide having UDP-Glucose dehydrogenase activity is obtained or derived from at least one of *Arabidopsis thaliana, Chlorella* virus PBCV1 and *Streptococcus zooepidemicus.*

9. The recombinant host cell (i) or the *S. cerevisiae* recombinant yeast cell (ii) according to claim 1, wherein the recombinant host cell (i) or the *S. cerevisiae* recombinant yeast cell (ii) further comprises a recombinant nucleic acid encoding one or more of:

(i) a polypeptide having glutamine-fructose-6-phosphate amidotransferase (GFA1) activity; and/or (ii) a polypeptide having UDP-N-acetylglucosamine pyrophosphorylase (QRI1) activity, and/or (iii) a polypeptide having Phosphoglucomutase-1 (PGM1) activity; and/or (iv) a polypeptide having UTP-glucose-1-phosphate uridylyltransferase (UGP1) activity; and/or (v) a polypeptide having Glucosamine-6-phosphate N-acetyltransferase (GNA1) activity; and/or (vi) a polypeptide having phosphoacetylglucosamine mutase (PCM1) activity.

10. The recombinant host cell (i) according to claim 1, wherein the recombinant host cell belongs to the Saccharomycesles order, and is selected from the group consisting of *Saccharomyces cerevisiae, Saccharomyces boulardii, Saccharomyces bayanus, Saccharomyces paradoxus, Saccharomyces mikatae, Saccharomyces castelli, Candida albicans, Candida glabrata, Candida tropicalis, Kluyveromyces lactis, Kluyveromyces marxianus, Kluyveromyces polysporus, Kluyveromyces thermotolerens, Ogataea polymorpha, Yarrowia lypolytica, Debaryomyces hansenii,* and *Ashbya gossypii.*

11. A method of producing hyaluronic acid (HA) of a desired molecular weight (HAMW) comprising:

(a) cultivating the recombinant host cell (i) or the *S. cerevisiae* recombinant yeast cell (ii) as defined in claim 1 in a cultivation medium for a time sufficient to produce hyaluronic acid (HA) of a desired molecular weight; and (b) optionally isolating or recovering the hyaluronic acid (HA) from the recombinant host cell (i) or the *S. cerevisiae* recombinant yeast cell (ii) and/or from the cultivation medium.

12. The method according to claim 11, wherein the HA has a molecular weight of from 20 kDa to 50 kDA, or from 20 kDa to 30 kDa, or from 30 kDa to 50 kDa, or from 50 kDa to 150 kDa, or from 150 kDa to 1500 kDa.

13. The method according to claim 11, wherein the recombinant host cell (i) or the *S. cerevisiae* recombinant yeast cell (ii) comprises at least one recombinant nucleic acid encoding one or more of:

(i) a polypeptide having glutamine-fructose-6-phosphate amidotransferase (GFA1) activity; and/or (ii) a polypeptide having UDP-N-acetylglucosamine pyrophosphorylase (QRI1) activity, and/or (iii) a polypeptide having Phosphoglucomutase-1 (PGM1) activity; and/or (iv) a polypeptide having UTP-glucose-1-phosphate uridylyltransferase (UGP1) activity;

(v) a polypeptide having Glucosamine-6-phosphate N-acetyltransferase (GNA1) activity; and/or (vi) a polypeptide having phosphoacetylglucosamine mutase (PCM1) activity.

14. The method according to claim 11, wherein the time sufficient to produce hyaluronic acid (HA) of the desired molecular weight is a period of from 35 hours to 50 hours, or from 40 hours to 50 hours or is 48 hours.

15. The method according to claim 11, wherein the molecular weight of the hyaluronic acid is controlled by regulating the pH of the cultivation medium.

16. The method according to claim 11, wherein the method is carried out on an industrial scale where the cultivation medium is at least 100 L, in a range of 1000 L to 3000 L, or is 10,000 L, or is 100,000 L, or is 250,000 L.

17. A method for producing hyaluronic acid comprising the steps of:

(a) culturing a recombinant host cell (i) or a *S. cerevisiae* recombinant yeast cell (ii) as defined in claim 1 in a culture medium; and (b) recovering the hyaluronic acid from said culture medium, wherein the hyaluronic acid recovered in step (b) has a molecular weight controlled through the selection of:

the nature and origin of the nucleic acid encoding the hyaluronidase of the recombinant yeast, the nature and origin of the promoter controlling the expression of the nucleic acid encoding the hyaluronidase(s) of the recombinant yeast, the presence of an anchoring and/or of a secretion signal associated with the encoded hyaluronidase(s) of the recombinant yeast, the pH of the culture medium during the step of culturing the recombinant yeast, and/or the duration of the culturing of the recombinant yeast.

* * * * *